(12) United States Patent
Doxsey

(10) Patent No.: US 7,279,566 B2
(45) Date of Patent: Oct. 9, 2007

(54) CENTROSOME PROTEINS AND USES THEREOF

(75) Inventor: Stephen J. Doxsey, Princeton, MA (US)

(73) Assignee: University of Massachusetts, Boston, MA (US)

( * ) Notice: Subject to any disclaimer, the term of this patent is extended or adjusted under 35 U.S.C. 154(b) by 512 days.

(21) Appl. No.: 10/663,433

(22) Filed: Sep. 15, 2003

(65) Prior Publication Data

US 2004/0175721 A1 Sep. 9, 2004

Related U.S. Application Data

(60) Provisional application No. 60/410,520, filed on Sep. 13, 2002.

(51) Int. Cl.
*C07H 21/04* (2006.01)
*C07H 21/02* (2006.01)
*C12Q 1/68* (2006.01)
*C12N 15/00* (2006.01)

(52) U.S. Cl. .................. 536/23.5; 435/6; 435/91.1; 435/320.1; 536/23.1

(58) Field of Classification Search ................ 435/6, 435/91.1, 320.1; 536/23.1, 23.5
See application file for complete search history.

(56) References Cited

U.S. PATENT DOCUMENTS 6,812,339 B1 11/2004 Venter et al.

OTHER PUBLICATIONS

Adames et al., "The surveillance mechanism of the spindle position checkpoint in yeast," J. Cell. Biol. 153, 159-68 (2001).
Andreassen et al., "Tetraploid State Induces p53-dependent Arrest of Nontransformed Mammalian Cells in G1," Mol. Biol. Cell 12, 1315-28 (2001).
Balasubramani et al., "Isolation and characterization of new fission yeast cytokinesis mutants," Genetics 149, 1265-75 (1998).
Bardin and Amon, "Men and sin: what's the difference?," Nat. Rev. Mol. Cell. Biol. 2, 815-26 (2001).
Bardin et al., "A mechanism for coupling exit from mitosis to partitioning of the nucleus," Cell 102, 21-31 (2000).
Bloecher et al., "Anaphase spindle position is monitored by the BUB2 checkpoint," Nat. Cell. Biol. 2, 556-8 (2000).
Bobinnec et al., "Centriol disassembly in vivo and its effect on centrosome structure and function in vertebrate cells," J. Cell. Biol. 143, 1575-1589 (1998).
Chang and Gould, "Sid4p is required to localize components of the septation initiation pathway to the spindle pole body in fission yeast," Proc. Natl. Acad. Sci. USA 97, 5249-54 (2000).
Cuif et al., "Characterization of GAPCenA, a GTPase activating protein for Rab6, part of which associates with the centrosome," EMBO. J. 18, 1772-82 (1999).

Dictenberg et al., "Pericentrin and gamma tubulin form a protein complex and are organized into a novel lattice at the centrosome," J. Cell. Biol. 141, 163-174 (1998).
Diviani et al., "Pericentrin anchors protein kinase A at the centrosome through a newly identified RII-binding domain," Curr. Biol. 10, 417-20 (2000).
Doxsey, S.J. "Re-evaluating centrosome function," Nature Reviews in Molecular Biology 2 688-699 (2000).
Doxsey et al., "Pericentrin, a highly conserved protein of centrosomes involoved in microtubule orgainzation," Cell 76, 639-650 (1994).
Fankhauser et al., "The S. pombe cdc15 gene is a key element in the reorganization of F- actin at mitosis," Cell 82, 435-44 (1995).
Flory et al., "Identification of a human centrosomal calmodulin-binding protein that shares homology with pericentrin," Proc. Natl. Acad. Sci. USA 97, 5919-23 (2000).
Gergely et al., "The TACC domain identifies a family of centrosomal proteins that can interact with microtubules," Proc. Natl. Acad. Sci. USA 97, 14352-7 (2000).
Gillingham and Munro, "The PACT domain, a conserved centrosomal targeting motif in the coiled-coil proteins AKAP450 and pericentrin," EMBO Rep. 1, 524-9 (2000).
Gruneberg et al., "Nud1p links astral microtubule organization and the control of exit from mitosis," Embo. J. 19, 6475-88 (2000).
Guasch et al., FGFR1 is fused to the centrosome-associated protein CEP110 in the 8p12 stem cell myeloproliferative disorder with t(8;9)(p12;q33), Blood 95, 1788-96 (2000).
Guertin et al., "Cytokinesis in eukaryotes," Microbiol. Mol. Biol. Rev. 66, 155-78 (2002).
Hinchcliffe et al, "Requirement of a centrosomal activity for cell cycle progression through G1 into S phase," Sciene 291, 1547-50 (2001).
Hirota et al., "Zyxin, a regulator of actin filament assembly, target the mitotic apparatus by interacting with h-warts/LATS1 tumor suppressor," J. Cell. Biol. 149, 1073-86 (2000).
Khodjakov, A. and Rieder, C. L., "Centrosomes enchance the fidelity of cytokinesis in vertebrates and are required for cell cycle progression," J. Cell. Biol. 153, 237-42 (2001).
Krapp et al, "S. pombe cdc11p, together with sid4p, provides an anchor for septation initiation network proteins on the spindle pole body," Curr. Biol. 11, 1559-68 (2001).
Le Goff et al., "Controlling septation in fission yeast: finding the middle, and timing it right," Curr. Genet. 35, 571-84 (1999).
Le Goff et al., "Analysis of the cps1 gene provides evidence for a septation checkpoint in Schizosaccharomyces pombe," Mol. Gen. Genet. 262, 163-72 (1999b).
Lee et al., "Msps/XMAP215 interacts with the centrosomal protein D-TACC to regulate microtubule behaviour," Nat. Cell. Biol. 3, 643-9 (1999b).

(Continued)

*Primary Examiner*—Jane Zara
(74) *Attorney, Agent, or Firm*—Fish & Richardson P.C.

(57) ABSTRACT

The invention includes nucleic acids and polypeptides that play important roles in centrosomes and cellular functions involving centrosomes. In addition, the invention encompasses antibodies, ribozymes, antisense nucleic acids, RNAis, and siRNAs that can be used to modulate the function of the nucleic acids and polypeptides of the invention. Such modulation can be useful in detecting, diagnosing, and treating abnormal centrosome function.

4 Claims, 44 Drawing Sheets
(7 of 44 Drawing Sheet(s) Filed in Color)

OTHER PUBLICATIONS

Liu et al., "A checkpoint that monitors cytokinesis in Schizosaccharomyces pombe," J. Cell. Sci. 113, 1223-30 (2000).

Luca and Winey, "MOB1, an essential yeast gene required for completion of mitosis and maintenance of ploidy," Mol. Biol. Cell 9, 29-46 (1998).

Mailand et al., "Deregulated human Cdc14A phosphatase disrupts centrosome separation and chromosome segregation," Nat. Cell. Biol. 4, 318-22 (2002).

Matuliene and Kuriyama, "Kinesin-like protein CHO1 is required for the formation of midbody matrix and the completion of cytokinesis in mammalian cells," Mol. Biol. Cell 13(6):1832-45 (2002).

McCollum and Gould, "Timing is everything: regulation of mitotic exit and cytokinesis by the MEN and SIN," Trends Cell. Biol. 11, 89-95 (2001).

Meraldi et al., "Aurora-A overexpression reveals tetraploidization as a major route to centrosome amplification in p53-/-cells," Embo. J. 21, 483-92 (2002).

Mogensen et al., "Centrosomal deployment of gamma-tubulin and pericentrin: Evidence for a microtubule-nucleating domain and a munis-end docking domain in certain mouse epithelial cells," Cell. Motil. Cytoskel. 36, 276-290 (1997).

Mogensen et al., "Microtubule minus-end anchorage at centrosomal and non-centrosomal sites: the role of ninein," J. Cell. Sci. 113, 3013-23 (2000).

Mollinari et al., "PRC1 is a microtubule binding and bundling protein essential to maintain the mitotic spindle midzone," J. Cell. Biol. 157:1175-1186 (2002).

Morales et al., "Absene of cancer-associated changes in human fibroblasts immortalized with telomerase," Nat. Genet. 21, 115-8 (1999).

Pereira and Schiebel, "The role of the yeast spindle pole body and the mammalian centrosome in regulating late mitotic events," Curr. Opin. Cell. Biol. 13, 762-9 (2001).

Piel et al., "The respective contributions of the mother and daughter centrioles to centrosome activity and behavior in vertebrate cells," J. Cell. Biol. 149(2):317-30 (2000).

Purohit et al., "Direct interaction of pericentrin with cytoplasmic dynein light intermediate chain contributes to mitotic spindle organization," J. Cell. Biol. 147, 481-491 (1999).

Scheffner et al., "The E6 oncoprotein encoded by human papillomavirus types 16 and 18 promotes the degradation of p53," Cell 63, 1129-36 (1990).

Tomlin et al., "The spindle pole body protein cdc11p links sid4p to the fission yeast septation initiation network," Mol. Biol. Cell 13, 1203-14 (2002).

Trautmann et al., "Fission yeast Clp1p phosphatase regulates G2/M transition and coordination of cytokinesis with cell cycle progression," Curr. Biol. 11, 931-40 (2001).

Gromley et al., "A novel human protein of the maternal centriole is required for the final stages of cytokinesis and entry into S phase," J. Cell Biol. 161(3):535-45 (2003).

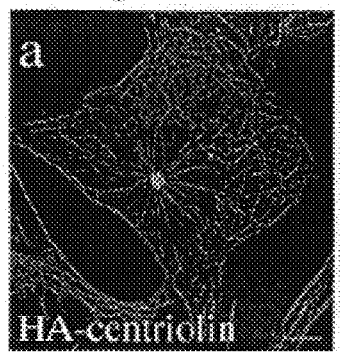
Figure 2A
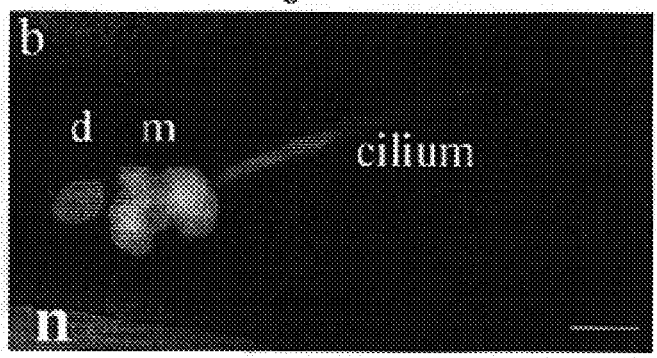
Figure 2B
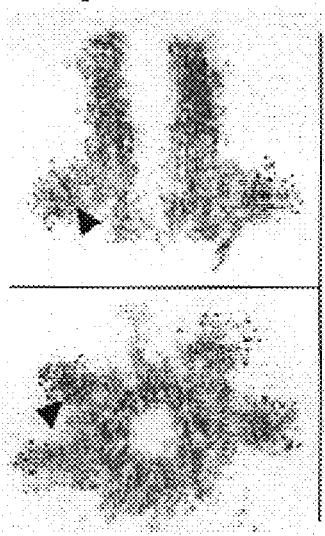
Figure 2C
Figure 2D
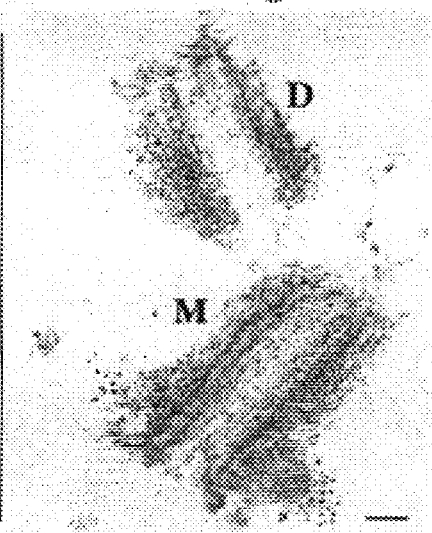
Figure 2E

SEQ ID NO:5
SEQ ID NO:6
SEQ ID NO:7

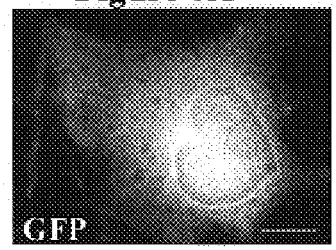
Figure 6A
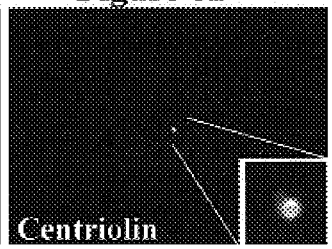
Figure 6B
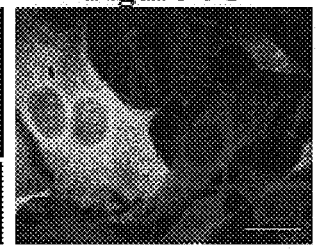
Figure 6C
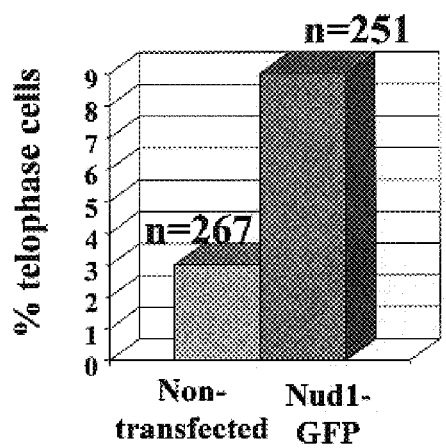
Figure 6D
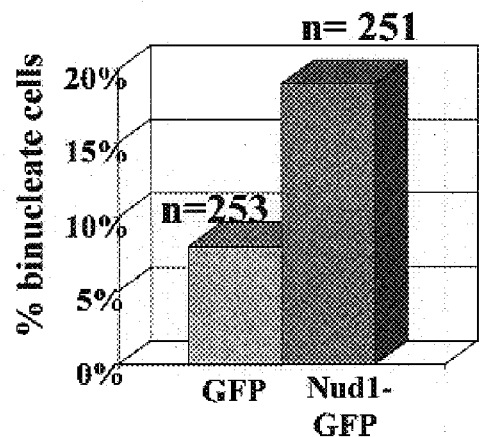
Figure 6E
Figure 7A
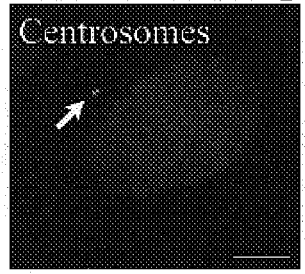
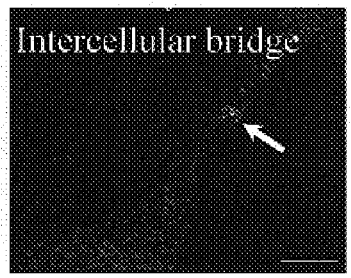

Centriolin

Pcnt-B

Serum starved

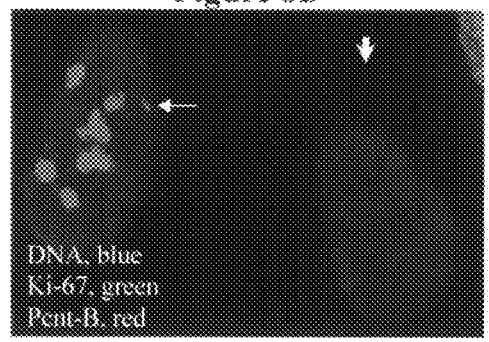
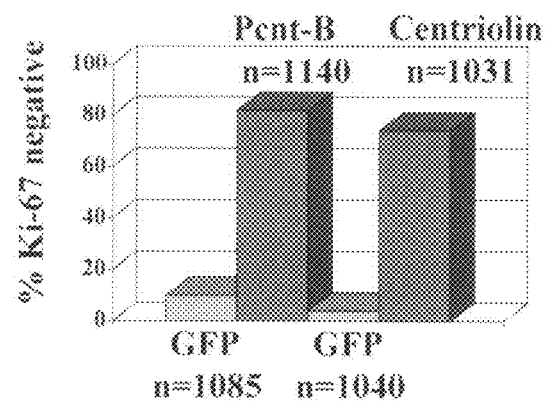
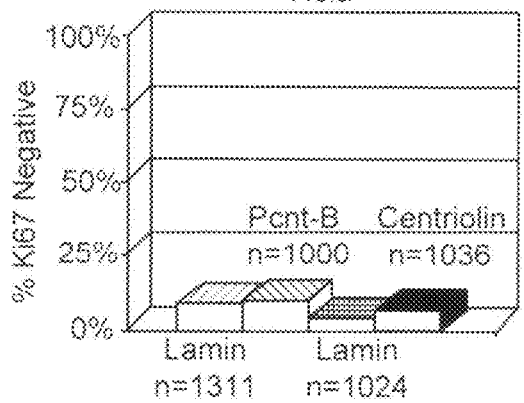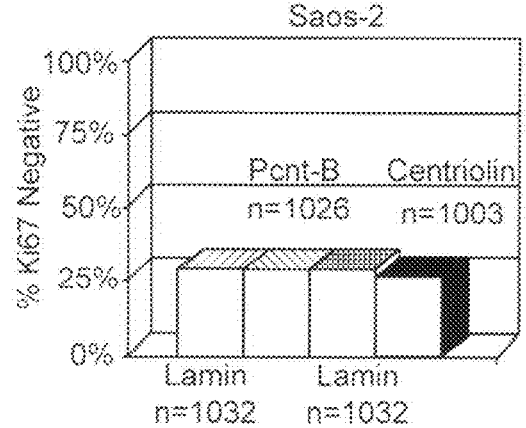

Figure 9

Without Nocodozole

|  | %G1 | %S | %G2 |
|---|---|---|---|
| Centriolin | 74 | 13 | 4 |
| Lamin (control) | 62 | 23 | 7 |
|  | %G1 | %S | %G2 |
| Pcnt-B | 70 | 13 | 14 |
| GFP (control) | 46 | 35 | 19 |

With Nocodozole

|  | %G1 | %S | %G2 |
|---|---|---|---|
| Centriolin | 49 | 13 | 23 |
| Lamin (control) | 19 | 19 | 46 |
|  | %G1 | %S | %G2 |
| Pcnt-B | 65 | 14 | 19 |
| GFP (control) | 24 | 15 | 60 |

Cell Cycle analysis of glow cytometry data (Fig. 8)

Figure 12A

| | |
|---|---:|
| atg aag aaa ggt tct caa caa aaa ata ttc tcc aaa gca aag ata cca<br>Met Lys Lys Gly Ser Gln Gln Lys Ile Phe Ser Lys Ala Lys Ile Pro<br>1                   5                           10                        15 | 48 |
| tca tca tct cac tct cct atc cca tca tct atg tcc aat atg aga tct<br>Ser Ser Ser His Ser Pro Ile Pro Ser Ser Met Ser Asn Met Arg Ser<br>                     20                         25                      30 | 96 |
| agg tca ctt tca cct ttg att gga tca gag act cta cct ttt cat tct<br>Arg Ser Leu Ser Pro Leu Ile Gly Ser Glu Thr Leu Pro Phe His Ser<br>           35                      40                      45 | 144 |
| gga gga cag tgg tgt gag caa att gag att gca gat gaa aac aat atg<br>Gly Gly Gln Trp Cys Glu Gln Ile Glu Ile Ala Asp Glu Asn Asn Met<br>        50                     55                    60 | 192 |
| ctt ttg gac tat caa gac cat aaa gga gct gat tca cat gca gga gtt<br>Leu Leu Asp Tyr Gln Asp His Lys Gly Ala Asp Ser His Ala Gly Val<br>65                    70                      75                    80 | 240 |
| aga tat att aca gag gcc ctc att aaa aaa ctt act aaa cag gat aat<br>Arg Tyr Ile Thr Glu Ala Leu Ile Lys Lys Leu Thr Lys Gln Asp Asn<br>                85                      90                    95 | 288 |
| ttg gct ttg ata aaa tct ctg aac ctt tca ctt tct aaa gac ggt ggc<br>Leu Ala Leu Ile Lys Ser Leu Asn Leu Ser Leu Ser Lys Asp Gly Gly<br>           100                   105                   110 | 336 |
| aag aaa ttt aag tat att gag aat ttg gaa aaa tgt gtt aaa ctt gaa<br>Lys Lys Phe Lys Tyr Ile Glu Asn Leu Glu Lys Cys Val Lys Leu Glu<br>           115                   120                   125 | 384 |
| gta ctg aat ctc agc tat aat cta ata ggg aag att gaa aag ttg gac<br>Val Leu Asn Leu Ser Tyr Asn Leu Ile Gly Lys Ile Glu Lys Leu Asp<br>           130                   135                   140 | 432 |
| aag ctg tta aaa tta cgt gaa ctc aac tta tca tat aac aaa atc agc<br>Lys Leu Leu Lys Leu Arg Glu Leu Asn Leu Ser Tyr Asn Lys Ile Ser<br>145                   150                   155                   160 | 480 |
| aaa att gaa ggc ata gaa aat atg tgt aat ctg caa aag ctt aac ctt<br>Lys Ile Glu Gly Ile Glu Asn Met Cys Asn Leu Gln Lys Leu Asn Leu<br>                  165                   170                   175 | 528 |
| gca gga aat gaa att gag cat att cca gta tgg tta ggg aag aag tta<br>Ala Gly Asn Glu Ile Glu His Ile Pro Val Trp Leu Gly Lys Lys Leu<br>           180                   185                   190 | 576 |
| aaa tct ttg cga gtc ctc aat ttg aaa ggc aac aag ata tca tcg ctc<br>Lys Ser Leu Arg Val Leu Asn Leu Lys Gly Asn Lys Ile Ser Ser Leu<br>           195                   200                   205 | 624 |
| caa gat ata agc aag ttg aaa ccg ctt caa gat ttg att tct ctg atc<br>Gln Asp Ile Ser Lys Leu Lys Pro Leu Gln Asp Leu Ile Ser Leu Ile<br>           210                   215                   220 | 672 |
| cta gtt gaa aat cca gtt gtg acc ctt cct cat tac ctc cag ttt acc<br>Leu Val Glu Asn Pro Val Val Thr Leu Pro His Tyr Leu Gln Phe Thr<br>225                   230                   235                   240 | 720 |

Figure 12B

| | |
|---|---|
| att ttc cac ctc cgt tca ttg gaa agt ttg gaa ggt cag cca gta acc<br>Ile Phe His Leu Arg Ser Leu Glu Ser Leu Glu Gly Gln Pro Val Thr<br>245                             250                        255 | 768 |
| act cag gat aga cag gag gct ttt gag aga ttc agt tta gaa gag gta<br>Thr Gln Asp Arg Gln Glu Ala Phe Glu Arg Phe Ser Leu Glu Glu Val<br>           260                       265                    270 | 816 |
| gaa aga ctg gaa aga gac cta gaa aaa aag atg ata gaa act gaa gag<br>Glu Arg Leu Glu Arg Asp Leu Glu Lys Lys Met Ile Glu Thr Glu Glu<br>      275                       280                   285 | 864 |
| ctt aag agc aaa caa aca agg ttc ctt gag gaa att aaa aat caa gat<br>Leu Lys Ser Lys Gln Thr Arg Phe Leu Glu Glu Ile Lys Asn Gln Asp<br>      290                       295                 300 | 912 |
| aaa ttg aat aaa tca tta aaa gag gag gcc atg tta cag aaa cag agc<br>Lys Leu Asn Lys Ser Leu Lys Glu Glu Ala Met Leu Gln Lys Gln Ser<br>305                       310                   315               320 | 960 |
| tgt gag gaa ctc aag agt gac tta aac aca aaa aat gaa ttg cta aaa<br>Cys Glu Glu Leu Lys Ser Asp Leu Asn Thr Lys Asn Glu Leu Leu Lys<br>           325                       330                   335 | 1008 |
| cag aag acc ata gaa tta aca cga gca tgt cag aag caa tat gag ctg<br>Gln Lys Thr Ile Glu Leu Thr Arg Ala Cys Gln Lys Gln Tyr Glu Leu<br>           340                       345                   350 | 1056 |
| gaa cag gaa ttg gcc ttt tat aaa att gat gct aaa ttt gag cca cta<br>Glu Gln Glu Leu Ala Phe Tyr Lys Ile Asp Ala Lys Phe Glu Pro Leu<br>      355                       360                 365 | 1104 |
| aat tat tat cca tca gag tat gct gaa att gat aaa gcc cca gat gaa<br>Asn Tyr Tyr Pro Ser Glu Tyr Ala Glu Ile Asp Lys Ala Pro Asp Glu<br>370                     375                    380 | 1152 |
| agc cct tac att ggc aaa tcc aga tac aag aga aat atg ttt gcc aca<br>Ser Pro Tyr Ile Gly Lys Ser Arg Tyr Lys Arg Asn Met Phe Ala Thr<br>385                     390                   395               400 | 1200 |
| gag agt tat att att gac agt gct cag gca gta cag atc aag aag atg<br>Glu Ser Tyr Ile Ile Asp Ser Ala Gln Ala Val Gln Ile Lys Lys Met<br>           405                       410                   415 | 1248 |
| gag cca gat gaa caa ctt aga aat gat cac atg aac ttg aga ggc cac<br>Glu Pro Asp Glu Gln Leu Arg Asn Asp His Met Asn Leu Arg Gly His<br>               420                       425                 430 | 1296 |
| aca cca ctg gac acg caa ctg gaa gac aaa gaa aaa aaa ata agt gca<br>Thr Pro Leu Asp Thr Gln Leu Glu Asp Lys Glu Lys Lys Ile Ser Ala<br>           435                       440                   445 | 1344 |
| gca caa act cga cta tca gaa ctg cat gat gaa ata gaa aag gca gaa<br>Ala Gln Thr Arg Leu Ser Glu Leu His Asp Glu Ile Glu Lys Ala Glu<br>450                     455                    460 | 1392 |
| caa caa att ttg aga gct act gaa gaa ttt aaa caa ctg gaa gaa gct<br>Gln Gln Ile Leu Arg Ala Thr Glu Glu Phe Lys Gln Leu Glu Glu Ala<br>465                     470                   475               480 | 1440 |

Figure 12C

```
ata caa cta aaa aag att tca gaa gca ggg aaa gac ctt ctt tac aag        1488
Ile Gln Leu Lys Lys Ile Ser Glu Ala Gly Lys Asp Leu Leu Tyr Lys
            485                 490                 495 cag ttg agt ggt aga cta caa ctt gta aat aaa tta cgc cag gaa gct        1536
Gln Leu Ser Gly Arg Leu Gln Leu Val Asn Lys Leu Arg Gln Glu Ala
            500                 505                 510 ctg gat cta gaa ctg cag atg gaa aag caa aag cag gaa att gcc gga        1584
Leu Asp Leu Glu Leu Gln Met Glu Lys Gln Lys Gln Glu Ile Ala Gly
            515                 520                 525 aag cag aag gag att aag gac ctg caa ata gcc ata gat agc ctg gat        1632
Lys Gln Lys Glu Ile Lys Asp Leu Gln Ile Ala Ile Asp Ser Leu Asp
530                 535                 540 tcc aaa gac cca aaa cat tcc cat atg aag gct caa aag agc ggt aaa        1680
Ser Lys Asp Pro Lys His Ser His Met Lys Ala Gln Lys Ser Gly Lys
545                 550                 555                 560 gaa caa cag ctt gac att atg aac aag cag tac caa caa ctt gaa agt        1728
Glu Gln Gln Leu Asp Ile Met Asn Lys Gln Tyr Gln Gln Leu Glu Ser
            565                 570                 575 cgt ttg gat gag ata ctt tct aga att gct aag gaa acg gaa gag att        1776
Arg Leu Asp Glu Ile Leu Ser Arg Ile Ala Lys Glu Thr Glu Glu Ile
            580                 585                 590 aag gac ctt gaa gaa cag ctt act gaa ggc cag ata gca gca aat gaa        1824
Lys Asp Leu Glu Glu Gln Leu Thr Glu Gly Gln Ile Ala Ala Asn Glu
            595                 600                 605 gcc ctg aag aag gat tta gaa ggt gtt atc agt ggg ttg caa gaa tac        1872
Ala Leu Lys Lys Asp Leu Glu Gly Val Ile Ser Gly Leu Gln Glu Tyr
610                 615                 620 ctg ggg acc att aaa ggc cag gca act cag gcc cag aat gag tgc agg        1920
Leu Gly Thr Ile Lys Gly Gln Ala Thr Gln Ala Gln Asn Glu Cys Arg
625                 630                 635                 640 aag ctg cgg gat gag aaa gag aca ttg ttg cag aga ttg aca gaa gtc        1968
Lys Leu Arg Asp Glu Lys Glu Thr Leu Leu Gln Arg Leu Thr Glu Val
            645                 650                 655 gag cag gag aga gac cag ctg gaa ata gtt gcc atg gat gca gaa aat        2016
Glu Gln Glu Arg Asp Gln Leu Glu Ile Val Ala Met Asp Ala Glu Asn
            660                 665                 670 atg agg aag gag ctt gca gag cta gaa agt gcc ctc caa gag cag cat        2064
Met Arg Lys Glu Leu Ala Glu Leu Glu Ser Ala Leu Gln Glu Gln His
            675                 680                 685 gag gtg aat gca tct ttg cag cag acc cag gga gat ctc agt gcc tat        2112
Glu Val Asn Ala Ser Leu Gln Gln Thr Gln Gly Asp Leu Ser Ala Tyr
            690                 695                 700 gaa gct gag cta gag gct cgg cta aac cta agg gat gct gaa gcc aac        2160
Glu Ala Glu Leu Glu Ala Arg Leu Asn Leu Arg Asp Ala Glu Ala Asn
705                 710                 715                 720
```

Figure 12D

```
cag ctc aag gaa gag ttg gaa aaa gta aca aga ctt acc cag tta gaa    2208
Gln Leu Lys Glu Glu Leu Glu Lys Val Thr Arg Leu Thr Gln Leu Glu
            725                 730                 735 caa tca gcc ctt caa gca gaa ctt gag aag gaa agg caa gcc ctc aag    2256
Gln Ser Ala Leu Gln Ala Glu Leu Glu Lys Glu Arg Gln Ala Leu Lys
            740                 745                 750 aat gcc ctt gga aaa gcc cag ttc tca gaa gaa aag gag caa gag aac    2304
Asn Ala Leu Gly Lys Ala Gln Phe Ser Glu Glu Lys Glu Gln Glu Asn
            755                 760                 765 agt gag ctc cat gca aaa ctt aaa cac ttg cag gat gac aat aat ctg    2352
Ser Glu Leu His Ala Lys Leu Lys His Leu Gln Asp Asp Asn Asn Leu
            770                 775                 780 tta aaa cag caa ctt aaa gat ttc cag aat cac ctt aac cat gtg gtt    2400
Leu Lys Gln Gln Leu Lys Asp Phe Gln Asn His Leu Asn His Val Val
785                 790                 795                 800 gat ggt ttg gtt cgt cca gaa gaa gtg gca gct cgt gtg gat gag cta    2448
Asp Gly Leu Val Arg Pro Glu Glu Val Ala Ala Arg Val Asp Glu Leu
            805                 810                 815 aga aga aaa ctg aaa tta gga act ggg gaa atg aac atc cat agt cct    2496
Arg Arg Lys Leu Lys Leu Gly Thr Gly Glu Met Asn Ile His Ser Pro
            820                 825                 830 tca gat gtc tta ggg aaa agt ctt gct gat tta cag aaa caa ttc agt    2544
Ser Asp Val Leu Gly Lys Ser Leu Ala Asp Leu Gln Lys Gln Phe Ser
            835                 840                 845 gaa att ctt gca cgc tcc aag tgg gaa aga gat gaa gca caa gtt aga    2592
Glu Ile Leu Ala Arg Ser Lys Trp Glu Arg Asp Glu Ala Gln Val Arg
            850                 855                 860 gag aga aaa ctc caa gaa gaa atg gct ctg cag caa gag aaa ctg gca    2640
Glu Arg Lys Leu Gln Glu Glu Met Ala Leu Gln Gln Glu Lys Leu Ala
865                 870                 875                 880 act gga caa gaa gag ttc agg cag gcc tgt gag aga gcc ctg gaa gca    2688
Thr Gly Gln Glu Glu Phe Arg Gln Ala Cys Glu Arg Ala Leu Glu Ala
            885                 890                 895 aga atg aat ttt gat aag agg caa cat gaa gca aga atc cag caa atg    2736
Arg Met Asn Phe Asp Lys Arg Gln His Glu Ala Arg Ile Gln Gln Met
            900                 905                 910 gag aat gaa att cac tat ttg caa gaa aat cta aaa agt atg gag gaa    2784
Glu Asn Glu Ile His Tyr Leu Gln Glu Asn Leu Lys Ser Met Glu Glu
            915                 920                 925 atc caa ggc ctt aca gat ctc caa ctt cag gaa gct gat gaa gag aag    2832
Ile Gln Gly Leu Thr Asp Leu Gln Leu Gln Glu Ala Asp Glu Glu Lys
            930                 935                 940 gag aga att ctg gcc caa ctc cga gag tta gag aaa aag aag aaa ctt    2880
Glu Arg Ile Leu Ala Gln Leu Arg Glu Leu Glu Lys Lys Lys Lys Leu
945                 950                 955                 960
```

Figure 12E

```
gaa gat gcc aaa tct cag gag caa gtt ttt ggt tta gat aaa gaa ctg      2928
Glu Asp Ala Lys Ser Gln Glu Gln Val Phe Gly Leu Asp Lys Glu Leu
            965                 970                 975 aag aaa cta aag aaa gcc gtg gcc acc tct gat aag cta gcc aca gct      2976
Lys Lys Leu Lys Lys Ala Val Ala Thr Ser Asp Lys Leu Ala Thr Ala
            980                 985                 990 gag ctc acc att gcc aaa gac cag ctg aag tcc ctt cat gga act gtt      3024
Glu Leu Thr Ile Ala Lys Asp Gln Leu Lys Ser Leu His Gly Thr Val
        995                 1000                1005 atg aaa att aac cag gag cga gca gag gag ttg cag gaa gca gag agg      3072
Met Lys Ile Asn Gln Glu Arg Ala Glu Glu Leu Gln Glu Ala Glu Arg
    1010                1015                1020 ttc agc aga aag gca gca caa gca gcc aga gat ctc acc cga gca gaa      3120
Phe Ser Arg Lys Ala Ala Gln Ala Ala Arg Asp Leu Thr Arg Ala Glu
1025                1030                1035                1040 gct gag atc gaa ctc ctg cag aat ctc ctc agg cag aag ggg gag cag      3168
Ala Glu Ile Glu Leu Leu Gln Asn Leu Leu Arg Gln Lys Gly Glu Gln
                1045                1050                1055 ttt cga ctt gag atg gag aaa aca ggt gta ggt act gga gca aac tca      3216
Phe Arg Leu Glu Met Glu Lys Thr Gly Val Gly Thr Gly Ala Asn Ser
            1060                1065                1070 cag gtc cta gaa att gag aaa ctg aat gag aca atg gaa cga caa agg      3264
Gln Val Leu Glu Ile Glu Lys Leu Asn Glu Thr Met Glu Arg Gln Arg
        1075                1080                1085 aca gag att gca agg ctg cag aat gta cta gac ctc act gga agt gac      3312
Thr Glu Ile Ala Arg Leu Gln Asn Val Leu Asp Leu Thr Gly Ser Asp
    1090                1095                1100 aac aaa gga ggc ttt gaa aat gtt tta gaa gaa att gct gaa ctt cga      3360
Asn Lys Gly Gly Phe Glu Asn Val Leu Glu Glu Ile Ala Glu Leu Arg
1105                1110                1115                1120 cgt gaa gtt tct tat cag aat gat tac ata agc agc atg gca gat cct      3408
Arg Glu Val Ser Tyr Gln Asn Asp Tyr Ile Ser Ser Met Ala Asp Pro
                1125                1130                1135 ttc aaa aga cga ggc tat tgg tac ttt atg cca cca cca cca tca tca      3456
Phe Lys Arg Arg Gly Tyr Trp Tyr Phe Met Pro Pro Pro Pro Ser Ser
            1140                1145                1150 aaa gtt tcc agc cat agt tcc cag gcc acc aag gac tct ggt gtt ggc      3504
Lys Val Ser Ser His Ser Ser Gln Ala Thr Lys Asp Ser Gly Val Gly
        1155                1160                1165 ctt aag tac tca gcc tca act cct gtt aga aaa cca cgc cct ggg cag      3552
Leu Lys Tyr Ser Ala Ser Thr Pro Val Arg Lys Pro Arg Pro Gly Gln
    1170                1175                1180 cag gat ggg aag gaa ggc agt caa cct ccc cct gcc tca gga tac tgg      3600
Gln Asp Gly Lys Glu Gly Ser Gln Pro Pro Pro Ala Ser Gly Tyr Trp
1185                1190                1195                1200
```

Figure 12F

```
gtt tat tct ccc atc agg agt ggg tta cat aaa ctg ttt cca agt aga    3648
Val Tyr Ser Pro Ile Arg Ser Gly Leu His Lys Leu Phe Pro Ser Arg
            1205                1210                1215 gat gca gac agt gga gga gat agt cag gaa gag agt gag ctg gat gac    3696
Asp Ala Asp Ser Gly Gly Asp Ser Gln Glu Glu Ser Glu Leu Asp Asp
            1220                1225                1230 caa gaa gaa ccc cca ttt gtg cct cct cct gga tac atg atg tat act    3744
Gln Glu Glu Pro Pro Phe Val Pro Pro Pro Gly Tyr Met Met Tyr Thr
        1235                1240                1245 gtg ctt cct gat ggt tct cct gta ccc cag ggc atg gcc ctg tat gca    3792
Val Leu Pro Asp Gly Ser Pro Val Pro Gln Gly Met Ala Leu Tyr Ala
        1250                1255                1260 cca cct cct ccc ttg cca aac aat agc cga cct ctc acc cct ggc act    3840
Pro Pro Pro Pro Leu Pro Asn Asn Ser Arg Pro Leu Thr Pro Gly Thr
1265                1270                1275                1280 gtt gtt tat ggc cca cct cct gct ggg gcc ccc atg gtg tat ggg cct    3888
Val Val Tyr Gly Pro Pro Pro Ala Gly Ala Pro Met Val Tyr Gly Pro
            1285                1290                1295 cca ccc ccc aac ttc tcc atc ccc ttc atc cct atg ggt gtg ctg cat    3936
Pro Pro Pro Asn Phe Ser Ile Pro Phe Ile Pro Met Gly Val Leu His
            1300                1305                1310 tgc aac gtc cct gaa cac cat aac tta gag aat gaa gtt tct aga tta    3984
Cys Asn Val Pro Glu His His Asn Leu Glu Asn Glu Val Ser Arg Leu
            1315                1320                1325 gaa gac ata atg cag cat tta aaa tca aag aag cgg gaa gaa agg tgg    4032
Glu Asp Ile Met Gln His Leu Lys Ser Lys Lys Arg Glu Glu Arg Trp
            1330                1335                1340 atg aga gca tcc aag cgg cag tcg gag aaa gaa atg gaa gaa ctg cat    4080
Met Arg Ala Ser Lys Arg Gln Ser Glu Lys Glu Met Glu Glu Leu His
1345                1350                1355                1360 cat aat att gat gat ctt ttg caa gag aag aaa agc tta gag tgt gaa    4128
His Asn Ile Asp Asp Leu Leu Gln Glu Lys Lys Ser Leu Glu Cys Glu
            1365                1370                1375 gta gaa gaa tta cat aga act gtc cag aaa cgt caa cag caa aag gac    4176
Val Glu Glu Leu His Arg Thr Val Gln Lys Arg Gln Gln Gln Lys Asp
            1380                1385                1390 ttc att gat gga aat gtt gag agt ctt atg act gaa cta gaa ata gaa    4224
Phe Ile Asp Gly Asn Val Glu Ser Leu Met Thr Glu Leu Glu Ile Glu
        1395                1400                1405 aaa tca ctc aaa cat cat gaa gat att gta gat gaa att gag tgc att    4272
Lys Ser Leu Lys His His Glu Asp Ile Val Asp Glu Ile Glu Cys Ile
1410                1415                1420 gag aag act ctt ctg aaa cgt cgc tca gag ctc agg gaa gct gac cga    4320
Glu Lys Thr Leu Leu Lys Arg Arg Ser Glu Leu Arg Glu Ala Asp Arg
1425                1430                1435                1440
```

Figure 12G

```
ctc ctg gca gag gct gag agt gaa ctt tca tgc act aaa gaa aag aca      4368
Leu Leu Ala Glu Ala Glu Ser Glu Leu Ser Cys Thr Lys Glu Lys Thr
            1445            1450             1455 aaa aat gct gtt gaa aag ttc act gat gcc aag aga agt tta ttg caa      4416
Lys Asn Ala Val Glu Lys Phe Thr Asp Ala Lys Arg Ser Leu Leu Gln
            1460            1465             1470 act gag tca gat gct gag gaa tta gaa agg aga gct cag gaa act gct     4464
Thr Glu Ser Asp Ala Glu Glu Leu Glu Arg Arg Ala Gln Glu Thr Ala
            1475            1480             1485 gtt aac ctc gtc aaa gct gat cag cag cta aga tcg ctc cag gct gat      4512
Val Asn Leu Val Lys Ala Asp Gln Gln Leu Arg Ser Leu Gln Ala Asp
        1490            1495             1500 gca aag gat ttg gag cag cac aaa atc aag caa gaa gaa atc ttg aaa      4560
Ala Lys Asp Leu Glu Gln His Lys Ile Lys Gln Glu Glu Ile Leu Lys
1505            1510                1515            1520 gaa ata aac aaa att gta gca gca aaa gac tca gac ttc caa tgt tta     4608
Glu Ile Asn Lys Ile Val Ala Ala Lys Asp Ser Asp Phe Gln Cys Leu
            1525            1530             1535 agc aag aag aag gaa aaa ctg aca gaa gag ctt cag aaa cta cag aaa      4656
Ser Lys Lys Lys Glu Lys Leu Thr Glu Glu Leu Gln Lys Leu Gln Lys
            1540            1545             1550 gac ata gag atg gca gaa cgc aat gag gat cac cac ctg cag gtc ctt     4704
Asp Ile Glu Met Ala Glu Arg Asn Glu Asp His His Leu Gln Val Leu
            1555            1560             1565 aaa gaa tct gag gtg ctt ctt cag gcc aaa aga gcc gag ctg gaa aag      4752
Lys Glu Ser Glu Val Leu Leu Gln Ala Lys Arg Ala Glu Leu Glu Lys
            1570            1575             1580 ctg aaa agc cag gtg aca agt cag cag cag gag atg gct gtc ttg gac      4800
Leu Lys Ser Gln Val Thr Ser Gln Gln Gln Glu Met Ala Val Leu Asp
1585            1590            1595                    1600 agg cag tta ggg cat aaa aag gag gag ctg cat cta ctc caa gga agc      4848
Arg Gln Leu Gly His Lys Lys Glu Glu Leu His Leu Leu Gln Gly Ser
            1605            1610             1615 atg gtc cag gca aaa gct gac ctc cag gaa gct ctg aga ctg gga gag      4896
Met Val Gln Ala Lys Ala Asp Leu Gln Glu Ala Leu Arg Leu Gly Glu
            1620            1625             1630 act gaa gta act gag aag tgc aat cac att agg gaa gta aaa tct ctt      4944
Thr Glu Val Thr Glu Lys Cys Asn His Ile Arg Glu Val Lys Ser Leu
            1635            1640             1645 ctg gaa gaa ctg agt ttt cag aaa gga gaa cta aat gtt cag att agt      4992
Leu Glu Glu Leu Ser Phe Gln Lys Gly Glu Leu Asn Val Gln Ile Ser
        1650            1655             1660 gaa aga aaa act caa ctt aca ctt ata aag cag gaa att gaa aaa gag      5040
Glu Arg Lys Thr Gln Leu Thr Leu Ile Lys Gln Glu Ile Glu Lys Glu
1665            1670            1675                    1680
```

Figure 12H

```
gaa gaa aat ctt cag gtt gtt tta agg cag atg tct aaa cat aaa acc      5088
Glu Glu Asn Leu Gln Val Val Leu Arg Gln Met Ser Lys His Lys Thr
            1685                1690                1695 gaa cta aag aat att ctg gac atg ttg caa ctt gaa aac cat gag cta      5136
Glu Leu Lys Asn Ile Leu Asp Met Leu Gln Leu Glu Asn His Glu Leu
            1700                1705                1710 caa ggt ttg aag cta caa cat gac caa agg gta tct gaa tta gag aag      5184
Gln Gly Leu Lys Leu Gln His Asp Gln Arg Val Ser Glu Leu Glu Lys
            1715                1720                1725 act cag gtg gca gtg cta gag gag aaa ctg gag tta gag aat ttg cag      5232
Thr Gln Val Ala Val Leu Glu Glu Lys Leu Glu Leu Glu Asn Leu Gln
            1730                1735                1740 cag ata tcc cag cag cag aaa ggg gaa ata gag tgg cag aag cag ctc      5280
Gln Ile Ser Gln Gln Gln Lys Gly Glu Ile Glu Trp Gln Lys Gln Leu
1745                1750                1755                1760 ctt gag agg gat aaa cga gaa ata gaa cga atg act gct gag tcc cga      5328
Leu Glu Arg Asp Lys Arg Glu Ile Glu Arg Met Thr Ala Glu Ser Arg
            1765                1770                1775 gct tta caa tcg tgt gtt gag tgt ttg agc aaa gaa aag gaa gat ctc      5376
Ala Leu Gln Ser Cys Val Glu Cys Leu Ser Lys Glu Lys Glu Asp Leu
            1780                1785                1790 caa gag aaa tgt gac att tgg gaa aaa aag ttg gca caa acc aaa agg      5424
Gln Glu Lys Cys Asp Ile Trp Glu Lys Lys Leu Ala Gln Thr Lys Arg
            1795                1800                1805 gtt tta gca gca gca gaa gaa aat agc aaa atg gag caa tca aac tta      5472
Val Leu Ala Ala Ala Glu Glu Asn Ser Lys Met Glu Gln Ser Asn Leu
            1810                1815                1820 gaa aag ttg gaa ttg aat gtc aga aaa ctg cag cag gaa cta gac caa      5520
Glu Lys Leu Glu Leu Asn Val Arg Lys Leu Gln Gln Glu Leu Asp Gln
1825                1830                1835                1840 cta aac aga gac aag ttg tca ctg cat aac gac att tca gca atg caa      5568
Leu Asn Arg Asp Lys Leu Ser Leu His Asn Asp Ile Ser Ala Met Gln
            1845                1850                1855 cag cag ctc caa gaa aaa cga gaa gca gta aac tca ctg cag gag gaa      5616
Gln Gln Leu Gln Glu Lys Arg Glu Ala Val Asn Ser Leu Gln Glu Glu
            1860                1865                1870 cta gct aat gtc caa gac cat ttg aac cta gca aaa cag gac ctg ctt      5664
Leu Ala Asn Val Gln Asp His Leu Asn Leu Ala Lys Gln Asp Leu Leu
            1875                1880                1885 cac acc acc aag cat cag gat gtg ttg ctc agt gag cag acc cga ctc      5712
His Thr Thr Lys His Gln Asp Val Leu Leu Ser Glu Gln Thr Arg Leu
            1890                1895                1900 cag aag gac atc agt gaa tgg gca aat agg ttt gaa gac tgt cag aaa      5760
Gln Lys Asp Ile Ser Glu Trp Ala Asn Arg Phe Glu Asp Cys Gln Lys
1905                1910                1915                1920
```

Figure 12I

| | | |
|---|---|---|
| gaa gag gag aca aaa caa caa caa ctt caa gtg ctt cag aat gag att<br>Glu Glu Glu Thr Lys Gln Gln Gln Leu Gln Val Leu Gln Asn Glu Ile<br>                 1925                  1930                1935 | 5808 |
| gaa gaa aac aag ctc aaa cta gtc caa caa gaa atg atg ttt cag aga<br>Glu Glu Asn Lys Leu Lys Leu Val Gln Gln Glu Met Met Phe Gln Arg<br>          1940                1945                1950 | 5856 |
| ctc cag aaa gag aga gaa agt gaa gaa agc aaa tta gaa acc agt aaa<br>Leu Gln Lys Glu Arg Glu Ser Glu Glu Ser Lys Leu Glu Thr Ser Lys<br>       1955                1960                1965 | 5904 |
| gtg aca ctg aag gag caa cag cac cag ctg gaa aag gaa tta aca gac<br>Val Thr Leu Lys Glu Gln Gln His Gln Leu Glu Lys Glu Leu Thr Asp<br>    1970                  1975                1980 | 5952 |
| cag aaa agc aaa ctg gac caa gtg ctc tca aag gtg ctg gca gct gaa<br>Gln Lys Ser Lys Leu Asp Gln Val Leu Ser Lys Val Leu Ala Ala Glu<br>1985              1990                1995              2000 | 6000 |
| gag cgt gtt agg act ctg cag gaa gag gag agg tgg tgt gag agc ctg<br>Glu Arg Val Arg Thr Leu Gln Glu Glu Arg Trp Cys Glu Ser Leu<br>              2005                2010              2015 | 6048 |
| gag aag aca ctc tcc caa act aaa cgg cag ctt tca gaa agg gag cag<br>Glu Lys Thr Leu Ser Gln Thr Lys Arg Gln Leu Ser Glu Arg Glu Gln<br>           2020                2025              2030 | 6096 |
| caa ttg gtg gag aaa tca ggt gag ctg ttg gcc ctc cag aaa gag gca<br>Gln Leu Val Glu Lys Ser Gly Glu Leu Leu Ala Leu Gln Lys Glu Ala<br>         2035                2040              2045 | 6144 |
| gat tct atg agg gca gac ttc agc ctt ctg cgg aac cag ttc ttg aca<br>Asp Ser Met Arg Ala Asp Phe Ser Leu Leu Arg Asn Gln Phe Leu Thr<br>     2050                2055                2060 | 6192 |
| gaa aga aag aaa gct gag aag cag gtg gcc agc ctg aag gaa gca ctt<br>Glu Arg Lys Lys Ala Glu Lys Gln Val Ala Ser Leu Lys Glu Ala Leu<br>2065              2070              2075              2080 | 6240 |
| aag atc cag cgg agc cag ctg gag aaa aac ctt ctt gag caa aaa cag<br>Lys Ile Gln Arg Ser Gln Leu Glu Lys Asn Leu Leu Glu Gln Lys Gln<br>              2085              2090              2095 | 6288 |
| gag aac agc tgc ata caa aag gaa atg gca aca att gaa ctg gta gcc<br>Glu Asn Ser Cys Ile Gln Lys Glu Met Ala Thr Ile Glu Leu Val Ala<br>             2100                2105              2110 | 6336 |
| cag gac aac cat gag cgg gcc agg cgc ctg atg aag gag ctc aac cag<br>Gln Asp Asn His Glu Arg Ala Arg Arg Leu Met Lys Glu Leu Asn Gln<br>         2115                2120              2125 | 6384 |
| atg cag tat gag tac acg gag ctc aag aaa cag atg gca aac caa aaa<br>Met Gln Tyr Glu Tyr Thr Glu Leu Lys Lys Gln Met Ala Asn Gln Lys<br>       2130                2135              2140 | 6432 |
| gat ttg gag aga aga caa atg gaa atc agt gat gca atg agg aca ctt<br>Asp Leu Glu Arg Arg Gln Met Glu Ile Ser Asp Ala Met Arg Thr Leu<br>2145              2150              2155              2160 | 6480 |

Figure 12J

```
aaa tct gag gtg aag gat gaa atc aga acc agc ttg aag aat ctt aat        6528
Lys Ser Glu Val Lys Asp Glu Ile Arg Thr Ser Leu Lys Asn Leu Asn
            2165                2170                2175 cag ttt ctt cca gaa cta cca gca gat cta gaa gct att ttg gaa aga        6576
Gln Phe Leu Pro Glu Leu Pro Ala Asp Leu Glu Ala Ile Leu Glu Arg
            2180                2185                2190 aac gaa aac cta gaa gga gaa ttg gaa agc ttg aaa gag aac ctt cca        6624
Asn Glu Asn Leu Glu Gly Glu Leu Glu Ser Leu Lys Glu Asn Leu Pro
            2195                2200                2205 ttt acc atg aat gag gga cct ttt gaa gaa aaa ctg aac ttt tcc caa        6672
Phe Thr Met Asn Glu Gly Pro Phe Glu Glu Lys Leu Asn Phe Ser Gln
            2210                2215                2220 gtt cac ata atg gat gaa cac tgg cgt gga gaa gca ctc cgg gag aaa        6720
Val His Ile Met Asp Glu His Trp Arg Gly Glu Ala Leu Arg Glu Lys
2225                2230                2235                2240 ctg cgt cac cgg gaa gac cga ctc aag gcc caa ctc cga cac tgt atg        6768
Leu Arg His Arg Glu Asp Arg Leu Lys Ala Gln Leu Arg His Cys Met
            2245                2250                2255 tcc aag caa gca gaa gta tta att aaa gga aag cgg cag aca gag ggc        6816
Ser Lys Gln Ala Glu Val Leu Ile Lys Gly Lys Arg Gln Thr Glu Gly
            2260                2265                2270 act tta cac agt ttg agg aga caa gta gat gct tta ggg gaa ttg gtc        6864
Thr Leu His Ser Leu Arg Arg Gln Val Asp Ala Leu Gly Glu Leu Val
            2275                2280                2285 acc agc acc tct gca gat tca gcg tca tca ccc agt ctg tct cag ctg        6912
Thr Ser Thr Ser Ala Asp Ser Ala Ser Ser Pro Ser Leu Ser Gln Leu
            2290                2295                2300 gag tct tcc ctc aca gag gac tct caa ctt gga caa aat cag gaa aag        6960
Glu Ser Ser Leu Thr Glu Asp Ser Gln Leu Gly Gln Asn Gln Glu Lys
2305                2310                2315                2320 aat gcc tca gcc aga tga        6978        (SEQ ID NO:1)
Asn Ala Ser Ala Arg                        (SEQ ID NO:2)
            2325
```

Figure 13A

| | |
|---|---|
| atg gaa gtt gag caa gag cag cgg cgc aga aag gtg gag gcc ggg agg<br>Met Glu Val Glu Gln Glu Gln Arg Arg Arg Lys Val Glu Ala Gly Arg<br>1                 5                   10                 15 | 48 |
| acg aag ctt gct cac ttc cga cag aga aaa aca aaa ggt gac agt tcg<br>Thr Lys Leu Ala His Phe Arg Gln Arg Lys Thr Lys Gly Asp Ser Ser<br>                  20                   25                   30 | 96 |
| cat tcg gag aaa aag acg gcg aag agg aag ggc tcg gct gtc gat gcg<br>His Ser Glu Lys Lys Thr Ala Lys Arg Lys Gly Ser Ala Val Asp Ala<br>        35                   40                   45 | 144 |
| tct gtc cag gag gag agt ccg gta acc aag gag gac agc gca ctc tgt<br>Ser Val Gln Glu Glu Ser Pro Val Thr Lys Glu Asp Ser Ala Leu Cys<br>        50                   55                   60 | 192 |
| gga gga ggg gac att tgc aaa agc aca tca tgt gac gac acc cct gat<br>Gly Gly Gly Asp Ile Cys Lys Ser Thr Ser Cys Asp Asp Thr Pro Asp<br>65                  70                   75                   80 | 240 |
| ggg gca gga ggg gcc ttt gca gct cag ccg gag gac tgt gat gga gag<br>Gly Ala Gly Gly Ala Phe Ala Ala Gln Pro Glu Asp Cys Asp Gly Glu<br>                  85                   90                   95 | 288 |
| aag aga gag gac ttg gaa cag ctg cag cag aag caa gtc aat gac cat<br>Lys Arg Glu Asp Leu Glu Gln Leu Gln Gln Lys Gln Val Asn Asp His<br>                100                  105                 110 | 336 |
| cct cca gag cag tgt ggg atg ttc aca gtc agt gac cac cca cca gaa<br>Pro Pro Glu Gln Cys Gly Met Phe Thr Val Ser Asp His Pro Pro Glu<br>        115                  120                 125 | 384 |
| cag cat ggg atg ttc aca gtc ggt gac cac cca cca gaa cag cgt ggg<br>Gln His Gly Met Phe Thr Val Gly Asp His Pro Pro Glu Gln Arg Gly<br>        130                  135                 140 | 432 |
| atg ttc aca gtc agt gac cac cca cca gaa cag cat ggg atg ttc aca<br>Met Phe Thr Val Ser Asp His Pro Pro Glu Gln His Gly Met Phe Thr<br>145                  150                  155                 160 | 480 |
| gtc agt gac cac cca cca gaa cag cgt ggg atg ttc aca atc agt gac<br>Val Ser Asp His Pro Pro Glu Gln Arg Gly Met Phe Thr Ile Ser Asp<br>                165                  170                 175 | 528 |
| cac caa ccg gaa cag cgt ggg atg ttc aca gtc agt gac cac aca cca<br>His Gln Pro Glu Gln Arg Gly Met Phe Thr Val Ser Asp His Thr Pro<br>        180                  185                 190 | 576 |
| gaa cag cgt ggg atc ttc aca atc agt gac cac cca gca gaa cag cgt<br>Glu Gln Arg Gly Ile Phe Thr Ile Ser Asp His Pro Ala Glu Gln Arg<br>        195                  200                 205 | 624 |
| ggg atg ttc aca aag gag tgt gaa caa gaa tgt gaa ctt gcc att act<br>Gly Met Phe Thr Lys Glu Cys Glu Gln Glu Cys Glu Leu Ala Ile Thr<br>        210                  215                 220 | 672 |
| gac ctg gag agc ggc cgt gaa gat gag gct ggc ctg cat cag agt cag<br>Asp Leu Glu Ser Gly Arg Glu Asp Glu Ala Gly Leu His Gln Ser Gln<br>225                  230                  235                 240 | 720 |

Figure 13B

```
gcc gtg cat ggc ctt gag ctg gag gcg ctg cgc ctg agt ctg agc aac       768
Ala Val His Gly Leu Glu Leu Glu Ala Leu Arg Leu Ser Leu Ser Asn
            245                 250                 255 atg cac acg gcg cag ctg gag ctg aca cag gcc aac ctc cag aag gag       816
Met His Thr Ala Gln Leu Glu Leu Thr Gln Ala Asn Leu Gln Lys Glu
            260                 265                 270 aag gag acg gca ttg acg gag ctg cgg gag atg ctc aac agc cgg cgt       864
Lys Glu Thr Ala Leu Thr Glu Leu Arg Glu Met Leu Asn Ser Arg Arg
            275                 280                 285 gcc cag gag ctg gcc ctg cta cag agc agg cag cag cac gag ctg gag       912
Ala Gln Glu Leu Ala Leu Leu Gln Ser Arg Gln Gln His Glu Leu Glu
        290                 295                 300 ctc ctc agg gag cag cac gca cgg gag aag gag gag gtg gtg ctc agg       960
Leu Leu Arg Glu Gln His Ala Arg Glu Lys Glu Glu Val Val Leu Arg
305                 310                 315                 320 tgt gga cag gaa gca gct gag ctg aag gag aag tta caa tca gaa atg      1008
Cys Gly Gln Glu Ala Ala Glu Leu Lys Glu Lys Leu Gln Ser Glu Met
            325                 330                 335 gag aaa aac gcc cag ata gta aag acc ctg aag gaa gat tgg gaa tct      1056
Glu Lys Asn Ala Gln Ile Val Lys Thr Leu Lys Glu Asp Trp Glu Ser
            340                 345                 350 gaa aaa gat tta tgt tta gaa aat cta cgc aaa gaa ctg tct gca aag      1104
Glu Lys Asp Leu Cys Leu Glu Asn Leu Arg Lys Glu Leu Ser Ala Lys
            355                 360                 365 cat caa tca gaa atg gag gat tta caa aac cag ttt cag aaa gaa ttg      1152
His Gln Ser Glu Met Glu Asp Leu Gln Asn Gln Phe Gln Lys Glu Leu
        370                 375                 380 gca gaa cag aga gct gag ttg gag aag att ttt caa gac aaa aac cag      1200
Ala Glu Gln Arg Ala Glu Leu Glu Lys Ile Phe Gln Asp Lys Asn Gln
385                 390                 395                 400 gct gaa cgg gcc ctt agg aac ctg gag agt cat cat caa gca gcc att      1248
Ala Glu Arg Ala Leu Arg Asn Leu Glu Ser His His Gln Ala Ala Ile
            405                 410                 415 gag aag tta cgt gaa gac ctg cag tcc gag cac ggc cgg tgt tta gaa      1296
Glu Lys Leu Arg Glu Asp Leu Gln Ser Glu His Gly Arg Cys Leu Glu
            420                 425                 430 gac ttg gag ttc aag ttc aaa gag agc gag aaa gaa aaa cag ctg gag      1344
Asp Leu Glu Phe Lys Phe Lys Glu Ser Glu Lys Glu Lys Gln Leu Glu
            435                 440                 445 tta gag aat ctt caa gca tca tat gaa gac ctg aag gca caa tca caa      1392
Leu Glu Asn Leu Gln Ala Ser Tyr Glu Asp Leu Lys Ala Gln Ser Gln
        450                 455                 460 gaa gag atc agg cgc ttg tgg tcc cag ctt gat tct gcc agg acc agt      1440
Glu Glu Ile Arg Arg Leu Trp Ser Gln Leu Asp Ser Ala Arg Thr Ser
465                 470                 475                 480
```

Figure 13C

```
aga cag gaa ttg agt gag cta cat gag caa ctc ctg gcg cgc acc tct    1488
Arg Gln Glu Leu Ser Glu Leu His Glu Gln Leu Leu Ala Arg Thr Ser
            485                 490                 495 cgt gtg gaa gat tta gaa cag ctg aag cag cga gaa aaa acc cag cat    1536
Arg Val Glu Asp Leu Glu Gln Leu Lys Gln Arg Glu Lys Thr Gln His
            500                 505                 510 gag tcc gaa ctg gag caa ctg agg att tat ttt gaa aag aag tta agg    1584
Glu Ser Glu Leu Glu Gln Leu Arg Ile Tyr Phe Glu Lys Lys Leu Arg
            515                 520                 525 gat gct gag aaa act tac caa gaa gac cta acc ctg tta cag cag agg    1632
Asp Ala Glu Lys Thr Tyr Gln Glu Asp Leu Thr Leu Leu Gln Gln Arg
            530                 535                 540 ctg cag ggg gcg agg gaa gat gct ctt ctg gac tct gtg gaa gtt ggg    1680
Leu Gln Gly Ala Arg Glu Asp Ala Leu Leu Asp Ser Val Glu Val Gly
545                 550                 555                 560 ttg tcc tgt gtg ggt tta gaa gag aaa cct gag aaa gga aga aaa gat    1728
Leu Ser Cys Val Gly Leu Glu Glu Lys Pro Glu Lys Gly Arg Lys Asp
            565                 570                 575 cac gtt gat gaa ctc gag cct gag cga cat aag gag agc ctg cca cgc    1776
His Val Asp Glu Leu Glu Pro Glu Arg His Lys Glu Ser Leu Pro Arg
            580                 585                 590 ttc cag gcg gag tta gaa gaa agc cac agg cac cag ctg gaa gcg ctg    1824
Phe Gln Ala Glu Leu Glu Glu Ser His Arg His Gln Leu Glu Ala Leu
            595                 600                 605 gag tct ccc ctc tgc atc cag cac gag ggg cat gtc tca gac aga tgc    1872
Glu Ser Pro Leu Cys Ile Gln His Glu Gly His Val Ser Asp Arg Cys
            610                 615                 620 tgc gta gag act tca gca ttg gga cac gag tgg cgt ctg gaa ccc tct    1920
Cys Val Glu Thr Ser Ala Leu Gly His Glu Trp Arg Leu Glu Pro Ser
625                 630                 635                 640 gaa ggg cac agc caa gag ctt ccc tgg gtg cat ctc cag ggt gtg cag    1968
Glu Gly His Ser Gln Glu Leu Pro Trp Val His Leu Gln Gly Val Gln
            645                 650                 655 gac ggg gac ttg gag gcc gac aca gag cgg gca gcc aga gtc ttg ggt    2016
Asp Gly Asp Leu Glu Ala Asp Thr Glu Arg Ala Ala Arg Val Leu Gly
            660                 665                 670 ctg gaa act gag cac aag gtg caa ctt tcg ctt ctt cag act gag ctc    2064
Leu Glu Thr Glu His Lys Val Gln Leu Ser Leu Leu Gln Thr Glu Leu
            675                 680                 685 aaa gaa gaa att gaa ctc cta aaa ata gaa aat aga aat ttg tat gag    2112
Lys Glu Glu Ile Glu Leu Leu Lys Ile Glu Asn Arg Asn Leu Tyr Glu
            690                 695                 700 aag ttg cag cat gaa act cgt ctg aag gac gat ttg gag aag gta aaa    2160
Lys Leu Gln His Glu Thr Arg Leu Lys Asp Asp Leu Glu Lys Val Lys
705                 710                 715                 720
```

Figure 13D

| | | | | | | | | | | | | | | | | |
|---|---|---|---|---|---|---|---|---|---|---|---|---|---|---|---|---|
| cac | aat | cta | att | gaa | gac | cac | cag | aag | gaa | cta | aat | aat | gct | aag | caa | 2208 |
| His | Asn | Leu | Ile | Glu | Asp | His | Gln | Lys | Glu | Leu | Asn | Asn | Ala | Lys | Gln | |
| | | | 725 | | | | | 730 | | | | | 735 | | | |
| aag | act | gag | ctg | atg | aaa | cag | gaa | ttc | caa | aga | aaa | gaa | acg | gac | tgg | 2256 |
| Lys | Thr | Glu | Leu | Met | Lys | Gln | Glu | Phe | Gln | Arg | Lys | Glu | Thr | Asp | Trp | |
| | | | 740 | | | | | 745 | | | | | 750 | | | |
| aaa | gtt | atg | aag | gag | gag | cta | cag | cgg | gaa | gct | gag | gag | aag | tta | aca | 2304 |
| Lys | Val | Met | Lys | Glu | Glu | Leu | Gln | Arg | Glu | Ala | Glu | Glu | Lys | Leu | Thr | |
| | | | 755 | | | | | 760 | | | | | 765 | | | |
| ttg | atg | cta | ctt | gaa | ctg | aga | gaa | aag | gct | gaa | tcc | gag | aaa | cag | acc | 2352 |
| Leu | Met | Leu | Leu | Glu | Leu | Arg | Glu | Lys | Ala | Glu | Ser | Glu | Lys | Gln | Thr | |
| | | | 770 | | | | | 775 | | | | | 780 | | | |
| atc | ata | aac | aag | ttt | gag | ctt | cga | gaa | gct | gaa | atg | agg | cag | ctt | cag | 2400 |
| Ile | Ile | Asn | Lys | Phe | Glu | Leu | Arg | Glu | Ala | Glu | Met | Arg | Gln | Leu | Gln | |
| 785 | | | | | 790 | | | | | 795 | | | | | 800 | |
| gac | caa | cag | gca | gcc | cag | atc | ctg | gat | ctg | gag | agg | tcc | ttg | acg | gag | 2448 |
| Asp | Gln | Gln | Ala | Ala | Gln | Ile | Leu | Asp | Leu | Glu | Arg | Ser | Leu | Thr | Glu | |
| | | | 805 | | | | | 810 | | | | | 815 | | | |
| cag | cag | ggc | cgc | ctg | cag | cag | ctg | gaa | cag | gac | ctc | act | tca | gac | gac | 2496 |
| Gln | Gln | Gly | Arg | Leu | Gln | Gln | Leu | Glu | Gln | Asp | Leu | Thr | Ser | Asp | Asp | |
| | | | 820 | | | | | 825 | | | | | 830 | | | |
| gcc | ctg | cat | tgc | agc | cag | tgt | ggg | cgg | gag | ccg | ccc | aca | gcc | cag | gac | 2544 |
| Ala | Leu | His | Cys | Ser | Gln | Cys | Gly | Arg | Glu | Pro | Pro | Thr | Ala | Gln | Asp | |
| | | | 835 | | | | | 840 | | | | | 845 | | | |
| ggg | gag | ctt | gcc | gcg | ctc | cac | gtg | aag | gaa | gac | tgc | gcc | ctg | cag | ctg | 2592 |
| Gly | Glu | Leu | Ala | Ala | Leu | His | Val | Lys | Glu | Asp | Cys | Ala | Leu | Gln | Leu | |
| | | | 850 | | | | | 855 | | | | | 860 | | | |
| atg | ctg | gcc | cgg | agc | agg | ttt | tta | gag | gaa | cgt | aaa | gag | atc | acc | gag | 2640 |
| Met | Leu | Ala | Arg | Ser | Arg | Phe | Leu | Glu | Glu | Arg | Lys | Glu | Ile | Thr | Glu | |
| 865 | | | | | 870 | | | | | 875 | | | | | 880 | |
| aaa | ttc | agt | gcg | gaa | caa | gat | gcc | ttc | ctg | cag | gag | gcc | cag | gag | cag | 2688 |
| Lys | Phe | Ser | Ala | Glu | Gln | Asp | Ala | Phe | Leu | Gln | Glu | Ala | Gln | Glu | Gln | |
| | | | 885 | | | | | 890 | | | | | 895 | | | |
| cat | gcc | cgt | gag | ctg | cag | ctc | ctc | cag | gag | aga | cac | cag | cag | cag | ctc | 2736 |
| His | Ala | Arg | Glu | Leu | Gln | Leu | Leu | Gln | Glu | Arg | His | Gln | Gln | Gln | Leu | |
| | | | 900 | | | | | 905 | | | | | 910 | | | |
| ctg | tca | gtg | acg | gcg | gag | ctc | gag | gcc | aga | cac | cag | gcc | gcg | ttg | ggc | 2784 |
| Leu | Ser | Val | Thr | Ala | Glu | Leu | Glu | Ala | Arg | His | Gln | Ala | Ala | Leu | Gly | |
| | | | 915 | | | | | 920 | | | | | 925 | | | |
| gag | ctg | aca | gcc | tcc | tta | gag | agc | aag | cag | ggg | gct | ctg | ctg | gct | gca | 2832 |
| Glu | Leu | Thr | Ala | Ser | Leu | Glu | Ser | Lys | Gln | Gly | Ala | Leu | Leu | Ala | Ala | |
| | | | 930 | | | | | 935 | | | | | 940 | | | |
| cgt | gtg | gcc | gaa | ctg | cag | aca | aaa | cac | gct | gcc | gac | ctc | ggc | gct | ctg | 2880 |
| Arg | Val | Ala | Glu | Leu | Gln | Thr | Lys | His | Ala | Ala | Asp | Leu | Gly | Ala | Leu | |
| 945 | | | | | 950 | | | | | 955 | | | | | 960 | |

Figure 13E

```
gag acc aga cat ctg tcc agc ctt gat tct ttg gaa tcc tgt tac ctc        2928
Glu Thr Arg His Leu Ser Ser Leu Asp Ser Leu Glu Ser Cys Tyr Leu
            965                 970                 975 tct gaa ttt cag acc atc cgt gag gag cac agg cag gcc cta gag ctc        2976
Ser Glu Phe Gln Thr Ile Arg Glu Glu His Arg Gln Ala Leu Glu Leu
            980                 985                 990 tta cga gca gac ttt gag gaa caa ctg tgg aaa aag gac tct ctt cac        3024
Leu Arg Ala Asp Phe Glu Glu Gln Leu Trp Lys Lys Asp Ser Leu His
            995                 1000                1005 caa acg att ttg act caa gag ttg gag aaa ctg aag cgg aaa cac gaa        3072
Gln Thr Ile Leu Thr Gln Glu Leu Glu Lys Leu Lys Arg Lys His Glu
        1010                1015                1020 ggg gag cta cag tct gtg cgg gac cac ctg cga acc gaa gtg agc aca        3120
Gly Glu Leu Gln Ser Val Arg Asp His Leu Arg Thr Glu Val Ser Thr
1025                1030                1035                1040 gag ctc gcc gga acc gtg gct cac gag ctg cag gga gtg cac cag ggt        3168
Glu Leu Ala Gly Thr Val Ala His Glu Leu Gln Gly Val His Gln Gly
                1045                1050                1055 gaa ttt gga agt gaa aag aaa act gct ttg cat gaa aaa gag gag aca        3216
Glu Phe Gly Ser Glu Lys Lys Thr Ala Leu His Glu Lys Glu Glu Thr
                1060                1065                1070 ctt cgg ctt cag agt gca cag gca cag cct ttt cac caa gag gag aaa        3264
Leu Arg Leu Gln Ser Ala Gln Ala Gln Pro Phe His Gln Glu Glu Lys
            1075                1080                1085 gag tct ttg tct ctg cag ctt caa aag aag aat cac caa gtc cag cag        3312
Glu Ser Leu Ser Leu Gln Leu Gln Lys Lys Asn His Gln Val Gln Gln
        1090                1095                1100 ctg aaa gac cag gtt tta tcc tta agt cac gag ata gaa gag tgc cgc        3360
Leu Lys Asp Gln Val Leu Ser Leu Ser His Glu Ile Glu Glu Cys Arg
1105                1110                1115                1120 tcc gag ttg gag gtg ctg cag cag agg cgg gag cgg gag aac cgg gaa        3408
Ser Glu Leu Glu Val Leu Gln Gln Arg Arg Glu Arg Glu Asn Arg Glu
                1125                1130                1135 ggc gca aac ctc ctc tcc atg ctc aag gcc gac gtc aac ctg tcc cac        3456
Gly Ala Asn Leu Leu Ser Met Leu Lys Ala Asp Val Asn Leu Ser His
                1140                1145                1150 agc gaa aga ggg gcc ctc cag gac gcc ctg cgc agg ctg ctg ggt ttg        3504
Ser Glu Arg Gly Ala Leu Gln Asp Ala Leu Arg Arg Leu Leu Gly Leu
            1155                1160                1165 ttt gga gag acg ctg agg gca gcc gtc acc ctg agg agc cgg atc ggg        3552
Phe Gly Glu Thr Leu Arg Ala Ala Val Thr Leu Arg Ser Arg Ile Gly
        1170                1175                1180 gag cgc gtg ggg ctc tgc ctg gat gac gcg ggc gca ggc ctg gcc ctg        3600
Glu Arg Val Gly Leu Cys Leu Asp Asp Ala Gly Ala Gly Leu Ala Leu
1185                1190                1195                1200
```

Figure 13F

```
tcg aca gct ccg gcg ctg gag gag aca tgg tct gat gtg gcc ctc ccg      3648
Ser Thr Ala Pro Ala Leu Glu Glu Thr Trp Ser Asp Val Ala Leu Pro
            1205                1210                1215 gag ttg gac aga act ttg tct gaa tgt gca gag atg tct tcc gtg gct      3696
Glu Leu Asp Arg Thr Leu Ser Glu Cys Ala Glu Met Ser Ser Val Ala
            1220                1225                1230 gaa att agc agc cac atg cgt gaa agc ttt ctc atg agc cca gaa agt      3744
Glu Ile Ser Ser His Met Arg Glu Ser Phe Leu Met Ser Pro Glu Ser
            1235                1240                1245 gtg cgg gag tgt gag cag ccc atc cgg agg gtc ttc cag agc ctc agc      3792
Val Arg Glu Cys Glu Gln Pro Ile Arg Arg Val Phe Gln Ser Leu Ser
            1250                1255                1260 ctg gcc gtg gac ggc ctc atg gag atg gcc ctg gac tcc agc agg cag      3840
Leu Ala Val Asp Gly Leu Met Glu Met Ala Leu Asp Ser Ser Arg Gln
1265                1270                1275                1280 ctg gaa gaa gca cgc caa att cat tct cgt ttt gaa aaa gaa ttt agt      3888
Leu Glu Glu Ala Arg Gln Ile His Ser Arg Phe Glu Lys Glu Phe Ser
            1285                1290                1295 ttt aag aat gag gag aca gca cag gtt gtc agg aag cac cag gag ctg      3936
Phe Lys Asn Glu Glu Thr Ala Gln Val Val Arg Lys His Gln Glu Leu
            1300                1305                1310 ctg gag tgt ttg aag gag gag agc gca gca aag gca gag ctg gcg ctg      3984
Leu Glu Cys Leu Lys Glu Glu Ser Ala Ala Lys Ala Glu Leu Ala Leu
            1315                1320                1325 gag ctg cac aag act cag ggt acc ctt gag gga ttc aag gtg gag aca      4032
Glu Leu His Lys Thr Gln Gly Thr Leu Glu Gly Phe Lys Val Glu Thr
            1330                1335                1340 gca gat ctg aag gag gtg ctg gcc ggg aag gag gat tcc gag cac cgt      4080
Ala Asp Leu Lys Glu Val Leu Ala Gly Lys Glu Asp Ser Glu His Arg
1345                1350                1355                1360 ctg gtg ctg gag ctg gag agc ctg aga cgg cag ctg cag cag gcg gcc      4128
Leu Val Leu Glu Leu Glu Ser Leu Arg Arg Gln Leu Gln Gln Ala Ala
            1365                1370                1375 cag gag cag gcg gcg ctg agg gag gag tgc acc cgt ctg tgg agt cgg      4176
Gln Glu Gln Ala Ala Leu Arg Glu Glu Cys Thr Arg Leu Trp Ser Arg
            1380                1385                1390 ggg gag gcc aca gcc acg gac gcc gag gcc aga gaa gct gct ctc cgg      4224
Gly Glu Ala Thr Ala Thr Asp Ala Glu Ala Arg Glu Ala Ala Leu Arg
            1395                1400                1405 aag gaa gtg gag gat ctg acc aaa gaa cag tcg gag acc agg aag cag      4272
Lys Glu Val Glu Asp Leu Thr Lys Glu Gln Ser Glu Thr Arg Lys Gln
1410                    1415                1420 gct gag aag gac cgc tca gcc ctg ctc tcc cag atg aag att ttg gag      4320
Ala Glu Lys Asp Arg Ser Ala Leu Leu Ser Gln Met Lys Ile Leu Glu
1425                1430                1435                1440
```

Figure 13G

```
tct gag tta gaa gaa cag ctg tct cag cat cgc ggg tgt gcc aag cag        4368
Ser Glu Leu Glu Glu Gln Leu Ser Gln His Arg Gly Cys Ala Lys Gln
            1445                1450                1455 gcg gag gcc gtc act gcc ctg gaa cag cag gtg gca tct ctg gac aag        4416
Ala Glu Ala Val Thr Ala Leu Glu Gln Gln Val Ala Ser Leu Asp Lys
        1460                1465                1470 cat ttg cgc aac cag cgg caa ttc atg gat gag cag gca gcc gag cgg        4464
His Leu Arg Asn Gln Arg Gln Phe Met Asp Glu Gln Ala Ala Glu Arg
        1475                1480                1485 gag cac gag cgc gag gag ttc cag cag gag att cag agg ctg gag ggg        4512
Glu His Glu Arg Glu Glu Phe Gln Gln Glu Ile Gln Arg Leu Glu Gly
        1490                1495                1500 cag ctc cgc cag gcg gcc aag ccg cag ccc tgg ggc cct cgc gac agc        4560
Gln Leu Arg Gln Ala Ala Lys Pro Gln Pro Trp Gly Pro Arg Asp Ser
1505                1510                1515                1520 cag cag gcg ccg ctg gat gga gag gtt gag ttg tta caa caa aag ttg        4608
Gln Gln Ala Pro Leu Asp Gly Glu Val Glu Leu Leu Gln Gln Lys Leu
            1525                1530                1535 aga gaa aag ttg gat gaa ttt aat gaa ttg gct ata cag aaa gag tcg        4656
Arg Glu Lys Leu Asp Glu Phe Asn Glu Leu Ala Ile Gln Lys Glu Ser
            1540                1545                1550 gca gat aga caa gtg tta atg cag gaa gaa gaa att aaa cgt ctg gag        4704
Ala Asp Arg Gln Val Leu Met Gln Glu Glu Glu Ile Lys Arg Leu Glu
        1555                1560                1565 gag atg aac atc aac atc agg aaa aaa gtg gcc cag ctc cag gaa gaa        4752
Glu Met Asn Ile Asn Ile Arg Lys Lys Val Ala Gln Leu Gln Glu Glu
    1570                1575                1580 gtg gaa aaa cag aaa aac atc gtg aaa ggg ctg gaa cag gat aaa gag        4800
Val Glu Lys Gln Lys Asn Ile Val Lys Gly Leu Glu Gln Asp Lys Glu
1585                1590                1595                1600 gtg tta aag aaa cag cag atg agt agc ttg ctt ctg gcg tcc acg ttg        4848
Val Leu Lys Lys Gln Gln Met Ser Ser Leu Leu Leu Ala Ser Thr Leu
                1605                1610                1615 cag tct aca cta gat gca ggc aga tgt ccc gag cct cct tcg ggc agc        4896
Gln Ser Thr Leu Asp Ala Gly Arg Cys Pro Glu Pro Pro Ser Gly Ser
            1620                1625                1630 cct cct gag ggt cca gaa ata cag tta gag gtg aca cag aga gca ctc        4944
Pro Pro Glu Gly Pro Glu Ile Gln Leu Glu Val Thr Gln Arg Ala Leu
        1635                1640                1645 ctg cgg cgc gag agc gag gtt ttg gac tta aaa gaa cag cta gaa aag        4992
Leu Arg Arg Glu Ser Glu Val Leu Asp Leu Lys Glu Gln Leu Glu Lys
        1650                1655                1660 atg aaa ggt gac tta gaa agt aaa aat gaa gaa ata cta cat ctg aac        5040
Met Lys Gly Asp Leu Glu Ser Lys Asn Glu Glu Ile Leu His Leu Asn
1665                1670                1675                1680
```

Figure 13H

```
tta aaa ttg gac atg cag aac agc cag act gct gtc agc ctc aga gaa          5088
Leu Lys Leu Asp Met Gln Asn Ser Gln Thr Ala Val Ser Leu Arg Glu
            1685                1690                1695 ctt gag gaa gag aac acg agc ttg aag gtc ata tat acc aga agt tct          5136
Leu Glu Glu Glu Asn Thr Ser Leu Lys Val Ile Tyr Thr Arg Ser Ser
        1700                1705                1710 gag att gaa gag ctg aaa gcc act att gaa aat ctg caa gag aat cag          5184
Glu Ile Glu Glu Leu Lys Ala Thr Ile Glu Asn Leu Gln Glu Asn Gln
        1715                1720                1725 aaa cga tta caa aag gag aaa gca gag gaa att gaa caa ctc cat gaa          5232
Lys Arg Leu Gln Lys Glu Lys Ala Glu Glu Ile Glu Gln Leu His Glu
        1730                1735                1740 gtc att gag aag ctg cag cac gag ctg tcc ctc atg ggg cct gtg gtg          5280
Val Ile Glu Lys Leu Gln His Glu Leu Ser Leu Met Gly Pro Val Val
1745                1750                1755                1760 cac gaa gtc agc gac agt cag gct ggc agt ctg cag agc gag ctg ctc          5328
His Glu Val Ser Asp Ser Gln Ala Gly Ser Leu Gln Ser Glu Leu Leu
            1765                1770                1775 tgc tcc cag gcc ggg ggc cct cgt ggg cag gcc cta cag ggc gag ctc          5376
Cys Ser Gln Ala Gly Gly Pro Arg Gly Gln Ala Leu Gln Gly Glu Leu
            1780                1785                1790 gag gct gcg ctg gaa gcc aag gag gcc ctg agc cgg ctg ctg gct gac          5424
Glu Ala Ala Leu Glu Ala Lys Glu Ala Leu Ser Arg Leu Leu Ala Asp
        1795                1800                1805 cag gag cgc agg cac agc cag gcc ctg gag gcc ctg cag cag cgc ctc          5472
Gln Glu Arg Arg His Ser Gln Ala Leu Glu Ala Leu Gln Gln Arg Leu
        1810                1815                1820 cag ggc gca gag gag gct gcg gag cta cag ctg gct gag ctg gag cgc          5520
Gln Gly Ala Glu Glu Ala Ala Glu Leu Gln Leu Ala Glu Leu Glu Arg
1825                1830                1835                1840 aat gta gcc ctc agg gag gct gag gtc gaa gac atg gcc tcc cgg atc          5568
Asn Val Ala Leu Arg Glu Ala Glu Val Glu Asp Met Ala Ser Arg Ile
            1845                1850                1855 cag gag ttc gaa gcg gcc ctg aaa gca aag gaa gcg acg att gcc gag          5616
Gln Glu Phe Glu Ala Ala Leu Lys Ala Lys Glu Ala Thr Ile Ala Glu
            1860                1865                1870 aga aat tta gaa atc gac gct ctg aac cag cgg aag gcg gcc cac tct          5664
Arg Asn Leu Glu Ile Asp Ala Leu Asn Gln Arg Lys Ala Ala His Ser
            1875                1880                1885 gcc gag ctg gag gcc gtc ctg ttg gcc ttg gcc cgc atc cgc cgc gcc          5712
Ala Glu Leu Glu Ala Val Leu Leu Ala Leu Ala Arg Ile Arg Arg Ala
        1890                1895                1900 ctg gag cag cag ccc ctg gca gcc ggg gcg gcg cct ccc gag ctg cag          5760
Leu Glu Gln Gln Pro Leu Ala Ala Gly Ala Ala Pro Pro Glu Leu Gln
1905                1910                1915                1920
```

Figure 13I

```
tgg ctc cga gcg cag tgt gcc cgc ctc agc cgc cag ctg cag gtg ctg     5808
Trp Leu Arg Ala Gln Cys Ala Arg Leu Ser Arg Gln Leu Gln Val Leu
                1925                1930                1935 cac cag cgg ttc ctg agg tgc cag gtg gag ctg gac agg cgg cag gcc     5856
His Gln Arg Phe Leu Arg Cys Gln Val Glu Leu Asp Arg Arg Gln Ala
            1940                1945                1950 cgc aga gcc aca gct cac aca cgg gtg ccc ggg gcc cac cca cag cct     5904
Arg Arg Ala Thr Ala His Thr Arg Val Pro Gly Ala His Pro Gln Pro
        1955                1960                1965 cgc atg gat ggt ggc gcc aag gcc cag gtc acc ggc gac gtg gag gcc     5952
Arg Met Asp Gly Gly Ala Lys Ala Gln Val Thr Gly Asp Val Glu Ala
        1970                1975                1980 tcc cat gat gct gct ttg gag ccg gtt gtc cct gac cca cag ggt gat     6000
Ser His Asp Ala Ala Leu Glu Pro Val Val Pro Asp Pro Gln Gly Asp
1985                1990                1995                2000 ctg cag cct gtc ctg gtg acg ttg aag gat gca cct ctc tgc aag caa     6048
Leu Gln Pro Val Leu Val Thr Leu Lys Asp Ala Pro Leu Cys Lys Gln
            2005                2010                2015 gaa ggc gtg atg tca gtg ctc acc gtc tgc cag agg cag ctg cag tcg     6096
Glu Gly Val Met Ser Val Leu Thr Val Cys Gln Arg Gln Leu Gln Ser
            2020                2025                2030 gag ctg ctc ttg gtg aaa aat gaa atg cgc ctg agt ctg gag gac ggc     6144
Glu Leu Leu Leu Val Lys Asn Glu Met Arg Leu Ser Leu Glu Asp Gly
            2035                2040                2045 ggc aag ggt aaa gaa aaa gta ctg gaa gat tgt cag ctg ccg aag gtc     6192
Gly Lys Gly Lys Glu Lys Val Leu Glu Asp Cys Gln Leu Pro Lys Val
        2050                2055                2060 gat ctc gta gct cag gtg aaa cag ctt cag gaa aaa ctg aac cgt ttg     6240
Asp Leu Val Ala Gln Val Lys Gln Leu Gln Glu Lys Leu Asn Arg Leu
2065                2070                2075                2080 ctg tat tcc atg acc ttc cag aat gtg gat gct gcc gac acc aaa tct     6288
Leu Tyr Ser Met Thr Phe Gln Asn Val Asp Ala Ala Asp Thr Lys Ser
            2085                2090                2095 ctg tgg ccc atg gcc tca gca cac ctg ttg gag agc agc tgg agt gat     6336
Leu Trp Pro Met Ala Ser Ala His Leu Leu Glu Ser Ser Trp Ser Asp
            2100                2105                2110 gat tcc tgt gac gga gaa gag cct gac ata tca ccc cac ata gac aca     6384
Asp Ser Cys Asp Gly Glu Glu Pro Asp Ile Ser Pro His Ile Asp Thr
            2115                2120                2125 tgt gat gcc aat aca gcc acg ggg ggt gta act gat gtt atc aaa aat     6432
Cys Asp Ala Asn Thr Ala Thr Gly Gly Val Thr Asp Val Ile Lys Asn
        2130                2135                2140 cag gcc ata gac gcg tgt gat gcc aat aca acc cca ggg ggt gta act     6480
Gln Ala Ile Asp Ala Cys Asp Ala Asn Thr Thr Pro Gly Gly Val Thr
2145                2150                2155                2160
```

Figure 13J

```
gat gtt atc aaa aat tgg gat tcc ttg ata cca gat gaa atg cca gat    6528
Asp Val Ile Lys Asn Trp Asp Ser Leu Ile Pro Asp Glu Met Pro Asp
            2165                2170                2175 tct ccc att caa gaa aaa tca gaa tgt cag gac atg tct ctt tct tca    6576
Ser Pro Ile Gln Glu Lys Ser Glu Cys Gln Asp Met Ser Leu Ser Ser
            2180                2185                2190 ccg acc agc gta ctt ggt ggc tcc cgc cac cag agc cac act gca gag    6624
Pro Thr Ser Val Leu Gly Gly Ser Arg His Gln Ser His Thr Ala Glu
            2195                2200                2205 gct ggg ccc cgg aag agc ccg gtc ggg atg ctg gac ctg tct tcc tgg    6672
Ala Gly Pro Arg Lys Ser Pro Val Gly Met Leu Asp Leu Ser Ser Trp
            2210                2215                2220 agc tcc cct gag gtc ctc agg aag gac tgg acc ctg gag ccc tgg ccc    6720
Ser Ser Pro Glu Val Leu Arg Lys Asp Trp Thr Leu Glu Pro Trp Pro
2225                2230                2235                2240 agc ctc ccc gtg aca ccc cac tca gga gcc ctg agc ctg tgc agt gcc    6768
Ser Leu Pro Val Thr Pro His Ser Gly Ala Leu Ser Leu Cys Ser Ala
            2245                2250                2255 gac aca tcc ctg ggg gac agg gcg gac acc tcg ctg cca cag acc cag    6816
Asp Thr Ser Leu Gly Asp Arg Ala Asp Thr Ser Leu Pro Gln Thr Gln
            2260                2265                2270 ggg ccg ggg ctg ctt tgt tcc cca ggc gtg tct gca gca gcg ctg gca    6864
Gly Pro Gly Leu Leu Cys Ser Pro Gly Val Ser Ala Ala Ala Leu Ala
            2275                2280                2285 ctg cag tgg gcc gag tct ccg ccg gct gac gac cac cat gtg cag agg    6912
Leu Gln Trp Ala Glu Ser Pro Pro Ala Asp Asp His His Val Gln Arg
            2290                2295                2300 acg gct gtg gag aaa gat gtc gaa gat ttt atc aca aca tcc ttt gat    6960
Thr Ala Val Glu Lys Asp Val Glu Asp Phe Ile Thr Thr Ser Phe Asp
2305                2310                2315                2320 tct caa gaa aca tta agt tca cct cct cct gga tta gaa gga aaa gct    7008
Ser Gln Glu Thr Leu Ser Ser Pro Pro Pro Gly Leu Glu Gly Lys Ala
            2325                2330                2335 gat aga agt gag aaa agt gac ggc tcg ggt ttt gga gca aga ctg agc    7056
Asp Arg Ser Glu Lys Ser Asp Gly Ser Gly Phe Gly Ala Arg Leu Ser
            2340                2345                2350 ccg ggg tca gga ggc cct gag gct caa act gct ggt cct gtg acc cct    7104
Pro Gly Ser Gly Gly Pro Glu Ala Gln Thr Ala Gly Pro Val Thr Pro
            2355                2360                2365 gct tcc atc tct gga agg ttt cag ccg ctg ccg gaa gcc atg aag gag    7152
Ala Ser Ile Ser Gly Arg Phe Gln Pro Leu Pro Glu Ala Met Lys Glu
            2370                2375                2380 aag gaa gtg cgt ccg aag cac gtg aag gct tta ctg cag atg gtg cgt    7200
Lys Glu Val Arg Pro Lys His Val Lys Ala Leu Leu Gln Met Val Arg
            2385                2390                2395                2400
```

Figure 13K

```
gac gag agc cac cag atc ctg gcg ctg tca gaa ggc ctt gca ccc cca    7248
Asp Glu Ser His Gln Ile Leu Ala Leu Ser Glu Gly Leu Ala Pro Pro
            2405                2410                2415 agc ggc gag cca cac cca ccc cgg aag gaa gac gag ata cag gac atc    7296
Ser Gly Glu Pro His Pro Pro Arg Lys Glu Asp Glu Ile Gln Asp Ile
            2420                2425                2430 tcg ctc cat ggg gga aag acg cag gaa gtg ccc acc gcg tgc ccc gat    7344
Ser Leu His Gly Gly Lys Thr Gln Glu Val Pro Thr Ala Cys Pro Asp
            2435                2440                2445 tgg aga ggg gac ctt ctg cag gtt gtg caa gag gcc ttt gaa aaa gag    7392
Trp Arg Gly Asp Leu Leu Gln Val Val Gln Glu Ala Phe Glu Lys Glu
            2450                2455                2460 cag gag atg cag ggg gtt gag ctg cag ccc cga ctc agt ggc tca gat    7440
Gln Glu Met Gln Gly Val Glu Leu Gln Pro Arg Leu Ser Gly Ser Asp
2465                2470                2475                2480 ctg ggg ggt cac agc tcc ctg ctc gaa agg ctg gag aag atc atc cgt    7488
Leu Gly Gly His Ser Ser Leu Leu Glu Arg Leu Glu Lys Ile Ile Arg
            2485                2490                2495 gag cag gga gac ctg cag gaa aag tcc ctg gag cat ctt cgc ttg ccg    7536
Glu Gln Gly Asp Leu Gln Glu Lys Ser Leu Glu His Leu Arg Leu Pro
            2500                2505                2510 gac cgg agc agc ctg ctg tcc gag atc cag gcg ctg cgt gcc cag ctg    7584
Asp Arg Ser Ser Leu Leu Ser Glu Ile Gln Ala Leu Arg Ala Gln Leu
            2515                2520                2525 cgc atg acg cac ctg cag aac cag gag aag ctg cag cac ttg cgc acg    7632
Arg Met Thr His Leu Gln Asn Gln Glu Lys Leu Gln His Leu Arg Thr
            2530                2535                2540 gcg ctg aca agc gca gag gcg cgc ggg agc cag cag gag cac cag ctg    7680
Ala Leu Thr Ser Ala Glu Ala Arg Gly Ser Gln Gln Glu His Gln Leu
2545                2550                2555                2560 cgc agg cag gtt gaa ctg ctg gct tat aaa gta gag cag gag aag tgc    7728
Arg Arg Gln Val Glu Leu Leu Ala Tyr Lys Val Glu Gln Glu Lys Cys
            2565                2570                2575 att gct ggt gac ttg cag aag acg ctg agt gaa gag caa gag aag gca    7776
Ile Ala Gly Asp Leu Gln Lys Thr Leu Ser Glu Glu Gln Glu Lys Ala
            2580                2585                2590 aac agc gtg cag aag ctc ctg gcg gcg gag cag act gta gtg cga gat    7824
Asn Ser Val Gln Lys Leu Leu Ala Ala Glu Gln Thr Val Val Arg Asp
            2595                2600                2605 ttg aag tcc gac ctc tgt gag agc agg cag aag agc gaa cag ctg tcc    7872
Leu Lys Ser Asp Leu Cys Glu Ser Arg Gln Lys Ser Glu Gln Leu Ser
            2610                2615                2620 cgg tcc ctc tgc gag gtg cag cag gag gtc ctc cag ctg aga tcc atg    7920
Arg Ser Leu Cys Glu Val Gln Gln Glu Val Leu Gln Leu Arg Ser Met
2625                2630                2635                2640
```

Figure 13L

```
ctg agc agt aag gag aac gag ctg aag gcc gcg ctt cag gag ctg gag      7968
Leu Ser Ser Lys Glu Asn Glu Leu Lys Ala Ala Leu Gln Glu Leu Glu
            2645                2650                2655 agt gag cag ggg aag ggg cgt gcc ctg cag agc cag ctg gag gag gag      8016
Ser Glu Gln Gly Lys Gly Arg Ala Leu Gln Ser Gln Leu Glu Glu Glu
            2660                2665                2670 cag ctg cgg cac ctg cag agg gag agc cag agt gcc aag gcc ctg gag      8064
Gln Leu Arg His Leu Gln Arg Glu Ser Gln Ser Ala Lys Ala Leu Glu
            2675                2680                2685 gag ctg cgg gcg tct ttg gag aca cag cgt gct cag agc agt cga ctc      8112
Glu Leu Arg Ala Ser Leu Glu Thr Gln Arg Ala Gln Ser Ser Arg Leu
            2690                2695                2700 tgc gtg gca ctg aaa cac gag cag acg gcc aag gac aac ctg cag aag      8160
Cys Val Ala Leu Lys His Glu Gln Thr Ala Lys Asp Asn Leu Gln Lys
2705                2710                2715                2720 gag ctg cgt atc gag cac tca cgc tgc gag gcc ttg ctg gct cag gag      8208
Glu Leu Arg Ile Glu His Ser Arg Cys Glu Ala Leu Leu Ala Gln Glu
            2725                2730                2735 cgg agc cag ctc tct gag ctc cag aag gac ctt gcg gct gag aag agc      8256
Arg Ser Gln Leu Ser Glu Leu Gln Lys Asp Leu Ala Ala Glu Lys Ser
            2740                2745                2750 cgc acc ctg gag ctg tca gag gcc ttg cgg cac gag cgg ctc ctg acc      8304
Arg Thr Leu Glu Leu Ser Glu Ala Leu Arg His Glu Arg Leu Leu Thr
            2755                2760                2765 gag cag ctg agc cag agg aca cag gag gct tgc gtg cac cag gac aca      8352
Glu Gln Leu Ser Gln Arg Thr Gln Glu Ala Cys Val His Gln Asp Thr
            2770                2775                2780 cag gcc cat cac gct ctg ctg cag aag ctg aag gag gag aag tcc cgg      8400
Gln Ala His His Ala Leu Leu Gln Lys Leu Lys Glu Glu Lys Ser Arg
2785                2790                2795                2800 gtg gtg gac ttg caa gcg atg ctt gaa aag gtg cag cag caa gcc ctg      8448
Val Val Asp Leu Gln Ala Met Leu Glu Lys Val Gln Gln Gln Ala Leu
            2805                2810                2815 cat tct cag cag cag ctt gag gct gag gct cag aag cac tgt gag gcg      8496
His Ser Gln Gln Gln Leu Glu Ala Glu Ala Gln Lys His Cys Glu Ala
            2820                2825                2830 ctc agg aga gag aag gag gta agt gcc aca ctg aag tcg acg gtg gaa      8544
Leu Arg Arg Glu Lys Glu Val Ser Ala Thr Leu Lys Ser Thr Val Glu
            2835                2840                2845 gcc ctg cac acc caa aaa cga gag ctg aga tgc tct ctg gag aga gag      8592
Ala Leu His Thr Gln Lys Arg Glu Leu Arg Cys Ser Leu Glu Arg Glu
            2850                2855                2860 agg gag aaa cca gcg tgg ttg cag gca gaa tta gag cag tca cac cca      8640
Arg Glu Lys Pro Ala Trp Leu Gln Ala Glu Leu Glu Gln Ser His Pro
2865                2870                2875                2880
```

Figure 13M

```
cgg ttg aaa gag caa gaa gga cgc aag gct gcg agg agg agc gcg gag      8688
Arg Leu Lys Glu Gln Glu Gly Arg Lys Ala Ala Arg Arg Ser Ala Glu
            2885                2890                2895 gcc agg cag agc cca gcg gct gcg gag cag tgg agg aag tgg cag aga      8736
Ala Arg Gln Ser Pro Ala Ala Ala Glu Gln Trp Arg Lys Trp Gln Arg
    2900                2905                2910 gac aag gag aag ctg cga gaa tta gaa ctg cag cgt cag cgt gac ttg      8784
Asp Lys Glu Lys Leu Arg Glu Leu Glu Leu Gln Arg Gln Arg Asp Leu
            2915                2920                2925 cat aag atc aag cag ctt cag cag aca gtg aga gac ctg gag tcg aag      8832
His Lys Ile Lys Gln Leu Gln Gln Thr Val Arg Asp Leu Glu Ser Lys
        2930                2935                2940 gac gag gtg cct ggc agc cgc ctc cac cta ggt tct gcc cgc agg gct      8880
Asp Glu Val Pro Gly Ser Arg Leu His Leu Gly Ser Ala Arg Arg Ala
2945                2950                2955                2960 gcc ggc tcg gat gcg gac cac ctc cgg gaa cag cag cga gag ctg gag      8928
Ala Gly Ser Asp Ala Asp His Leu Arg Glu Gln Gln Arg Glu Leu Glu
            2965                2970                2975 gcg atg agg cag cgg ctg ctc tct gcc gcc cgg ctt ctc acc agc ttc      8976
Ala Met Arg Gln Arg Leu Leu Ser Ala Ala Arg Leu Leu Thr Ser Phe
        2980                2985                2990 acc agc cag gcc gtg gac agg aca gtt aat gat tgg acg tca tcc aat      9024
Thr Ser Gln Ala Val Asp Arg Thr Val Asn Asp Trp Thr Ser Ser Asn
            2995                3000                3005 gag aaa gca gtg atg tct tta ctg cac acg ttg gag gag ctg aag tct      9072
Glu Lys Ala Val Met Ser Leu Leu His Thr Leu Glu Glu Leu Lys Ser
    3010                3015                3020 gac ttg agc agg ccc acc tcc tcc cag aaa aaa atg gca gca gag ctg      9120
Asp Leu Ser Arg Pro Thr Ser Ser Gln Lys Lys Met Ala Ala Glu Leu
3025                3030                3035                3040 cag ttc cag ttt gtg gac gtc ctg ctg aaa gac aat gtt tcc ctc aca      9168
Gln Phe Gln Phe Val Asp Val Leu Leu Lys Asp Asn Val Ser Leu Thr
            3045                3050                3055 aaa gcg ctc agc acg gtg acc cag gag aag ctg gag ctg agc aga gcc      9216
Lys Ala Leu Ser Thr Val Thr Gln Glu Lys Leu Glu Leu Ser Arg Ala
        3060                3065                3070 gtg tct aag ctt gag aag ttg ctg aag cac cat ctg cag aag ggc tgc      9264
Val Ser Lys Leu Glu Lys Leu Leu Lys His His Leu Gln Lys Gly Cys
        3075                3080                3085 agc cca agc agg tcg gaa agg tct gct tgg aag cca gac gaa acg gct      9312
Ser Pro Ser Arg Ser Glu Arg Ser Ala Trp Lys Pro Asp Glu Thr Ala
    3090                3095                3100 cca cag agt tcc ctg agg cgc cca gac ccc ggc cgg ctt cca cca gct      9360
Pro Gln Ser Ser Leu Arg Arg Pro Asp Pro Gly Arg Leu Pro Pro Ala
3105                3110                3115                3120
```

Figure 13N

```
gcc agc gag gaa gca cac acc agc aat gtc aag atg gaa aaa ttg tac      9408
Ala Ser Glu Glu Ala His Thr Ser Asn Val Lys Met Glu Lys Leu Tyr
            3125                3130                3135 ctg cat tac ttg aga gca gag agc ttt aga aaa gct ctg att tat caa      9456
Leu His Tyr Leu Arg Ala Glu Ser Phe Arg Lys Ala Leu Ile Tyr Gln
            3140                3145                3150 aag aag tat ctt ttg ctg ttg att ggt gga ttc cag gat tct gaa caa      9504
Lys Lys Tyr Leu Leu Leu Leu Ile Gly Gly Phe Gln Asp Ser Glu Gln
            3155                3160                3165 gaa aca ctc tcc atg att gcc cat ttg ggg gta ttt cct tcc aaa gca      9552
Glu Thr Leu Ser Met Ile Ala His Leu Gly Val Phe Pro Ser Lys Ala
            3170                3175                3180 gaa cgg aaa atc aca tct cgt cct ttc acc agg ttc cgc acg gcc gtc      9600
Glu Arg Lys Ile Thr Ser Arg Pro Phe Thr Arg Phe Arg Thr Ala Val
3185                3190                3195                3200 agg gtg gtc att gca ata tta aga tta cgt ttt ttg gtt aag aaa tgg      9648
Arg Val Val Ile Ala Ile Leu Arg Leu Arg Phe Leu Val Lys Lys Trp
            3205                3210                3215 caa gaa gta gat cgg aaa gga gct ctg gca caa ggc aaa gcc cct cgc      9696
Gln Glu Val Asp Arg Lys Gly Ala Leu Ala Gln Gly Lys Ala Pro Arg
            3220                3225                3230 cca ggg ccc cga gca cga cag ccg cag tct cca ccc aga acc aga gag      9744
Pro Gly Pro Arg Ala Arg Gln Pro Gln Ser Pro Pro Arg Thr Arg Glu
            3235                3240                3245 tcc ccc cca acc cgg gat gta ccc tct ggc cac acc agg gac cct gcc      9792
Ser Pro Pro Thr Arg Asp Val Pro Ser Gly His Thr Arg Asp Pro Ala
            3250                3255                3260 aga ggc cgc aga ctg gca gca gca gcc tcc cca cac agt ggg gga aga      9840
Arg Gly Arg Arg Leu Ala Ala Ala Ala Ser Pro His Ser Gly Gly Arg
3265                3270                3275                3280 gcc act cca tcc cca aat tca aga tta gaa aga tcc ctg act gct tct      9888
Ala Thr Pro Ser Pro Asn Ser Arg Leu Glu Arg Ser Leu Thr Ala Ser
            3285                3290                3295 caa gat cca gaa cat tcc ttg aca gag tat att cac cat tta gaa gtg      9936
Gln Asp Pro Glu His Ser Leu Thr Glu Tyr Ile His His Leu Glu Val
            3300                3305                3310 atc cag caa aga ttg gga ggg gta cta cca gat tct act tca aag aaa      9984
Ile Gln Gln Arg Leu Gly Gly Val Leu Pro Asp Ser Thr Ser Lys Lys
            3315                3320                3325 tcc tgc cac ccg atg att aaa cag tga    10011        (SEQ ID NO:3)
Ser Cys His Pro Met Ile Lys Gln                     (SEQ ID NO:4)
            3330                3335
```

Figure 14
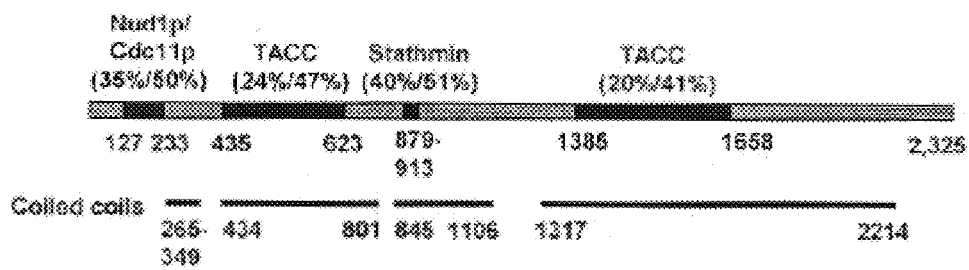
Figure 15A
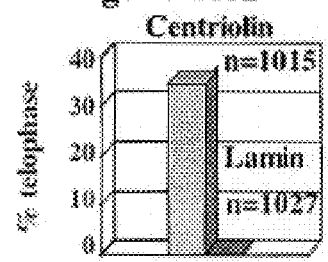
| Figure 15B | Figure 15C | Figure 15D |
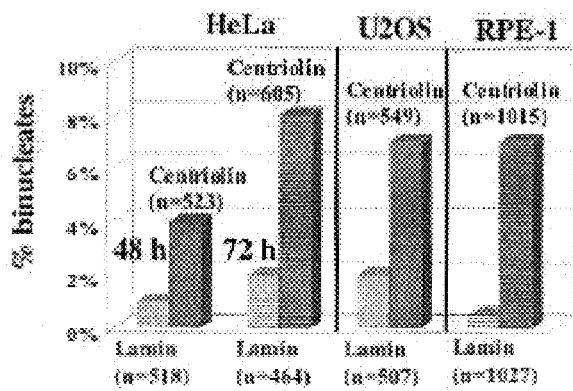

Figures 15E-N
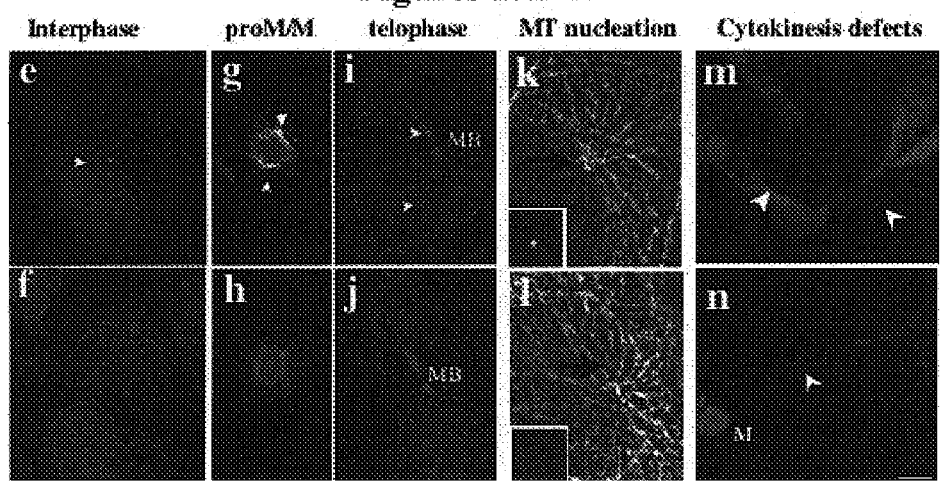
Figure 16A
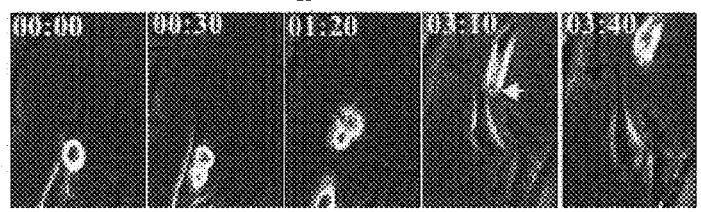
Figure 16B
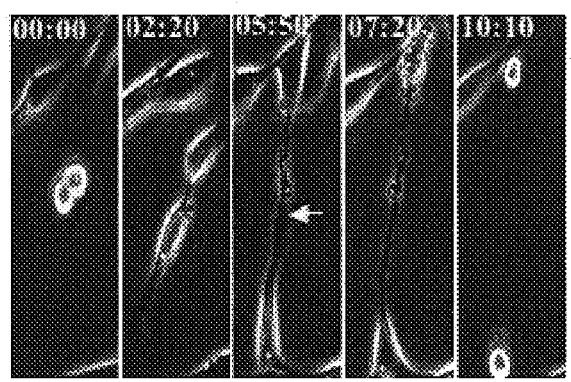

SEQUENCE LISTING

```
<160> NUMBER OF SEQ ID NOS: 30

<210> SEQ ID NO 1
<211> LENGTH: 6978
<212> TYPE: DNA
<213> ORGANISM: Homo sapiens
<220> FEATURE:
<221> NAME/KEY: CDS
<222> LOCATION: (1)...(6975)

<400> SEQUENCE: 1 atg aag aaa ggt tct caa caa aaa ata ttc tcc aaa gca aag ata cca      48
Met Lys Lys Gly Ser Gln Gln Lys Ile Phe Ser Lys Ala Lys Ile Pro
  1               5                  10                  15 tca tca tct cac tct cct atc cca tca tct atg tcc aat atg aga tct      96
Ser Ser Ser His Ser Pro Ile Pro Ser Ser Met Ser Asn Met Arg Ser
             20                  25                  30 agg tca ctt tca cct ttg att gga tca gag act cta cct ttt cat tct     144
Arg Ser Leu Ser Pro Leu Ile Gly Ser Glu Thr Leu Pro Phe His Ser
         35                  40                  45
```

-continued

| | |
|---|---|
| gga gga cag tgg tgt gag caa att gag att gca gat gaa aac aat atg<br>Gly Gly Gln Trp Cys Glu Gln Ile Glu Ile Ala Asp Glu Asn Asn Met<br>50              55                  60 | 192 |
| ctt ttg gac tat caa gac cat aaa gga gct gat tca cat gca gga gtt<br>Leu Leu Asp Tyr Gln Asp His Lys Gly Ala Asp Ser His Ala Gly Val<br>65              70                  75              80 | 240 |
| aga tat att aca gag gcc ctc att aaa aaa ctt act aaa cag gat aat<br>Arg Tyr Ile Thr Glu Ala Leu Ile Lys Lys Leu Thr Lys Gln Asp Asn<br>                85                  90                  95 | 288 |
| ttg gct ttg ata aaa tct ctg aac ctt tca ctt tct aaa gac ggt ggc<br>Leu Ala Leu Ile Lys Ser Leu Asn Leu Ser Leu Ser Lys Asp Gly Gly<br>            100                 105                 110 | 336 |
| aag aaa ttt aag tat att gag aat ttg gaa aaa tgt gtt aaa ctt gaa<br>Lys Lys Phe Lys Tyr Ile Glu Asn Leu Glu Lys Cys Val Lys Leu Glu<br>        115                 120                 125 | 384 |
| gta ctg aat ctc agc tat aat cta ata ggg aag att gaa aag ttg gac<br>Val Leu Asn Leu Ser Tyr Asn Leu Ile Gly Lys Ile Glu Lys Leu Asp<br>130                 135                 140 | 432 |
| aag ctg tta aaa tta cgt gaa ctc aac tta tca tat aac aaa atc agc<br>Lys Leu Leu Lys Leu Arg Glu Leu Asn Leu Ser Tyr Asn Lys Ile Ser<br>145                 150                 155                 160 | 480 |
| aaa att gaa ggc ata gaa aat atg tgt aat ctg caa aag ctt aac ctt<br>Lys Ile Glu Gly Ile Glu Asn Met Cys Asn Leu Gln Lys Leu Asn Leu<br>                165                 170                 175 | 528 |
| gca gga aat gaa att gag cat att cca gta tgg tta ggg aag aag tta<br>Ala Gly Asn Glu Ile Glu His Ile Pro Val Trp Leu Gly Lys Lys Leu<br>            180                 185                 190 | 576 |
| aaa tct ttg cga gtc ctc aat ttg aaa ggc aac aag ata tca tcg ctc<br>Lys Ser Leu Arg Val Leu Asn Leu Lys Gly Asn Lys Ile Ser Ser Leu<br>        195                 200                 205 | 624 |
| caa gat ata agc aag ttg aaa ccg ctt caa gat ttg att tct ctg atc<br>Gln Asp Ile Ser Lys Leu Lys Pro Leu Gln Asp Leu Ile Ser Leu Ile<br>210                 215                 220 | 672 |
| cta gtt gaa aat cca gtt gtg acc ctt cct cat tac ctc cag ttt acc<br>Leu Val Glu Asn Pro Val Val Thr Leu Pro His Tyr Leu Gln Phe Thr<br>225                 230                 235                 240 | 720 |
| att ttc cac ctc cgt tca ttg gaa agt ttg gaa ggt cag cca gta acc<br>Ile Phe His Leu Arg Ser Leu Glu Ser Leu Glu Gly Gln Pro Val Thr<br>                245                 250                 255 | 768 |
| act cag gat aga cag gag gct ttt gag aga ttc agt tta gaa gag gta<br>Thr Gln Asp Arg Gln Glu Ala Phe Glu Arg Phe Ser Leu Glu Glu Val<br>            260                 265                 270 | 816 |
| gaa aga ctg gaa aga gac cta gaa aaa aag atg ata gaa act gaa gag<br>Glu Arg Leu Glu Arg Asp Leu Glu Lys Lys Met Ile Glu Thr Glu Glu<br>        275                 280                 285 | 864 |
| ctt aag agc aaa caa aca agg ttc ctt gag gaa att aaa aat caa gat<br>Leu Lys Ser Lys Gln Thr Arg Phe Leu Glu Glu Ile Lys Asn Gln Asp<br>290                 295                 300 | 912 |
| aaa ttg aat aaa tca tta aaa gag gag gcc atg tta cag aaa cag agc<br>Lys Leu Asn Lys Ser Leu Lys Glu Glu Ala Met Leu Gln Lys Gln Ser<br>305                 310                 315                 320 | 960 |
| tgt gag gaa ctc aag agt gac tta aac aca aaa aat gaa ttg cta aaa<br>Cys Glu Glu Leu Lys Ser Asp Leu Asn Thr Lys Asn Glu Leu Leu Lys<br>                325                 330                 335 | 1008 |
| cag aag acc ata gaa tta aca cga gca tgt cag aag caa tat gag ctg<br>Gln Lys Thr Ile Glu Leu Thr Arg Ala Cys Gln Lys Gln Tyr Glu Leu<br>            340                 345                 350 | 1056 |
| gaa cag gaa ttg gcc ttt tat aaa att gat gct aaa ttt gag cca cta<br>Glu Gln Glu Leu Ala Phe Tyr Lys Ile Asp Ala Lys Phe Glu Pro Leu<br>        355                 360                 365 | 1104 |

-continued

| | | |
|---|---|---|
| aat tat tat cca tca gag tat gct gaa att gat aaa gcc cca gat gaa<br>Asn Tyr Tyr Pro Ser Glu Tyr Ala Glu Ile Asp Lys Ala Pro Asp Glu<br>370                        375                      380 | 1152 |
| agc cct tac att ggc aaa tcc aga tac aag aga aat atg ttt gcc aca<br>Ser Pro Tyr Ile Gly Lys Ser Arg Tyr Lys Arg Asn Met Phe Ala Thr<br>385                        390                      395                      400 | 1200 |
| gag agt tat att att gac agt gct cag gca gta cag atc aag aag atg<br>Glu Ser Tyr Ile Ile Asp Ser Ala Gln Ala Val Gln Ile Lys Lys Met<br>                        405                      410                      415 | 1248 |
| gag cca gat gaa caa ctt aga aat gat cac atg aac ttg aga ggc cac<br>Glu Pro Asp Glu Gln Leu Arg Asn Asp His Met Asn Leu Arg Gly His<br>420                        425                      430 | 1296 |
| aca cca ctg gac acg caa ctg gaa gac aaa gaa aaa aaa ata agt gca<br>Thr Pro Leu Asp Thr Gln Leu Glu Asp Lys Glu Lys Lys Ile Ser Ala<br>                        435                      440                      445 | 1344 |
| gca caa act cga cta tca gaa ctg cat gat gaa ata gaa aag gca gaa<br>Ala Gln Thr Arg Leu Ser Glu Leu His Asp Glu Ile Glu Lys Ala Glu<br>450                        455                      460 | 1392 |
| caa caa att ttg aga gct act gaa gaa ttt aaa caa ctg gaa gaa gct<br>Gln Gln Ile Leu Arg Ala Thr Glu Glu Phe Lys Gln Leu Glu Glu Ala<br>465                        470                      475                      480 | 1440 |
| ata caa cta aaa aag att tca gaa gca ggg aaa gac ctt ctt tac aag<br>Ile Gln Leu Lys Lys Ile Ser Glu Ala Gly Lys Asp Leu Leu Tyr Lys<br>                        485                      490                      495 | 1488 |
| cag ttg agt ggt aga cta caa ctt gta aat aaa tta cgc cag gaa gct<br>Gln Leu Ser Gly Arg Leu Gln Leu Val Asn Lys Leu Arg Gln Glu Ala<br>                500                      505                      510 | 1536 |
| ctg gat cta gaa ctg cag atg gaa aag caa aag cag gaa att gcc gga<br>Leu Asp Leu Glu Leu Gln Met Glu Lys Gln Lys Gln Glu Ile Ala Gly<br>                515                      520                      525 | 1584 |
| aag cag aag gag att aag gac ctg caa ata gcc ata gat agc ctg gat<br>Lys Gln Lys Glu Ile Lys Asp Leu Gln Ile Ala Ile Asp Ser Leu Asp<br>530                        535                      540 | 1632 |
| tcc aaa gac cca aaa cat tcc cat atg aag gct caa aag agc ggt aaa<br>Ser Lys Asp Pro Lys His Ser His Met Lys Ala Gln Lys Ser Gly Lys<br>545                        550                      555                      560 | 1680 |
| gaa caa cag ctt gac att atg aac aag cag tac caa caa ctt gaa agt<br>Glu Gln Gln Leu Asp Ile Met Asn Lys Gln Tyr Gln Gln Leu Glu Ser<br>                565                      570                      575 | 1728 |
| cgt ttg gat gag ata ctt tct aga att gct aag gaa acg gaa gag att<br>Arg Leu Asp Glu Ile Leu Ser Arg Ile Ala Lys Glu Thr Glu Glu Ile<br>                        580                      585                      590 | 1776 |
| aag gac ctt gaa gaa cag ctt act gaa ggc cag ata gca gca aat gaa<br>Lys Asp Leu Glu Glu Gln Leu Thr Glu Gly Gln Ile Ala Ala Asn Glu<br>595                        600                      605 | 1824 |
| gcc ctg aag aag gat tta gaa ggt gtt atc agt ggg ttg caa gaa tac<br>Ala Leu Lys Lys Asp Leu Glu Gly Val Ile Ser Gly Leu Gln Glu Tyr<br>610                        615                      620 | 1872 |
| ctg ggg acc att aaa ggc cag gca act cag gcc cag aat gag tgc agg<br>Leu Gly Thr Ile Lys Gly Gln Ala Thr Gln Ala Gln Asn Glu Cys Arg<br>625                        630                      635                      640 | 1920 |
| aag ctg cgg gat gag aaa gag aca ttg ttg cag aga ttg aca gaa gtc<br>Lys Leu Arg Asp Glu Lys Glu Thr Leu Leu Gln Arg Leu Thr Glu Val<br>                        645                      650                      655 | 1968 |
| gag cag gag aga gac cag ctg gaa ata gtt gcc atg gat gca gaa aat<br>Glu Gln Glu Arg Asp Gln Leu Glu Ile Val Ala Met Asp Ala Glu Asn<br>                660                      665                      670 | 2016 |
| atg agg aag gag ctt gca gag cta gaa agt gcc ctc caa gag cag cat<br>Met Arg Lys Glu Leu Ala Glu Leu Glu Ser Ala Leu Gln Glu Gln His | 2064 |

-continued

```
            675                 680                 685
gag gtg aat gca tct ttg cag cag acc cag gga gat ctc agt gcc tat      2112
Glu Val Asn Ala Ser Leu Gln Gln Thr Gln Gly Asp Leu Ser Ala Tyr
        690                 695                 700 gaa gct gag cta gag gct cgg cta aac cta agg gat gct gaa gcc aac      2160
Glu Ala Glu Leu Glu Ala Arg Leu Asn Leu Arg Asp Ala Glu Ala Asn
705                 710                 715                 720 cag ctc aag gaa gag ttg gaa aaa gta aca aga ctt acc cag tta gaa      2208
Gln Leu Lys Glu Glu Leu Glu Lys Val Thr Arg Leu Thr Gln Leu Glu
                725                 730                 735 caa tca gcc ctt caa gca gaa ctt gag aag gaa agg caa gcc ctc aag      2256
Gln Ser Ala Leu Gln Ala Glu Leu Glu Lys Glu Arg Gln Ala Leu Lys
            740                 745                 750 aat gcc ctt gga aaa gcc cag ttc tca gaa gaa aag gag caa gag aac      2304
Asn Ala Leu Gly Lys Ala Gln Phe Ser Glu Glu Lys Glu Gln Glu Asn
        755                 760                 765 agt gag ctc cat gca aaa ctt aaa cac ttg cag gat gac aat aat ctg      2352
Ser Glu Leu His Ala Lys Leu Lys His Leu Gln Asp Asp Asn Asn Leu
    770                 775                 780 tta aaa cag caa ctt aaa gat ttc cag aat cac ctt aac cat gtg gtt      2400
Leu Lys Gln Gln Leu Lys Asp Phe Gln Asn His Leu Asn His Val Val
785                 790                 795                 800 gat ggt ttg gtt cgt cca gaa gaa gtg gca gct cgt gtg gat gag cta      2448
Asp Gly Leu Val Arg Pro Glu Glu Val Ala Ala Arg Val Asp Glu Leu
                805                 810                 815 aga aga aaa ctg aaa tta gga act ggg gaa atg aac atc cat agt cct      2496
Arg Arg Lys Leu Lys Leu Gly Thr Gly Glu Met Asn Ile His Ser Pro
            820                 825                 830 tca gat gtc tta ggg aaa agt ctt gct gat tta cag aaa caa ttc agt      2544
Ser Asp Val Leu Gly Lys Ser Leu Ala Asp Leu Gln Lys Gln Phe Ser
        835                 840                 845 gaa att ctt gca cgc tcc aag tgg gaa aga gat gaa gca caa gtt aga      2592
Glu Ile Leu Ala Arg Ser Lys Trp Glu Arg Asp Glu Ala Gln Val Arg
    850                 855                 860 gag aga aaa ctc caa gaa gaa atg gct ctg cag caa gag aaa ctg gca      2640
Glu Arg Lys Leu Gln Glu Glu Met Ala Leu Gln Gln Glu Lys Leu Ala
865                 870                 875                 880 act gga caa gaa gag ttc agg cag gcc tgt gag aga gcc ctg gaa gca      2688
Thr Gly Gln Glu Glu Phe Arg Gln Ala Cys Glu Arg Ala Leu Glu Ala
                885                 890                 895 aga atg aat ttt gat aag agg caa cat gaa gca aga atc cag caa atg      2736
Arg Met Asn Phe Asp Lys Arg Gln His Glu Ala Arg Ile Gln Gln Met
            900                 905                 910 gag aat gaa att cac tat ttg caa gaa aat cta aaa agt atg gag gaa      2784
Glu Asn Glu Ile His Tyr Leu Gln Glu Asn Leu Lys Ser Met Glu Glu
        915                 920                 925 atc caa ggc ctt aca gat ctc caa ctt cag gaa gct gat gaa gag aag      2832
Ile Gln Gly Leu Thr Asp Leu Gln Leu Gln Glu Ala Asp Glu Glu Lys
    930                 935                 940 gag aga att ctg gcc caa ctc cga gag tta gag aaa aag aag aaa ctt      2880
Glu Arg Ile Leu Ala Gln Leu Arg Glu Leu Glu Lys Lys Lys Lys Leu
945                 950                 955                 960 gaa gat gcc aaa tct cag gag caa gtt ttt ggt tta gat aaa gaa ctg      2928
Glu Asp Ala Lys Ser Gln Glu Gln Val Phe Gly Leu Asp Lys Glu Leu
                965                 970                 975 aag aaa cta aag aaa gcc gtg gcc acc tct gat aag cta gcc aca gct      2976
Lys Lys Leu Lys Lys Ala Val Ala Thr Ser Asp Lys Leu Ala Thr Ala
            980                 985                 990 gag ctc acc att gcc aaa gac cag ctg aag tcc ctt cat gga act gtt      3024
```

```
                    -continued

Glu Leu Thr Ile Ala Lys Asp Gln Leu Lys Ser Leu His Gly Thr Val
            995                 1000                1005 atg aaa att aac cag gag cga gca gag gag ttg cag gaa gca gag agg        3072
Met Lys Ile Asn Gln Glu Arg Ala Glu Glu Leu Gln Glu Ala Glu Arg
    1010                1015                1020 ttc agc aga aag gca gca caa gca gcc aga gat ctc acc cga gca gaa        3120
Phe Ser Arg Lys Ala Ala Gln Ala Ala Arg Asp Leu Thr Arg Ala Glu
1025                1030                1035                1040 gct gag atc gaa ctc ctg cag aat ctc ctc agg cag aag ggg gag cag        3168
Ala Glu Ile Glu Leu Leu Gln Asn Leu Leu Arg Gln Lys Gly Glu Gln
            1045                1050                1055 ttt cga ctt gag atg gag aaa aca ggt gta ggt act gga gca aac tca        3216
Phe Arg Leu Glu Met Glu Lys Thr Gly Val Gly Thr Gly Ala Asn Ser
        1060                1065                1070 cag gtc cta gaa att gag aaa ctg aat gag aca atg gaa cga caa agg        3264
Gln Val Leu Glu Ile Glu Lys Leu Asn Glu Thr Met Glu Arg Gln Arg
    1075                1080                1085 aca gag att gca agg ctg cag aat gta cta gac ctc act gga agt gac        3312
Thr Glu Ile Ala Arg Leu Gln Asn Val Leu Asp Leu Thr Gly Ser Asp
1090                1095                1100 aac aaa gga ggc ttt gaa aat gtt tta gaa gaa att gct gaa ctt cga        3360
Asn Lys Gly Gly Phe Glu Asn Val Leu Glu Glu Ile Ala Glu Leu Arg
1105                1110                1115                1120 cgt gaa gtt tct tat cag aat gat tac ata agc agc atg gca gat cct        3408
Arg Glu Val Ser Tyr Gln Asn Asp Tyr Ile Ser Ser Met Ala Asp Pro
            1125                1130                1135 ttc aaa aga cga ggc tat tgg tac ttt atg cca cca cca cca tca tca        3456
Phe Lys Arg Arg Gly Tyr Trp Tyr Phe Met Pro Pro Pro Pro Ser Ser
        1140                1145                1150 aaa gtt tcc agc cat agt tcc cag gcc acc aag gac tct ggt gtt ggc        3504
Lys Val Ser Ser His Ser Ser Gln Ala Thr Lys Asp Ser Gly Val Gly
    1155                1160                1165 ctt aag tac tca gcc tca act cct gtt aga aaa cca cgc cct ggg cag        3552
Leu Lys Tyr Ser Ala Ser Thr Pro Val Arg Lys Pro Arg Pro Gly Gln
1170                1175                1180 cag gat ggg aag gaa ggc agt caa cct ccc cct gcc tca gga tac tgg        3600
Gln Asp Gly Lys Glu Gly Ser Gln Pro Pro Pro Ala Ser Gly Tyr Trp
1185                1190                1195                1200 gtt tat tct ccc atc agg agt ggg tta cat aaa ctg ttt cca agt aga        3648
Val Tyr Ser Pro Ile Arg Ser Gly Leu His Lys Leu Phe Pro Ser Arg
            1205                1210                1215 gat gca gac agt gga gga gat agt cag gaa gag agt gag ctg gat gac        3696
Asp Ala Asp Ser Gly Gly Asp Ser Gln Glu Glu Ser Glu Leu Asp Asp
        1220                1225                1230 caa gaa gaa ccc cca ttt gtg cct cct cct gga tac atg atg tat act        3744
Gln Glu Glu Pro Pro Phe Val Pro Pro Pro Gly Tyr Met Met Tyr Thr
    1235                1240                1245 gtg ctt cct gat ggt tct cct gta ccc cag ggc atg gcc ctg tat gca        3792
Val Leu Pro Asp Gly Ser Pro Val Pro Gln Gly Met Ala Leu Tyr Ala
1250                1255                1260 cca cct cct ccc ttg cca aac aat agc cga cct ctc acc cct ggc act        3840
Pro Pro Pro Pro Leu Pro Asn Asn Ser Arg Pro Leu Thr Pro Gly Thr
1265                1270                1275                1280 gtt gtt tat ggc cca cct cct gct ggg gcc ccc atg gtg tat ggg cct        3888
Val Val Tyr Gly Pro Pro Pro Ala Gly Ala Pro Met Val Tyr Gly Pro
            1285                1290                1295 cca ccc ccc aac ttc tcc atc ccc ttc atc cct atg ggt gtg ctg cat        3936
Pro Pro Pro Asn Phe Ser Ile Pro Phe Ile Pro Met Gly Val Leu His
        1300                1305                1310
```

-continued

| | |
|---|---|
| tgc aac gtc cct gaa cac cat aac tta gag aat gaa gtt tct aga tta<br>Cys Asn Val Pro Glu His His Asn Leu Glu Asn Glu Val Ser Arg Leu<br>        1315                  1320                      1325 | 3984 |
| gaa gac ata atg cag cat tta aaa tca aag aag cgg gaa gaa agg tgg<br>Glu Asp Ile Met Gln His Leu Lys Ser Lys Lys Arg Glu Glu Arg Trp<br>1330                      1335                      1340 | 4032 |
| atg aga gca tcc aag cgg cag tcg gag aaa gaa atg gaa gaa ctg cat<br>Met Arg Ala Ser Lys Arg Gln Ser Glu Lys Glu Met Glu Glu Leu His<br>1345                      1350                      1355                      1360 | 4080 |
| cat aat att gat gat ctt ttg caa gag aag aaa agc tta gag tgt gaa<br>His Asn Ile Asp Asp Leu Leu Gln Glu Lys Lys Ser Leu Glu Cys Glu<br>        1365                  1370                      1375 | 4128 |
| gta gaa gaa tta cat aga act gtc cag aaa cgt caa cag caa aag gac<br>Val Glu Glu Leu His Arg Thr Val Gln Lys Arg Gln Gln Gln Lys Asp<br>        1380                  1385                      1390 | 4176 |
| ttc att gat gga aat gtt gag agt ctt atg act gaa cta gaa ata gaa<br>Phe Ile Asp Gly Asn Val Glu Ser Leu Met Thr Glu Leu Glu Ile Glu<br>        1395                  1400                      1405 | 4224 |
| aaa tca ctc aaa cat cat gaa gat att gta gat gaa att gag tgc att<br>Lys Ser Leu Lys His His Glu Asp Ile Val Asp Glu Ile Glu Cys Ile<br>        1410                  1415                      1420 | 4272 |
| gag aag act ctt ctg aaa cgt cgc tca gag ctc agg gaa gct gac cga<br>Glu Lys Thr Leu Leu Lys Arg Arg Ser Glu Leu Arg Glu Ala Asp Arg<br>1425                      1430                      1435                      1440 | 4320 |
| ctc ctg gca gag gct gag agt gaa ctt tca tgc act aaa gaa aag aca<br>Leu Leu Ala Glu Ala Glu Ser Glu Leu Ser Cys Thr Lys Glu Lys Thr<br>                      1445                      1450                      1455 | 4368 |
| aaa aat gct gtt gaa aag ttc act gat gcc aag aga agt tta ttg caa<br>Lys Asn Ala Val Glu Lys Phe Thr Asp Ala Lys Arg Ser Leu Leu Gln<br>        1460                  1465                      1470 | 4416 |
| act gag tca gat gct gag gaa tta gaa agg aga gct cag gaa act gct<br>Thr Glu Ser Asp Ala Glu Glu Leu Glu Arg Arg Ala Gln Glu Thr Ala<br>        1475                  1480                      1485 | 4464 |
| gtt aac ctc gtc aaa gct gat cag cag cta aga tcg ctc cag gct gat<br>Val Asn Leu Val Lys Ala Asp Gln Gln Leu Arg Ser Leu Gln Ala Asp<br>        1490                  1495                      1500 | 4512 |
| gca aag gat ttg gag cag cac aaa atc aag caa gaa gaa atc ttg aaa<br>Ala Lys Asp Leu Glu Gln His Lys Ile Lys Gln Glu Glu Ile Leu Lys<br>1505                      1510                      1515                      1520 | 4560 |
| gaa ata aac aaa att gta gca gca aaa gac tca gac ttc caa tgt tta<br>Glu Ile Asn Lys Ile Val Ala Ala Lys Asp Ser Asp Phe Gln Cys Leu<br>        1525                  1530                      1535 | 4608 |
| agc aag aag aag gaa aaa ctg aca gaa gag ctt cag aaa cta cag aaa<br>Ser Lys Lys Lys Glu Lys Leu Thr Glu Glu Leu Gln Lys Leu Gln Lys<br>                      1540                      1545                      1550 | 4656 |
| gac ata gag atg gca gaa cgc aat gag gat cac cac ctg cag gtc ctt<br>Asp Ile Glu Met Ala Glu Arg Asn Glu Asp His His Leu Gln Val Leu<br>        1555                  1560                      1565 | 4704 |
| aaa gaa tct gag gtg ctt ctt cag gcc aaa aga gcc gag ctg gaa aag<br>Lys Glu Ser Glu Val Leu Leu Gln Ala Lys Arg Ala Glu Leu Glu Lys<br>        1570                  1575                      1580 | 4752 |
| ctg aaa agc cag gtg aca agt cag cag cag gag atg gct gtc ttg gac<br>Leu Lys Ser Gln Val Thr Ser Gln Gln Gln Glu Met Ala Val Leu Asp<br>1585                      1590                      1595                      1600 | 4800 |
| agg cag tta ggg cat aaa aag gag gag ctg cat cta ctc caa gga agc<br>Arg Gln Leu Gly His Lys Lys Glu Glu Leu His Leu Leu Gln Gly Ser<br>        1605                  1610                      1615 | 4848 |
| atg gtc cag gca aaa gct gac ctc cag gaa gct ctg aga ctg gga gag<br>Met Val Gln Ala Lys Ala Asp Leu Gln Glu Ala Leu Arg Leu Gly Glu<br>        1620                  1625                      1630 | 4896 |

-continued

```
act gaa gta act gag aag tgc aat cac att agg gaa gta aaa tct ctt    4944
Thr Glu Val Thr Glu Lys Cys Asn His Ile Arg Glu Val Lys Ser Leu
    1635                1640                1645 ctg gaa gaa ctg agt ttt cag aaa gga gaa cta aat gtt cag att agt    4992
Leu Glu Glu Leu Ser Phe Gln Lys Gly Glu Leu Asn Val Gln Ile Ser
1650                1655                1660 gaa aga aaa act caa ctt aca ctt ata aag cag gaa att gaa aaa gag    5040
Glu Arg Lys Thr Gln Leu Thr Leu Ile Lys Gln Glu Ile Glu Lys Glu
1665                1670                1675                1680 gaa gaa aat ctt cag gtt gtt tta agg cag atg tct aaa cat aaa acc    5088
Glu Glu Asn Leu Gln Val Val Leu Arg Gln Met Ser Lys His Lys Thr
            1685                1690                1695 gaa cta aag aat att ctg gac atg ttg caa ctt gaa aac cat gag cta    5136
Glu Leu Lys Asn Ile Leu Asp Met Leu Gln Leu Glu Asn His Glu Leu
        1700                1705                1710 caa ggt ttg aag cta caa cat gac caa agg gta tct gaa tta gag aag    5184
Gln Gly Leu Lys Leu Gln His Asp Gln Arg Val Ser Glu Leu Glu Lys
    1715                1720                1725 act cag gtg gca gtg cta gag gag aaa ctg gag tta gag aat ttg cag    5232
Thr Gln Val Ala Val Leu Glu Glu Lys Leu Glu Leu Glu Asn Leu Gln
1730                1735                1740 cag ata tcc cag cag cag aaa ggg gaa ata gag tgg cag aag cag ctc    5280
Gln Ile Ser Gln Gln Gln Lys Gly Glu Ile Glu Trp Gln Lys Gln Leu
1745                1750                1755                1760 ctt gag agg gat aaa cga gaa ata gaa cga atg act gct gag tcc cga    5328
Leu Glu Arg Asp Lys Arg Glu Ile Glu Arg Met Thr Ala Glu Ser Arg
            1765                1770                1775 gct tta caa tcg tgt gtt gag tgt ttg agc aaa gaa aag gaa gat ctc    5376
Ala Leu Gln Ser Cys Val Glu Cys Leu Ser Lys Glu Lys Glu Asp Leu
        1780                1785                1790 caa gag aaa tgt gac att tgg gaa aaa aag ttg gca caa acc aaa agg    5424
Gln Glu Lys Cys Asp Ile Trp Glu Lys Lys Leu Ala Gln Thr Lys Arg
    1795                1800                1805 gtt tta gca gca gca gaa gaa aat agc aaa atg gag caa tca aac tta    5472
Val Leu Ala Ala Ala Glu Glu Asn Ser Lys Met Glu Gln Ser Asn Leu
1810                1815                1820 gaa aag ttg gaa ttg aat gtc aga aaa ctg cag cag gaa cta gac caa    5520
Glu Lys Leu Glu Leu Asn Val Arg Lys Leu Gln Gln Glu Leu Asp Gln
1825                1830                1835                1840 cta aac aga gac aag ttg tca ctg cat aac gac att tca gca atg caa    5568
Leu Asn Arg Asp Lys Leu Ser Leu His Asn Asp Ile Ser Ala Met Gln
            1845                1850                1855 cag cag ctc caa gaa aaa cga gaa gca gta aac tca ctg cag gag gaa    5616
Gln Gln Leu Gln Glu Lys Arg Glu Ala Val Asn Ser Leu Gln Glu Glu
        1860                1865                1870 cta gct aat gtc caa gac cat ttg aac cta gca aaa cag gac ctg ctt    5664
Leu Ala Asn Val Gln Asp His Leu Asn Leu Ala Lys Gln Asp Leu Leu
    1875                1880                1885 cac acc acc aag cat cag gat gtg ttg ctc agt gag cag acc cga ctc    5712
His Thr Thr Lys His Gln Asp Val Leu Leu Ser Glu Gln Thr Arg Leu
1890                1895                1900 cag aag gac atc agt gaa tgg gca aat agg ttt gaa gac tgt cag aaa    5760
Gln Lys Asp Ile Ser Glu Trp Ala Asn Arg Phe Glu Asp Cys Gln Lys
1905                1910                1915                1920 gaa gag gag aca aaa caa caa caa ctt caa gtg ctt cag aat gag att    5808
Glu Glu Glu Thr Lys Gln Gln Gln Leu Gln Val Leu Gln Asn Glu Ile
            1925                1930                1935 gaa gaa aac aag ctc aaa cta gtc caa caa gaa atg atg ttt cag aga    5856
Glu Glu Asn Lys Leu Lys Leu Val Gln Gln Glu Met Met Phe Gln Arg
```

-continued

```
                       1940                1945                 1950
ctc cag aaa gag aga gaa agt gaa gaa agc aaa tta gaa acc agt aaa              5904
Leu Gln Lys Glu Arg Glu Ser Glu Glu Ser Lys Leu Glu Thr Ser Lys
            1955                1960                1965 gtg aca ctg aag gag caa cag cac cag ctg gaa aag gaa tta aca gac              5952
Val Thr Leu Lys Glu Gln Gln His Gln Leu Glu Lys Glu Leu Thr Asp
        1970                1975                1980 cag aaa agc aaa ctg gac caa gtg ctc tca aag gtg ctg gca gct gaa              6000
Gln Lys Ser Lys Leu Asp Gln Val Leu Ser Lys Val Leu Ala Ala Glu
1985                1990                1995                2000 gag cgt gtt agg act ctg cag gaa gag gag agg tgg tgt gag agc ctg              6048
Glu Arg Val Arg Thr Leu Gln Glu Glu Glu Arg Trp Cys Glu Ser Leu
            2005                2010                2015 gag aag aca ctc tcc caa act aaa cgg cag ctt tca gaa agg gag cag              6096
Glu Lys Thr Leu Ser Gln Thr Lys Arg Gln Leu Ser Glu Arg Glu Gln
            2020                2025                2030 caa ttg gtg gag aaa tca ggt gag ctg ttg gcc ctc cag aaa gag gca              6144
Gln Leu Val Glu Lys Ser Gly Glu Leu Leu Ala Leu Gln Lys Glu Ala
            2035                2040                2045 gat tct atg agg gca gac ttc agc ctt ctg cgg aac cag ttc ttg aca              6192
Asp Ser Met Arg Ala Asp Phe Ser Leu Leu Arg Asn Gln Phe Leu Thr
        2050                2055                2060 gaa aga aag aaa gct gag aag cag gtg gcc agc ctg aag gaa gca ctt              6240
Glu Arg Lys Lys Ala Glu Lys Gln Val Ala Ser Leu Lys Glu Ala Leu
2065                2070                2075                2080 aag atc cag cgg agc cag ctg gag aaa aac ctt ctt gag caa aaa cag              6288
Lys Ile Gln Arg Ser Gln Leu Glu Lys Asn Leu Leu Glu Gln Lys Gln
            2085                2090                2095 gag aac agc tgc ata caa aag gaa atg gca aca att gaa ctg gta gcc              6336
Glu Asn Ser Cys Ile Gln Lys Glu Met Ala Thr Ile Glu Leu Val Ala
        2100                2105                2110 cag gac aac cat gag cgg gcc agg cgc ctg atg aag gag ctc aac cag              6384
Gln Asp Asn His Glu Arg Ala Arg Arg Leu Met Lys Glu Leu Asn Gln
        2115                2120                2125 atg cag tat gag tac acg gag ctc aag aaa cag atg gca aac caa aaa              6432
Met Gln Tyr Glu Tyr Thr Glu Leu Lys Lys Gln Met Ala Asn Gln Lys
        2130                2135                2140 gat ttg gag aga aga caa atg gaa atc agt gat gca atg agg aca ctt              6480
Asp Leu Glu Arg Arg Gln Met Glu Ile Ser Asp Ala Met Arg Thr Leu
2145                2150                2155                2160 aaa tct gag gtg aag gat gaa atc aga acc agc ttg aag aat ctt aat              6528
Lys Ser Glu Val Lys Asp Glu Ile Arg Thr Ser Leu Lys Asn Leu Asn
            2165                2170                2175 cag ttt ctt cca gaa cta cca gca gat cta gaa gct att ttg gaa aga              6576
Gln Phe Leu Pro Glu Leu Pro Ala Asp Leu Glu Ala Ile Leu Glu Arg
        2180                2185                2190 aac gaa aac cta gaa gga gaa ttg gaa agc ttg aaa gag aac ctt cca              6624
Asn Glu Asn Leu Glu Gly Glu Leu Glu Ser Leu Lys Glu Asn Leu Pro
        2195                2200                2205 ttt acc atg aat gag gga cct ttt gaa gaa aaa ctg aac ttt tcc caa              6672
Phe Thr Met Asn Glu Gly Pro Phe Glu Glu Lys Leu Asn Phe Ser Gln
        2210                2215                2220 gtt cac ata atg gat gaa cac tgg cgt gga gaa gca ctc cgg gag aaa              6720
Val His Ile Met Asp Glu His Trp Arg Gly Glu Ala Leu Arg Glu Lys
2225                2230                2235                2240 ctg cgt cac cgg gaa gac cga ctc aag gcc caa ctc cga cac tgt atg              6768
Leu Arg His Arg Glu Asp Arg Leu Lys Ala Gln Leu Arg His Cys Met
            2245                2250                2255 tcc aag caa gca gaa gta tta att aaa gga aag cgg cag aca gag ggc              6816
```

```
                                                -continued

Ser Lys Gln Ala Glu Val Leu Ile Lys Gly Lys Arg Gln Thr Glu Gly
            2260                2265                2270 act tta cac agt ttg agg aga caa gta gat gct tta ggg gaa ttg gtc      6864
Thr Leu His Ser Leu Arg Arg Gln Val Asp Ala Leu Gly Glu Leu Val
        2275                2280                2285 acc agc acc tct gca gat tca gcg tca tca ccc agt ctg tct cag ctg      6912
Thr Ser Thr Ser Ala Asp Ser Ala Ser Ser Pro Ser Leu Ser Gln Leu
    2290                2295                2300 gag tct tcc ctc aca gag gac tct caa ctt gga caa aat cag gaa aag      6960
Glu Ser Ser Leu Thr Glu Asp Ser Gln Leu Gly Gln Asn Gln Glu Lys
2305                2310                2315                2320 aat gcc tca gcc aga tga                                              6978
Asn Ala Ser Ala Arg
            2325

<210> SEQ ID NO 2
<211> LENGTH: 2325
<212> TYPE: PRT
<213> ORGANISM: Homo sapiens

<400> SEQUENCE: 2

Met Lys Lys Gly Ser Gln Gln Lys Ile Phe Ser Lys Ala Lys Ile Pro
1               5                   10                  15

Ser Ser Ser His Ser Pro Ile Pro Ser Ser Met Ser Asn Met Arg Ser
            20                  25                  30

Arg Ser Leu Ser Pro Leu Ile Gly Ser Glu Thr Leu Pro Phe His Ser
        35                  40                  45

Gly Gly Gln Trp Cys Glu Gln Ile Glu Ile Ala Asp Glu Asn Asn Met
    50                  55                  60

Leu Leu Asp Tyr Gln Asp His Lys Gly Ala Asp Ser His Ala Gly Val
65              70                  75                  80

Arg Tyr Ile Thr Glu Ala Leu Ile Lys Lys Leu Thr Lys Gln Asp Asn
            85                  90                  95

Leu Ala Leu Ile Lys Ser Leu Asn Leu Ser Leu Ser Lys Asp Gly Gly
            100                 105                 110

Lys Lys Phe Lys Tyr Ile Glu Asn Leu Glu Lys Cys Val Lys Leu Glu
        115                 120                 125

Val Leu Asn Leu Ser Tyr Asn Leu Ile Gly Lys Ile Glu Lys Leu Asp
    130                 135                 140

Lys Leu Leu Lys Leu Arg Glu Leu Asn Leu Ser Tyr Asn Lys Ile Ser
145                 150                 155                 160

Lys Ile Glu Gly Ile Glu Asn Met Cys Asn Leu Gln Lys Leu Asn Leu
            165                 170                 175

Ala Gly Asn Glu Ile Glu His Ile Pro Val Trp Leu Gly Lys Lys Leu
        180                 185                 190

Lys Ser Leu Arg Val Leu Asn Leu Lys Gly Asn Lys Ile Ser Ser Leu
    195                 200                 205

Gln Asp Ile Ser Lys Leu Lys Pro Leu Gln Asp Leu Ile Ser Leu Ile
    210                 215                 220

Leu Val Glu Asn Pro Val Thr Leu Pro His Tyr Leu Gln Phe Thr
225                 230                 235                 240

Ile Phe His Leu Arg Ser Leu Glu Ser Leu Glu Gly Gln Pro Val Thr
            245                 250                 255

Thr Gln Asp Arg Gln Glu Ala Phe Glu Arg Phe Ser Leu Glu Glu Val
            260                 265                 270

Glu Arg Leu Glu Arg Asp Leu Glu Lys Lys Met Ile Glu Thr Glu Glu
```

-continued

```
                275                 280                 285
Leu Lys Ser Lys Gln Thr Arg Phe Leu Glu Glu Ile Lys Asn Gln Asp
    290                 295                 300

Lys Leu Asn Lys Ser Leu Lys Glu Ala Met Leu Gln Lys Gln Ser
305                 310                 315                 320

Cys Glu Glu Leu Lys Ser Asp Leu Asn Thr Lys Asn Glu Leu Leu Lys
                325                 330                 335

Gln Lys Thr Ile Glu Leu Thr Arg Ala Cys Gln Lys Gln Tyr Glu Leu
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Ala Glu Ile Asp Lys Ala Pro Asp Glu
    370                 375                 380

Ser Pro Tyr Ile Gly Lys Ser Arg Tyr Lys Arg Asn Met Phe Ala Thr
385                 390                 395                 400

Glu Ser Tyr Ile Ile Asp Ser Ala Gln Ala Val Gln Ile Lys Lys Met
                405                 410                 415

Glu Pro Asp Glu Gln Leu Arg Asn Asp His Met Asn Leu Arg Gly His
            420                 425                 430

Thr Pro Leu Asp Thr Gln Leu Glu Asp Lys Glu Lys Lys Ile Ser Ala
        435                 440                 445

Ala Gln Thr Arg Leu Ser Glu Leu His Asp Glu Ile Glu Lys Ala Glu
    450                 455                 460

Gln Gln Ile Leu Arg Ala Thr Glu Glu Phe Lys Gln Leu Glu Glu Ala
465                 470                 475                 480

Ile Gln Leu Lys Lys Ile Ser Glu Ala Gly Lys Asp Leu Leu Tyr Lys
                485                 490                 495

Gln Leu Ser Gly Arg Leu Gln Leu Val Asn Lys Leu Arg Gln Glu Ala
            500                 505                 510

Leu Asp Leu Glu Leu Gln Met Glu Lys Gln Lys Gln Glu Ile Ala Gly
        515                 520                 525

Lys Gln Lys Glu Ile Lys Asp Leu Gln Ile Ala Ile Asp Ser Leu Asp
    530                 535                 540

Ser Lys Asp Pro Lys His Ser His Met Lys Ala Gln Lys Ser Gly Lys
545                 550                 555                 560

Glu Gln Gln Leu Asp Ile Met Asn Lys Gln Tyr Gln Leu Glu Ser
                565                 570                 575

Arg Leu Asp Glu Ile Leu Ser Arg Ile Ala Lys Glu Thr Glu Glu Ile
            580                 585                 590

Lys Asp Leu Glu Glu Gln Leu Thr Glu Gly Gln Ile Ala Ala Asn Glu
        595                 600                 605

Ala Leu Lys Lys Asp Leu Glu Gly Val Ile Ser Gly Leu Gln Glu Tyr
    610                 615                 620

Leu Gly Thr Ile Lys Gly Gln Ala Thr Gln Ala Asn Glu Cys Arg
625                 630                 635                 640

Lys Leu Arg Asp Glu Lys Glu Thr Leu Leu Gln Arg Leu Thr Glu Val
                645                 650                 655

Glu Gln Glu Arg Asp Gln Leu Glu Ile Val Ala Met Asp Ala Glu Asn
            660                 665                 670

Met Arg Lys Glu Leu Ala Glu Leu Glu Ser Ala Leu Gln Glu Gln His
        675                 680                 685

Glu Val Asn Ala Ser Leu Gln Gln Thr Gln Gly Asp Leu Ser Ala Tyr
    690                 695                 700
```

```
Glu Ala Glu Leu Glu Ala Arg Leu Asn Leu Arg Asp Ala Glu Ala Asn
705                 710                 715                 720

Gln Leu Lys Glu Glu Leu Glu Lys Val Thr Arg Leu Thr Gln Leu Glu
                725                 730                 735

Gln Ser Ala Leu Gln Ala Glu Leu Glu Lys Glu Arg Gln Ala Leu Lys
            740                 745                 750

Asn Ala Leu Gly Lys Ala Gln Phe Ser Glu Lys Glu Gln Glu Asn
            755                 760                 765

Ser Glu Leu His Ala Lys Leu Lys His Leu Gln Asp Asp Asn Asn Leu
770                 775                 780

Leu Lys Gln Gln Leu Lys Asp Phe Gln Asn His Leu Asn His Val Val
785                 790                 795                 800

Asp Gly Leu Val Arg Pro Glu Glu Val Ala Ala Arg Val Asp Glu Leu
                805                 810                 815

Arg Arg Lys Leu Lys Leu Gly Thr Gly Glu Met Asn Ile His Ser Pro
                820                 825                 830

Ser Asp Val Leu Gly Lys Ser Leu Ala Asp Leu Gln Lys Gln Phe Ser
            835                 840                 845

Glu Ile Leu Ala Arg Ser Lys Trp Glu Arg Asp Glu Ala Gln Val Arg
850                 855                 860

Glu Arg Lys Leu Gln Glu Glu Met Ala Leu Gln Gln Glu Lys Leu Ala
865                 870                 875                 880

Thr Gly Gln Glu Glu Phe Arg Gln Ala Cys Glu Arg Ala Leu Glu Ala
                885                 890                 895

Arg Met Asn Phe Asp Lys Arg Gln His Glu Ala Arg Ile Gln Gln Met
                900                 905                 910

Glu Asn Glu Ile His Tyr Leu Gln Glu Asn Leu Lys Ser Met Glu Glu
            915                 920                 925

Ile Gln Gly Leu Thr Asp Leu Gln Leu Gln Glu Ala Asp Glu Glu Lys
            930                 935                 940

Glu Arg Ile Leu Ala Gln Leu Arg Glu Leu Glu Lys Lys Lys Lys Leu
945                 950                 955                 960

Glu Asp Ala Lys Ser Gln Glu Gln Val Phe Gly Leu Asp Lys Glu Leu
                965                 970                 975

Lys Lys Leu Lys Lys Ala Val Ala Thr Ser Asp Lys Leu Ala Thr Ala
            980                 985                 990

Glu Leu Thr Ile Ala Lys Asp Gln Leu Lys Ser Leu His Gly Thr Val
            995                 1000                1005

Met Lys Ile Asn Gln Glu Arg Ala Glu Glu Leu Gln Glu Ala Glu Arg
1010                1015                1020

Phe Ser Arg Lys Ala Ala Gln Ala Ala Arg Asp Leu Thr Arg Ala Glu
1025                1030                1035                1040

Ala Glu Ile Glu Leu Leu Gln Asn Leu Leu Arg Gln Lys Gly Glu Gln
                1045                1050                1055

Phe Arg Leu Glu Met Glu Lys Thr Gly Val Gly Thr Gly Ala Asn Ser
                1060                1065                1070

Gln Val Leu Glu Ile Glu Lys Leu Asn Glu Thr Met Glu Arg Gln Arg
            1075                1080                1085

Thr Glu Ile Ala Arg Leu Gln Asn Val Leu Asp Leu Thr Gly Ser Asp
            1090                1095                1100

Asn Lys Gly Gly Phe Glu Asn Val Leu Glu Glu Ile Ala Glu Leu Arg
1105                1110                1115                1120
```

```
Arg Glu Val Ser Tyr Gln Asn Asp Tyr Ile Ser Ser Met Ala Asp Pro
            1125                1130                1135

Phe Lys Arg Arg Gly Tyr Trp Tyr Phe Met Pro Pro Pro Ser Ser
            1140                1145                1150

Lys Val Ser Ser His Ser Ser Gln Ala Thr Lys Asp Ser Gly Val Gly
            1155                1160                1165

Leu Lys Tyr Ser Ala Ser Thr Pro Val Arg Lys Pro Arg Pro Gly Gln
        1170                1175                1180

Gln Asp Gly Lys Glu Gly Ser Gln Pro Pro Ala Ser Gly Tyr Trp
1185                1190                1195                1200

Val Tyr Ser Pro Ile Arg Ser Gly Leu His Lys Leu Phe Pro Ser Arg
            1205                1210                1215

Asp Ala Asp Ser Gly Gly Asp Ser Gln Glu Glu Ser Glu Leu Asp Asp
            1220                1225                1230

Gln Glu Glu Pro Pro Phe Val Pro Pro Gly Tyr Met Met Tyr Thr
        1235                1240                1245

Val Leu Pro Asp Gly Ser Pro Val Pro Gln Gly Met Ala Leu Tyr Ala
            1250                1255                1260

Pro Pro Pro Pro Leu Pro Asn Asn Ser Arg Pro Leu Thr Pro Gly Thr
1265                1270                1275                1280

Val Val Tyr Gly Pro Pro Pro Ala Gly Ala Pro Met Val Tyr Gly Pro
            1285                1290                1295

Pro Pro Pro Asn Phe Ser Ile Pro Phe Ile Pro Met Gly Val Leu His
            1300                1305                1310

Cys Asn Val Pro Glu His His Asn Leu Glu Asn Glu Val Ser Arg Leu
            1315                1320                1325

Glu Asp Ile Met Gln His Leu Lys Ser Lys Arg Glu Glu Arg Trp
        1330                1335                1340

Met Arg Ala Ser Lys Arg Gln Ser Glu Lys Glu Met Glu Glu Leu His
1345                1350                1355                1360

His Asn Ile Asp Asp Leu Leu Gln Glu Lys Lys Ser Leu Glu Cys Glu
            1365                1370                1375

Val Glu Glu Leu His Arg Thr Val Gln Lys Arg Gln Gln Lys Asp
            1380                1385                1390

Phe Ile Asp Gly Asn Val Glu Ser Leu Met Thr Glu Leu Glu Ile Glu
        1395                1400                1405

Lys Ser Leu Lys His His Glu Asp Ile Val Asp Glu Ile Glu Cys Ile
        1410                1415                1420

Glu Lys Thr Leu Leu Lys Arg Arg Ser Glu Leu Arg Glu Ala Asp Arg
1425                1430                1435                1440

Leu Leu Ala Glu Ala Glu Ser Glu Leu Ser Cys Thr Lys Glu Lys Thr
            1445                1450                1455

Lys Asn Ala Val Glu Lys Phe Thr Asp Ala Lys Arg Ser Leu Leu Gln
            1460                1465                1470

Thr Glu Ser Asp Ala Glu Glu Leu Glu Arg Arg Ala Gln Glu Thr Ala
            1475                1480                1485

Val Asn Leu Val Lys Ala Asp Gln Gln Leu Arg Ser Leu Gln Ala Asp
            1490                1495                1500

Ala Lys Asp Leu Glu Gln His Lys Ile Lys Gln Glu Ile Leu Lys
1505                1510                1515                1520

Glu Ile Asn Lys Ile Val Ala Ala Lys Asp Ser Asp Phe Gln Cys Leu
            1525                1530                1535

Ser Lys Lys Lys Glu Lys Leu Thr Glu Glu Leu Gln Lys Leu Gln Lys
```

-continued

```
               1540                1545                1550
Asp Ile Glu Met Ala Glu Arg Asn Glu Asp His His Leu Gln Val Leu
         1555                1560                1565
Lys Glu Ser Glu Val Leu Leu Gln Ala Lys Arg Ala Glu Leu Glu Lys
1570                1575                1580
Leu Lys Ser Gln Val Thr Ser Gln Gln Gln Glu Met Ala Val Leu Asp
1585                1590                1595                1600
Arg Gln Leu Gly His Lys Lys Glu Leu His Leu Leu Gln Gly Ser
             1605                1610                1615
Met Val Gln Ala Lys Ala Asp Leu Gln Glu Ala Leu Arg Leu Gly Glu
         1620                1625                1630
Thr Glu Val Thr Glu Lys Cys Asn His Ile Arg Glu Val Lys Ser Leu
         1635                1640                1645
Leu Glu Glu Leu Ser Phe Gln Lys Gly Glu Leu Asn Val Gln Ile Ser
         1650                1655                1660
Glu Arg Lys Thr Gln Leu Thr Leu Ile Lys Gln Ile Glu Lys Glu
1665                1670                1675                1680
Glu Glu Asn Leu Gln Val Val Leu Arg Gln Met Ser Lys His Lys Thr
             1685                1690                1695
Glu Leu Lys Asn Ile Leu Asp Met Leu Gln Leu Glu Asn His Glu Leu
         1700                1705                1710
Gln Gly Leu Lys Leu Gln His Asp Gln Arg Val Ser Glu Leu Glu Lys
         1715                1720                1725
Thr Gln Val Ala Val Leu Glu Glu Lys Leu Glu Leu Glu Asn Leu Gln
         1730                1735                1740
Gln Ile Ser Gln Gln Gln Lys Gly Glu Ile Glu Trp Gln Lys Gln Leu
1745                1750                1755                1760
Leu Glu Arg Asp Lys Arg Glu Ile Glu Arg Met Thr Ala Glu Ser Arg
             1765                1770                1775
Ala Leu Gln Ser Cys Val Glu Cys Leu Ser Lys Glu Lys Glu Asp Leu
         1780                1785                1790
Gln Glu Lys Cys Asp Ile Trp Glu Lys Lys Leu Ala Gln Thr Lys Arg
         1795                1800                1805
Val Leu Ala Ala Ala Glu Glu Asn Ser Lys Met Glu Gln Ser Asn Leu
         1810                1815                1820
Glu Lys Leu Glu Leu Asn Val Arg Lys Leu Gln Gln Glu Leu Asp Gln
1825                1830                1835                1840
Leu Asn Arg Asp Lys Leu Ser Leu His Asn Asp Ile Ser Ala Met Gln
             1845                1850                1855
Gln Gln Leu Gln Glu Lys Arg Glu Ala Val Asn Ser Leu Gln Glu Glu
         1860                1865                1870
Leu Ala Asn Val Gln Asp His Leu Asn Leu Ala Lys Gln Asp Leu Leu
         1875                1880                1885
His Thr Thr Lys His Gln Asp Val Leu Leu Ser Glu Gln Thr Arg Leu
         1890                1895                1900
Gln Lys Asp Ile Ser Glu Trp Ala Asn Arg Phe Glu Asp Cys Gln Lys
1905                1910                1915                1920
Glu Glu Glu Thr Lys Gln Gln Gln Leu Gln Val Leu Gln Asn Glu Ile
                 1925                1930                1935
Glu Glu Asn Lys Leu Lys Leu Val Gln Gln Glu Met Met Phe Gln Arg
             1940                1945                1950
Leu Gln Lys Glu Arg Glu Ser Glu Glu Ser Lys Leu Glu Thr Ser Lys
         1955                1960                1965
```

```
Val Thr Leu Lys Glu Gln Gln His Gln Leu Glu Lys Glu Leu Thr Asp
    1970                1975                1980

Gln Lys Ser Lys Leu Asp Gln Val Leu Ser Lys Val Leu Ala Ala Glu
1985                1990                1995                2000

Glu Arg Val Arg Thr Leu Gln Glu Glu Arg Trp Cys Glu Ser Leu
            2005                2010                2015

Glu Lys Thr Leu Ser Gln Thr Lys Arg Gln Leu Ser Gly Arg Glu Gln
        2020                2025                2030

Gln Leu Val Glu Lys Ser Gly Glu Leu Leu Ala Leu Gln Lys Glu Ala
            2035                2040                2045

Asp Ser Met Arg Ala Asp Phe Ser Leu Leu Arg Asn Gln Phe Leu Thr
        2050                2055                2060

Glu Arg Lys Lys Ala Glu Lys Gln Val Ala Ser Leu Lys Glu Ala Leu
2065                2070                2075                2080

Lys Ile Gln Arg Ser Gln Leu Glu Lys Asn Leu Leu Gln Lys Gln
            2085                2090                2095

Glu Asn Ser Cys Ile Gln Lys Glu Met Ala Thr Ile Glu Leu Val Ala
            2100                2105                2110

Gln Asp Asn His Glu Arg Ala Arg Arg Leu Met Lys Glu Leu Asn Gln
        2115                2120                2125

Met Gln Tyr Glu Tyr Thr Glu Leu Lys Lys Gln Met Ala Asn Gln Lys
        2130                2135                2140

Asp Leu Glu Arg Arg Gln Met Glu Ile Ser Asp Ala Met Arg Thr Leu
2145                2150                2155                2160

Lys Ser Glu Val Lys Asp Glu Ile Arg Thr Ser Leu Lys Asn Leu Asn
            2165                2170                2175

Gln Phe Leu Pro Glu Leu Pro Ala Asp Leu Glu Ala Ile Leu Glu Arg
            2180                2185                2190

Asn Glu Asn Leu Glu Gly Glu Leu Glu Ser Leu Lys Glu Asn Leu Pro
            2195                2200                2205

Phe Thr Met Asn Glu Gly Pro Phe Glu Glu Lys Leu Asn Phe Ser Gln
        2210                2215                2220

Val His Ile Met Asp Glu His Trp Arg Gly Glu Ala Leu Arg Glu Lys
2225                2230                2235                2240

Leu Arg His Arg Glu Asp Arg Leu Lys Ala Gln Leu Arg His Cys Met
            2245                2250                2255

Ser Lys Gln Ala Glu Val Leu Ile Lys Gly Lys Arg Gln Thr Glu Gly
            2260                2265                2270

Thr Leu His Ser Leu Arg Arg Gln Val Asp Ala Leu Gly Glu Leu Val
        2275                2280                2285

Thr Ser Thr Ser Ala Asp Ser Ala Ser Ser Pro Ser Leu Ser Gln Leu
    2290                2295                2300

Glu Ser Ser Leu Thr Glu Asp Ser Gln Leu Gly Gln Asn Gln Glu Lys
2305                2310                2315                2320

Asn Ala Ser Ala Arg
            2325

<210> SEQ ID NO 3
<211> LENGTH: 10011
<212> TYPE: DNA
<213> ORGANISM: Homo sapiens
<220> FEATURE:
<221> NAME/KEY: CDS
<222> LOCATION: (1)...(10008)
```

```
<400> SEQUENCE: 3 atg gaa gtt gag caa gag cag cgg cgc aga aag gtg gag gcc ggg agg     48
Met Glu Val Glu Gln Glu Gln Arg Arg Arg Lys Val Glu Ala Gly Arg
 1               5                  10                  15 acg aag ctt gct cac ttc cga cag aga aaa aca aaa ggt gac agt tcg     96
Thr Lys Leu Ala His Phe Arg Gln Arg Lys Thr Lys Gly Asp Ser Ser
             20                  25                  30 cat tcg gag aaa aag acg gcg aag agg aag ggc tcg gct gtc gat gcg    144
His Ser Glu Lys Lys Thr Ala Lys Arg Lys Gly Ser Ala Val Asp Ala
         35                  40                  45 tct gtc cag gag gag agt ccg gta acc aag gag gac agc gca ctc tgt    192
Ser Val Gln Glu Glu Ser Pro Val Thr Lys Glu Asp Ser Ala Leu Cys
     50                  55                  60 gga gga ggg gac att tgc aaa agc aca tca tgt gac gac acc cct gat    240
Gly Gly Gly Asp Ile Cys Lys Ser Thr Ser Cys Asp Asp Thr Pro Asp
 65                  70                  75                  80 ggg gca gga ggg gcc ttt gca gct cag ccg gag gac tgt gat gga gag    288
Gly Ala Gly Gly Ala Phe Ala Ala Gln Pro Glu Asp Cys Asp Gly Glu
                 85                  90                  95 aag aga gag gac ttg gaa cag ctg cag cag aag caa gtc aat gac cat    336
Lys Arg Glu Asp Leu Glu Gln Leu Gln Gln Lys Gln Val Asn Asp His
            100                 105                 110 cct cca gag cag tgt ggg atg ttc aca gtc agt gac cac cca cca gaa    384
Pro Pro Glu Gln Cys Gly Met Phe Thr Val Ser Asp His Pro Pro Glu
        115                 120                 125 cag cat ggg atg ttc aca gtc ggt gac cac cca cca gaa cag cgt ggg    432
Gln His Gly Met Phe Thr Val Gly Asp His Pro Pro Glu Gln Arg Gly
    130                 135                 140 atg ttc aca gtc agt gac cac cca cca gaa cag cat ggg atg ttc aca    480
Met Phe Thr Val Ser Asp His Pro Pro Glu Gln His Gly Met Phe Thr
145                 150                 155                 160 gtc agt gac cac cca cca gaa cag cgt ggg atg ttc aca atc agt gac    528
Val Ser Asp His Pro Pro Glu Gln Arg Gly Met Phe Thr Ile Ser Asp
                165                 170                 175 cac caa ccg gaa cag cgt ggg atg ttc aca gtc agt gac cac aca cca    576
His Gln Pro Glu Gln Arg Gly Met Phe Thr Val Ser Asp His Thr Pro
            180                 185                 190 gaa cag cgt ggg atc ttc aca atc agt gac cac cca gca gaa cag cgt    624
Glu Gln Arg Gly Ile Phe Thr Ile Ser Asp His Pro Ala Glu Gln Arg
        195                 200                 205 ggg atg ttc aca aag gag tgt gaa caa gaa tgt gaa ctt gcc att act    672
Gly Met Phe Thr Lys Glu Cys Glu Gln Glu Cys Glu Leu Ala Ile Thr
    210                 215                 220 gac ctg gag agc ggc cgt gaa gat gag gct ggc ctg cat cag agt cag    720
Asp Leu Glu Ser Gly Arg Glu Asp Glu Ala Gly Leu His Gln Ser Gln
225                 230                 235                 240 gcc gtg cat ggc ctt gag ctg gag gcg ctg cgc ctg agt ctg agc aac    768
Ala Val His Gly Leu Glu Leu Glu Ala Leu Arg Leu Ser Leu Ser Asn
                245                 250                 255 atg cac acg gcg cag ctg gag ctg aca cag gcc aac ctc cag aag gag    816
Met His Thr Ala Gln Leu Glu Leu Thr Gln Ala Asn Leu Gln Lys Glu
            260                 265                 270 aag gag acg gca ttg acg gag ctg cgg gag atg ctc aac agc cgg cgt    864
Lys Glu Thr Ala Leu Thr Glu Leu Arg Glu Met Leu Asn Ser Arg Arg
        275                 280                 285 gcc cag gag ctg gcc ctg cta cag agc agg cag cag cac gag ctg gag    912
Ala Gln Glu Leu Ala Leu Leu Gln Ser Arg Gln Gln His Glu Leu Glu
    290                 295                 300 ctc ctc agg gag cag cac gca cgg gag aag gag gag gtg gtg ctc agg    960
```

```
                                                      -continued

Leu Leu Arg Glu Gln His Ala Arg Glu Lys Glu Glu Val Val Leu Arg
305                 310                 315                 320 tgt gga cag gaa gca gct gag ctg aag gag aag tta caa tca gaa atg    1008
Cys Gly Gln Glu Ala Ala Glu Leu Lys Glu Lys Leu Gln Ser Glu Met
                325                 330                 335 gag aaa aac gcc cag ata gta aag acc ctg aag gaa gat tgg gaa tct    1056
Glu Lys Asn Ala Gln Ile Val Lys Thr Leu Lys Glu Asp Trp Glu Ser
            340                 345                 350 gaa aaa gat tta tgt tta gaa aat cta cgc aaa gaa ctg tct gca aag    1104
Glu Lys Asp Leu Cys Leu Glu Asn Leu Arg Lys Glu Leu Ser Ala Lys
        355                 360                 365 cat caa tca gaa atg gag gat tta caa aac cag ttt cag aaa gaa ttg    1152
His Gln Ser Glu Met Glu Asp Leu Gln Asn Gln Phe Gln Lys Glu Leu
    370                 375                 380 gca gaa cag aga gct gag ttg gag aag att ttt caa gac aaa aac cag    1200
Ala Glu Gln Arg Ala Glu Leu Glu Lys Ile Phe Gln Asp Lys Asn Gln
385                 390                 395                 400 gct gaa cgg gcc ctt agg aac ctg gag agt cat cat caa gca gcc att    1248
Ala Glu Arg Ala Leu Arg Asn Leu Glu Ser His His Gln Ala Ala Ile
                405                 410                 415 gag aag tta cgt gaa gac ctg cag tcc gag cac ggc cgg tgt tta gaa    1296
Glu Lys Leu Arg Glu Asp Leu Gln Ser Glu His Gly Arg Cys Leu Glu
            420                 425                 430 gac ttg gag ttc aag ttc aaa gag agc gag aaa gaa aaa cag ctg gag    1344
Asp Leu Glu Phe Lys Phe Lys Glu Ser Glu Lys Glu Lys Gln Leu Glu
        435                 440                 445 tta gag aat ctt caa gca tca tat gaa gac ctg aag gca caa tca caa    1392
Leu Glu Asn Leu Gln Ala Ser Tyr Glu Asp Leu Lys Ala Gln Ser Gln
    450                 455                 460 gaa gag atc agg cgc ttg tgg tcc cag ctt gat tct gcc agg acc agt    1440
Glu Glu Ile Arg Arg Leu Trp Ser Gln Leu Asp Ser Ala Arg Thr Ser
465                 470                 475                 480 aga cag gaa ttg agt gag cta cat gag caa ctc ctg gcg cgc acc tct    1488
Arg Gln Glu Leu Ser Glu Leu His Glu Gln Leu Leu Ala Arg Thr Ser
                485                 490                 495 cgt gtg gaa gat tta gaa cag ctg aag cag cga gaa aaa acc cag cat    1536
Arg Val Glu Asp Leu Glu Gln Leu Lys Gln Arg Glu Lys Thr Gln His
            500                 505                 510 gag tcc gaa ctg gag caa ctg agg att tat ttt gaa aag aag tta agg    1584
Glu Ser Glu Leu Glu Gln Leu Arg Ile Tyr Phe Glu Lys Lys Leu Arg
        515                 520                 525 gat gct gag aaa act tac caa gaa gac cta acc ctg tta cag cag agg    1632
Asp Ala Glu Lys Thr Tyr Gln Glu Asp Leu Thr Leu Leu Gln Gln Arg
    530                 535                 540 ctg cag ggg gcg agg gaa gat gct ctt ctg gac tct gtg gaa gtt ggg    1680
Leu Gln Gly Ala Arg Glu Asp Ala Leu Leu Asp Ser Val Glu Val Gly
545                 550                 555                 560 ttg tcc tgt gtg ggt tta gaa gag aaa cct gag aaa gga aga aaa gat    1728
Leu Ser Cys Val Gly Leu Glu Glu Lys Pro Glu Lys Gly Arg Lys Asp
                565                 570                 575 cac gtt gat gaa ctc gag cct gag cga cat aag gag agc ctg cca cgc    1776
His Val Asp Glu Leu Glu Pro Glu Arg His Lys Glu Ser Leu Pro Arg
            580                 585                 590 ttc cag gcg gag tta gaa gaa agc cac agg cac cag ctg gaa gcg ctg    1824
Phe Gln Ala Glu Leu Glu Glu Ser His Arg His Gln Leu Glu Ala Leu
        595                 600                 605 gag tct ccc ctc tgc atc cag cac gag ggg cat gtc tca gac aga tgc    1872
Glu Ser Pro Leu Cys Ile Gln His Glu Gly His Val Ser Asp Arg Cys
    610                 615                 620
```

-continued

```
tgc gta gag act tca gca ttg gga cac gag tgg cgt ctg gaa ccc tct      1920
Cys Val Glu Thr Ser Ala Leu Gly His Glu Trp Arg Leu Glu Pro Ser
625                 630                 635                 640 gaa ggg cac agc caa gag ctt ccc tgg gtg cat ctc cag ggt gtg cag      1968
Glu Gly His Ser Gln Glu Leu Pro Trp Val His Leu Gln Gly Val Gln
                645                 650                 655 gac ggg gac ttg gag gcc gac aca gag cgg gca gcc aga gtc ttg ggt      2016
Asp Gly Asp Leu Glu Ala Asp Thr Glu Arg Ala Ala Arg Val Leu Gly
            660                 665                 670 ctg gaa act gag cac aag gtg caa ctt tcg ctt ctt cag act gag ctc      2064
Leu Glu Thr Glu His Lys Val Gln Leu Ser Leu Leu Gln Thr Glu Leu
        675                 680                 685 aaa gaa gaa att gaa ctc cta aaa ata gaa aat aga aat ttg tat gag      2112
Lys Glu Glu Ile Glu Leu Leu Lys Ile Glu Asn Arg Asn Leu Tyr Glu
690                 695                 700 aag ttg cag cat gaa act cgt ctg aag gac gat ttg gag aag gta aaa      2160
Lys Leu Gln His Glu Thr Arg Leu Lys Asp Asp Leu Glu Lys Val Lys
705                 710                 715                 720 cac aat cta att gaa gac cac cag aag gaa cta aat aat gct aag caa      2208
His Asn Leu Ile Glu Asp His Gln Lys Glu Leu Asn Asn Ala Lys Gln
                725                 730                 735 aag act gag ctg atg aaa cag gaa ttc caa aga aaa gaa acg gac tgg      2256
Lys Thr Glu Leu Met Lys Gln Glu Phe Gln Arg Lys Glu Thr Asp Trp
            740                 745                 750 aaa gtt atg aag gag gag cta cag cgg gaa gct gag gag aag tta aca      2304
Lys Val Met Lys Glu Glu Leu Gln Arg Glu Ala Glu Glu Lys Leu Thr
        755                 760                 765 ttg atg cta ctt gaa ctg aga gaa aag gct gaa tcc gag aaa cag acc      2352
Leu Met Leu Leu Glu Leu Arg Glu Lys Ala Glu Ser Glu Lys Gln Thr
770                 775                 780 atc ata aac aag ttt gag ctt cga gaa gct gaa atg agg cag ctt cag      2400
Ile Ile Asn Lys Phe Glu Leu Arg Glu Ala Glu Met Arg Gln Leu Gln
785                 790                 795                 800 gac caa cag gca gcc cag atc ctg gat ctg gag agg tcc ttg acg gag      2448
Asp Gln Gln Ala Ala Gln Ile Leu Asp Leu Glu Arg Ser Leu Thr Glu
                805                 810                 815 cag cag ggc cgc ctg cag cag ctg gaa cag gac ctc act tca gac gac      2496
Gln Gln Gly Arg Leu Gln Gln Leu Glu Gln Asp Leu Thr Ser Asp Asp
            820                 825                 830 gcc ctg cat tgc agc cag tgt ggg cgg gag ccg ccc aca gcc cag gac      2544
Ala Leu His Cys Ser Gln Cys Gly Arg Glu Pro Pro Thr Ala Gln Asp
        835                 840                 845 ggg gag ctt gcc gcg ctc cac gtg aag gaa gac tgc gcc ctg cag ctg      2592
Gly Glu Leu Ala Ala Leu His Val Lys Glu Asp Cys Ala Leu Gln Leu
850                 855                 860 atg ctg gcc cgg agc agg ttt tta gag gaa cgt aaa gag atc acc gag      2640
Met Leu Ala Arg Ser Arg Phe Leu Glu Glu Arg Lys Glu Ile Thr Glu
865                 870                 875                 880 aaa ttc agt gcg gaa caa gat gcc ttc ctg cag gag gcc cag gag cag      2688
Lys Phe Ser Ala Glu Gln Asp Ala Phe Leu Gln Glu Ala Gln Glu Gln
                885                 890                 895 cat gcc cgt gag ctg cag ctc ctc cag gag aga cac cag cag cag ctc      2736
His Ala Arg Glu Leu Gln Leu Leu Gln Glu Arg His Gln Gln Gln Leu
            900                 905                 910 ctg tca gtg acg gcg gag ctc gag gcc aga cac cag gcc gcg ttg ggc      2784
Leu Ser Val Thr Ala Glu Leu Glu Ala Arg His Gln Ala Ala Leu Gly
        915                 920                 925 gag ctg aca gcc tcc tta gag agc aag cag ggg gct ctg ctg gct gca      2832
Glu Leu Thr Ala Ser Leu Glu Ser Lys Gln Gly Ala Leu Leu Ala Ala
930                 935                 940
```

-continued

```
cgt gtg gcc gaa ctg cag aca aaa cac gct gcc gac ctc ggc gct ctg     2880
Arg Val Ala Glu Leu Gln Thr Lys His Ala Ala Asp Leu Gly Ala Leu
945                 950                 955                 960 gag acc aga cat ctg tcc agc ctt gat tct ttg gaa tcc tgt tac ctc     2928
Glu Thr Arg His Leu Ser Ser Leu Asp Ser Leu Glu Ser Cys Tyr Leu
            965                 970                 975 tct gaa ttt cag acc atc cgt gag gag cac agg cag gcc cta gag ctc     2976
Ser Glu Phe Gln Thr Ile Arg Glu Glu His Arg Gln Ala Leu Glu Leu
        980                 985                 990 tta cga gca gac ttt gag gaa caa ctg tgg aaa aag gac tct ctt cac     3024
Leu Arg Ala Asp Phe Glu Glu Gln Leu Trp Lys Lys Asp Ser Leu His
    995                 1000                1005 caa acg att ttg act caa gag ttg gag aaa ctg aag cgg aaa cac gaa     3072
Gln Thr Ile Leu Thr Gln Glu Leu Glu Lys Leu Lys Arg Lys His Glu
1010                1015                1020 ggg gag cta cag tct gtg cgg gac cac ctg cga acc gaa gtg agc aca     3120
Gly Glu Leu Gln Ser Val Arg Asp His Leu Arg Thr Glu Val Ser Thr
1025                1030                1035                1040 gag ctc gcc gga acc gtg gct cac gag ctg cag gga gtg cac cag ggt     3168
Glu Leu Ala Gly Thr Val Ala His Glu Leu Gln Gly Val His Gln Gly
                1045                1050                1055 gaa ttt gga agt gaa aag aaa act gct ttg cat gaa aaa gag gag aca     3216
Glu Phe Gly Ser Glu Lys Lys Thr Ala Leu His Glu Lys Glu Glu Thr
            1060                1065                1070 ctt cgg ctt cag agt gca cag gca cag cct ttt cac caa gag gag aaa     3264
Leu Arg Leu Gln Ser Ala Gln Ala Gln Pro Phe His Gln Glu Glu Lys
        1075                1080                1085 gag tct ttg tct ctg cag ctt caa aag aag aat cac caa gtc cag cag     3312
Glu Ser Leu Ser Leu Gln Leu Gln Lys Lys Asn His Gln Val Gln Gln
    1090                1095                1100 ctg aaa gac cag gtt tta tcc tta agt cac gag ata gaa gag tgc cgc     3360
Leu Lys Asp Gln Val Leu Ser Leu Ser His Glu Ile Glu Glu Cys Arg
1105                1110                1115                1120 tcc gag ttg gag gtg ctg cag cag agg cgg gag cgg gag aac cgg gaa     3408
Ser Glu Leu Glu Val Leu Gln Gln Arg Arg Glu Arg Glu Asn Arg Glu
                1125                1130                1135 ggc gca aac ctc ctc tcc atg ctc aag gcc gac gtc aac ctg tcc cac     3456
Gly Ala Asn Leu Leu Ser Met Leu Lys Ala Asp Val Asn Leu Ser His
            1140                1145                1150 agc gaa aga ggg gcc ctc cag gac gcc ctg cgc agg ctg ctg ggt tty     3504
Ser Glu Arg Gly Ala Leu Gln Asp Ala Leu Arg Arg Leu Leu Gly Leu
        1155                1160                1165 ttt gga gag acg ctg agg gca gcc gtc acc ctg agg agc cgg atc ggg     3552
Phe Gly Glu Thr Leu Arg Ala Ala Val Thr Leu Arg Ser Arg Ile Gly
    1170                1175                1180 gag cgc gtg ggg ctc tgc ctg gat gac gcg ggc gca ggc ctg gcc ctg     3600
Glu Arg Val Gly Leu Cys Leu Asp Asp Ala Gly Ala Gly Leu Ala Leu
1185                1190                1195                1200 tcg aca gct ccg gcg ctg gag gag aca tgg tct gat gtg gcc ctc ccg     3648
Ser Thr Ala Pro Ala Leu Glu Glu Thr Trp Ser Asp Val Ala Leu Pro
                1205                1210                1215 gag ttg gac aga act ttg tct gaa tgt gca gag atg tct tcc gtg gct     3696
Glu Leu Asp Arg Thr Leu Ser Glu Cys Ala Glu Met Ser Ser Val Ala
            1220                1225                1230 gaa att agc agc cac atg cgt gaa agc ttt ctc atg agc cca gaa agt     3744
Glu Ile Ser Ser His Met Arg Glu Ser Phe Leu Met Ser Pro Glu Ser
        1235                1240                1245 gtg cgg gag tgt gag cag ccc atc cgg agg gtc ttc cag agc ctc agc     3792
Val Arg Glu Cys Glu Gln Pro Ile Arg Arg Val Phe Gln Ser Leu Ser
```

```
                                                                -continued
      1250                  1255                  1260
ctg gcc gtg gac ggc ctc atg gag atg gcc ctg gac tcc agc agg cag        3840
Leu Ala Val Asp Gly Leu Met Glu Met Ala Leu Asp Ser Ser Arg Gln
1265                  1270                  1275                  1280 ctg gaa gaa gca cgc caa att cat tct cgt ttt gaa aaa gaa ttt agt        3888
Leu Glu Glu Ala Arg Gln Ile His Ser Arg Phe Glu Lys Glu Phe Ser
                  1285                  1290                  1295 ttt aag aat gag gag aca gca cag gtt gtc agg aag cac cag gag ctg        3936
Phe Lys Asn Glu Glu Thr Ala Gln Val Val Arg Lys His Gln Glu Leu
            1300                  1305                  1310 ctg gag tgt ttg aag gag gag agc gca gca aag gca gag ctg gcg ctg        3984
Leu Glu Cys Leu Lys Glu Glu Ser Ala Ala Lys Ala Glu Leu Ala Leu
        1315                  1320                  1325 gag ctg cac aag act cag ggt acc ctt gag gga ttc aag gtg gag aca        4032
Glu Leu His Lys Thr Gln Gly Thr Leu Glu Gly Phe Lys Val Glu Thr
    1330                  1335                  1340 gca gat ctg aag gag gtg ctg gcc ggg aag gag gat tcc gag cac cgt        4080
Ala Asp Leu Lys Glu Val Leu Ala Gly Lys Glu Asp Ser Glu His Arg
1345                  1350                  1355                  1360 ctg gtg ctg gag ctg gag agc ctg aga cgg cag ctg cag cag gcg gcc        4128
Leu Val Leu Glu Leu Glu Ser Leu Arg Arg Gln Leu Gln Gln Ala Ala
                  1365                  1370                  1375 cag gag cag gcg gcg ctg agg gag gag tgc acc cgt ctg tgg agt cgg        4176
Gln Glu Gln Ala Ala Leu Arg Glu Glu Cys Thr Arg Leu Trp Ser Arg
            1380                  1385                  1390 ggg gag gcc aca gcc acg gac gcc gag gcc aga gaa gct gct ctc cgg        4224
Gly Glu Ala Thr Ala Thr Asp Ala Glu Ala Arg Glu Ala Ala Leu Arg
        1395                  1400                  1405 aag gaa gtg gag gat ctg acc aaa gaa cag tcg gag acc agg aag cag        4272
Lys Glu Val Glu Asp Leu Thr Lys Glu Gln Ser Glu Thr Arg Lys Gln
    1410                  1415                  1420 gct gag aag gac cgc tca gcc ctg ctc tcc cag atg aag att ttg gag        4320
Ala Glu Lys Asp Arg Ser Ala Leu Leu Ser Gln Met Lys Ile Leu Glu
1425                  1430                  1435                  1440 tct gag tta gaa gaa cag ctg tct cag cat cgc ggg tgt gcc aag cag        4368
Ser Glu Leu Glu Glu Gln Leu Ser Gln His Arg Gly Cys Ala Lys Gln
                  1445                  1450                  1455 gcg gag gcc gtc act gcc ctg gaa cag cag gtg gca tct ctg gac aag        4416
Ala Glu Ala Val Thr Ala Leu Glu Gln Gln Val Ala Ser Leu Asp Lys
            1460                  1465                  1470 cat ttg cgc aac cag cgg caa ttc atg gat gag cag gca gcc gag cgg        4464
His Leu Arg Asn Gln Arg Gln Phe Met Asp Glu Gln Ala Ala Glu Arg
        1475                  1480                  1485 gag cac gag cgc gag gag ttc cag cag gag att cag agg ctg gag ggg        4512
Glu His Glu Arg Glu Glu Phe Gln Gln Glu Ile Gln Arg Leu Glu Gly
    1490                  1495                  1500 cag ctc cgc cag gcg gcc aag ccg cag ccc tgg ggc cct cgc gac agc        4560
Gln Leu Arg Gln Ala Ala Lys Pro Gln Pro Trp Gly Pro Arg Asp Ser
1505                  1510                  1515                  1520 cag cag gcg ccg ctg gat gga gag gtt gag ttg tta caa caa aag ttg        4608
Gln Gln Ala Pro Leu Asp Gly Glu Val Glu Leu Leu Gln Gln Lys Leu
                  1525                  1530                  1535 aga gaa aag ttg gat gaa ttt aat gaa ttg gct ata cag aaa gag tcg        4656
Arg Glu Lys Leu Asp Glu Phe Asn Glu Leu Ala Ile Gln Lys Glu Ser
            1540                  1545                  1550 gca gat aga caa gtg tta atg cag gaa gaa gaa att aaa cgt ctg gag        4704
Ala Asp Arg Gln Val Leu Met Gln Glu Glu Glu Ile Lys Arg Leu Glu
        1555                  1560                  1565 gag atg aac atc aac atc agg aaa aaa gtg gcc cag ctc cag gaa gaa        4752
```

```
                Glu Met Asn Ile Asn Ile Arg Lys Lys Val Ala Gln Leu Gln Glu Glu
                    1570                1575                1580 gtg gaa aaa cag aaa aac atc gtg aaa ggg ctg gaa cag gat aaa gag        4800
Val Glu Lys Gln Lys Asn Ile Val Lys Gly Leu Glu Gln Asp Lys Glu
1585                1590                1595                1600 gtg tta aag aaa cag cag atg agc agc ttg ctt ctg gcg tcc acg ttg        4848
Val Leu Lys Lys Gln Gln Met Ser Ser Leu Leu Leu Ala Ser Thr Leu
                1605                1610                1615 cag tct aca cta gat gca ggc aga tgt ccc gag cct cct tcg ggc agc        4896
Gln Ser Thr Leu Asp Ala Gly Arg Cys Pro Glu Pro Pro Ser Gly Ser
                1620                1625                1630 cct cct gag ggt cca gaa ata cag tta gag gtg aca cag aga gca ctc        4944
Pro Pro Glu Gly Pro Glu Ile Gln Leu Glu Val Thr Gln Arg Ala Leu
            1635                1640                1645 ctg cgg cgc gag agc gag gtt ttg gac tta aaa gaa cag cta gaa aag        4992
Leu Arg Arg Glu Ser Glu Val Leu Asp Leu Lys Glu Gln Leu Glu Lys
        1650                1655                1660 atg aaa ggt gac tta gaa agt aaa aat gaa gaa ata cta cat ctg aac        5040
Met Lys Gly Asp Leu Glu Ser Lys Asn Glu Glu Ile Leu His Leu Asn
1665                1670                1675                1680 tta aaa ttg gac atg cag aac agc cag act gct gtc agc ctc aga gaa        5088
Leu Lys Leu Asp Met Gln Asn Ser Gln Thr Ala Val Ser Leu Arg Glu
                1685                1690                1695 ctt gag gaa gag aac acg agc ttg aag gtc ata tat acc aga agt tct        5136
Leu Glu Glu Glu Asn Thr Ser Leu Lys Val Ile Tyr Thr Arg Ser Ser
                1700                1705                1710 gag att gaa gag ctg aaa gcc act att gaa aat ctg caa gag aat cag        5184
Glu Ile Glu Glu Leu Lys Ala Thr Ile Glu Asn Leu Gln Glu Asn Gln
            1715                1720                1725 aaa cga tta caa aag gag aaa gca gag gaa att gaa caa ctc cat gaa        5232
Lys Arg Leu Gln Lys Glu Lys Ala Glu Glu Ile Glu Gln Leu His Glu
        1730                1735                1740 gtc att gag aag ctg cag cac gag ctg tcc ctc atg ggg cct gtg gtg        5280
Val Ile Glu Lys Leu Gln His Glu Leu Ser Leu Met Gly Pro Val Val
1745                1750                1755                1760 cac gaa gtc agc gac agt cag gct ggc agt ctg cag agc gag ctg ctc        5328
His Glu Val Ser Asp Ser Gln Ala Gly Ser Leu Gln Ser Glu Leu Leu
                1765                1770                1775 tgc tcc cag gcc ggg ggc cct cgt ggg cag gcc cta cag ggc gag ctc        5376
Cys Ser Gln Ala Gly Gly Pro Arg Gly Gln Ala Leu Gln Gly Glu Leu
                1780                1785                1790 gag gct gcg ctg gaa gcc aag gag gcc ctg agc cgg ctg ctg gct gac        5424
Glu Ala Ala Leu Glu Ala Lys Glu Ala Leu Ser Arg Leu Leu Ala Asp
            1795                1800                1805 cag gag cgc agg cac agc cag gcc ctg gag gcc ctg cag cag cgc ctc        5472
Gln Glu Arg Arg His Ser Gln Ala Leu Glu Ala Leu Gln Gln Arg Leu
        1810                1815                1820 cag ggc gca gag gag gct gcg gag cta cag ctg gct gag ctg gag cgc        5520
Gln Gly Ala Glu Glu Ala Ala Glu Leu Gln Leu Ala Glu Leu Glu Arg
1825                1830                1835                1840 aat gta gcc ctc agg gag gct gag gtc gaa gac atg gcc tcc cgg atc        5568
Asn Val Ala Leu Arg Glu Ala Glu Val Glu Asp Met Ala Ser Arg Ile
                1845                1850                1855 cag gag ttc gaa gcg gcc ctg aaa gca aag gaa gcg acg att gcc gag        5616
Gln Glu Phe Glu Ala Ala Leu Lys Ala Lys Glu Ala Thr Ile Ala Glu
                1860                1865                1870 aga aat tta gaa atc gac gct ctg aac cag cgg aag gcg gcc cac tct        5664
Arg Asn Leu Glu Ile Asp Ala Leu Asn Gln Arg Lys Ala Ala His Ser
            1875                1880                1885
```

-continued

| | |
|---|---|
| gcc gag ctg gag gcc gtc ctg ttg gcc ttg gcc cgc atc cgc cgc gcc<br>Ala Glu Leu Glu Ala Val Leu Leu Ala Leu Ala Arg Ile Arg Arg Ala<br>              1890                          1895                        1900 | 5712 |
| ctg gag cag cag ccc ctg gca gcc ggg gcg gcg cct ccc gag ctg cag<br>Leu Glu Gln Gln Pro Leu Ala Ala Gly Ala Ala Pro Pro Glu Leu Gln<br>1905                        1910                        1915                        1920 | 5760 |
| tgg ctc cga gcg cag tgt gcc cgc ctc agc cgc cag ctg cag gtg ctg<br>Trp Leu Arg Ala Gln Cys Ala Arg Leu Ser Arg Gln Leu Gln Val Leu<br>                      1925                        1930                        1935 | 5808 |
| cac cag cgg ttc ctg agg tgc cag gtg gag ctg gac agg cgg cag gcc<br>His Gln Arg Phe Leu Arg Cys Gln Val Glu Leu Asp Arg Arg Gln Ala<br>              1940                        1945                        1950 | 5856 |
| cgc aga gcc aca gct cac aca cgg gtg ccc ggg gcc cac cca cag cct<br>Arg Arg Ala Thr Ala His Thr Arg Val Pro Gly Ala His Pro Gln Pro<br>                    1955                        1960                        1965 | 5904 |
| cgc atg gat ggt ggc gcc aag gcc cag gtc acc ggc gac gtg gag gcc<br>Arg Met Asp Gly Gly Ala Lys Ala Gln Val Thr Gly Asp Val Glu Ala<br>          1970                        1975                        1980 | 5952 |
| tcc cat gat gct gct ttg gag ccg gtt gtc cct gac cca cag ggt gat<br>Ser His Asp Ala Ala Leu Glu Pro Val Val Pro Asp Pro Gln Gly Asp<br>1985                        1990                        1995                        2000 | 6000 |
| ctg cag cct gtc ctg gtg acg ttg aag gat gca cct ctc tgc aag caa<br>Leu Gln Pro Val Leu Val Thr Leu Lys Asp Ala Pro Leu Cys Lys Gln<br>                      2005                        2010                        2015 | 6048 |
| gaa ggc gtg atg tca gtg ctc acc gtc tgc cag agg cag ctg cag tcg<br>Glu Gly Val Met Ser Val Leu Thr Val Cys Gln Arg Gln Leu Gln Ser<br>                2020                        2025                        2030 | 6096 |
| gag ctg ctc ttg gtg aaa aat gaa atg cgc ctg agt ctg gag gac ggc<br>Glu Leu Leu Leu Val Lys Asn Glu Met Arg Leu Ser Leu Glu Asp Gly<br>            2035                        2040                        2045 | 6144 |
| ggc aag ggt aaa gaa aaa gta ctg gaa gat tgt cag ctg ccg aag gtc<br>Gly Lys Gly Lys Glu Lys Val Leu Glu Asp Cys Gln Leu Pro Lys Val<br>        2050                        2055                        2060 | 6192 |
| gat ctc gta gct cag gtg aaa cag ctt cag gaa aaa ctg aac cgt ttg<br>Asp Leu Val Ala Gln Val Lys Gln Leu Gln Glu Lys Leu Asn Arg Leu<br>2065                        2070                        2075                        2080 | 6240 |
| ctg tat tcc atg acc ttc cag aat gtg gat gct gcc gac acc aaa tct<br>Leu Tyr Ser Met Thr Phe Gln Asn Val Asp Ala Ala Asp Thr Lys Ser<br>                    2085                        2090                        2095 | 6288 |
| ctg tgg ccc atg gcc tca gca cac ctg ttg gag agc agc tgg agt gat<br>Leu Trp Pro Met Ala Ser Ala His Leu Leu Glu Ser Ser Trp Ser Asp<br>              2100                        2105                        2110 | 6336 |
| gat tcc tgt gac gga gaa gag cct gac ata tca ccc cac ata gac aca<br>Asp Ser Cys Asp Gly Glu Glu Pro Asp Ile Ser Pro His Ile Asp Thr<br>          2115                        2120                        2125 | 6384 |
| tgt gat gcc aat aca gcc acg ggg ggt gta act gat gtt atc aaa aat<br>Cys Asp Ala Asn Thr Ala Thr Gly Gly Val Thr Asp Val Ile Lys Asn<br>2130                        2135                        2140 | 6432 |
| cag gcc ata gac gcg tgt gat gcc aat aca acc cca ggg ggt gta act<br>Gln Ala Ile Asp Ala Cys Asp Ala Asn Thr Thr Pro Gly Gly Val Thr<br>2145                        2150                        2155                        2160 | 6480 |
| gat gtt atc aaa aat tgg gat tcc tta ata cca gat gaa atg cca gat<br>Asp Val Ile Lys Asn Trp Asp Ser Leu Ile Pro Asp Glu Met Pro Asp<br>                    2165                        2170                        2175 | 6528 |
| tct ccc att caa gaa aaa tca gaa tgt cag gac atg tct ctt tct tca<br>Ser Pro Ile Gln Glu Lys Ser Glu Cys Gln Asp Met Ser Leu Ser Ser<br>              2180                        2185                        2190 | 6576 |
| ccg acc agc gta ctt ggt ggc tcc cgc cac cag agc cac act gca gag<br>Pro Thr Ser Val Leu Gly Gly Ser Arg His Gln Ser His Thr Ala Glu<br>          2195                        2200                        2205 | 6624 |

-continued

| | | |
|---|---|---|
| gct ggg ccc cgg aag agc ccg gtc ggg atg ctg gac ctg tct tcc tgg<br>Ala Gly Pro Arg Lys Ser Pro Val Gly Met Leu Asp Leu Ser Ser Trp<br>    2210                        2215                        2220 | 6672 |
| agc tcc cct gag gtc ctc agg aag gac tgg acc ctg gag ccc tgg ccc<br>Ser Ser Pro Glu Val Leu Arg Lys Asp Trp Thr Leu Glu Pro Trp Pro<br>2225                      2230                    2235                      2240 | 6720 |
| agc ctc ccc gtg aca ccc cac tca gga gcc ctg agc ctg tgc agt gcc<br>Ser Leu Pro Val Thr Pro His Ser Gly Ala Leu Ser Leu Cys Ser Ala<br>                 2245                        2250                        2255 | 6768 |
| gac aca tcc ctg ggg gac agg gcg gac acc tcg ctg cca cag acc cag<br>Asp Thr Ser Leu Gly Asp Arg Ala Asp Thr Ser Leu Pro Gln Thr Gln<br>            2260                        2265                        2270 | 6816 |
| ggg ccg ggg ctg ctt tgt tcc cca ggc gtg tct gca gcg ctg gca<br>Gly Pro Gly Leu Leu Cys Ser Pro Gly Val Ser Ala Ala Ala Leu Ala<br>                 2275                        2280                        2285 | 6864 |
| ctg cag tgg gcc gag tct ccg ccg gct gac gac cac cat gtg cag agg<br>Leu Gln Trp Ala Glu Ser Pro Pro Ala Asp Asp His His Val Gln Arg<br>            2290                        2295                        2300 | 6912 |
| acg gct gtg gag aaa gat gtc gaa gat ttt atc aca aca tcc ttt gat<br>Thr Ala Val Glu Lys Asp Val Glu Asp Phe Ile Thr Thr Ser Phe Asp<br>2305                      2310                    2315                      2320 | 6960 |
| tct caa gaa aca tta agt tca cct cct cct gga tta gaa gga aaa gct<br>Ser Gln Glu Thr Leu Ser Ser Pro Pro Pro Gly Leu Glu Gly Lys Ala<br>                 2325                        2330                        2335 | 7008 |
| gat aga agt gag aaa agt gac ggc tcg ggt ttt gga gca aga ctg agc<br>Asp Arg Ser Glu Lys Ser Asp Gly Ser Gly Phe Gly Ala Arg Leu Ser<br>            2340                        2345                        2350 | 7056 |
| ccg ggg tca gga ggc cct gag gct caa act gct ggt cct gtg acc cct<br>Pro Gly Ser Gly Gly Pro Glu Ala Gln Thr Ala Gly Pro Val Thr Pro<br>                 2355                        2360                        2365 | 7104 |
| gct tcc atc tct gga agg ttt cag ccg ctg ccg gaa gcc atg aag gag<br>Ala Ser Ile Ser Gly Arg Phe Gln Pro Leu Pro Glu Ala Met Lys Glu<br>            2370                        2375                        2380 | 7152 |
| aag gaa gtg cgt ccg aag cac gtg aag gct tta ctg cag atg gtg cgt<br>Lys Glu Val Arg Pro Lys His Val Lys Ala Leu Leu Gln Met Val Arg<br>2385                      2390                    2395                      2400 | 7200 |
| gac gag agc cac cag atc ctg gcg ctg tca gaa ggc ctt gca ccc cca<br>Asp Glu Ser His Gln Ile Leu Ala Leu Ser Glu Gly Leu Ala Pro Pro<br>                 2405                        2410                        2415 | 7248 |
| agc ggc gag cca cac cca ccc cgg aag gaa gac gag ata cag gac atc<br>Ser Gly Glu Pro His Pro Pro Arg Lys Glu Asp Glu Ile Gln Asp Ile<br>            2420                        2425                        2430 | 7296 |
| tcg ctc cat ggg gga aag acg cag gaa gtg ccc acc gcg tgc ccc gat<br>Ser Leu His Gly Gly Lys Thr Gln Glu Val Pro Thr Ala Cys Pro Asp<br>                 2435                        2440                        2445 | 7344 |
| tgg aga ggg gac ctt ctg cag gtt gtg caa gag gcc ttt gaa aaa gag<br>Trp Arg Gly Asp Leu Leu Gln Val Val Gln Glu Ala Phe Glu Lys Glu<br>            2450                        2455                        2460 | 7392 |
| cag gag atg cag ggg gtt gag ctg cag ccc cga ctc agt ggc tca gat<br>Gln Glu Met Gln Gly Val Glu Leu Gln Pro Arg Leu Ser Gly Ser Asp<br>2465                      2470                    2475                      2480 | 7440 |
| ctg ggg ggt cac agc tcc ctg ctc gaa agg ctg gag aag atc atc cgt<br>Leu Gly Gly His Ser Ser Leu Leu Glu Arg Leu Glu Lys Ile Ile Arg<br>                 2485                        2490                        2495 | 7488 |
| gag cag gga gac ctg cag gaa aag tcc ctg gag cat ctt cgc ttg ccg<br>Glu Gln Gly Asp Leu Gln Glu Lys Ser Leu Glu His Leu Arg Leu Pro<br>            2500                        2505                        2510 | 7536 |
| gac cgg agc agc ctg ctg tcc gag atc cag gcg ctg cgt gcc cag ctg<br>Asp Arg Ser Ser Leu Leu Ser Glu Ile Gln Ala Leu Arg Ala Gln Leu | 7584 |

```
                2515                2520                2525
cgc atg acg cac ctg cag aac cag gag aag ctg cag cac ttg cgc acg       7632
Arg Met Thr His Leu Gln Asn Gln Glu Lys Leu Gln His Leu Arg Thr
    2530                2535                2540 gcg ctg aca agc gca gag gcg cgc ggg agc cag cag gag cac cag ctg       7680
Ala Leu Thr Ser Ala Glu Ala Arg Gly Ser Gln Gln Glu His Gln Leu
2545                2550                2555                2560 cgc agg cag gtt gaa ctg ctg gct tat aaa gta gag cag gag aag tgc       7728
Arg Arg Gln Val Glu Leu Leu Ala Tyr Lys Val Glu Gln Glu Lys Cys
                2565                2570                2575 att gct ggt gac ttg cag aag acg ctg agt gaa gag caa gag aag gca       7776
Ile Ala Gly Asp Leu Gln Lys Thr Leu Ser Glu Glu Gln Glu Lys Ala
            2580                2585                2590 aac agc gtg cag aag ctc ctg gcg gcg gag cag act gta gtg cga gat       7824
Asn Ser Val Gln Lys Leu Leu Ala Ala Glu Gln Thr Val Val Arg Asp
        2595                2600                2605 ttg aag tcc gac ctc tgt gag agc agg cag aag agc gaa cag ctg tcc       7872
Leu Lys Ser Asp Leu Cys Glu Ser Arg Gln Lys Ser Glu Gln Leu Ser
    2610                2615                2620 cgg tcc ctc tgc gag gtg cag cag gag gtc ctc cag ctg aga tcc atg       7920
Arg Ser Leu Cys Glu Val Gln Gln Glu Val Leu Gln Leu Arg Ser Met
2625                2630                2635                2640 ctg agc agt aag gag aac gag ctg aag gcc gcg ctt cag gag ctg gag       7968
Leu Ser Ser Lys Glu Asn Glu Leu Lys Ala Ala Leu Gln Glu Leu Glu
                2645                2650                2655 agt gag cag ggg aag ggg cgt gcc ctg cag agc cag ctg gag gag gag       8016
Ser Glu Gln Gly Lys Gly Arg Ala Leu Gln Ser Gln Leu Glu Glu Glu
            2660                2665                2670 cag ctg cgg cac ctg cag agg gag agc cag agt gcc aag gcc ctg gag       8064
Gln Leu Arg His Leu Gln Arg Glu Ser Gln Ser Ala Lys Ala Leu Glu
        2675                2680                2685 gag ctg cgg gcg tct ttg gag aca cag cgt gct cag agc agt cga ctc       8112
Glu Leu Arg Ala Ser Leu Glu Thr Gln Arg Ala Gln Ser Ser Arg Leu
    2690                2695                2700 tgc gtg gca ctg aaa cac gag cag acg gcc aag gac aac ctg cag aag       8160
Cys Val Ala Leu Lys His Glu Gln Thr Ala Lys Asp Asn Leu Gln Lys
2705                2710                2715                2720 gag ctg cgt atc gag cac tca cgc tgc gag gcc ttg ctg gct cag gag       8208
Glu Leu Arg Ile Glu His Ser Arg Cys Glu Ala Leu Leu Ala Gln Glu
                2725                2730                2735 cgg agc cag ctc tct gag ctc cag aag gac ctt gcg gct gag aag agc       8256
Arg Ser Gln Leu Ser Glu Leu Gln Lys Asp Leu Ala Ala Glu Lys Ser
            2740                2745                2750 cgc acc ctg gag ctg tca gag gcc ttg cgg cac gag cgg ctc ctg acc       8304
Arg Thr Leu Glu Leu Ser Glu Ala Leu Arg His Glu Arg Leu Leu Thr
        2755                2760                2765 gag cag ctg agc cag agg aca cag gag gct tgc gtg cac cag gac aca       8352
Glu Gln Leu Ser Gln Arg Thr Gln Glu Ala Cys Val His Gln Asp Thr
    2770                2775                2780 cag gcc cat cac gct ctg ctg cag aag ctg aag gag gag aag tcc cgg       8400
Gln Ala His His Ala Leu Leu Gln Lys Leu Lys Glu Glu Lys Ser Arg
2785                2790                2795                2800 gtg gtg gac ttg caa gcg atg ctt gaa aag gtg cag cag caa gcc ctg       8448
Val Val Asp Leu Gln Ala Met Leu Glu Lys Val Gln Gln Gln Ala Leu
                2805                2810                2815 cat tct cag cag cag ctt gag gct gag gct cag aag cac tgt gag gcg       8496
His Ser Gln Gln Gln Leu Glu Ala Glu Ala Gln Lys His Cys Glu Ala
            2820                2825                2830 ctc agg aga gag aag gag gta agt gcc aca ctg aag tcg acg gtg gaa       8544
```

```
Leu Arg Arg Glu Lys Glu Val Ser Ala Thr Leu Lys Ser Thr Val Glu
        2835                2840                2845 gcc ctg cac acc caa aaa cga gag ctg aga tgc tct ctg gag aga gag      8592
Ala Leu His Thr Gln Lys Arg Glu Leu Arg Cys Ser Leu Glu Arg Glu
    2850                2855                2860 agg gag aaa cca gcg tgg ttg cag gca gaa tta gag cag tca cac cca      8640
Arg Glu Lys Pro Ala Trp Leu Gln Ala Glu Leu Glu Gln Ser His Pro
2865                2870                2875                2880 cgg ttg aaa gag caa gaa gga cgc aag gct gcg agg agg agc gcg gag      8688
Arg Leu Lys Glu Gln Glu Gly Arg Lys Ala Ala Arg Arg Ser Ala Glu
            2885                2890                2895 gcc agg cag agc cca gcg gct gcg gag cag tgg agg aag tgg cag aga      8736
Ala Arg Gln Ser Pro Ala Ala Ala Glu Gln Trp Arg Lys Trp Gln Arg
        2900                2905                2910 gac aag gag aag ctg cga gaa tta gaa ctg cag cgt cag cgt gac ttg      8784
Asp Lys Glu Lys Leu Arg Glu Leu Glu Leu Gln Arg Gln Arg Asp Leu
    2915                2920                2925 cat aag atc aag cag ctt cag cag aca gtg aga gac ctg gag tcg aag      8832
His Lys Ile Lys Gln Leu Gln Gln Thr Val Arg Asp Leu Glu Ser Lys
2930                2935                2940 gac gag gtg cct ggc agc cgc ctc cac cta ggt tct gcc cgc agg gct      8880
Asp Glu Val Pro Gly Ser Arg Leu His Leu Gly Ser Ala Arg Arg Ala
2945                2950                2955                2960 gcc ggc tcg gat gcg gac cac ctc cgg gaa cag cag cga gag ctg gag      8928
Ala Gly Ser Asp Ala Asp His Leu Arg Glu Gln Gln Arg Glu Leu Glu
            2965                2970                2975 gcg atg agg cag cgg ctg ctc tct gcc gcc cgg ctt ctc acc agc ttc      8976
Ala Met Arg Gln Arg Leu Leu Ser Ala Ala Arg Leu Leu Thr Ser Phe
        2980                2985                2990 acc agc cag gcc gtg gac agg aca gtt aat gat tgg acg tca tcc aat      9024
Thr Ser Gln Ala Val Asp Arg Thr Val Asn Asp Trp Thr Ser Ser Asn
    2995                3000                3005 gag aaa gca gtg atg tct tta ctg cac acg ttg gag gag ctg aag tct      9072
Glu Lys Ala Val Met Ser Leu Leu His Thr Leu Glu Glu Leu Lys Ser
3010                3015                3020 gac ttg agc agg ccc acc tcc tcc cag aaa aaa atg gca gca gag ctg      9120
Asp Leu Ser Arg Pro Thr Ser Ser Gln Lys Lys Met Ala Ala Glu Leu
3025                3030                3035                3040 cag ttc cag ttt gtg gac gtc ctg ctg aaa gac aat gtt tcc ctc aca      9168
Gln Phe Gln Phe Val Asp Val Leu Leu Lys Asp Asn Val Ser Leu Thr
            3045                3050                3055 aaa gcg ctc agc acg gtg acc cag gag aag ctg gag ctg agc aga gcc      9216
Lys Ala Leu Ser Thr Val Thr Gln Glu Lys Leu Glu Leu Ser Arg Ala
        3060                3065                3070 gtg tct aag ctt gag aag ttg ctg aag cac cat ctg cag aag ggc tgc      9264
Val Ser Lys Leu Glu Lys Leu Leu Lys His His Leu Gln Lys Gly Cys
    3075                3080                3085 agc cca agc agg tcg gaa agg tct gct tgg aag cca gac gaa acg gct      9312
Ser Pro Ser Arg Ser Glu Arg Ser Ala Trp Lys Pro Asp Glu Thr Ala
3090                3095                3100 cca cag agt tcc ctg agg cgc cca gac ccc ggc cgg ctt cca cca gct      9360
Pro Gln Ser Ser Leu Arg Arg Pro Asp Pro Gly Arg Leu Pro Pro Ala
3105                3110                3115                3120 gcc agc gag gaa gca cac acc agc aat gtc aag atg gaa aaa ttg tac      9408
Ala Ser Glu Glu Ala His Thr Ser Asn Val Lys Met Glu Lys Leu Tyr
            3125                3130                3135 ctg cat tac ttg aga gca gag agc ttt aga aaa gct ctg att tat caa      9456
Leu His Tyr Leu Arg Ala Glu Ser Phe Arg Lys Ala Leu Ile Tyr Gln
        3140                3145                3150
```

-continued

| | | |
|---|---|---|
| aag aag tat ctt ttg ctg ttg att ggt gga ttc cag gat tct gaa caa<br>Lys Lys Tyr Leu Leu Leu Leu Ile Gly Gly Phe Gln Asp Ser Glu Gln<br>             3155                        3160                        3165 | 9504 |
| gaa aca ctc tcc atg att gcc cat ttg ggg gta ttt cct tcc aaa gca<br>Glu Thr Leu Ser Met Ile Ala His Leu Gly Val Phe Pro Ser Lys Ala<br>3170                         3175                         3180 | 9552 |
| gaa cgg aaa atc aca tct cgt cct ttc acc agg ttc cgc acg gcc gtc<br>Glu Arg Lys Ile Thr Ser Arg Pro Phe Thr Arg Phe Arg Thr Ala Val<br>3185                       3190                      3195                    3200 | 9600 |
| agg gtg gtc att gca ata tta aga tta cgt ttt ttg gtt aag aaa tgg<br>Arg Val Val Ile Ala Ile Leu Arg Leu Arg Phe Leu Val Lys Lys Trp<br>                    3205                      3210                    3215 | 9648 |
| caa gaa gta gat cgg aaa gga gct ctg gca caa ggc aaa gcc cct cgc<br>Gln Glu Val Asp Arg Lys Gly Ala Leu Ala Gln Gly Lys Ala Pro Arg<br>3220                       3225                      3230 | 9696 |
| cca ggg ccc cga gca cga cag ccg cag tct cca ccc aga acc aga gag<br>Pro Gly Pro Arg Ala Arg Gln Pro Gln Ser Pro Pro Arg Thr Arg Glu<br>                    3235                      3240                    3245 | 9744 |
| tcc ccc cca acc cgg gat gta ccc tct ggc cac acc agg gac cct gcc<br>Ser Pro Pro Thr Arg Asp Val Pro Ser Gly His Thr Arg Asp Pro Ala<br>3250                       3255                      3260 | 9792 |
| aga ggc cgc aga ctg gca gca gca gcc tcc cca cac agt ggg gga aga<br>Arg Gly Arg Arg Leu Ala Ala Ala Ala Ser Pro His Ser Gly Gly Arg<br>3265                       3270                      3275                    3280 | 9840 |
| gcc act cca tcc cca aat tca aga tta gaa aga tcc ctg act gct tct<br>Ala Thr Pro Ser Pro Asn Ser Arg Leu Glu Arg Ser Leu Thr Ala Ser<br>                    3285                      3290                    3295 | 9888 |
| caa gat cca gaa cat tcc ttg aca gag tat att cac cat tta gaa gtg<br>Gln Asp Pro Glu His Ser Leu Thr Glu Tyr Ile His His Leu Glu Val<br>3300                       3305                      3310 | 9936 |
| atc cag caa aga ttg gga ggg gta cta cca gat tct act tca aag aaa<br>Ile Gln Gln Arg Leu Gly Gly Val Leu Pro Asp Ser Thr Ser Lys Lys<br>                    3315                      3320                    3325 | 9984 |
| tcc tgc cac ccg atg att aaa cag tga<br>Ser Cys His Pro Met Ile Lys Gln<br>3330                       3335 | 10011 |

<210> SEQ ID NO 4
<211> LENGTH: 3336
<212> TYPE: PRT
<213> ORGANISM: Homo sapiens

<400> SEQUENCE: 4

Met Glu Val Glu Gln Gln Arg Arg Arg Lys Val Glu Ala Gly Arg
1               5                   10                  15

Thr Lys Leu Ala His Phe Arg Gln Arg Lys Thr Lys Gly Asp Ser Ser
            20                  25                  30

His Ser Glu Lys Lys Thr Ala Lys Arg Lys Gly Ser Ala Val Asp Ala
        35                  40                  45

Ser Val Gln Glu Glu Ser Pro Val Thr Lys Glu Asp Ser Ala Leu Cys
    50                  55                  60

Gly Gly Gly Asp Ile Cys Lys Ser Thr Ser Cys Asp Thr Pro Asp
65                  70                  75                  80

Gly Ala Gly Gly Ala Phe Ala Ala Gln Pro Glu Asp Cys Asp Gly Glu
                85                  90                  95

Lys Arg Glu Asp Leu Glu Gln Leu Gln Gln Lys Gln Val Asn Asp His
            100                 105                 110

Pro Pro Glu Gln Cys Gly Met Phe Thr Val Ser Asp His Pro Pro Glu
        115                 120                 125

```
Gln His Gly Met Phe Thr Val Gly Asp His Pro Glu Gln Arg Gly
    130                 135                 140

Met Phe Thr Val Ser Asp His Pro Glu Gln His Gly Met Phe Thr
145                 150                 155                 160

Val Ser Asp His Pro Glu Gln Arg Gly Met Phe Thr Ile Ser Asp
                165                 170                 175

His Gln Pro Glu Gln Arg Gly Met Phe Thr Val Ser Asp His Thr Pro
            180                 185                 190

Glu Gln Arg Gly Ile Phe Thr Ile Ser Asp His Pro Ala Glu Gln Arg
        195                 200                 205

Gly Met Phe Thr Lys Glu Cys Glu Gln Glu Cys Glu Leu Ala Ile Thr
    210                 215                 220

Asp Leu Glu Ser Gly Arg Glu Asp Glu Ala Gly Leu His Gln Ser Gln
225                 230                 235                 240

Ala Val His Gly Leu Glu Leu Glu Ala Leu Arg Leu Ser Leu Ser Asn
                245                 250                 255

Met His Thr Ala Gln Leu Glu Leu Thr Gln Ala Asn Leu Gln Lys Glu
            260                 265                 270

Lys Glu Thr Ala Leu Thr Glu Leu Arg Glu Met Leu Asn Ser Arg Arg
        275                 280                 285

Ala Gln Glu Leu Ala Leu Leu Gln Ser Arg Gln His Glu Leu Glu
    290                 295                 300

Leu Leu Arg Glu Gln His Ala Arg Glu Lys Glu Glu Val Val Leu Arg
305                 310                 315                 320

Cys Gly Gln Glu Ala Ala Glu Leu Lys Glu Lys Leu Gln Ser Glu Met
                325                 330                 335

Glu Lys Asn Ala Gln Ile Val Lys Thr Leu Lys Glu Asp Trp Glu Ser
            340                 345                 350

Glu Lys Asp Leu Cys Leu Glu Asn Leu Arg Lys Glu Leu Ser Ala Lys
        355                 360                 365

His Gln Ser Glu Met Glu Asp Leu Gln Asn Gln Phe Gln Lys Glu Leu
    370                 375                 380

Ala Glu Gln Arg Ala Glu Leu Glu Lys Ile Phe Gln Asp Lys Asn Gln
385                 390                 395                 400

Ala Glu Arg Ala Leu Arg Asn Leu Glu Ser His His Gln Ala Ala Ile
                405                 410                 415

Glu Lys Leu Arg Glu Asp Leu Gln Ser Glu His Gly Arg Cys Leu Glu
            420                 425                 430

Asp Leu Glu Phe Lys Phe Lys Glu Ser Glu Lys Glu Lys Gln Leu Glu
        435                 440                 445

Leu Glu Asn Leu Gln Ala Ser Tyr Glu Asp Leu Lys Ala Gln Ser Gln
    450                 455                 460

Glu Glu Ile Arg Arg Leu Trp Ser Gln Leu Asp Ser Ala Arg Thr Ser
465                 470                 475                 480

Arg Gln Glu Leu Ser Glu Leu His Glu Gln Leu Leu Ala Arg Thr Ser
                485                 490                 495

Arg Val Glu Asp Leu Glu Gln Leu Lys Gln Arg Glu Lys Thr Gln His
            500                 505                 510

Glu Ser Glu Leu Glu Gln Leu Arg Ile Tyr Phe Glu Lys Lys Leu Arg
        515                 520                 525

Asp Ala Glu Lys Thr Tyr Gln Glu Asp Leu Thr Leu Leu Gln Gln Arg
530                 535                 540
```

```
Leu Gln Gly Ala Arg Glu Asp Ala Leu Leu Asp Ser Val Glu Val Gly
545                 550                 555                 560

Leu Ser Cys Val Gly Leu Glu Glu Lys Pro Glu Lys Gly Arg Lys Asp
                565                 570                 575

His Val Asp Glu Leu Glu Pro Glu Arg His Lys Glu Ser Leu Pro Arg
            580                 585                 590

Phe Gln Ala Glu Leu Glu Glu Ser His Arg His Gln Leu Glu Ala Leu
        595                 600                 605

Glu Ser Pro Leu Cys Ile Gln His Glu Gly His Val Ser Asp Arg Cys
    610                 615                 620

Cys Val Glu Thr Ser Ala Leu Gly His Glu Trp Arg Leu Glu Pro Ser
625                 630                 635                 640

Glu Gly His Ser Gln Glu Leu Pro Trp Val His Leu Gln Gly Val Gln
                645                 650                 655

Asp Gly Asp Leu Glu Ala Asp Thr Glu Arg Ala Ala Arg Val Leu Gly
            660                 665                 670

Leu Glu Thr Glu His Lys Val Gln Leu Ser Leu Leu Gln Thr Glu Leu
        675                 680                 685

Lys Glu Glu Ile Glu Leu Lys Ile Glu Asn Arg Asn Leu Tyr Glu
    690                 695                 700

Lys Leu Gln His Glu Thr Arg Leu Lys Asp Asp Leu Glu Lys Val Lys
705                 710                 715                 720

His Asn Leu Ile Glu Asp His Gln Lys Glu Leu Asn Asn Ala Lys Gln
                725                 730                 735

Lys Thr Glu Leu Met Lys Gln Glu Phe Gln Arg Lys Glu Thr Asp Trp
            740                 745                 750

Lys Val Met Lys Glu Glu Leu Gln Arg Glu Ala Glu Glu Lys Leu Thr
        755                 760                 765

Leu Met Leu Leu Glu Leu Arg Glu Lys Ala Glu Ser Glu Lys Gln Thr
770                 775                 780

Ile Ile Asn Lys Phe Glu Leu Arg Glu Ala Glu Met Arg Gln Leu Gln
785                 790                 795                 800

Asp Gln Gln Ala Ala Gln Ile Leu Asp Leu Glu Arg Ser Leu Thr Glu
                805                 810                 815

Gln Gln Gly Arg Leu Gln Gln Leu Glu Gln Asp Leu Thr Ser Asp Asp
            820                 825                 830

Ala Leu His Cys Ser Gln Cys Gly Arg Glu Pro Pro Thr Ala Gln Asp
        835                 840                 845

Gly Glu Leu Ala Ala Leu His Val Lys Glu Asp Cys Ala Leu Gln Leu
850                 855                 860

Met Leu Ala Arg Ser Arg Phe Leu Glu Glu Arg Lys Glu Ile Thr Glu
865                 870                 875                 880

Lys Phe Ser Ala Glu Gln Asp Ala Phe Leu Gln Glu Ala Gln Glu Gln
                885                 890                 895

His Ala Arg Glu Leu Gln Leu Leu Gln Glu Arg His Gln Gln Gln Leu
            900                 905                 910

Leu Ser Val Thr Ala Glu Leu Glu Ala Arg His Gln Ala Ala Leu Gly
        915                 920                 925

Glu Leu Thr Ala Ser Leu Glu Ser Lys Gln Gly Ala Leu Leu Ala Ala
930                 935                 940

Arg Val Ala Glu Leu Gln Thr Lys His Ala Ala Asp Leu Gly Ala Leu
945                 950                 955                 960

Glu Thr Arg His Leu Ser Ser Leu Asp Ser Leu Glu Ser Cys Tyr Leu
```

-continued

```
                965                 970                 975
Ser Glu Phe Gln Thr Ile Arg Glu Glu His Arg Gln Ala Leu Glu Leu
            980                 985                 990
Leu Arg Ala Asp Phe Glu Glu Gln Leu Trp Lys Lys Asp Ser Leu His
            995                1000                1005
Gln Thr Ile Leu Thr Gln Glu Leu Lys Leu Lys Arg Lys His Glu
           1010                1015                1020
Gly Glu Leu Gln Ser Val Arg Asp His Leu Arg Thr Glu Val Ser Thr
1025                1030                1035                1040
Glu Leu Ala Gly Thr Val Ala His Glu Leu Gln Gly Val His Gln Gly
           1045                1050                1055
Glu Phe Gly Ser Glu Lys Lys Thr Ala Leu His Glu Lys Glu Glu Thr
           1060                1065                1070
Leu Arg Leu Gln Ser Ala Gln Ala Gln Pro Phe His Gln Glu Glu Lys
           1075                1080                1085
Glu Ser Leu Ser Leu Gln Leu Lys Lys Asn His Gln Val Gln Gln
           1090                1095                1100
Leu Lys Asp Gln Val Leu Ser Leu Ser His Glu Ile Glu Glu Cys Arg
1105                1110                1115                1120
Ser Glu Leu Glu Val Leu Gln Gln Arg Arg Glu Arg Glu Asn Arg Glu
           1125                1130                1135
Gly Ala Asn Leu Leu Ser Met Leu Lys Ala Asp Val Asn Leu Ser His
           1140                1145                1150
Ser Glu Arg Gly Ala Leu Gln Asp Ala Leu Arg Leu Leu Gly Leu
           1155                1160                1165
Phe Gly Glu Thr Leu Arg Ala Ala Val Thr Leu Arg Ser Arg Ile Gly
           1170                1175                1180
Glu Arg Val Gly Leu Cys Leu Asp Asp Ala Gly Ala Gly Leu Ala Leu
1185                1190                1195                1200
Ser Thr Ala Pro Ala Leu Glu Glu Thr Trp Ser Asp Val Ala Leu Pro
           1205                1210                1215
Glu Leu Asp Arg Thr Leu Ser Glu Cys Ala Glu Met Ser Ser Val Ala
           1220                1225                1230
Glu Ile Ser Ser His Met Arg Glu Ser Phe Leu Met Ser Pro Glu Ser
           1235                1240                1245
Val Arg Glu Cys Glu Gln Pro Ile Arg Arg Val Phe Gln Ser Leu Ser
           1250                1255                1260
Leu Ala Val Asp Gly Leu Met Glu Met Ala Leu Asp Ser Ser Arg Gln
1265                1270                1275                1280
Leu Glu Glu Ala Arg Gln Ile His Ser Arg Phe Glu Lys Glu Phe Ser
           1285                1290                1295
Phe Lys Asn Glu Glu Thr Ala Gln Val Val Arg Lys His Gln Glu Leu
           1300                1305                1310
Leu Glu Cys Leu Lys Glu Glu Ser Ala Ala Lys Ala Glu Leu Ala Leu
           1315                1320                1325
Glu Leu His Lys Thr Gln Gly Thr Leu Glu Gly Phe Lys Val Glu Thr
           1330                1335                1340
Ala Asp Leu Lys Glu Val Leu Ala Gly Lys Glu Asp Ser Glu His Arg
1345                1350                1355                1360
Leu Val Leu Glu Leu Glu Ser Leu Arg Arg Gln Leu Gln Gln Ala Ala
           1365                1370                1375
Gln Glu Gln Ala Ala Leu Arg Glu Glu Cys Thr Arg Leu Trp Ser Arg
           1380                1385                1390
```

-continued

```
Gly Glu Ala Thr Ala Thr Asp Ala Glu Ala Arg Glu Ala Ala Leu Arg
    1395                1400                1405
Lys Glu Val Glu Asp Leu Thr Lys Glu Gln Ser Glu Thr Arg Lys Gln
    1410                1415                1420
Ala Glu Lys Asp Arg Ser Ala Leu Leu Ser Gln Met Lys Ile Leu Glu
1425                1430                1435                1440
Ser Glu Leu Glu Glu Gln Leu Ser Gln His Arg Gly Cys Ala Lys Gln
                1445                1450                1455
Ala Glu Ala Val Thr Ala Leu Glu Gln Gln Val Ala Ser Leu Asp Lys
                1460                1465                1470
His Leu Arg Asn Gln Arg Gln Phe Met Asp Glu Gln Ala Ala Glu Arg
    1475                1480                1485
Glu His Glu Arg Glu Glu Phe Gln Gln Glu Ile Gln Arg Leu Glu Gly
    1490                1495                1500
Gln Leu Arg Gln Ala Ala Lys Pro Gln Pro Trp Gly Pro Arg Asp Ser
1505                1510                1515                1520
Gln Gln Ala Pro Leu Asp Gly Glu Val Glu Leu Leu Gln Gln Lys Leu
                1525                1530                1535
Arg Glu Lys Leu Asp Glu Phe Asn Glu Leu Ala Ile Gln Lys Glu Ser
    1540                1545                1550
Ala Asp Arg Gln Val Leu Met Gln Glu Glu Ile Lys Arg Leu Glu
    1555                1560                1565
Glu Met Asn Ile Asn Ile Arg Lys Lys Val Ala Gln Leu Gln Glu Glu
    1570                1575                1580
Val Glu Lys Gln Lys Asn Ile Val Lys Gly Leu Glu Gln Asp Lys Glu
1585                1590                1595                1600
Val Leu Lys Lys Gln Gln Met Ser Ser Leu Leu Leu Ala Ser Thr Leu
                1605                1610                1615
Gln Ser Thr Leu Asp Ala Gly Arg Cys Pro Glu Pro Ser Gly Ser
    1620                1625                1630
Pro Pro Glu Gly Pro Glu Ile Gln Leu Glu Val Thr Gln Arg Ala Leu
    1635                1640                1645
Leu Arg Arg Glu Ser Glu Val Leu Asp Leu Lys Glu Gln Leu Glu Lys
    1650                1655                1660
Met Lys Gly Asp Leu Glu Ser Lys Asn Glu Glu Ile Leu His Leu Asn
1665                1670                1675                1680
Leu Lys Leu Asp Met Gln Asn Ser Gln Thr Ala Val Ser Leu Arg Glu
                1685                1690                1695
Leu Glu Glu Glu Asn Thr Ser Leu Lys Val Ile Tyr Thr Arg Ser Ser
    1700                1705                1710
Glu Ile Glu Glu Leu Lys Ala Thr Ile Glu Asn Leu Gln Glu Asn Gln
    1715                1720                1725
Lys Arg Leu Gln Lys Glu Lys Ala Glu Glu Ile Glu Gln Leu His Glu
    1730                1735                1740
Val Ile Glu Lys Leu Gln His Glu Leu Ser Leu Met Gly Pro Val Val
1745                1750                1755                1760
His Glu Val Ser Asp Ser Gln Ala Gly Ser Leu Gln Ser Glu Leu Leu
                1765                1770                1775
Cys Ser Gln Ala Gly Gly Pro Arg Gly Gln Ala Leu Gln Gly Glu Leu
                1780                1785                1790
Glu Ala Ala Leu Glu Ala Lys Glu Ala Leu Ser Arg Leu Leu Ala Asp
    1795                1800                1805
```

-continued

```
Gln Glu Arg Arg His Ser Gln Ala Leu Glu Ala Leu Gln Gln Arg Leu
         1810                1815                1820

Gln Gly Ala Glu Glu Ala Ala Glu Leu Gln Leu Ala Glu Leu Glu Arg
1825                1830                1835                1840

Asn Val Ala Leu Arg Glu Ala Glu Val Glu Asp Met Ala Ser Arg Ile
            1845                1850                1855

Gln Glu Phe Glu Ala Ala Leu Lys Ala Lys Glu Ala Thr Ile Ala Glu
            1860                1865                1870

Arg Asn Leu Glu Ile Asp Ala Leu Asn Gln Arg Lys Ala Ala His Ser
        1875                1880                1885

Ala Glu Leu Glu Ala Val Leu Leu Ala Leu Ala Arg Ile Arg Arg Ala
        1890                1895                1900

Leu Glu Gln Gln Pro Leu Ala Ala Gly Ala Ala Pro Pro Glu Leu Gln
1905                1910                1915                1920

Trp Leu Arg Ala Gln Cys Ala Arg Leu Ser Arg Gln Leu Gln Val Leu
            1925                1930                1935

His Gln Arg Phe Leu Arg Cys Gln Val Glu Leu Asp Arg Arg Gln Ala
            1940                1945                1950

Arg Arg Ala Thr Ala His Thr Arg Val Pro Gly Ala His Pro Gln Pro
        1955                1960                1965

Arg Met Asp Gly Gly Ala Lys Ala Gln Val Thr Gly Asp Val Glu Ala
    1970                1975                1980

Ser His Asp Ala Ala Leu Glu Pro Val Val Pro Asp Pro Gln Gly Asp
1985                1990                1995                2000

Leu Gln Pro Val Leu Val Thr Leu Lys Asp Ala Pro Leu Cys Lys Gln
            2005                2010                2015

Glu Gly Val Met Ser Val Leu Thr Val Cys Gln Arg Gln Leu Gln Ser
        2020                2025                2030

Glu Leu Leu Leu Val Lys Asn Glu Met Arg Leu Ser Leu Glu Asp Gly
        2035                2040                2045

Gly Lys Gly Lys Glu Lys Val Leu Glu Asp Cys Gln Leu Pro Lys Val
2050                2055                2060

Asp Leu Val Ala Gln Val Lys Gln Leu Gln Glu Lys Leu Asn Arg Leu
2065                2070                2075                2080

Leu Tyr Ser Met Thr Phe Gln Asn Val Asp Ala Ala Asp Thr Lys Ser
            2085                2090                2095

Leu Trp Pro Met Ala Ser Ala His Leu Leu Glu Ser Ser Trp Ser Asp
            2100                2105                2110

Asp Ser Cys Asp Gly Glu Pro Asp Ile Ser Pro His Ile Asp Thr
        2115                2120                2125

Cys Asp Ala Asn Thr Ala Thr Gly Gly Val Thr Asp Val Ile Lys Asn
    2130                2135                2140

Gln Ala Ile Asp Ala Cys Asp Ala Asn Thr Thr Pro Gly Gly Val Thr
2145                2150                2155                2160

Asp Val Ile Lys Asn Trp Asp Ser Leu Ile Pro Asp Glu Met Pro Asp
            2165                2170                2175

Ser Pro Ile Gln Glu Lys Ser Glu Cys Gln Asp Met Ser Leu Ser Ser
            2180                2185                2190

Pro Thr Ser Val Leu Gly Gly Ser Arg His Gln Ser His Thr Ala Glu
        2195                2200                2205

Ala Gly Pro Arg Lys Ser Pro Val Gly Met Leu Asp Leu Ser Ser Trp
    2210                2215                2220

Ser Ser Pro Glu Val Leu Arg Lys Asp Trp Thr Leu Glu Pro Trp Pro
```

```
                2225                2230                2235                2240
Ser Leu Pro Val Thr Pro His Ser Gly Ala Leu Ser Leu Cys Ser Ala
            2245                2250                2255
Asp Thr Ser Leu Gly Asp Arg Ala Asp Thr Ser Leu Pro Gln Thr Gln
            2260                2265                2270
Gly Pro Gly Leu Leu Cys Ser Pro Gly Val Ser Ala Ala Leu Ala
        2275                2280                2285
Leu Gln Trp Ala Glu Ser Pro Pro Ala Asp His His Val Gln Arg
        2290                2295                2300
Thr Ala Val Glu Lys Asp Val Glu Asp Phe Ile Thr Thr Ser Phe Asp
2305                2310                2315                2320
Ser Gln Glu Thr Leu Ser Ser Pro Pro Gly Leu Glu Gly Lys Ala
            2325                2330                2335
Asp Arg Ser Glu Lys Ser Asp Gly Ser Gly Phe Gly Ala Arg Leu Ser
            2340                2345                2350
Pro Gly Ser Gly Gly Pro Glu Ala Gln Thr Ala Gly Pro Val Thr Pro
            2355                2360                2365
Ala Ser Ile Ser Gly Arg Phe Gln Pro Leu Pro Glu Ala Met Lys Glu
            2370                2375                2380
Lys Glu Val Arg Pro Lys His Val Lys Ala Leu Leu Gln Met Val Arg
2385                2390                2395                2400
Asp Glu Ser His Gln Ile Leu Ala Leu Ser Glu Gly Leu Ala Pro Pro
            2405                2410                2415
Ser Gly Glu Pro His Pro Pro Arg Lys Glu Asp Glu Ile Gln Asp Ile
            2420                2425                2430
Ser Leu His Gly Gly Lys Thr Gln Glu Val Pro Thr Ala Cys Pro Asp
            2435                2440                2445
Trp Arg Gly Asp Leu Leu Gln Val Val Gln Glu Ala Phe Glu Lys Glu
            2450                2455                2460
Gln Glu Met Gln Gly Val Glu Leu Gln Pro Arg Leu Ser Gly Ser Asp
2465                2470                2475                2480
Leu Gly Gly His Ser Ser Leu Leu Glu Arg Leu Glu Lys Ile Ile Arg
            2485                2490                2495
Glu Gln Gly Asp Leu Gln Glu Lys Ser Leu Glu His Leu Arg Leu Pro
            2500                2505                2510
Asp Arg Ser Ser Leu Leu Ser Glu Ile Gln Ala Leu Arg Ala Gln Leu
            2515                2520                2525
Arg Met Thr His Leu Gln Asn Gln Glu Lys Leu Gln His Leu Arg Thr
            2530                2535                2540
Ala Leu Thr Ser Ala Glu Ala Arg Gly Ser Gln Gln Glu His Gln Leu
2545                2550                2555                2560
Arg Arg Gln Val Glu Leu Leu Ala Tyr Lys Val Glu Gln Lys Cys
            2565                2570                2575
Ile Ala Gly Asp Leu Gln Lys Thr Leu Ser Glu Gln Glu Lys Ala
            2580                2585                2590
Asn Ser Val Gln Lys Leu Leu Ala Ala Glu Gln Thr Val Val Arg Asp
            2595                2600                2605
Leu Lys Ser Asp Leu Cys Glu Ser Arg Gln Lys Ser Glu Gln Leu Ser
            2610                2615                2620
Arg Ser Leu Cys Glu Val Gln Gln Glu Val Leu Gln Leu Arg Ser Met
2625                2630                2635                2640
Leu Ser Ser Lys Glu Asn Glu Leu Lys Ala Ala Leu Gln Glu Leu Glu
            2645                2650                2655
```

-continued

Ser Glu Gln Gly Lys Gly Arg Ala Leu Gln Ser Gln Leu Glu Glu
                2660                2665                2670

Gln Leu Arg His Leu Gln Arg Glu Ser Gln Ser Ala Lys Ala Leu Glu
        2675                2680                2685

Glu Leu Arg Ala Ser Leu Glu Thr Gln Arg Ala Gln Ser Ser Arg Leu
        2690                2695                2700

Cys Val Ala Leu Lys His Glu Gln Thr Ala Lys Asp Asn Leu Gln Lys
2705                2710                2715                2720

Glu Leu Arg Ile Glu His Ser Arg Cys Glu Ala Leu Leu Ala Gln Glu
                2725                2730                2735

Arg Ser Gln Leu Ser Glu Leu Gln Lys Asp Leu Ala Ala Glu Lys Ser
            2740                2745                2750

Arg Thr Leu Glu Leu Ser Glu Ala Leu Arg His Glu Arg Leu Leu Thr
                2755                2760                2765

Glu Gln Leu Ser Gln Arg Thr Gln Glu Ala Cys Val His Gln Asp Thr
        2770                2775                2780

Gln Ala His His Ala Leu Leu Gln Lys Leu Lys Glu Glu Lys Ser Arg
2785                2790                2795                2800

Val Val Asp Leu Gln Ala Met Leu Glu Lys Val Gln Gln Ala Leu
                2805                2810                2815

His Ser Gln Gln Gln Leu Glu Ala Glu Ala Gln Lys His Cys Glu Ala
            2820                2825                2830

Leu Arg Arg Glu Lys Glu Val Ser Ala Thr Leu Lys Ser Thr Val Glu
                2835                2840                2845

Ala Leu His Thr Gln Lys Arg Glu Leu Arg Cys Ser Leu Glu Arg Glu
        2850                2855                2860

Arg Glu Lys Pro Ala Trp Leu Gln Ala Glu Leu Glu Gln Ser His Pro
2865                2870                2875                2880

Arg Leu Lys Glu Gln Glu Gly Arg Lys Ala Ala Arg Arg Ser Ala Glu
                2885                2890                2895

Ala Arg Gln Ser Pro Ala Ala Ala Glu Gln Trp Arg Lys Trp Gln Arg
        2900                2905                2910

Asp Lys Glu Lys Leu Arg Glu Leu Glu Leu Gln Arg Gln Arg Asp Leu
            2915                2920                2925

His Lys Ile Lys Gln Leu Gln Gln Thr Val Arg Asp Leu Glu Ser Lys
        2930                2935                2940

Asp Glu Val Pro Gly Ser Arg Leu His Leu Gly Ser Ala Arg Arg Ala
2945                2950                2955                2960

Ala Gly Ser Asp Ala Asp His Leu Arg Glu Gln Gln Arg Glu Leu Glu
            2965                2970                2975

Ala Met Arg Gln Arg Leu Leu Ser Ala Ala Arg Leu Leu Thr Ser Phe
        2980                2985                2990

Thr Ser Gln Ala Val Asp Arg Thr Val Asn Asp Trp Thr Ser Ser Asn
            2995                3000                3005

Glu Lys Ala Val Met Ser Leu Leu His Thr Leu Glu Glu Leu Lys Ser
        3010                3015                3020

Asp Leu Ser Arg Pro Thr Ser Ser Gln Lys Lys Met Ala Ala Glu Leu
3025                3030                3035                3040

Gln Phe Gln Phe Val Asp Val Leu Leu Lys Asp Asn Val Ser Leu Thr
                3045                3050                3055

Lys Ala Leu Ser Thr Val Thr Gln Glu Lys Leu Glu Leu Ser Arg Ala
            3060                3065                3070

-continued

Val Ser Lys Leu Glu Lys Leu Leu Lys His His Leu Gln Lys Gly Cys
        3075                3080                3085

Ser Pro Ser Arg Ser Glu Arg Ser Ala Trp Lys Pro Asp Glu Thr Ala
        3090                3095                3100

Pro Gln Ser Ser Leu Arg Arg Pro Asp Pro Gly Arg Leu Pro Pro Ala
3105                3110                3115                3120

Ala Ser Glu Glu Ala His Thr Ser Asn Val Lys Met Glu Lys Leu Tyr
        3125                3130                3135

Leu His Tyr Leu Arg Ala Glu Ser Phe Arg Lys Ala Leu Ile Tyr Gln
        3140                3145                3150

Lys Lys Tyr Leu Leu Leu Ile Gly Gly Phe Gln Asp Ser Glu Gln
        3155                3160                3165

Glu Thr Leu Ser Met Ile Ala His Leu Gly Val Phe Pro Ser Lys Ala
        3170                3175                3180

Glu Arg Lys Ile Thr Ser Arg Pro Phe Thr Arg Phe Arg Thr Ala Val
3185                3190                3195                3200

Arg Val Val Ile Ala Ile Leu Arg Leu Arg Phe Leu Val Lys Lys Trp
        3205                3210                3215

Gln Glu Val Asp Arg Lys Gly Ala Leu Ala Gln Gly Lys Ala Pro Arg
        3220                3225                3230

Pro Gly Pro Arg Ala Arg Gln Pro Gln Ser Pro Arg Thr Arg Glu
        3235                3240                3245

Ser Pro Pro Thr Arg Asp Val Pro Ser Gly His Thr Arg Asp Pro Ala
        3250                3255                3260

Arg Gly Arg Arg Leu Ala Ala Ala Ser Pro His Ser Gly Gly Arg
3265                3270                3275                3280

Ala Thr Pro Ser Pro Asn Ser Arg Leu Glu Arg Ser Leu Thr Ala Ser
        3285                3290                3295

Gln Asp Pro Glu His Ser Leu Thr Glu Tyr Ile His His Leu Glu Val
        3300                3305                3310

Ile Gln Gln Arg Leu Gly Gly Val Leu Pro Asp Ser Thr Ser Lys Lys
        3315                3320                3325

Ser Cys His Pro Met Ile Lys Gln
        3330                3335

<210> SEQ ID NO 5
<211> LENGTH: 126
<212> TYPE: PRT
<213> ORGANISM: Schizosaccharomyces pombe

<400> SEQUENCE: 5

Leu Gln Tyr Leu Asp Ile Ser Tyr Asn Gln Leu Glu Asp Leu Thr Gly
1               5                   10                  15

Leu Ser Ser Leu Ile His Leu Arg Glu Leu Lys Val Asp Ser Asn His
            20                  25                  30

Leu Trp Ser Leu Asp Gly Ile Gln His Leu Asp Gly Leu Leu Lys Leu
        35                  40                  45

Ser Ala Cys His Asn Arg Ile Lys Glu Leu Ser Phe Thr Asn Ser Asn
    50                  55                  60

Leu His Arg Leu Glu Glu Leu Leu Gly Asn Asn Glu Ile Glu Glu
65                  70                  75                  80

Ile Glu Glu Ile Ser Ser Leu Gln Asn Leu Met Val Leu Gln Leu Asp
                85                  90                  95

Asn Asn Lys Leu Thr Asn Leu Lys Ala Ser Gln Pro Met Ile His Leu
            100                 105                 110

Arg Ile Leu Arg Ile Ser Asn Asn Ala Ile His Gln Leu Glu
        115                 120                 125

<210> SEQ ID NO 6
<211> LENGTH: 113
<212> TYPE: PRT
<213> ORGANISM: Saccharomyces cerevisiae

<400> SEQUENCE: 6

Leu Glu Cys Leu Asp Leu Ser Tyr Asn Leu Leu Asn Thr Ser Leu Lys
 1               5                  10                  15

Phe Leu Ser Leu Cys His His Leu Gln Glu Val Asn Leu Ser Tyr Asn
            20                  25                  30

Ser Ile Gln Ser Leu Glu Gly Ile Gly Ser Ser Arg Met Lys Lys Leu
        35                  40                  45

Asn Leu Ser Asn Asn Glu Ile Asn Gly Ile Ile Asp Phe Glu Gln Leu
    50                  55                  60

Ile Leu Thr Asn Asn Ser Val Val Gly Gly Trp Leu Thr Val Glu Val
65                  70                  75                  80

Leu Asp Leu Ser Asn Asn Ile Ile Gly Val Arg Asn Ile Asn Cys
                85                  90                  95

Leu Pro Arg Leu Lys Val Leu Asn Leu Asn Gly Asn Pro Leu Val Ser
                100                 105                 110

Ile

<210> SEQ ID NO 7
<211> LENGTH: 121
<212> TYPE: PRT
<213> ORGANISM: Homo sapiens

<400> SEQUENCE: 7

Leu Glu Val Leu Asn Leu Ser Tyr Asn Leu Ile Gly Lys Ile Glu Lys
 1               5                  10                  15

Leu Asp Lys Leu Leu Lys Leu Arg Glu Leu Asn Leu Ser Tyr Asn Lys
            20                  25                  30

Ile Ser Lys Ile Glu Gly Ile Glu Asn Met Cys Asn Leu Gln Lys Leu
        35                  40                  45

Asn Leu Ala Gly Asn Glu Ile Glu His Ile Pro Val Trp Leu Gly Lys
    50                  55                  60

Lys Leu Lys Ser Leu Arg Val Leu Asn Leu Lys Gly Asn Lys Ile Ser
65                  70                  75                  80

Ser Leu Gln Asp Ile Ser Lys Leu Lys Pro Leu Gln Asp Leu Ile Ser
                85                  90                  95

Leu Ile Leu Val Glu Asn Pro Val Val Thr Leu Pro His Tyr Leu Gln
                100                 105                 110

Phe Thr Ile Phe His Leu Arg Ser Leu
            115                 120

<210> SEQ ID NO 8
<211> LENGTH: 19
<212> TYPE: RNA
<213> ORGANISM: Artificial Sequence
<220> FEATURE:
<223> OTHER INFORMATION: Centriolin siRNA sequence

<400> SEQUENCE: 8
ggaucagaga cucuaccuu                                                19

<210> SEQ ID NO 9
<211> LENGTH: 19
<212> TYPE: RNA
<213> ORGANISM: Artificial Sequence
<220> FEATURE:
<223> OTHER INFORMATION: Centriolin siRNA sequence

<400> SEQUENCE: 9
gcugauucac augcaggag                                                    19

<210> SEQ ID NO 10
<211> LENGTH: 19
<212> TYPE: RNA
<213> ORGANISM: Artificial Sequence
<220> FEATURE:
<223> OTHER INFORMATION: Centriolin siRNA sequence

<400> SEQUENCE: 10
gacgaggcua uugguacuu                                                    19

<210> SEQ ID NO 11
<211> LENGTH: 19
<212> TYPE: RNA
<213> ORGANISM: Artificial Sequence
<220> FEATURE:
<223> OTHER INFORMATION: Centriolin siRNA sequence

<400> SEQUENCE: 11
aagcaaagau accaucauc                                                    19

<210> SEQ ID NO 12
<211> LENGTH: 19
<212> TYPE: RNA
<213> ORGANISM: Artificial Sequence
<220> FEATURE:
<223> OTHER INFORMATION: Centriolin siRNA sequence

<400> SEQUENCE: 12
guggugugag caaauugag                                                    19

<210> SEQ ID NO 13
<211> LENGTH: 19
<212> TYPE: RNA
<213> ORGANISM: Artificial Sequence
<220> FEATURE:
<223> OTHER INFORMATION: Centriolin siRNA sequence

<400> SEQUENCE: 13
agaccauaaa ggagcugau                                                    19

<210> SEQ ID NO 14
<211> LENGTH: 19
<212> TYPE: RNA
<213> ORGANISM: Artificial Sequence
<220> FEATURE:
<223> OTHER INFORMATION: Centriolin siRNA sequence

<400> SEQUENCE: 14
gaccauaaag gagcugauu                                                    19

<210> SEQ ID NO 15
<211> LENGTH: 19
<212> TYPE: RNA
<213> ORGANISM: Artificial Sequence
<220> FEATURE:
<223> OTHER INFORMATION: Centriolin siRNA sequence

```
<400> SEQUENCE: 15
uucacaugca ggaguuaga                                              19

<210> SEQ ID NO 16
<211> LENGTH: 19
<212> TYPE: RNA
<213> ORGANISM: Artificial Sequence
<220> FEATURE:
<223> OTHER INFORMATION: Pericentrin-B siRNA sequence

<400> SEQUENCE: 16
uuggaacagc ugcagcaga                                              19

<210> SEQ ID NO 17
<211> LENGTH: 19
<212> TYPE: RNA
<213> ORGANISM: Artificial Sequence
<220> FEATURE:
<223> OTHER INFORMATION: Pericentrin-B siRNA sequence

<400> SEQUENCE: 17
agcugagcug aaggagaag                                              19

<210> SEQ ID NO 18
<211> LENGTH: 19
<212> TYPE: RNA
<213> ORGANISM: Artificial Sequence
<220> FEATURE:
<223> OTHER INFORMATION: Pericentrin-B siRNA sequence

<400> SEQUENCE: 18
gaaggagaag gagacggca                                              19

<210> SEQ ID NO 19
<211> LENGTH: 19
<212> TYPE: RNA
<213> ORGANISM: Artificial Sequence
<220> FEATURE:
<223> OTHER INFORMATION: Pericentrin-B siRNA sequence

<400> SEQUENCE: 19
aaaggugaca guucgcauu                                              19

<210> SEQ ID NO 20
<211> LENGTH: 19
<212> TYPE: RNA
<213> ORGANISM: Artificial Sequence
<220> FEATURE:
<223> OTHER INFORMATION: Pericentrin-B siRNA sequence

<400> SEQUENCE: 20
caguucgcau ucggagaaa                                              19

<210> SEQ ID NO 21
<211> LENGTH: 19
<212> TYPE: RNA
<213> ORGANISM: Artificial Sequence
<220> FEATURE:
<223> OTHER INFORMATION: Pericentrin-B siRNA sequence

<400> SEQUENCE: 21
gcagacugua gugcgagau                                              19

<210> SEQ ID NO 22
```

```
<211> LENGTH: 19
<212> TYPE: RNA
<213> ORGANISM: Artificial Sequence
<220> FEATURE:
<223> OTHER INFORMATION: Pericentrin-B siRNA sequence

<400> SEQUENCE: 22
gccgugucua agcuugaga                                                  19

<210> SEQ ID NO 23
<211> LENGTH: 19
<212> TYPE: RNA
<213> ORGANISM: Artificial Sequence
<220> FEATURE:
<223> OTHER INFORMATION: Pericentrin-B siRNA sequence

<400> SEQUENCE: 23
ucacaucucg uccuuucac                                                  19

<210> SEQ ID NO 24
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 24
tttgttgaga acctttcttc attgc                                           25

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
aacactctcc atgattgccc                                                 20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
taccctccca atctttgctg                                                 20

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
aaagatgtca atgctgcc                                                   18

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
```

```
tcctctcctt cttcctcac                                              19

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
ccatcatcat ctcactctc                                              19

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
cttccctaac catactgg                                               18
```

CENTROSOME PROTEINS AND USES THEREOF

CROSS-REFERENCE TO RELATED APPLICATION

This application claims benefit of priority from U.S. Provisional Patent Application Ser. No. 60/410,520, filed on Sep. 13, 2002, and to the U.S. patent application Ser. No. 10/663,443 filed on Sep. 15, 2003, claiming priority therefrom, both of which patent applications are incorporated herein by reference in their entireties.

FIELD OF THE INVENTION

This invention relates to the centriolin and pericentrin-B/kendrin genes, the polypeptides they encode, and their uses in the detection, diagnosis, and treatment of centrosomal and cell division diseases and disorders.

BACKGROUND OF THE INVENTION

Centrosomes are the major microtubule nucleating organelles in most animal cells. They nucleate and organize microtubules for spindle assembly during mitosis and establish microtubule arrays in interphase cells for numerous cellular functions. Centrosomes are comprised of two major structural elements, centrioles and the pericentriolar material/centrosome matrix. Centrioles are microtubule barrels present as pairs in each centrosome, and appear to organize the pericentriolar material (Bobinnec et al., *J. Cell Biol.*, 143:1575–1589, 1998) and anchor microtubules (Chretien et al., *J Cell Biol.*, 120:117–133, 1997; Piel et al., *J Cell Biol.*, 149:317–330, 2000). The pericentriolar material nucleates the growth of new microtubules and serves as a scaffold for molecules that regulate fundamental cellular processes.

SUMMARY OF THE INVENTION

The invention is based on the discovery that centriolin, together with pericentrin-B, plays a key roles in centrosome function. The invention provides new methods for diagnosing and treating centrosomal diseases.

The invention includes isolated nucleic acids that include SEQ ID NOs:1 and 3 (and complementary sequences, fragments, and analogs thereof), polypeptides encoded by SEQ ID NOs:1 and 3 (and degenerate sequences, fragments, or analogs thereof), polypeptides that include SEQ ID NOs:2 and 4 (and fragments or analogs thereof (e.g., those with conservative amino acid substitutions)), as well as biologically active fragments and analogs of any of SEQ ID NOs:1–4.

The invention also includes vectors comprising the nucleic acid molecules of SEQ ID NO:1 or 3, or fragments or analogs thereof), as well as cells comprising the nucleic acid molecules of SEQ ID NO:1 or 3, or fragments or analogs thereof.

The invention also features a method of reducing cell division by administering to a cell an amount of a centriolin or pericentrin-B modulator (e.g., an RNAi, siRNA (e.g., any one of SEQ ID NOs:8–23), antisense nucleic acid, ribozyme, or antibody (including those produced either in vivo or in vitro, as well as monoclonal antibodies)) effective to disrupt microtubule organization in the cell, in which cell division is reduced. The invention can be used to treat cancer, leukemia, psoriasis, Hodgkin's disease, lymphoma, myelofibrosis, polycythemia vera, or other cell proliferative disorders or diseases.

Furthermore, the invention encompasses a method of treating abnormal centrosome function in a cell by administering to the cell an amount of centriolin polypeptide or pericentrin-B polypeptide effective to restore normal centrosome function.

A centriolin or pericentrin-B modulator is any molecule or other substance capable of increasing or decreasing centriolin or pericentrin-B expression, respectively. Such modulators include, for example, polypeptides, ribozymes, antisense molecules, siRNA molecules, antibodies, and small molecules.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention has a number of advantages. First, it provides the nucleic acid and polypeptide sequences of centriolin and pericentrin-B. These nucleic acid sequences themselves have many uses, for example, in the production of hybridization probes to locate identical, homologous, or similar DNA or RNA sequences, within either humans or other organisms (especially mammals). The invention includes novel methods of modulating cell division, thus allowing treatment of associated diseases, disorders, or symptoms thereof, for which there have been few or no therapeutic options available. Another advantage provided by the invention involves methods for the diagnosis of abnormal centriolin and pericentrin-B expression or activity, thus allowing, for example, valuable insight into the etiology of diseases, disorders, or symptoms thereof that have previously defied medically useful explanation. Furthermore, the diagnosis of such diseases, disorders, or symptoms thereof can now be followed by previously unavailable methods of treatment. There are numerous advantages in addition to those listed here.

Other features and advantages of the invention will be apparent from the following detailed description, and from the claims.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 2A–G depict centriolin localized to maternal centrioles and noncentrosomal sites of microtubule anchoring.

FIG. 2A depicts HA-tagged centriolin overexpressed in COS-7 cells, which localizes to the centrosome (anti-HA, green) at the convergence of microtubules (red, anti-a tubulin). Bar, 10 μm.

FIG. 2B depicts an RPE1 cell immunostained with an antibody to polygluamylated tubulin (GT335) (Bobinnec et al., *J Cell Biol.*, 143:1575–1589, 1998) to label centrioles and the primary cilium (red) and for centriolin (green) that is localized to the maternal centriole (m) associated with the primary cilium (yellow in merge) but not on the daughter centriole (d). n, nucleus. Bar, 2 μm.

FIGS. 2C–E depict electron micrographs showing specific immunogold labeling of centriolin on subdistal appendages found on maternal but not daughter centrioles.

FIG. 2C depicts an electron micrograph showing a longitudinal section through maternal centrioles. An arrowhead shows striations characteristic of subdistal appendages. Bar, 100 nm.

FIG. 2D depicts an electron micrograph showing a cross-section through maternal centrioles. An arrowhead shows striations characteristic of subdistal appendages. Bar, 100 nm.

FIG. 2E depicts an electron micrograph showing a longitudinal section through both centrioles. The electron micrograph shows specific immunogold labeling of centriolin on subdistal appendages found on maternal (FIG. 2E, bottom) but not daughter centrioles (FIG. 2E, top). Bar, 100 nm.

FIG. 2F is a schematic diagram showing that centriolin is found at noncentrosomal sites of microtubule anchoring in pillar cells of the mouse cochlea (Mogensen et al., *Cell Motil Cytoskel*, 36:276–290, 1997) (arrow) (F, G, arrows). T centrosome and associated cilium is shown schematically at top of cell.

FIG. 2G depicts a centriolin immunofluorescence staining overlaid with phase contrast image showing that centriolin is found at noncentrosomal sites of microtubule anchoring in pillar cells of the mouse cochlea (Mogensen et al., *Cell Motil Cytoskel*, 36:276–290, 1997) (arrow). Bar, 10 μm.

FIG. 3A depicts a micrograph of Xenopus two cell embryos injected into one cell with ~50 nl anti-centriolin antibodies (2 mg/ml affinity purified) that fail to cleave (arrows) while noninjected cells (side opposite arrows) and cells injected with control rabbit IgG (2 mg/ml, top) cleave normally.

FIG. 3B is a graph depicting the quantification of results from injection experiments (average of 3 individual experiments). Unless otherwise specified for these and other experiments, n is the total number of cells counted.

FIG. 3C is a micrograph of a COS-7 cell in cytokinesis overexpressing HA-tagged centriolin (anti-HA, inset) showing persistent microtubule bundles in the intercellular bridge (main panel, α-tubulin staining) despite reformation of the nucleus and decondensation of chromatin (DNA, inset). Bar, 15 μm, and for insets, 35 μm.

FIG. 3D is a micrograph of a control COS-7 cell expressing HA alone (left inset) shows a narrow intercellular bridge and greatly diminished microtubule polymer (main panel), characteristic of cells that have reformed nuclei and decondensed DNA (right panel). Bar, 15 μm, and for insets, 35 μm.

FIG. 3E is a graph depicting a quantitative analysis showing the proportion of telophase cells in the presence of HA-centriolin of HA alone. Results are the average of 2 independent experiments. Unless otherwise specified for these and other experiments, n is the total number of cells counted.

FIG. 3F is a graph depicting a quantitative analysis showing the proportion of aberrant telophase cells (F, persistent microtubule bundles in late telophase/early G1) in the presence of HA-centriolin of HA alone. Results are the average of 2 independent experiments. Unless otherwise specified for these and other experiments, n is the total number of cells counted.

FIG. 3G is a graph depicting a quantitative analysis showing the proportion of binucleate cells in the presence of HA-centriolin of HA alone. Results are the average of 2 independent experiments. Unless otherwise specified for these and other experiments, n is the total number of cells counted.

FIG. 4A depicts an RT-PCR analysis showing that centriolin mRNA is reduced in RPE1 cells treated with centriolin-specific siRNAs but is unaffected in cells treated with siRNAs targeting lamins A/C (left, sequence identity confirmed). Control (a tubulin) RT-PCR was performed in the same reaction mixtures with centriolin and lamin (bottom panels).

FIG. 4B depicts immunofluorescence images of cells treated with siRNAs targeting centriolin showing a cell with reduced centriolin at the centrosome/centriole (green/white, lower) and a cell that is unaffected by the treatment (upper). Centrosomes are co-labeled with γ-tubulin (red). Insets: higher magnification of centrosomes in upper and lower cells. Bar, 12 μm, and for insets, 2 μm.

FIG. 4C depicts a graph showing the proportion of cells whose centrosomal centriolin staining is undetectable or markedly reduced in cells treated with centriolin and GFP siRNAs.

FIG. 4D depicts average fluorescence intensities at individual centrosomes in cells treated with lamin or centriolin siRNAs. The centrosome fluorescence in most centriolin siRNA-treated cells (83%, left of arrow) was below the lowest values observed in control cells.

FIG. 4E is a graph showing the percentage of abnormal telophase (wide intercellular bridges, cells that remain interconnected in G1) following treatment with centriolin siRNAs versus lamin siRNAs.

FIG. 4F is a graph showing the percentage of binucleate cells following treatment with centriolin siRNAs versus lamin siRNAs.

FIG. 4G is a series of graphs showing that progression of cells through prom/M in cells treated with centriolin siRNAs is similar to those treated with lamin siRNAs, while progression through telophase is delayed.

FIG. 5A is a schematic diagram showing centriolin coiled coil regions (boxes), noncoiled regions (lines) and domains homologous to budding and fission yeast Nud1p and Cdc11p, human stathmin and human and Drosophila TACC proteins.

FIG. 5B depicts an alignment of the centriolin Nud1 domain (SEQ ID NO:7) with the yeast Nud1p (SEQ ID NO:6)/Cdc11p (SEQ ID NO:5) proteins.

FIG. 5C depicts the position of the Nud1 domain and Cdc11p in centriolin and the homologous domains within the yeast proteins.

FIG. 5D is a depiction showing that the Nud1 domain interacts with budding yeast Bub2p by yeast two-hybrid analysis. The blue colony in blue box (middle bottom) and increased β-galactosidase activity (Bar 2 of graph) demonstrate a specific interaction between the human centriolin Nud1 domain (hNud1) and Bub2p. Bar 1, LexA-BUB2× transactivation domain (TAD), Bar 2, LexA-BUB×TAD-hNud1, Bar 3, LexA-BFA1×TAD, Bar 4, TAD-hNud1× LexA-BFA1, Bar 5, TAD-hNud1×LexA.

FIG. 5E depicts specific co-immunoprecipitation of HA-tagged hNud1 and Lex A-tagged yeast Bub2p from budding yeast cells. Co-precipitation was observed using antibodies to either protein and only when both were co-expressed (top middle panel in each group).

FIGS. 6A–E depict overexpression of the centriolin Nud1 domain, which induces cytokinesis defects but does not mislocalize centrosomal centriolin.

FIG. 6A depicts a micrograph showing the Nud1-GFP domain of centriolin expressed in a COS-7 cell. Bar, 10 μm.

FIG. 6B depicts a micrograph showing that the Nud1-GFP domain of centriolin expressed in a COS-7 cell does not affect localization of endogenous centriolin to centrosomes. Bar, 10 μm.

FIG. 6C depicts an image showing two nuclei (blue) in a cell expressing the Nud1-GFP domain of centriolin (green, appears yellow in merge) colabeled with microtubules (red). Bar, 15 μm.

FIG. 6D is a graphs showing percent telophase in cells overexpressing Nud1-GFP domain compared with nontransfected cells.

FIG. 6D is a graphs showing percent binucleates in cells overexpressing Nud1-GFP domain compared with GFP-expressing cells.

FIGS. 7A–G depict pericentrin-B, which co-localizes with centriolin, and reduction in its levels, which mislocalizes centriolin and induces delays and defects in cytokinesis.

FIG. 7A depicts an RPE cell showing pericentrin-B (red) colocalizing with centriolin (green, yellow in merge) at centrosomes (arrow) and intercellular bridges in telophase (second panel). Bar, 15 μm.

FIG. 7B depicts an RT-PCR analysis showing that pericentrin-B (Pcnt-B) siRNA treatment reduces pericentrin-B mRNA levels (upper left) while lamin siRNA has no effect (upper right, sequence confirmed). A tubulin RT-PCR was performed in the same reaction mixtures with pericentrin-B and lamin and serves as a control (bottom panels). Pcnt-B, pericentrin-B.

FIG. 7C is a graph showing the proportion of cells whose centrosomal staining for pericentrin-B is undetectable or markedly reduced in cells treated with pericentrin-B and GFP siRNAs. Pcnt-B, pericentrin-B.

FIG. 7D is a graph showing pericentrin-B fluorescence intensity at individual centrosomes (thin bars) in cells treated with lamin or pericentrin-B siRNAs. The centrosome fluorescence in most pericentrin-B siRNA-treated cells (87%, left of arrow) was below the lowest levels detected in control cells (lamin). Pcnt-B, pericentrin-B.

FIG. 7E depicts a micrograph of immunofluorescence images showing that pericentrin-B siRNA-treated cells with reduced centrosomal pericentrin-B (red, arrow) also have reduced levels of centriolin (yellow, arrow). Unaffected cell (bottom) stains for both proteins. Bar, 15 μm.

FIG. 7F is a graph showing the percentages of HeLa cells in telophase following treatment with pericentrin-B siRNAs and GFP siRNAs. Bars in A, E 15 mm. Pcnt-B, pericentrin-B.

FIG. 7G is a graph showing the percentages of aberrant telophase cells following treatment with pericentrin-B siRNAs and GFP siRNAs. Pcnt-B, pericentrin-B.

FIGS. 8A–G depict siRNAs targeting centriolin and pericentrin-B, which induces G1/G0 arrest.

FIG. 8A is a graph showing that RPE1 cells treated with centriolin or pericentrin-B siRNAs (blue line) do not shift into the G2/M peak following nocodazole treatment as seen for control lamin siRNA-treated cells (red line).

FIG. 8B is a graph showing that RPE1 cells treated with centriolin or pericentrin-B siRNAs (blue line) do not shift into the G2/M peak following nocodazole treatment as seen for control lamin siRNA-treated cells (red line). Pcnt-B, pericentrin-B.

FIG. 8C is a graph showing that the centriolin and pericentrin-B siRNA phenotype is similar to that observed in serum-starved cells (blue, serum starved; red, not starved).

FIG. 8D depicts a micrograph of Ki-67 staining of pericentrin-B siRNA-treated cells showing that a cell lacking pericentrin-B also lacks Ki-67 (arrowhead), compared with a cell that is unaffected (upper left) and stains for both pericentrin-B (red, arrow) and Ki-67 (green). Bar, 7.5 μm.

FIG. 8E is a graph showing quantification of Ki-67 staining in cells treated with siRNAs targeting pericentrin-B, centriolin and GFP. Pcnt-B, pericentrin-B.

FIG. 8F is a graph showing that HeLa cells, with abrogated p53 function, did not arrest when centriolin or pericentrin-B levels were reduced. The majority stained for Ki-67 and shifted into the G2 peak when treated with nocodazole.

FIG. 8G is a graph showing that Saos-2 cells, with abrogated p53 function, did not arrest when centriolin or pericentrin-B levels were reduced. The majority stained for Ki-67 and shifted into the G2 peak when treated with nocodazole.

FIG. 9 is a table that shows cell cycle analysis of flow cytometry data without nocodazole (above) and with nocodazole (below) (see FIGS. 8A–G).

FIGS. 12A-J depict the nucleotide sequence (SEQ ID NO:1) (above) and amino acid sequence (SEQ ID NO:2) (below) of centriolin.

FIGS. 13A-N depict the nucleotide sequence (SEQ ID NO:3) (above) and amino acid sequence (SEQ ID NO:4) (below) of pericentrin-B.

FIG. 14 is a schematic diagram of centriolin. It depicts centriolin domains that share homology with budding and fission yeast proteins Nud1p and Cdc11p, human stathmin, and human and Drosophila TACCs (above). Percentages represent identities and similarities of centriolin to the homologous proteins described above. It also depicts centriolin regions predicted to be coiled coil (below). Beneath each sequence are centriolin amino acid numbers.

FIGS. 15A–N are graphs and micrographs relating to RPE-1 cells treated with siRNAs targeting centriolin.

FIG. 15A is a graph showing the dramatic increase in the percentage of cells in telophase/cytokinesis after siRNA targeting of centriolin (~70-fold).
n=total number of cells counted (FIG. 15A–D).

FIG. 15B is a graph showing the increased percentage of binucleate cells in a HeLa cell line after treatment with centriolin siRNAs (4–15-fold greater than controls). Values represent data from a single experiment. The time analyzed was as follows: 48 hours and 72 hours.

FIG. 15C is a graph showing the increased percentage of binucleate cells in a U2OS cell line after treatment with centriolin siRNAs (4–15-fold greater than controls). Values represent data from a single experiment. The time analyzed was as follows: U2OS, 72 hours.

FIG. 15D is a graph showing the increased percentage of binucleate cells in an RPE-1 cell line after treatment with centriolin siRNAs (4–15-fold greater than controls). Values represent data from a single experiment. The time analyzed was as follows: RPE-1, 24 hours.

FIGS. 15E–J depict micrographs showing that microtubule organization (FIGS. 15E–J) and microtubule nucleation (FIGS. 15K and L) are not detectably altered in cells treated with centriolin siRNA (FIGS. 15F, H, J, and L) compared with cells treated with lamin siRNA (FIGS. 15E, G, I, and K). No centrosome staining is observed in centriolin siRNA-treated cells.

FIG. 15E depicts a micrograph showing microtubule organization of cells (in interphase) treated with lamin siRNA. Arrow indicates position of centrosome. Microtubules (red), centrosomes (green/yellow), and nuclei (blue). MB=midbody. Bar in FIG. 15N, 5 μm.

FIG. 15F depicts a micrograph showing microtubule organization of cells (in interphase, lower cell) treated with centriolin siRNA. Microtubules (red), centrosomes (green/yellow), and nuclei (blue). MB=midbody. Bar in FIG. 15N, 5 μm.

FIG. 15G depicts a micrograph showing microtubule organization of cells (prometaphase/metaphase (proM/M)) treated with lamin siRNA. Arrows indicate positions of centrosomes. Microtubules (red), centrosomes (green/yellow), and nuclei (blue). MB=midbody. Bar in FIG. 15N, 5 μm.

FIG. 15H depicts a micrograph showing microtubule organization of cells (prometaphase/metaphase (proM/M)) treated with centriolin siRNA. Microtubules (red), centrosomes (green/yellow), and nuclei (blue). MB=midbody. Bar in FIG. 15N, 5 μm.

FIG. 15I depicts a micrograph showing microtubule organization of cells (telophase) treated with lamin siRNA. Arrows indicate positions of centrosomes. Microtubules (red), centrosomes (green/yellow), and nuclei (blue). MB=midbody. Bar in FIG. 15N, 5 μm.

FIG. 15J depicts a micrograph showing microtubule organization of cells (telophase) treated with centriolin siRNA. Microtubules (red), centrosomes (green/yellow), and nuclei (blue). MB=midbody. Bar in FIG. 15N, 5 μm.

FIG. 15K depicts a micrograph showing microtubule nucleation of cells treated with lamin siRNA. Arrow indicates position of centrosome. Insets is an enlargement of centriolin staining at centrosomes (or microtubule convergence sites) at arrows. Bar in FIG. 15N, 5 μm (including inset).

FIG. 15L depicts a micrograph showing microtubule nucleation of cells treated with centriolin siRNA. Arrow indicates position of centrosome. Insets is an enlargement of centriolin staining at centrosomes (or microtubule convergence sites) at arrows. Bar in FIG. 15N, 5 μm (including inset)

FIGS. 15M and N depicts cells treated with siRNAs targeting centriolin stained for microtubules (red) and DNA (blue). Arrowheads indicate contiguous connections between two or more cells.

FIG. 15M depicts three interconnected cells forming a syncytium. Cells were treated with siRNAs targeting centriolin stained for microtubules (red) and DNA (blue). Arrowheads indicate contiguous connections between two or more cells. Bar, 15 μm.

FIG. 15N depicts one daughter of an interconnected pair of cells that has reentered mitosis (M). Cells were treated with siRNAs targeting centriolin stained for microtubules (red) and DNA (blue). Arrowhead indicates contiguous connections between two or more cells. Bar, 15 μm.

FIGS. 16A–F are depictions of time-lapse images of HeLa cells treated with centriolin siRNAs, revealing unique cytokinesis defects. Time in hours and minutes is included in each panel in FIGS. 16A–D. Time-lapse videos (Videos 1–3) of the series of images shown in FIGS. 16A–C are available at http://www.jcb.org/cgi/content/full/jcb.200301105/DC1.

FIG. 16A depicts a cell treated with control siRNAs targeting lamin moving apart, forming visible midbodies (arrow), and completing the final cleavage event with normal timing (1–3 hours after metaphase). Bar, 10 μm.

FIGS. 16B–D depict centriolin siRNA-treated cells that remain attached for extended periods of time through persistent intercellular bridges and sometimes do not show visible midbodies.

FIG. 16B depicts a cell that remains attached by a long intercellular bridge for at least 8 hours. The cell cleaves, both daughter cells round up, and at least one appears to undergo apoptotic cell death (upper cell, 7:20, extensive blebbing and decrease in size). Bar, 10 μm.

FIG. 16C depicts a dividing cell that has not completed cleavage and reenters the next mitosis. One cell rounds up and is drawn to the other. The other rounds-up and both undergo the early stages of cytokinesis to form a total of four cells; these progeny often remain attached by intercellular bridges forming syncytia. Bar, 10 μm.

FIG. 16D depicts a cell showing three failed attempts at cell cleavage over a 9.5-hour time period. Bar, 10 μm.

FIG. 16E is a graph showing time quantitation of cells treated with siRNAs targeting centriolin progress from nuclear envelope breakdown (NEB) to anaphase with normal timing, similar to lamin siRNA controls. Vertical bars represent recordings from single cells. Results represent recordings of individual cells from several independent experiments.

FIG. 16F is a graph showing time quantitation of centriolin siRNA-treated cells that are delayed in cytokinesis (~70%) compared with control lamin siRNA-treated cells, a value consistent with a 70–80% silencing efficiency. Vertical bars represent recordings from single cells. Results represent recordings of individual cells from several independent experiments.

Like reference symbols in the various drawings indicate like elements.

DETAILED DESCRIPTION OF THE INVENTION

Figure 1A:
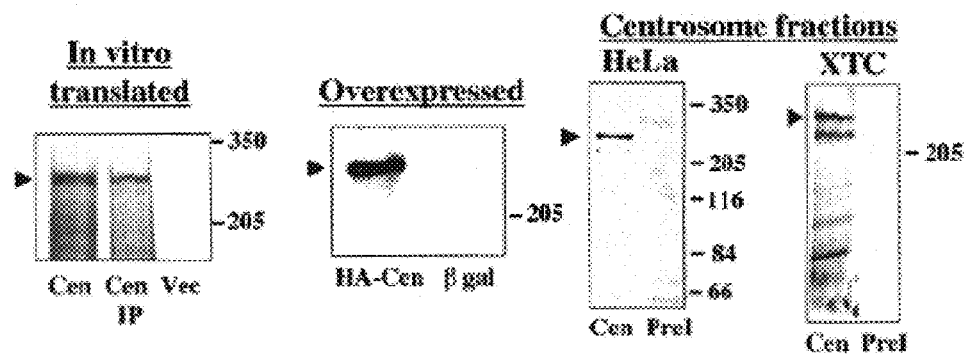
FIG. 1A is a representation of a series of SDS gels that show 35S(Methionine)-labeled HA-tagged centriolin (Cen) or empty vector (Vec) produced by in vitro translation and run on SDS gels directly or after immunoprecipitation with HA antibodies (Cen IP). Western blots were probed with anti-HA antibody showing overexpressed HA-tagged centriolin (HA-Cen) and its absence from cells overexpressing β-galactosidase (β gal). Centrosome fractions prepared from HeLa cells (panel 3) and *Xenopus* cells (XTC, panel 4) were blotted with antibodies to centriolin (Cen) and preimmune sera (PreI). Arrowheads show position of centriolin. In XTC cells, the band below centriolin appears to be a degradation product as a band of similar molecular weight is sometimes observed when the cDNA is translated in vitro or overexpressed. Bars represent positions of molecular weight markers (×10³).

The invention is based, in part, on the discovery of the interaction between centrosome polypeptide components, centriolin and pericentrin-B, whose disruption induces cytokinesis delays/defects and subsequent G1/G0 arrest. This phenotype is essentially the same as that observed when centrosomes are experimentally eliminated from vertebrate cells (Hinchcliffe et al., *Science*, 291:1547–1550, 2001; Khodjakov and Rieder, *J Cell Biol.*, 153:237–242, 2001). Taken together, these results demonstrate that centriolin and pericentrin-B represent core centrosome components required for progression through cytokinesis and entry into S phase.

Yeast Centrosomes

To ensure that each daughter cell receives one copy of each chromosome during cell division, exit from mitosis and cytokinesis must occur only after chromosomes are properly segregated. It is therefore essential that these events are precisely ordered. A role for centrosomes in defining the site of cell cleavage during cytokinesis has been suggested for some time (Rappaport, *Int Rev Cyctol*, 105:245–281, 1986). Recent studies with vertebrate cells provide evidence for a direct link between centrosome activity and completion of cytokinesis. Elimination of centrosomes from interphase cells by removal with a microneedle (Hinchcliffe et al., *Science*, 291:1547–1550, 2001) or from mitotic cells by laser ablation (Khodjakov and Rieder, *J Cell Biol.*, 153: 237–242, 2001), caused cytokinesis defects, arrest, or failure. It was also shown that during the final stages of cytokinesis the maternal centriole moved to the intercellular bridge, the microtubule-filled interconnection between nascent daughter cells. Centriole re-positioning correlated with bridge narrowing and microtubule depolymerization, and its subsequent movement away from the bridge correlated with cell cleavage. Taken together, these studies suggest that centrosomes either activate the final stages of cytokinesis or induce release of cells from a checkpoint that monitors completion of mitosis.

These studies are consistent with work in both fission and budding yeast that show that spindle pole body-anchored signaling pathways regulate cytokinesis. In budding yeast, a regulatory pathway called the mitotic exit network (MEN) controls anaphase progression by inactivating cyclin-dependent kinases (CDKs, for reviews see Bardin and Amon, *Nat Rev Mol Cell Biol*, 2:815–826, 2001; McCollum and Gould, *Trends Cell Biol.*, 11:89–95, 2001; Pereira and Schiebel, *Curr Opin Cell Biol.*, 13:762–769, 2001). Cells mutant for this GTPase-driven signaling network typically arrest in late anaphase. As cells enter late anaphase the spindle pole body (centrosome equivalent) moves into the nascent daughter cell (bud). This event brings into contact a GTP binding protein called Tem1p located on the spindle pole body nearest the bud and the guanine nucleotide exchange factor Lte1p located in the bud. Tem1p is converted to its active GTP form by Lte1p probably in combination with inactivation of the Bub2p GTPase activating protein (GAP). Activation of Tem1p, together with loss of microtubule contact with the bud neck and microtubule depolymerization at the bud neck, triggers exit from mitosis (Bardin et al., *Cell*, 102:21–31, 2000; Bloecher et al., *Nat Cell Biol.*, 2:556–558, 2000; Gruneberg et al., *Embo J*, 19:6475–6488, 2000; Adames et al., *J Cell Biol.*, 153:159–168, 2001). In addition to regulating mitotic exit, the MEN also appears to play a role in cytokinesis (see Bardin and Amon, *Nat Rev Mol Cell Biol*, 2:815–826, 2001; Guertin et al., *Microbiol Mol Biol Rev.*, 66:155–178, 2002; McCollum and Gould, *Trends Cell Biol.*, 11:89–95, 2001).

In fission yeast, a signal transduction pathway analogous to the MEN has been termed the septation initiation network (SIN) (see Bardin and Amon, *Nat Rev Mol Cell Biol*, 2:815–826, 2001; Le Goff et al., *Curr Genet*, 35:571–584, 1999a; McCollum and Gould, *Trends Cell Biol.*, 11:89–95, 2001). This pathway is anchored at the spindle pole body by Cdc11p, a protein homologous to the budding yeast Nud1p, and by sid4p (Chang and Gould, *Proc Natl Acad Sci USA*, 97:5249–5254, 2000; Krapp et al., *Curr Biol.*, 11:1559–1568, 2001; Tomlin et al., *Mol Biol Cell*, 13:1203–1214, 2002). SIN mutants fail in cytokinesis but continue to replicate their DNA and become elongated and multinucleate (Balasubramanian et al., *Genetics*, 149:1265–1275, 1998; Fankhauser et al., *Cell*, 82:435–444, 1995). A SIN-dependent checkpoint was recently identified that monitors completion of cytokinesis (Le Goff et al., *Mol Gen Genet.*, 262:163–172, 1999b; Liu et al., *J Cell Sci*, 113:1223–1230, 2000; Trautmann et al., *Curr Biol.*, 11:931–940, 2001). Cytokinesis failure causes cells to arrest prior to the next mitosis with two nuclei, thus preventing propagation of polyploid cells. Like the MEN, the SIN also may play a role in mitotic exit through inactivation of mitotic CDKs under certain circumstances (see Bardin and Amon, *Nat Rev Mol Cell Biol*, 2:815–826, 2001; McCollum and Gould, *Trends Cell Biol.*, 11, 89–95, 2001). Thus, both the SIN and MEN appear to regulate two steps in the latter stages of mitosis, mitotic exit and completion of cytokinesis. Consistent with their shared roles in mitosis, several components of the SIN and MEN share sequence homology (see Guertin et al., *Microbiol Mol Biol.*, 66:155–178, 2002).

Vertebrate Centrosomes

Although some of the late events in vertebrate cell mitosis appear similar to those in yeasts, there is little evidence for the existence of a signaling pathway homologous to the MEN or SIN in vertebrate cells. Although a few components related to yeast proteins have been identified in vertebrates, they have not been shown to possess activities and interactions of the SIN and MEN pathways (Cuif et al., *Embo J*, 18:1772–1782, 1999; Hirota et al., *J Cell Biol.*, 149:1073–1086, 2000; Luca and Winey, *Mol Biol Cell*, 9:29–46, 1998; Mailand et al., *Nat Cell Biol.*, 4:318–322, 2002).

In addition to their role in cytokinesis, centrosomes play a role in cell cycle progression. When centrosomes were removed from vertebrate cells, half completed mitosis but did not initiate DNA replication (Hinchcliffe et al., *Science*, 291:1547–1550, 2001; Khodjakov and Rieder, *J Cell Biol.*, 153:237–242, 2001). The authors suggested that centrosomes controlled entry into S phase by recruiting or concentrating "core" centrosome molecules required for this process or that they indirectly activated a cellular checkpoint that monitored aberrant centrosome number. Consistent with the checkpoint model are results from fission yeast showing that cytokinesis failure triggers a checkpoint that inhibits entry into the following mitotic cycle (see above). Moreover, vertebrate cells treated with cytochalasin D to inhibit actin-mediated cell cleavage, become tetraploid and subsequently arrest in G1 (Andreassen et al., *Mol Biol Cell*, 12:1315–1328, 2001). Elucidation of the mechanism by which centrosomes contribute to cell cycle progression in vertebrate cells will require identification of the molecular components and pathways that control these events.

The current invention is based, in part, on the identification of a novel human core centrosome/centriole component called centriolin. Modification of centriolin levels produces precisely the same phenotype observed when centrosomes are experimentally eliminated from cells, namely cytokinesis defects and G1 arrest. Centriolin shares homology with the yeast MEN/SIN components Nud1p/cdc11, is able to bind a yeast MEN component that interacts with Nud1p (Bub2), and is anchored to centrosomes by pericentrin-B, analogous to the anchoring of the SIN component cdc11 to spindle pole bodies by sid4. Reduction in levels of centriolin or pericentrin-B induces G1/G0 arrest.

The invention is based, at least in part, on the interaction of centriolin with pericentrin-B as components of a regulatory pathway in vertebrate cells that control progression through cytokinesis and into S phase. This invention discloses a molecular mechanism for cytokinesis defects and G1 arrest in vertebrate cells whose centrosomes are experimentally eliminated. It identifies core centrosome proteins involved in the final stages of cytokinesis that are members of a regulatory pathway analogous to the yeast SIN and MEN. It also demonstrates that reduction in expression or activity of these proteins arrests cells in G1/G0.

Identification of a Vertebrate Pathway that Regulates Cytokinesis

Regulatory pathways that control mitotic exit and cytokinesis have been described in budding and fission yeasts, but an analogous pathway in vertebrate cells has not been previously identified. The present invention elucidates such a pathway. Alteration of centriolin or pericentrin-B levels in vertebrate cells affects progression through cytokinesis just as mutation or overexpression of SIN or MEN proteins affects mitotic exit and cytokinesis in budding and fission yeasts. Centriolin shares homology with spindle pole body proteins in budding and fission yeasts (Nud1p, Cdc11p) that anchor downstream effectors of the MEN and SIN. Like Nud1p, the centriolin Nud1-related domain interacts with the MEN GAP, Bub2p. Both yeast and human proteins localize to microtubule organizing centers (centrosomes, spindle pole bodies). Overexpression of the Nud1-related domain of centriolin disrupts cytokinesis suggesting that it sequesters vertebrate homologue(s) of the MEN/SIN. Centriolin localizes to the maternal centriole and is translocated to the intercellular bridge during cytokinesis. It has recently been postulated that translocation of the maternal centriole to and subsequently away from the intercellular bridge is required to activate a regulatory network that controls cytokinesis in vertebrates in much the same way that movement of the spindle pole body into the bud triggers the MEN in budding yeast (Piel et al., *Science*, 291:1550–1553, 2001). This places centriolin at the right place at the right time to affect progression through the late stages of cytokinesis. Pericentrin-B anchors centriolin to centrosomes and reduction in its level mislocalizes centrosomal centriolin resulting in cytokinesis defects, just as loss or mutation of the fission yeast Sid4p mislocalizes Cdc11p and perturbs cytokinesis. Taken together, these results suggest a model in which centriolin and pericentrin-B define a vertebrate pathway analogous to the yeast MEN and SIN that is required for completion of cytokinesis. This pathway will be referred to as the cytokinesis activation network (CAN).

The vertebrate CAN appears to be more like the SIN than the MEN. Cells with defects in the SIN fail to septate but exit mitosis and grow to form elongated multinucleate cells. Similarly, vertebrate cells defective for the CAN often fail to cleave forming large binucleate cells. Like fission yeast, vertebrate cells with cytokinesis defects retain microtubule structures and midbodies suggesting that the defect is at the final stages of cell cleavage. In contrast, budding yeast cells defective for MEN function arrest in anaphase.

The terminal stage of arrest for these three pathways is different. Budding yeast arrest in late anaphase while vertebrate cells arrest in the following G1/G0. Although fission yeast do not undergo cell cycle arrest, recent studies have uncovered a SIN-dependent cytokinesis checkpoint that arrests cells in G2 when they fail to undergo septation and cytokinesis (see Bardin and Amon, *Nat Rev Mol Cell Biol.*, 2:815–826, 2001; McCollum and Gould, *Trends Cell Biol.*, 11:89–95, 2001). It is interesting to compare how similar pathways control mitotic exit, cytokinesis, and cell cycle progression in these different organisms.

Mechanism of Centriolin-Induced Cytokinesis Defects

Centriolin function was targeted using multiple strategies, cell types, and species. All produced cytokinesis defects including reduction and elevation of centriolin levels, ectopic expression of the centriolin Nud1-related domain, ectopic expression of the pericentrin-B centrosome targeting domain, injection of centriolin antibodies, and reduction of pericentrin-B levels. Although the precise cause for an effect on cytokinesis is not yet known, one possibility is that the effect is achieved by modulating localization of centriolin-bound components of the CAN. Perhaps the most compelling data supporting this model is that overexpression of the centriolin Nud1-related domain induces cytokinesis delays and defects. This domain binds to yeast Bub2p, lacks the potential microtubule modifying domains (stathmin, TACCs), and does not disrupt centrosomal localization of endogenous centriolin when overexpressed. Overexpression of this domain in vertebrate cells may sequester a vertebrate homolog of the MEN/SIN and affect progression of cytokinesis.

Centrosome Integrity Checkpoint

The invention is based, in part, on the discovery that vertebrate cells with reduced centriolin or pericentrin-B levels exhibit cytokinesis defects and subsequently arrest in G1/G0. Cytokinesis defects and G1 arrest occur when centrosomes are experimentally eliminated from vertebrate cells. One of the discoveries upon which this invention is based is of a different mechanism for centrosome-mediated G1 arrest: activation of a checkpoint that monitors centrosome composition and/or function. Several observations support this. Reduction in levels of centrosome proteins that have no detectable effect on cytokinesis cause a potent G1/G0 arrest, indicating that the arrest is unrelated to cytokinesis. Several centrosome proteins that function in pathways unrelated to the CAN/MEN/SIN induce G1/G0 arrest, demonstrating that the arrest is unrelated to this regulatory pathway. Even noncentrosome proteins that affect centrosome assembly and integrity induce G1/G0 arrest, such as members of the dynactin and dynein complexes.

G1 arrest is specific for centrosomes, as shown by the fact that targeting of proteins of other cellular organelles, such as the nucleus (e.g., lamin A/C), has no detectable effect on cell cycle progression. Alterations in centrosome composition, integrity, or function induce G1/G0 arrest even in cells with normal centrosome numbers. This demonstrates that vertebrate cells have a centrosome integrity checkpoint that monitors the composition and/or function of centrosomes. Inactivation of this pathway can lead to cytokinesis failure, aneuploidy, and tumor progression.

Centrosome Defects and the Induction of Exit from the Cell Cycle (G0)

Cells lacking centrosomes are unable to enter S phase and are arrested in G1 or G1/S (the restriction point). However, the invention is based, at least in part, on the discovery that cells with reduced centrosome protein levels exit the cell cycle and enter a quiescent G0 state. These cells were negative for antibodies that recognize cycling or cell cycle arrested cells, and not G0 or differentiated cells. Flow cytometry patterns in these cells were indistinguishable from serum-starved cells but different from cells in G1 or those arrested in G1/S. The G0 arrest phenotype was observed in multiple cell types including normal diploid cell lines (e.g., RPE, BJ-1), two genetically unstable tumor or tumor-like cell lines (i.e., HeLa, COS), cell lines with normal p53 (i.e., RPE, BJ-1) and altered p53 (i.e., HeLa), and cells of different tissue origins and species (e.g., human, monkey, mouse, hamster). Because the G0 state is more permanent and less subject to being overridden or reversed than cells arrested within the cell cycle, it can be exploited in cancer therapeutics by targeting centrosome proteins in tumor cells to induce exit from the cell cycle, and perhaps trigger re-differentiation.

Mechanism of G1/G0 Arrest

G1 arrest occurs when entire centrosomes are physically eliminated from vertebrate cells by laser ablation or microsurgery. It was demonstrated that even minor changes in centrosome composition can effectively inhibit cell cycle progression. However, the mechanism by which cells arrest occurs has been unknown. Possibilities include that the arrest is a downstream consequence of improper exit from cytokinesis/mitosis, that the CAN may control entry into S phase in addition to its role in cytokinesis, or that centriolin and pericentrin-B have dual roles in cytokinesis and S phase entry. The results of experiments carried out as part of the invention suggest that loss of centrosomal centriolin or pericentrin-B activates a checkpoint that monitors centrosome integrity (or number), thus preventing cells from entering S phase.

The G1/G0 arrest induced by reduction of centriolin or pericentrin-B is p53-dependent. The p53 pathway is also activated when cytokinesis is prevented by inhibiting actin ring formation or by overexpression of aurora-A kinase. The mechanism of p53 activation under these different experimental conditions is not yet understood.

Additional Roles for Centriolin and Pericentrin-B

Centriolin and pericentrin-B perform functions in addition to their roles in regulating completion of cytokinesis. Both are extraordinarily large proteins (260 kD, 350 kD, respectively) with a diversity of functional domains. Like other large centrosome-coiled coil proteins, both act as scaffolds for anchoring numerous proteins and activities. Centriolin has domains that may affect microtubule stability (stathmin, TACC) and microtubule anchoring (Nud1p). The microtubule bundles and other changes in microtubule organization observed in cells overexpressing full-length centriolin result from activation or suppression of these microtubule-modifying domains, and these microtubule structures are not observed when the Nud1-related domain is overexpressed. Additional functions for centriolin and pericentrin-B are also suggested by their re-localization from centrosomes to the intercellular bridge and midbody during cytokinesis, as this redistribution does not occur in the putative yeast homologues (Chang and Gould, *Proc Natl Acad Sci USA*, 97:5249–5254, 2000; Gruneberg et al., *Embo J*, 19:6475–6488, 2000; Krapp et al., *Curr Biol.*, 11:1559–1568, 2001).

Pericentrin-B shares homology with budding yeast spc110p, a spindle pole body protein that anchors g tubulin complexes (Flory et al., *Proc Natl Acad Sci USA*, 411: 494–498, 2000), and appears to be an isoform of pericentrin-A. Pericentrin-B may interact with the same molecules as pericentrin-A including g tubulin complexes (Dictenberg et al., *J Cell Biol.*, 141:163–174, 1998), PKA (Diviani et al., *Curr Biol.*, 10:417–420, 2000), and cytoplasmic dynein (Purohit et al., *J Cell Biol.*, 147:481–491, 1999). However, reduction of pericentrin-B levels does not prevent centrosomal association of g tubulin as would be expected if it interacted with the g tubulin complex.

Centriolin is a Marker for Maternal Centrioles and Centriole Maturation

Even though centrioles begin duplicating at G1/S, centriolin does not significantly accumulate at the new mother centriole until mitosis. It thus serves as a marker for centriole maturation, a characteristic shared with cenexin (Lange and Gull, *J Cell Biol.*, 130:919–927, 1995) and ninein (Mogensen et al., *J Cell Sci*, 113:3013–3023, 2000). Localization of centriolin to the subdistal appendages suggests that it may be involved in recruitment of other CAN components to these sites. It may also function in the anchoring of microtubules at these sites (Piel et al., *J Cell Biol.*, 149:317–330, 2000), or in maintaining the integrity of the appendages. Localization of centriolin to appendages could also facilitate its movement from the centriole to the intercellular bridge via microtubules anchored at these sites.

Genetic Instability Induced by Reduction in Centriolin or Pericentrin-B Levels

The formation of binucleate cells in cells with reduced centriolin or pericentrin-B demonstrates that these proteins affect the fidelity of partitioning chromosomes into daughter cells by interfering with cytokinesis. Because centrosome anomalies are implicated in the establishment of genetic instability associated with human tumors, functional changes in centriolin or pericentrin-B that affect centrosomes contribute to genetic instability. Moreover, the location of the centriolin gene to a chromosomal site often involved in translocations, and its presence as an oncogenic fusion protein with FGF-R, suggests another mechanism whereby centriolin can influence tumor progression.

Nucleic Acids

The invention encompasses nucleic acids that have sequences substantially identical to any one of the nucleic acid sequences of SEQ ID NOs:1 and 3. The nucleotide sequences of SEQ ID NOs:1 and 3 are shown in FIGS.

12A-J and FIGS. 13A-N respectively. A nucleic acid sequence that is "substantially identical" to a reference nucleic acid sequence has a sequence that has at least 85% identity to the reference sequence, e.g., the nucleic acid sequence of SEQ ID NOs:1 and 3. Of course, a substantially identical sequence can have a greater percentage of identity, e.g., 90%, 95%, 96%, or 99% identity.

The nucleic acid molecules of the invention can be cDNA, genomic DNA, synthetic DNA, or RNA, and can be double-stranded or single-stranded (i.e., either a sense or an antisense strand). Fragments of these molecules are also considered to be within the scope of the invention, and can be produced, for example, by the polymerase chain reaction (PCR) or generated by treatment with one or more restriction endonucleases. A ribonucleic acid (RNA) molecule can be produced by in vitro transcription.

The nucleic acid molecules of the invention can contain naturally occurring sequences, or sequences that differ from those that occur naturally, but, due to the degeneracy of the genetic code, encode the same polypeptide. In addition, these nucleic acid molecules are not limited to sequences that only encode polypeptides, and thus, can include some or all of the non-coding sequences that lie upstream or downstream from a coding sequence.

The nucleic acid molecules of the invention can be synthesized (for example, by phosphoramidite-based synthesis) or obtained from a biological cell. Combinations or modifications of the nucleotides within these types of nucleic acids are also encompassed.

In addition, the new isolated nucleic acid molecules encompass fragments that are not found as such in the natural state, but possess the same functions or uses as the full-length nucleic acids. The lengths of such fragments can range from very short to almost as long as the full-length nucleic acids of which they are fragments. For example, fragments of SEQ ID NOs:1 or 3 can range in length from 10 to 210 nucleic acids in length (e.g., 10, 20, 30, 40, 50, 60, 70, 80, 90, 100, 110, 120, 130, 140, 150, 160, 170, 180, 190, 200, or 210 nucleic acids). Thus, the invention encompasses recombinant molecules, such as those in which a nucleic acid molecule (for example, an isolated nucleic acid molecule such as SEQ ID NOs:1 or 3) is incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

In the event the nucleic acid molecules of the invention encode or act as antisense molecules, they can be used for example, to regulate translation of mRNA of the invention. Given target sequences, techniques associated with detection or regulation of expression of those target nucleic acids or target polypeptides are known to skilled artisans and can be used to diagnose and/or treat disorders associated with aberrant expression of nucleic acids or polypeptides of the invention.

The invention also encompasses nucleic acid molecules that hybridize under stringent conditions to a nucleic acid molecule encoding a polypeptide of the invention. The cDNA sequences described herein can be used to identify these hybridizing nucleic acids, which include, for example, nucleic acids that encode homologous polypeptides in other species, and splice variants of the genes of the invention. Accordingly, the invention features methods of detecting and isolating these nucleic acid molecules. Using these methods, a sample (for example, a nucleic acid library, such as a cDNA or genomic library) is contacted (or "screened") with a probe specific to a nucleotide of the invention (for example, a fragment of SEQ ID NOs:1 or 3 that is at least 25 or 50 or 100 nucleotides long). The probe will selectively hybridize to nucleic acids encoding related polypeptides (or to complementary sequences thereof). The probe, which can contain at least 25 (for example, 25, 50, 100, 200, 300, or more than 300 nucleotides) can be produced using any of several standard methods (see, for example, Ausubel et al., "Current Protocols in Molecular Biology, Vol. I," Green Publishing Associates, Inc., and John Wiley & Sons, Inc., NY, 1989). For example, the probe can be generated using PCR amplification methods in which oligonucleotide primers are used to amplify a nucleic acid sequence specific to a nucleic acid of the invention that can be used as a probe to screen a nucleic acid library and thereby detect nucleic acid molecules (within the library) that hybridize to the probe (e.g., probes with nucleotide sequences complementary to nucleotides at positions 40–65, 120–170, 390–490, and 670–1170 of SEQ ID NO:1, or positions 65–136, 450–610, 1100–1650, or 4006–5009 of SEQ ID NO:3).

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acids are hybridized at 42° C. in 2×SSC/0.1% SDS (sodium dodecylsulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

Once detected, the nucleic acid molecules can be isolated by any of a number of standard techniques (see, for example, Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any of the foregoing coding sequences (related to a polypeptide of the invention) and/or their complements (that is, "antisense" sequence); (b) expression vectors that contain any of the foregoing coding sequences (related to a polypeptide of the invention) operatively associated with a regulatory element (examples of which are given below) that directs the expression of the coding sequences; (c) expression vectors containing, in addition to sequences encoding a polypeptide of the invention, nucleic acid sequences that are unrelated to nucleic acid sequences encoding a polypeptide of the invention, such as molecules encoding a reporter or marker; and (d) genetically engineered host cells that contain any of the foregoing expression vectors and thereby express the nucleic acid molecules of the invention in the host cell.

The invention also encompasses heterologous fusions with endogenous human and murine genes. For example, many human oncogenes are hybrids comprised of a viral domain and a human domain. This suggests that, at some point, a virus integrated its sequence into a human, thus creating a chimeric sequence that is oncogenic.

Recombinant nucleic acid molecules can contain a sequence encoding a soluble polypeptide of the invention; mature polypeptide of the invention; or polypeptide of the invention having an added or endogenous signal sequence. A full-length polypeptide of the invention; a domain of a polypeptide of the invention; or a fragment thereof may be fused to additional polypeptides, as described below. Similarly, the nucleic acid molecules of the invention can encode the mature form of a polypeptide of the invention or a form that encodes a polypeptide that facilitates secretion. In the latter instance, the polypeptide is typically referred to as a proprotein (or preprotein), which can be converted into an active form by removal of the signal sequence, for example, within the host cell. Proproteins can be converted into the active form of the protein by removal of the inactivating sequence.

The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter. Generally, the hybrid polypeptide will include a first portion and a second portion; the first portion being a polypeptide of the invention and the second portion being, for example, the reporter described above or an immunoglobulin constant region.

The expression systems that may be used for purposes of the invention include, but are not limited to, microorganisms such as bacteria (for example, E. coli and Bacillus subtilis) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention (preferably containing the nucleic acid sequence encoding a polypeptide of the invention); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing nucleotide sequences of nucleic acids of the invention; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions containing polypeptides of the invention or for raising antibodies to those polypeptides, vectors that are capable of directing the expression of high levels of fusion protein products that are readily purified may be desirable. Such vectors include, but are not limited to, the E. coli expression vector pUR278 (Ruther et al., EMBO J. 2:1791, 1983), in which the coding sequence of the insert may be ligated individually into the vector in frame with the lacZ coding region so that a fusion protein is produced; pIN vectors (Inouye and Inouye, Nucleic Acids Res., 13:3101–3109, 1985; Van Heeke and Schuster, J. Biol. Chem., 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) can be used as a vector to express foreign genes. The virus grows in *Spodoptera frugiperda* cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (for example, see Smith el al, *J. Virol.*, 46:584, 1983; Smith, U.S. Pat. No. 4,215,051).

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1 or E3) will result in a recombinant virus that is viable and capable of expressing a gene product of the invention in infected hosts (for example, see Logan and Shenk, *Proc. Natl. Acad. Sci. USA*, 81:3655–3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.*, 153:516–544, 1987).

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. The mammalian cell types listed above are among those that could serve as suitable host cells.

For long-term, high-yield production of recombinant proteins, stable expression is preferred. For example, cell lines that stably express the sequences of nucleic acids or polypeptides of the invention described above may be engineered. Rather than using expression vectors that contain viral origins of replication, host cells can be transformed with DNA controlled by appropriate expression control elements (for example, promoter, enhancer sequences, transcription terminators, polyadenylation sites, etc.), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci that in turn can be cloned and expanded into cell lines. This method can advantageously be used to engineer cell lines that express nucleic acids or polypeptides of the invention. Such engineered cell lines may be particularly useful in screening and evaluation of compounds that affect the endogenous activity of the gene product.

A number of selection systems can be used. For example, the herpes simplex virus thymidine kinase (Wigler, et al., *Cell*, 11:223, 1977), hypoxanthine-guanine phosphoribosyltransferase (Szybalska and Szybalski, *Proc. Natl. Acad. Sci. USA*, 48:2026, 1962), and adenine phosphoribosyltransferase (Lowy et al., *Cell*, 22:817, 1980) genes can be employed in tk⁻, hgprt⁻ or aprt⁻ cells, respectively. Also, anti-metabolite resistance can be used as the basis of selection for the following genes: dhfr, which confers resistance to methotrexate (Wigler et al., *Proc. Natl. Acad. Sci. USA*, 77:3567, 1980; O'Hare et al., *Proc. Natl. Acad. Sci. USA*, 78:1527, 1981); gpt, which confers resistance to mycophenolic acid (Mulligan and Berg, *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1984).

The nucleic acid molecules of the invention are useful in the diagnosis and treatment of systemic sclerosis and other autoimmune disorders.

Polypeptides

The invention also includes polypeptides that have a sequence that is encoded by, or is substantially identical to the polypeptides encoded by, the nucleic acids of the invention (e.g., polypeptides that are substantially identical to a polypeptide encoded by either SEQ ID NO:1 or 3). The polypeptide sequences of centriolin (SEQ ID NO:2) and pericentrin-B (SEQ ID NO:4) are shown in FIGS. 12A-J and 13A-N, respectively. A polypeptide which is "substantially identical" to a given reference polypeptide is a polypeptide having a sequence that has at least 85% identity to the sequence of the given reference polypeptide sequence (e.g., the amino sequence of a polypeptide encoded either SEQ ID NO:1 or 3). Substantially identical polypeptides can also have a higher percentage identity, e.g., 90%, 95%, 98%, or 99%.

The terms "protein" and "polypeptide" are used herein interchangably to describe any chain of amino acids, regardless of length or post-translational modification (for example, glycosylation or phosphorylation). Thus, the term "polypeptides of the invention" includes: full-length, naturally occurring proteins of the invention; recombinantly or synthetically produced polypeptides that correspond to full-length naturally occurring proteins of the invention; or particular domains or portions of the naturally occurring proteins. The term also encompasses mature polypeptides that have an added amino-terminal methionine (useful for expression in prokaryotic cells).

The centriolin and pericentrin-B polypeptides described herein are encoded by any of the nucleic acid molecules described herein and include SEQ ID NOs:2 and 4, as well as fragments, mutants, truncated forms, and fusion proteins of polypeptides of the invention. These polypeptides can be prepared for a variety of uses, including, but not limited to, the generation of antibodies, as reagents in diagnostic assays, for the identification of other cellular gene products or compounds that can modulate the activity or expression of nucleic acids or polypeptides of the invention, and as pharmaceutical reagents useful for the treatment of disorders associated with aberrant expression or activity of nucleic acids or polypeptides of the invention.

Useful polypeptides are substantially pure polypeptides of the invention, including those that correspond to the polypeptide with an intact signal sequence, and the secreted form of the polypeptide. Especially useful polypeptides are soluble under normal physiological conditions.

The invention also encompasses polypeptides that are functionally equivalent to polypeptides of SEQ ID NOs:2 and 4. These polypeptides are functionally equivalent to polypeptides of SEQ ID NOs:2 and 4 in that they are capable of carrying out one or more of the functions of polypeptides of the invention in a biological system. Useful polypeptides of the invention have 60%, 75%, 80%, or even 90% of one or more of the biological activities of the full-length polypeptides of SEQ ID NOs:2 and 4. Such comparisons are generally based on an assay of biological activity in which equal concentrations of the polypeptides are used and compared. The comparison can also be based on the amount of the polypeptide required to reach 50% of the maximal stimulation obtainable.

Functionally equivalent polypeptides can be those, for example, that contain additional or substituted amino acid residues. Substitutions may be made on the basis of similarity in polarity, charge, solubility, hydrophobicity, hydrophilicity, and/or the amphipathic nature of the residues involved. For example, a functionally equivalent polypeptide is one in which 10% or fewer of the amino acids in a full-length, naturally occurring polypeptide are replaced by conservative amino acid substitutions, and the functionally equivalent polypeptide maintains at least 50% of the biological activity of the full-length polypeptide. Conservative amino acid substitution refers to the substitution of one amino acid for another amino acid of the same class (e.g., valine for glycine and arginine for lysine).

Polypeptides that are functionally equivalent to polypeptides of SEQ ID NOs:2 and 4 can be made using random mutagenesis on the encoding nucleic acids by techniques well known to those skilled in the art. It is more likely, however, that such polypeptides will be generated by site-directed mutagenesis (again using techniques well known to those skilled in the art). These polypeptides may have increased functionality or decreased functionality.

To design functionally equivalent polypeptides, it is useful to distinguish between conserved positions and variable positions. This can be done by aligning the amino acid sequence of a protein of the invention from one species with its homolog from another species. Skilled artisans will recognize that conserved amino acid residues are more likely to be necessary for preservation of function. Thus, it is preferable that conserved residues are not altered.

Mutations within the coding sequence of nucleic acid molecules of the invention can be made to generate variant genes that are better suited for expression in a selected host cell. For example, N-linked glycosylation sites can be altered or eliminated to achieve, for example, expression of a homogeneous product that is more easily recovered and purified from yeast hosts that are known to hyperglycosylate N-linked sites. To this end, a variety of amino acid substitutions at one or both of the first or third amino acid positions of any one or more of the glycosylation recognition sequences which occur, and/or an amino acid deletion at the second position of any one or more of such recognition sequences, will prevent glycosylation at the modified tripeptide sequence (see, for example, Miyajima et al., *EMBO J.*, 5:1193, 1986).

The polypeptides of SEQ ID NOs:2 and 4 can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

A fusion protein may be readily purified by utilizing an antibody specific for the fusion protein being expressed. For example, a system described by Janknecht et al. allows for the ready purification of non-denatured fusion proteins expressed in human cell lines (*Proc. Natl. Acad. Sci. USA*, 88: 8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

The polypeptides of SEQ ID NOs:2 and 4 can be chemically synthesized (for example, see Creighton, "Proteins: Structures and Molecular Principles," W.H. Freeman & Co., NY, 1983), or, perhaps more advantageously, produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

The invention also features polypeptides that interact with nucleic acids or polypeptides of the invention (and the genes that encode them) and thereby alter the function of nucleic acids or polypeptides of the invention. Interacting polypeptides can be identified using methods known to those skilled in the art. One suitable method is the "two-hybrid system," which detects protein interactions in vivo (Chien et al., *Proc. Natl. Acad. Sci. USA*, 88:9578, 1991). A kit for practicing this method is available from Clontech (Palo Alto, Calif.).

The invention also encompasses small polypeptides that can be used to inhibit specific interactions of two proteins (e.g., a viral membrane protein and a host cell receptor). By virtue of their size, small polypeptides can have many useful properties. For example, they can be membrane-permeable if necessary, or they can be used at high concentration because of their specificity. Small polypeptides can also be used to generate very specific antibodies.

Antibodies

Polypeptides of the invention (or immunogenic fragments or analogs thereof) can be used to raise antibodies useful in the invention; such polypeptides can be produced by recombinant techniques or synthesized (see, for example, "Solid Phase Peptide Synthesis," supra; Ausubel et al., supra). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with a polypeptide of the invention. Host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*. Polyclonal antibodies are heterogeneous populations of antibody molecules that are contained in the sera of the immunized animals.

Antibodies within the invention include polyclonal antibodies and, in addition, monoclonal antibodies, humanized or chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the polypeptides of the invention described above and standard hybridoma technology (see, for example, Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific recognition of polypeptides of the invention by Western blot or immunoprecipitation analysis by standard methods, e.g., as described in Ausubel et al., supra. Antibodies that specifically recognize and bind to polypeptides of the invention are useful in the invention. For example, such antibodies can be used in an immunoassay to monitor the level of a polypeptide of the invention produced by a mammal (for example, to determine the amount or subcellular location of a polypeptide of the invention).

Preferably, antibodies of the invention are produced using fragments of the protein of the invention that lie outside highly conserved regions and appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antisera may also be checked for its ability to immunoprecipitate recombinant proteins of the invention or control proteins, such as glucocorticoid receptor, CAT, or luciferase.

In addition to their therapeutic uses, the new antibodies can be used, for example, in the detection of the polypeptide of the invention in a biological sample as part of a diagnostic assay. Antibodies also can be used in a screening assay to measure the effect of a candidate compound on expression or localization of a polypeptide of the invention. Additionally, such antibodies can be used in conjunction with the gene therapy techniques described to, for example, evaluate normal and/or genetically engineered cells that express nucleic acids or polypeptides of the invention prior to their introduction into the patient. Such antibodies additionally can be used in a method for inhibiting abnormal activity of nucleic acids or polypeptides of the invention.

In other embodiments, techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). A method for lipidation of antibodies is described by Cruikshank et al. (*J. Acquired Immune Deficiency Syndromes and Human Retrovirology*, 14:193, 1997).

Alternatively, techniques described for the production of single chain antibodies (U.S. Pat. Nos. 4,946,778, 4,946,778, and 4,704,692) can be adapted to produce single chain antibodies against polypeptides of the invention. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Antibodies to polypeptides of the invention can, in turn, be used to generate anti-idiotype antibodies that resemble a portion of the protein of the invention using techniques well known to those skilled in the art (see, e.g., Greenspan et al., FASEB J., 7:437, 1993; Nissinoff, J. Immunol., 147:2429, 1991). For example, antibodies that bind to the protein of the invention and competitively inhibit the binding of a binding partner of the protein can be used to generate anti-idiotypes that resemble a binding partner binding domain of the protein and, therefore, bind and neutralize a binding partner of the protein. Such neutralizing anti-idiotypic antibodies or Fab fragments of such anti-idiotypic antibodies can be used in therapeutic regimens.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., Nature Genetics, 7:13–21, 1994; see also U.S. Pat. Nos. 5,545,806 and 5,569,825).

The methods described herein in which anti-polypeptide-of-the-invention antibodies are employed may be performed, for example, by utilizing pre-packaged diagnostic kits comprising at least one specific polypeptide-of-the-invention antibody reagent described herein, which may be conveniently used, for example, in clinical settings, to diagnose patients exhibiting symptoms of disorders associated with aberrant expression of nucleic acids or polypeptides of the invention.

An antibody (or fragment thereof) can be conjugated to a therapeutic moiety such as a cytotoxin, a therapeutic agent, or a radioactive agent (e.g., a radioactive metal ion). Cytotoxins and cytotoxic agents include any agent that is detrimental to cells. Examples of such agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin {formerly designated daunomycin} and doxorubicin), antibiotics (e.g., dactinomycin {formerly designated actinomycin}, bleomycin, mithramycin, and anthramycin), and anti-mitotic agents (e.g., vincristine and vinblastine).

Conjugated antibodies (i.e., antibodies joined to a moiety of a drug molecule) of the invention can be used for modifying a given biological response. The conjugated drug moiety need not be limited to classical chemical therapeutic agents. For example, the drug moiety can be a protein or polypeptide possessing a desired biological activity. Such proteins include, for example, toxins such as abrin, ricin A, Pseudomonas exotoxin, or Diphtheria toxin; proteins such as tumor necrosis factor, alpha-interferon, beta-interferon, nerve growth factor, platelet derived growth factor, tissue plasminogen activator; and biological response modifiers such as lymphokines, interleukin-1, interleukin-2, interleukin-6, granulocyte macrophage colony stimulating factor, granulocyte colony stimulating factor, or other growth factors.

Techniques for conjugating a therapeutic moiety to an antibody are well known (see, e.g., Arnon et al., 1985, "Monoclonal Antibodies For Immunotargeting Of Drugs In Cancer Therapy", in Monoclonal Antibodies And Cancer Therapy, Reisfeld et al., Eds., Alan R. Liss, Inc. pp. 243–256; Hellstrom et al., 1987, "Antibodies For Drug Delivery", in Controlled Drug Delivery, 2nd ed., Robinson et al., Eds., Marcel Dekker, Inc., pp. 623–653; Thorpe, 1985, "Antibody Carriers Of Cytotoxic Agents In Cancer Therapy: A Review", in Monoclonal Antibodies '84: Biological And Clinical Applications, Pinchera et al., Eds., pp. 475–506; "Analysis, Results, And Future Prospective Of The Therapeutic Use Of Radiolabeled Antibody In Cancer Therapy", in Monoclonal Antibodies For Cancer Detection And Therapy, Baldwin et al., Eds., Academic Press, pp. 303–316, 1985; and Thorpe et al., 1982, Immunol. Rev., 62:119–158). Alternatively, an antibody can be conjugated to a second antibody to form an antibody heteroconjugate as described by Segal in U.S. Pat. No. 4,676,980.

Antisense Nucleic Acids

Treatment regimes based on an "antisense" approach involve the design of oligonucleotides (either DNA or RNA) that are complementary to mRNA complementary to DNA sequences of the invention (e.g., SEQ ID NO:1 or 3, or portions of these sequences). These oligonucleotides bind to the complementary mRNA transcripts of the invention and prevent translation. Absolute complementarity, although preferred, is not required. A sequence "complementary" to a portion of an RNA, as referred to herein, means a sequence having sufficient complementarily to be able to hybridize with the RNA in vivo, forming a stable duplex; in the case of double-stranded antisense nucleic acids, a single strand of the duplex DNA may be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, Nature, 372:333, 1984). Thus, oligonucleotides complementary to either the 5' or 3' non-translated, non-coding regions of the gene or mRNA could be used in an antisense approach to inhibit translation of endogenous mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5', 3', or coding region of an mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., Proc. Natl. Acad. Sci. USA, 86:6553, 1989; Lemaitre et al., Proc. Natl. Acad. Sci. USA, 84:648, 1987; PCT Publication No. WO 88/09810) or the blood-brain barrier (see, for example, PCT Publication No. WO 89/10134), or hybridization-triggered cleavage agents (see, for example, Krol et al., BioTechniques, 6:958, 1988), or intercalating agents (see, for example, Zon, Pharm. Res., 5:539, 1988). To this end, the oligonucleotide can be conjugated to another molecule, for example, a peptide, hybridization triggered cross-linking agent, transport agent, or hybridization-triggered cleavage agent.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids. Res., 15:6625, 1987). The oligonucleotide is a 2'-0-methylribonucleotide (Inoue et al., Nucl. Acids Res., 15:6131, 1987), or a chimeric RNA-DNA analog (Inoue et al., FEBS Lett., 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (Nucl. Acids Res., 16:3209, 1988), and methylphosphonate oligonucleotides can be prepared by use of controlled pore glass polymer supports (Sarin et al., Proc. Natl. Acad. Sci. USA, 85:7448, 1988). Examples of antisense molecules that can be used in the methods of the invention include RNA molecules identical to the sequences stretching from nucleotide positions 101–203, 509–725, 2002–2310, and 3907–4702 of SEQ ID NO:1 or positions 567–734, 2346–2678, 3006–3123, and 3634–4201 of SEQ ID NO:3, with U's substituted for all T's. Many other such examples of antisense molecules are also available.

The antisense molecules should be delivered to cells that express nucleic acids or polypeptides of the invention in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense molecule sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcripts of nucleic acids of the invention and thereby prevent translation of the endogenous mRNA. The invention encompasses the construction of an antisense RNA using the complementary strand as a template. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist et al., Nature 290: 304, 1981); the promoter contained in the 3' long terminal repeat of Rous sarcoma virus (Yamamoto et al., Cell, 22:787–797, 1988); the herpes thymidine kinase promoter (Wagner et al., Proc. Natl. Acad. Sci. USA, 78:1441, 1981); or the regulatory sequences of the metallothionein gene (Brinster et al., Nature, 296:39, 1988).

Gene Silencing

Double-stranded nucleic acid molecules can be used to silence or inhibit expression of a gene of the invention (e.g., SEQ ID NO:1 or 3). RNA interference (RNAi) is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an extremely powerful method for making targeted knockouts or "knockdowns" at the RNA level. RNAi has proven successful in human cells, including human embryonic kidney and HeLa cells (see, e.g., Elbashir et al., *Nature*, 411:494–8, 2001). In one embodiment, gene silencing can be induced in mammalian cells by enforcing endogenous expression of RNA hairpins (see Paddison et al., *PNAS*, 99:1443–1448, PNAS). In another embodiment, transfection of small (21–23 nt) dsRNA specifically inhibits gene expression (reviewed in Caplen, *Trends in Biotechnology*, 20:49–51, 2002).

Briefly, RNAi is thought to work as follows. dsRNA corresponding to a portion of a gene to be silenced is introduced into a cell. The dsRNA is digested into 21–23 nucleotide siRNAs, or short interfering RNAs. The siRNA duplexes bind to a nuclease complex to form what is known as the RNA-induced silencing complex, or RISC. The RISC targets the homologous transcript by base pairing interactions between one of the siRNA strands and the endogenous mRNA. It then cleaves the mRNA ~12 nucleotides from the 3' terminus of the siRNA (reviewed in Sharp et al., *Genes Dev*, 15:485–490, 2001; Hammond et al., *Nature Rev Gen*, 2:110–119, 2001).

RNAi technology in gene silencing utilizes standard molecular biology methods. dsRNA corresponding to the sequence from a target gene to be inactivated can be produced by standard methods, e.g., by simultaneous transcription of both strands of a template DNA (corresponding to the target sequence) with T7 RNA polymerase. Kits for production of dsRNA for use in RNAi are available commercially (e.g., from New England Biolabs, Inc.). Methods of transfection of dsRNA or plasmids engineered to make dsRNA are routine in the art.

Gene silencing effects similar to those of RNAi have been reported in mammalian cells with transfection of a mRNA-cDNA hybrid construct (Lin et al., *Biochem Biophys Res Commun*, 281(3):639–44, 2001), providing yet another strategy for gene silencing.

SiRNA sequences to centriolin and pericentrin-B can be designed, for example, using siDESIGN Center or the Custom SMARTPool siRNA Design Service (Dharmacon Research, Inc.).

Centriolin siRNA sequences that can be used in the invention include the following (all listed from 5' to 3': GGAUCAGAGACUCUACCUU (SEQ ID NO:8), GCUGAUUCACAUGCAGGAG (SEQ ID NO:9), GACGAGGCUAUUGGUACUU (SEQ ID NO:10), AAGCAAAGAUACCAUCAUC (SEQ ID NO:11), GUGGUGUGAGCAAAUUGAG (SEQ ID NO:12), AGACCAUAAAGGAGCUGAU (SEQ ID NO:13), GACCAUAAAGGAGCUGAUU (SEQ ID NO:14), and UUCACAUGCAGGAGUUAGA (SEQ ID NO:15). These are merely included as a representative sample of the many centriolin siRNA sequences that can be employed in the invention.

Pericentrin-B siRNA sequences that can be used in the invention include the following (all listed from 5' to 3': UUGGAACAGCUGCAGCAGA (SEQ ID NO:16), AGCUGAGCUGAAGGAGAAG (SEQ ID NO:17), GAAGGAGAAGGAGACGGCA (SEQ ID NO:18), AAAGGUGACAGUUCGCAUU (SEQ ID NO:19), CAGUUCGCAUUCGGAGAAA (SEQ ID NO:20), GCAGACUGUAGUGCGAGAU (SEQ ID NO:21), GCCGUGUCUAAGCUUGAGA (SEQ ID NO:22), and UCACAUCUCGUCCUUUCAC (SEQ ID NO:23). These are merely included as a representative sample of the many centriolin siRNA sequences that can be employed in the invention.

Ribozymes

Ribozyme molecules designed to catalytically cleave mRNA transcripts of nucleic acids of the invention (e.g., SEQ ID NOs:1 or 3 depicted in FIGS. 12A-J and 13A-N, respectively) can be used to prevent translation and expression of mRNA of the invention. (see, e.g., PCT Publication WO 90/11364; Saraver et al., *Science*, 247:1222, 1990). While various ribozymes that cleave mRNA at site-specific recognition sequences can be used to destroy mRNAs of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., *Nature*, 334:585, 1988). Preferably, the ribozyme is engineered so that the cleavage recognition site is located near the 5' end of the mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in *Tetrahymena thermophila* (known as the IVS or L-19 IVS RNA), and which has been extensively described by Cech and his collaborators (Zaug et al., *Science*, 224:574, 1984; Zaug et al., *Science*, 231:470, 1986; Zug et al., *Nature*, 324:429, 1986; PCT Application No. WO 88/04300; and Been et al., *Cell*, 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in nucleic acids of the invention.

As in the antisense approach, the ribozymes can be composed of modified oligonucleotides (e.g., for improved stability, targeting, etc.), and should be delivered to cells that express nucleic acids or polypeptides of the invention in vivo. A preferred method of delivery involves using a DNA construct "encoding" the ribozyme under the control of a strong constitutive pol III or pol II promoter, so that transfected cells will produce sufficient quantities of the ribozyme to destroy endogenous messages and inhibit translation. Because ribozymes, unlike antisense molecules, are catalytic, a lower intracellular concentration is required for efficiency.

Screening Assays

Compounds with unknown function can be screened to determine whether they specifically bind to nucleic acids or polypeptides of the invention using any standard binding assay. For example, candidate compounds can be bound to a solid support. A nucleic acid or polypeptide of the invention is then exposed to the immobilized compound and binding is measured (e.g., as done in European Patent Application 84/03564).

In one embodiment, the invention provides assays for screening candidate or test compounds that bind with or modulate the activity of the membrane-bound form of a polypeptide of the invention or biologically active portion thereof. The test, or "candidate", compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam, *Anticancer Drug Des.*, 12:145, 1997).

Examples of methods useful for the synthesis of molecular libraries can be found in the art, for example in: DeWitt et al., *Proc. Natl. Acad. Sci. USA*, 90:6909, 1993; Erb et al., *Proc. Natl. Acad. Sci. USA*, 91:11422, 1994; Zuckermann et al., *J. Med. Chem.*, 37:2678, 1994; Cho et al., *Science*, 261:1303, 1993; Carrell et al., *Angew. Chem. Int. Ed. Engl.*, 33:2059, 1994; Carell et al., *Angew. Chem. Int. Ed. Engl.*, 33:2061, 1994; and Gallop et al., *J. Med. Chem.*, 37:1233, 1994.

Libraries of compounds can be presented in solution (e.g., Houghten, *Bio/Techniques*, 13:412–421, 1992), or on beads (Lam, *Nature*, 354:82–84, 1991), chips (Fodor, *Nature*, 364:555–556, 1993), bacteria (U.S. Pat. No. 5,223,409), spores (U.S. Pat. Nos. 5,571,698; 5,403,484; and 5,223,409), plasmids (Cull et al., *Proc. Natl. Acad. Sci. USA*, 89:1865–1869, 1992) or phage (Scott and Smith, *Science*, 249:386–390, 1990; Devlin, *Science*, 249:404–406, 1990; Cwirla et al., *Proc. Natl. Acad. Sci. USA*, 87:6378–6382, 1990; and Felici, *J. Mol. Biol.*, 222:301–310, 1991).

In one embodiment, an assay is a cell-based assay in which a cell that expresses a membrane-bound form of a polypeptide of the invention, or a biologically active portion thereof, on the cell surface is contacted with a test compound and the ability of the test compound to bind with the polypeptide is determined. The cell, for example, can be a yeast cell or a cell of mammalian origin. Determining the ability of the test compound to bind with the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radio-emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of a polypeptide of the invention, or a biologically active portion thereof, on the cell surface with a known compound that binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind with the polypeptide or biologically active portion thereof as compared to the known compound.

In another embodiment, the assay involves assessment of an activity characteristic of the polypeptide, wherein binding of the test compound with the polypeptide or a biologically active portion thereof alters (i.e., increases or decreases) the activity of the polypeptide.

Methods of Use

The invention provides the nucleic acid and polypeptide sequences of centriolin and pericentrin-B. These nucleic acid sequences themselves have many uses, for example, in the production of hybridization probes to locate identical, homologous, or similar DNA or RNA sequences, within either humans or other organisms (especially mammals).

The invention includes methods of reducing or preventing cell division by, for example, blocking the replication, expression, or translation of centriolin or pericentrin-B, or by, for example, interfering with the activity of centriolin or pericentrin-B polypeptide. Abnormalities in cell division have been linked to numerous debilitating diseases and disorders, including cell proliferation disorders, not the least of which are cancers, leukemia, psoriasis, and leukemia. Because of their pivotal role in modulating cell division, centriolin and pericentrin-B can be used to treat such diseases and disorders at the subcellular level of causation. For example, methods of the invention can be used to treat cancer by modulating centriolin or pericentrin-B (e.g., via RNAi, siRNA, antisense nucleic acids, ribozymes, antibodies) so as to drive cancer cells into cell-cycle arrest. For example, the siRNA molecules of SEQ ID NOs:8, 9, and 10 can be used effectively to arrest the cell-cycle by interfering with centriolin. In a patient with a cell proliferative disorder (e.g., psoriasis, cancers, leukemia, Hodgkin's disease, lymphomas, myelofibrosis, polycythemia vera), these molecules can be delivered to the patient to stop cell proliferation, thereby ameliorating the symptoms of the disease and slowing or stopping its progression. Similarly, siRNA molecules of SEQ ID NOs:16, 17, and 18 can be used effectively to arrest the cell-cycle by interfering with pericentrin-B. Such molecules can also be delivered to particular tissues most affected by unhealthy cell proliferation, thus localizing cell-cycle arrest.

In addition, the invention provides methods of restoring normal centriolin or pericentrin-B function (e.g., to cells in which centriolin or pericentrin-B expression or activity is inadequate to sustain a normal cell division cycle) by administering therapeutically effective amounts of centriolin or pericentrin-B polypeptides. This provides a method of treatment for debilitating diseases in which cell proliferation is inadequate for healthy bodily functioning (e.g., in healing of wounds or replacement of epithelial cells).

The invention also provides a method for the diagnosis of abnormal centriolin and pericentrin-B expression or activity, thus allowing, for example, valuable insight into the etiology of diseases, disorders, or symptoms thereof that have previously defied medically useful explanation. Having linked any such disease, disorder, or symptom thereof to abnormal centriolin and pericentrin-B expression or activity, methods of the invention then provide treatments heretofore unavailable or unknown.

Effective Dose

Toxicity and therapeutic efficacy of the molecules disclosed in the invention (e.g., nucleic acids, polypeptides, ribozymes, antibodies etc.) and the compounds that modulate their expression or activity can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other compounds that exhibit large therapeutic indices are preferred. While compounds that exhibit toxic side effects may be used, care should be taken to design a delivery system that targets such compounds to the site of affected tissue to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

The compounds may also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The nucleic acids, polypeptides, antibodies, or modulatory compounds of the invention can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences". It is expected that the preferred route of administration will be intravenous.

It is recognized that the pharmaceutical compositions and methods described herein can be used independently or in combination with one another. That is, subjects can be administered one or more of the pharmaceutical compositions, e.g., pharmaceutical compositions comprising a nucleic acid molecule or protein of the invention or a modulator thereof, subjected to one or more of the therapeutic methods described herein, or both, in temporally overlapping or non-overlapping regimens. When therapies overlap temporally, the therapies may generally occur in any order and can be simultaneous (e.g., administered simultaneously together in a composite composition or simultaneously but as separate compositions) or interspersed. By way of example, a subject afflicted with a disorder described herein can be simultaneously or sequentially administered both a cytotoxic agent which selectively kills aberrant cells and an antibody (e.g., an antibody of the invention) which can, in one embodiment, be conjugated or linked with a therapeutic agent, a cytotoxic agent, an imaging agent, or the like.

EXAMPLES

The invention is further described in the following examples, which do not limit the scope of the invention described in the claims. The general experimental procedures are described first.

Experimental Procedures

Western Blotting

Western blotting was carried out in centrosome fractions prepared from HeLa cells. The IF method was employed. Embryos were processed as described in Doxsey et al. (*Cell*, 76:639–650, 1994). RT-PCR bands were sequenced.

Cell Culture and Transfections

The cells used primarily in this study were diploid, telomerase-immortalized human retinal pigment epithelial cells (hTERT-RPE1s, Clontech) (Morales et al., *Nat Genet*, 21:115–118, 1999). Other cells included HeLa, COS-7, hTERT-HME1 (human mammary epithelia), Saos, U2OS and *Xenopus* tissue culture cells (XTC). All were grown as described (American Type Culture Collection). COS-7 cells were transfected with cDNAs encoding centriolin, the Nud1 domain, and the pericentrin-B centrosome localization domain as described (Lipofectamine, InVitrogen).

Antibody Production

Amino acids 268–903 or centriolin were fused with glutathione-S-transferase (GST, Clontech), overexpressed in *E. coli* and purified as described (Doxsey et al., *Cell*, 76:639–650, 1994). Antibodies raised in rabbits were affinity-purified by passing sera over a GST column to remove anti-GST antibodies then over a GST-centriolin column. Antibodies to the following proteins were also used in this study: lamin A/C (Cell Signaling Technology), a and g tubulins, (Sigma), LexA (Santa Cruz), GAL4 TAD (Clontech), pericentrin-B (T. Davis, R. Balczon), Ki-67, hemagglutinin (BD Biosciences).

Aster Formation Assays

*Xenopus* mitotic egg extracts were obtained as described in Doxsey (1994 #131). Asters were formed by adding 1 ul of sperm (104) to 8.8 µl of crude egg extract containing 0.2 ul of 10 mg/ml rhodamine tubulin (Cytoskeleton). This mixture was incubated at 25° C. for 7 minutes then affinity-purified centriolin antibody or rabbit IgG (Sigma) were added to reach a final concentration of 50 ug/ml. At 0, 5, 10 and 15 minutes after antibody addition, samples were prepared as described in Doxsey (1994), and immediately viewed for the presence of asters under a Zeiss Axiophot fluorescence microscope equipped with DAPI and rhodamine filters. The number of asters associated with sperm were recorded for each timepoint.

Immunofluorescence and Electron Microscopy

Cells were prepared for immunofluorescence and imaged as described (Dictenberg et al., *J Cell Biol.*, 141:163–174, 1998) then deconvolved using Metamorph software (Universal Imaging Corp.). Immunogold electron microscopy was performed as described (Doxsey et al., *Cell*, 76:639–650, 1994) using centrosome fractions from HeLa cells (Blomberg and Doxsey, *Meth Enzymol*, 298:228–238, 1998) and antibodies to centriolin followed by antibodies coupled to 5 nm gold particles (Amersham).

Centriolin and Pericentrin-B Cloning and Sequencing

A cDNA of ~1.7 kB was identified by screening a human placenta expression library with serum from individuals with scleroderma (Doxsey et al., *Cell*, 76:639–650, 1994). The nucleotide sequence was compared with others (blastn) in the human genome database (NCBI) and revealed a sequence with 99% identity on chromosome 9 q34.11–34.13 (Genbank accession # AF513978). Genscan predicted a ~7 kb gene comprising 40 exons. PCR primers were used to obtain a ~7 Kb cDNA in a human testes cDNA library. The 5' end, obtained by rapid amplification of cDNA ends (RACE), was identical to the predicted sequence. A full-length HA-tagged centriolin was obtained by inserting an HA tag (YPYDVPDYASL) 5' to the RACE fragment and ligating the HA-centriolin cDNA to the original fragment. The full length centriolin cDNA contained 6,975 nucleotides with an ORF of 2,325 amino acids and predicted molecular mass of 269 kD, consistent with the molecular mass of endogenous centriolin.

Regions flanking the ORF had a translational start (Kozak sequence), polyadenylation sequence, poly-A tail and multiple upstream and downstream stop codons. The construct was inserted into pcDNA 3.1 Zeo (+) (InVitrogen) using BamHI and NotI restriction sites. Centriolin was translated in vitro (TNT, Promega) and expressed in cultured cells using conventional procedures (Lipofectamine, InVitrogen). Centriolin amino acids 435–623 and 1385–1658 were 24% identical/47% similar and 20% identical/41% similar to the COOH-terminal half of TACCs, respectively. Amino acids 879–913 were 40% identical/51% similar to amino acids 72–106 of human stathmin. Amino acids 126–234 were 31–35% identical/47%–50% similar to Nud1p and Cdc11p.

Using the cDNA sequence of the human pericentrin-B (GenBank accession numbers U52962 &XM_036857), the 10,011 bp cDNA was cloned using a combination of library screening and RT-PCR. A clone containing ~4 kB of the 3' pericentrin-B sequence was isolated from a human lung cDNA library by screening with a short cDNA, and the remaining ~6 kb was obtained by RT-PCR from human testis mRNA in 1 kB sections. An HA tag was added 5' to the start methionine and the resulting cDNA was cloned into the pcDNA3.1 vector between the Nhe I and Not I sites (Cytomyx, Cambridge UK). Both strands of the cDNA were sequenced.

siRNAs and Morpholino Antisense siRNAs targeting centriolin, pericentrin-B, lamin A/C, and GFP mRNAs were made as complimentary single stranded 19-mer siRNAs with 3' dTdT overhangs (Dharmacon Research), deprotected, annealed and delivered into cells (Oligofectamine, Invitrogen). A 400 mM stock was used to increase the efficiency of gene silencing observed using published stocks. Nucleotides targeted: in centriolin, 117–136 (FIG. 4A–G) and 145–163, in pericentrin-B, 301–319 (FIG. 7A–G) and 975–993, in lamin A/C, 608–630 (Genbank Acc. No. X03444) and pEGFP-C1 (Clontech), 233–252.

Fluorescein-conjugated morpholino antisense DNA oligonucleotides (Gene Tools) targeting the start codon of centriolin (5'-TTTGTTGAGAACCTTTCTTCATTGC) (SEQ ID NO:24) were introduced into cells using the EPEI agent (Gene Tools). The inverse sequence was used as control.

Time-Lapse Imaging

HeLa cells plated on coverslips (25 mm diameter) were treated with siRNAs targeting centriolin for 50 h. They were placed in a chamber (PDMI-2; Harvard Apparatus) in complete medium with $CO_2$ exchange (0.5 liters/min) at 37° C. Cells were imaged every 10 min for 12–20 h using a 20× or 40× phase contrast lens with a green interference filter on an inverted microscope (Olympus IX-70). Images were captured on a CoolSnap HQ CCD camera (Roper Scientific) and concatenated using Metamorph software (Universal Imaging Corp.).

RT-PCR to Determine mRNA Levels following siRNA Treatment

RNA was extracted and purified (Ologotex Direct mRNA miniKit, QIAGEN) and mRNA levels were assessed by the reverse transcription polymerase chain reaction (RT-PCR) with 10 ml of mRNA using OneStep RT-PCR Kit (QIAGEN). Alpha tubulin was amplified in the same tubes as the experimental sample to serve as an internal control. PCR products were subjected to electrophoresis in 1% agarose gel and stained with ethidium bromide. Product authenticity was confirmed by DNA sequencing. Primers used were for pericentrin-B, forward 5'-AACACTCTCCATGATTGCCC-3' (SEQ ID NO:25) and reverse 5'-TACCCTCCCAATCTTTGCTG-3' (SEQ ID NO:26) (GenBank Acc. No. XM_036857).

Cell Synchronization and Cell Cycle Analysis hTERT-RPE1 cells treated with siRNAs and nocodazole (100 ng/ml) for 10 hrs, were washed free of drug and grown for various times before being prepared for immunofluorescence. To examine mitotic cells only, nocodazole-treated mitotic cells were released from plates, washed and re-plated on coverslips. After they adhered (~90 min) most were in telophase; FIG. 4A–G shows cells at the end of the wave of cytokinesis. Flow cytometry was performed on cells stained with propidium iodide (Sigma) using FACScan (Becton Dickinson) and FloJo software.

Primary Cilium Formation

Primary cilia were induced by culturing hTERT-RPE1 cells in medium with 0.25% serum for 48 hrs and identified using the GT335 antibody raised to polygluatamylated α- and β-tubulins (Bobinnec et al., *J Cell Biol.*, 143:1575–1589, 1998). Microtubule nucleation was performed as previously described (Purohit et al., *J. Cell Biol.*, 147:481–491, 1999) by treatment with nocodazole (1 mg/ml) for 1 h at 37° C., fixing cells at various times after washing out drug, and then staining for microtubules.

RT-PCR

Centriolin and pericentrin-B mRNA levels were assayed by reverse transcription polymerase chain reaction (RT-PCR) using 10 µl mRNA (OneStep RT-PCR, Qiagen); α-tubulin served as an internal control in the same reaction. Alls products were sequenced. Primers: specific for pericentrin-B (and not pericentrin-A), forward 5'-AACACTCTC-CATGATTGCCC-3' (SEQ ID NO:25) and reverse 5'-TAC-CCTCCCAATCTTTGCTG-3' (SEQ ID NO:26) (GeneBank Acc. No. XM036857); for human a tubulin, forward 5'-AAAGATGTCAATGCTGCC-3' (SEQ ID NO:27) and reverse 5'-TCCTCTCCTTCTTCCTCAC-3' (SEQ ID NO:28); for centriolin, forward 5'-CCATCATCATCT-CACTCTC-3' (SEQ ID NO:29) and reverse 5'-CTTC-CCTAACCATACTGG-3' (SEQ ID NO:30).

Yeast Two Hybrid Analysis and Immunoprecipitations

A 321 base pair fragment containing amino acids 127–233 of centriolin were cloned into EcoR I and Sal I sites of pGADT7 (Clontech) to produce a fusion with the GAL4 transactivation domain (TAD). Constructs pEG202 (LexA), pGP69 (LexA-BUB2), pGP122 (LexA-BFA1) and the yeast strain SGY37 were from Elmar Schiebel (Paterson Institute for Cancer Research, Manchester, U.K.). SGY37, which contains a LacZ reporter gene under control of a LexA operator, was transformed with plasmid DNA using LiAc (Ito et al., *J Bacteriol*, 153:163–168, 1983) and transformants selected for on dropout medium. Methods used were semi-quantitative β-galactosidase assays (Schramm et al., *Methods Cell Biol.*, 67:71–94, 2001) and more quantitative β-galactosidase assays with CPRG (chlorophenol red-b-D-galactopyranoside, Roche) as a substrate per the manufacturer's instructions (Clontech Yeast Protocols Handbook). Co-immunoprecipitation of LexA and GAL4 TAD fusion proteins were carried out as previously described (Schramm et al., *Methods Cell Biol.*, 67:71–94, 2001).

Semi-quantitative β-galactosidase assays were performed by growing yeast on selective media and overlaying with a solution of 0.4% agarose, 145 mM Na2HPO4, 106 mM NaH2PO4 (pH7.0), 0.5% SDS, 10 mM KCl, 1 mM MgCl2, 0.4 mg/ml 5-bromo-4-chloro-indolyl-b-D galactopyranoside (Sigma) that had been allowed to cool to 40° C. After the agarose had solidified the plates were incubated at 30° C. until a color change was observed.

Quantitative β-galactosidase assays were performed using chlorophenol red-b-D-galactopyranoside (CPRG) as a substrate. Transformed yeast were used to inoculate 2 ml of SD-L-H medium and grown overnight at 30° C. with shaking at 280 rpm. The cultures were then diluted 1:5 with YPDA and grown until the OD600 nm was between 0.5 and 0.8. A 3 ml volume of culture was removed, the cells pelleted by centrifugation at 14,000 rpm for 1 minute and the supernatant discarded. A single wash with CPRG assay buffer (0.05% Tween 20, 1% BSA, 100 mM HEPES, 154 mM NaCl, 4.5 mM L-aspartate) was carried out, the cells re-suspended in 0.6 ml CPRG assay buffer and aliquoted in 0.1 ml volumes into 1.5 ml Eppendorf tubes. The cells were lysed by repeatedly snap freezing in liquid nitrogen and thawing in a 37° C. water bath for a total of three times. A 0.7 ml volume of CPRG substrate buffer (2.23 mM CPRG, 0.05% Tween 20, 1% BSA, 100 mM HEPES, 154 mM NaCl, 4.5 mM L-aspartate) was added to each tube, the contents briefly mixed by vortexing and the samples incubated at 30° C. until a color change was observed. Reactions were stopped by adding 0.5 ml of 3 mM ZnCl2 and pelleting the cellular debris by centrifugation at 14,000 rpm for 2 minutes. The OD578 nm measured against a blank and used to calculate the number of β-galactosidase units produced.

Yeast cells expressing the indicated proteins either alone or in combination were used for immunoprecipitations. The hNud1-β-galactosidase fusion protein or β-galactosidase alone were immunoprecipitated using antibodies to β-galactosidase. LexA-Bub2p and LexA-Bfa1p fusion proteins and LexA alone were immunoprecipitated using an anti-LexA antibody. Following immunoprecipitation with one antibody, the other antibody was used to detect proteins that co-immunoprecipitate by Western blotting. Conditions and buffers for Ips were those specified in (Ito et al., *J. Bacteriol*, 153:163–168, 1983).

Flow Cytometry

Cells treated with siRNAs for 50–70 h were treated with 100 ng/ml for 12 h, removed from plates, and fixed in methanol. Cells stained with propidium iodide were analyzed for flow cytometry (FACSCAN®; Becton Dickinson) using Flojo software (Tree Star, Inc.).

GenBank/EMBL/DDBJ Accession Numbers

The GenBank/EMBL/DDBJ accession number for centriolin is AF513978. The accession number for lamin A/C is X03444. And, the accession numbers for pericentrin-B are U52962 and XM_036857.

Example 1

Identification and Cloning of a 260 kD Protein Localized to the Maternal Centriole and Intercellular Bridge Using sera from patients with the autoimmune disease scleroderma that react with centrosomes (Doxsey et al., Cell, 76:639–650, 1994) a human placenta lgt11 cDNA expression library was screened to identify genes encoding the autoantigens. Of the 3×10⁶ clones screened, only one of 1.7 Kb was identified indicating that the mRNA for this molecule was rare. The protein encoded by the cDNA was called centriolin. Antibodies raised against recombinant centriolin recognized a band of ~270 kD on Western blots of isolated centrosome fractions from cells of a wide range of species including human and *Xenopus* (FIG. 1A); preimmune sera showed no specific bands. The protein was not detected by Western blotting of whole-cell lysates, consistent with the probable low abundance of this and other centrosome autoantigens (Doxsey et al., *Cell*, 76:639–650, 1994). In vitro translation and overexpression of the protein in mammalian cells using the full-length cDNA produced a protein with a molecular weight similar to the endogenous protein (FIG. 1A).

Figure 1B:
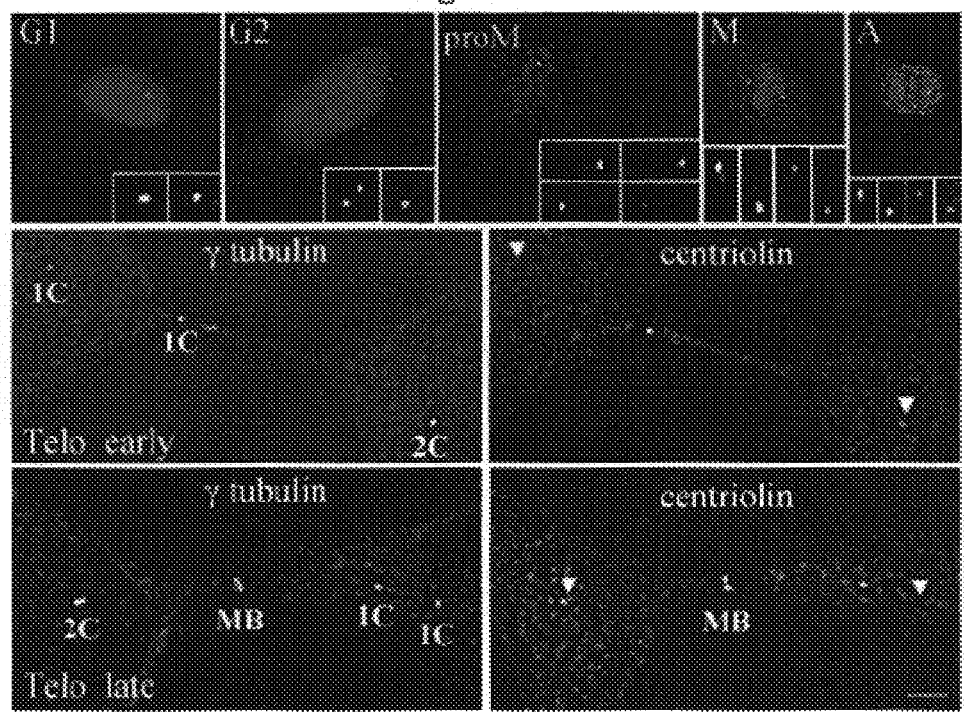
FIG. 1B depicts immunofluorescence images of endogenous centriolin in RPE1 cells through the cell cycle. Upper panels are merged images of centriolin (green), g tubulin (red) and nuclei (blue) from cells in G1, G2, proM, M and anaphase (A). Insets, higher magnifications of centrosomes stained for g tubulin (left panels) and centriolin (right panels). Staining of one of the two centrosomes is demonstrated most clearly in the G2 cell. Lower panels (Telo early, Telo late) show separate images of g tubulin staining (left) and centriolin (right). In these images γ-tubulin marks the centrioles that have separated in some cases. Centriolin staining is confined to one of two centrioles in each centrosome and sometimes appears at the intercellular bridge (Telo early). Centrioles lacking centriolin are indicated by arrowheads in right panels. C, centriole, MB, midbody. Bar in bottom right of B, 10 mm for all except insets, 3 mm.
Figures 2F, 2G:
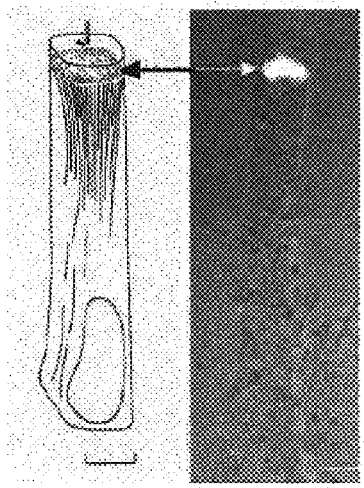

Immunofluorescence microscopy demonstrated that centriolin was localized to centrosomes in a wide variety of species including human, monkey, hamster, mouse, and *Xenopus* (FIGS. 1A–B and 2A–G). Centrosome localization was confirmed by showing that a hemagglutinin (HA)-tagged centriolin protein ectopically expressed in COS cells localized to centrosomes (FIG. 2A). The endogenous protein was present on the centrosome throughout the cell cycle. In late G1/early S phase centrosomes begin to duplicate and by G2/M duplication is completed. During the duplication process, centriolin was present on only one of the two duplicating centrosomes although other proteins such as g tubulin were found on both (FIG. 1B). Beginning at prometaphase, dim staining was observed next to a brightly-stained centrosome. By metaphase when centrosomes become "mature" (Lange and Gull, *J Cell Biol.*, 130:919–927, 1995), both centrosomes had equally high levels of centriolin and were higher than any other cell cycle stage. At the metaphase to anaphase transition, centriolin staining was rapidly reduced at centrosomes and reached its lowest levels by late anaphase/telophase. During cytokinesis, centriolin appeared at the intercellular bridge, initially as one or two dots adjacent to the bridge (FIG. 1B, Telo early) suggesting that the centrosome/centriole had moved to this site. The staining pattern was consistent with recent time lapse imaging experiments showing that the maternal centriole translocates to the intercellular bridge during cytokinesis (Piel et al., *Science*, 291:1550–1553, 2001). Centriolin next appeared as diffusely organized material within the intercellular bridge and then became concentrated at the midbody (FIG. 1B, Telo late).

The organization of centriolin at the centrosome was more precisely determined by serum-starving cells to induce growth of a primary cilium from the maternal centriole (Vorobjev and Chentsov, *J Cell Biol.*, 93:938–949, 1982). In these cells, centriolin staining was confined to the maternal centriole underlying the cilium (FIG. 2B). Immunogold electron microscopy on centrosome fractions (Blomberg and Doxsey, *Meth Enzymol*, 298:228–238, 1998; Doxsey et al., *Cell*, 76:639–650, 1994) confirmed localization to the maternal centriole (FIG. 2E) and further demonstrated that the protein was concentrated on subdistal appendages, specialized substructures of the maternal centriole implicated in microtubule anchoring (FIG. 2C–E) (Chretien et al., *J Struct Biol.*, 120:117–133, 1997; Piel et al., *J Cell Biol.*, 149: 317–330, 2000). Based on its centriolar localization the protein was named centriolin. Centriolin was also found at noncentrosomal apical bands of material in specialized epithelial cells that lack proteins involved in microtubule nucleation (g tubulin) and appear to anchor the minus ends of microtubules (Mogensen et al., *Cell Motil Cytoskel,* 36:276–290, 1997) (FIGS. 2F and G).

Example 2

Figure 3A:
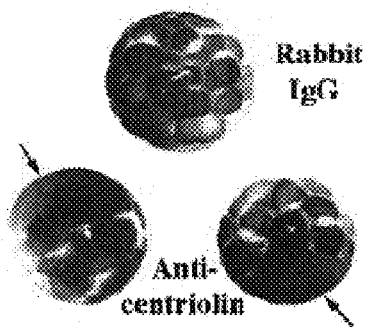
FIGS. 3A–G depict centriolin antibodies and protein overexpression, which disrupts cytokinesis.
Figure 3B:
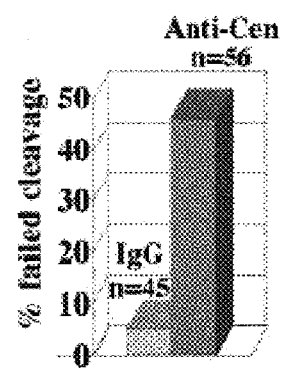

Centriolin Antibodies and Altered Centriolin Levels Induce Delays and Defects in Cytokinesis As an initial test of centriolin function, the effects of affinity-purified anti-centriolin antibodies were examined following microinjection into developing *Xenopus* embryos. A centriolin antibody that cross-reacted with the *Xenopus* protein on Western blots and stained *Xenopus* tissue culture cells by immunofluorescence (FIG. 1A) was injected into one cell of two-cell embryos as described (Doxsey et al., *Cell,* 76:639–650, 1994). Uninjected and preimmune IgG-injected cells divided normally, while cells injected with centriolin antibodies failed to cleave or cleaved a few times then arrested (FIGS. 3A and B). Centriolin antibody-injected cells arrested with two nuclei and two microtubule asters indicating that they had accomplished chromosome segregation, nuclear reformation and centrosome duplication, but failed to complete cytokinesis.

Figure 3C:
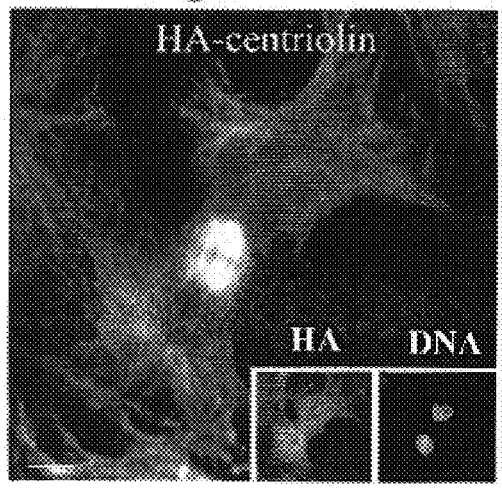
Figure 3D:
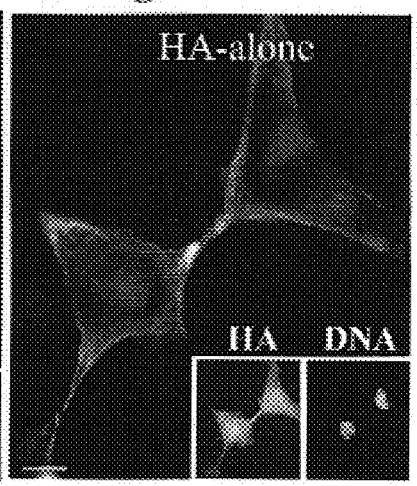
Figure 3E:
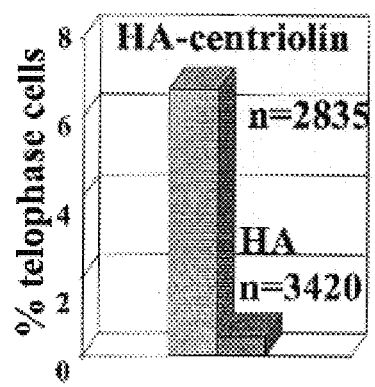
Figure 3F:
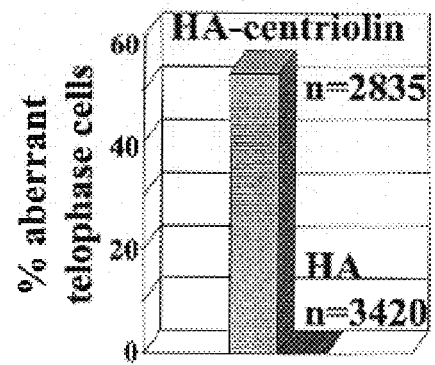
Figure 3G:
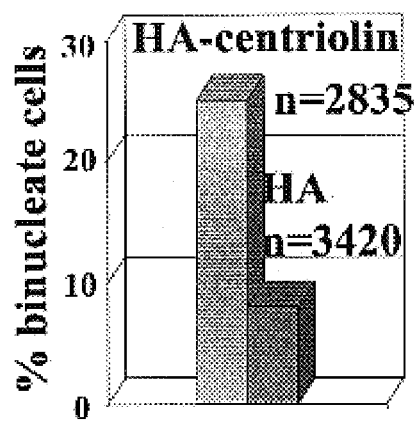

Centriolin function was next tested in vertebrate cells by ectopically expressing protein from a full-length centriolin cDNA. The population of cells expressing hemagglutinin-tagged (HA) centriolin had a significantly higher percentage of telophase cells compared to cells expressing HA alone (FIG. 3E). A striking feature of these cells was the presence of microtubule bundles located within intercellular bridges despite the fact that the nuclei had reformed and contained decondensed chromatin (FIGS. 3C and F). In control cells, nuclei with similar features were seen only in late-stage telophase cells with narrow intercellular bridges and midbodies, or in G1 cells (FIGS. 3D and F). This suggested that cells expressing centriolin had exited mitosis but had not yet cleaved. One consequence of these delays and defects in cytokinesis was formation of binucleate cells apparently by coalescence of two nascent daughter cells into one (FIG. 3G).

Figure 4A:
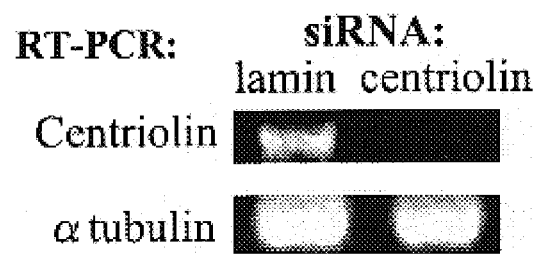
FIGS. 4A–G depict siRNAs targeting centriolin, which induces cytokinesis defects and delays in RPE cells.
Figure 4B:
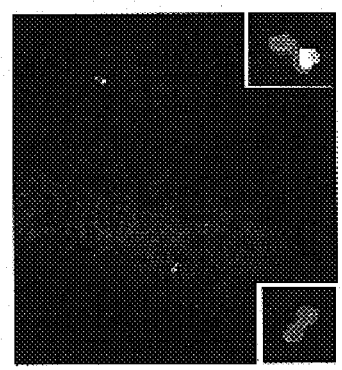
Figure 4C:
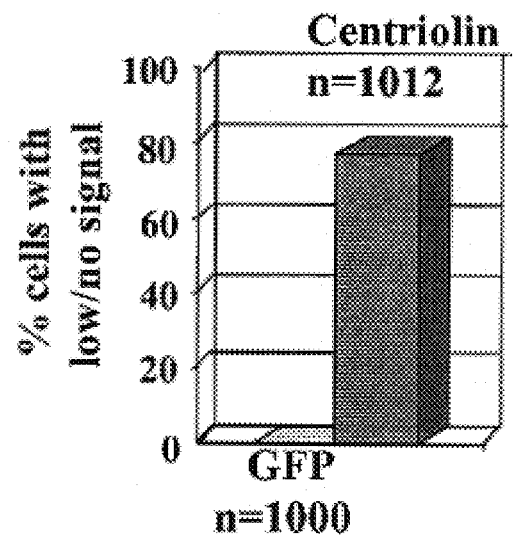
Figure 4D:
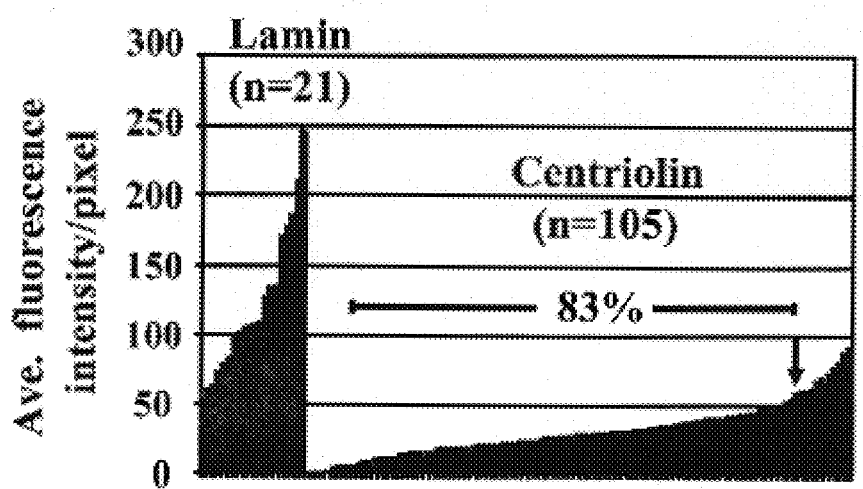

To test the requirement of centriolin protein in cytokinesis we reduced its levels using small interfering RNAs (siRNAs) (Elbashir et al., *Nature,* 411:494–498, 2001). Treatment of telomerase-immortalized diploid human retinal pigment epithelial cells (RPE1) (Morales et al., *Nat Genet,* 21:115–118, 1999) with centriolin-specific siRNAs caused a ~5-fold reduction in centriolin mRNA levels (FIG. 4A). Although we were unable to examine protein levels by Western blotting of whole cell lysates due to the rare nature of this and other centrosome autoantigens (Doxsey et al., Cell, 76:639–650, 1994), immunofluorescence staining demonstrated that centriolin was undetectable or greatly reduced at centrosomes in most cells (FIG. 4B). Quantitative analysis showed that immunofluorescence signals at individual centrosomes was significantly below those in cells treated with control lamin A/C siRNA despite severe disruption of the nuclear lamina in the latter (FIGS. 4C and D, Elbashir et al., Nature, 411:494–498, 2001).

Figure 4E:
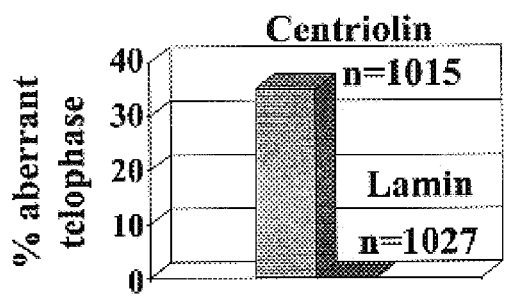
Figure 4F:
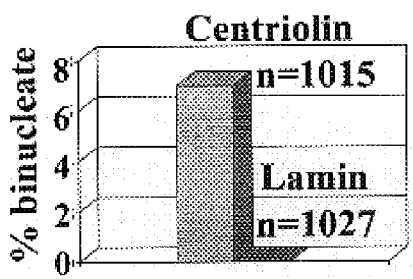
Figure 4G:
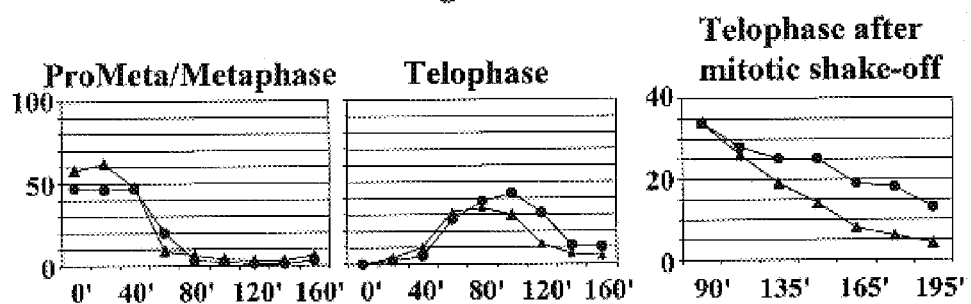

Twenty four hours after treating RPE1 cells with siRNAs targeting centriolin an increase was observed in the percentage of cells in cytokinesis, the appearance of cells undergoing abnormal cytokinesis (wide intercellular bridges, persistent intercellular connections into G1), and formation of binucleate cells (FIGS. 4E and F). Progression through mitosis was also examined by synchronizing a subpopulation of cells. Cells were first treated with siRNAs then with nocodazole to induce mitotic arrest. Upon removal of the drug, cells treated with lamin siRNAs transited through mitosis and completed cytokinesis within 60–80 minutes (similar to untreated cells). In contrast, cells treated with siRNAs targeting centriolin transited normally through prometaphase, metaphase, and early anaphase but were delayed in telophase by up to 20–40 minutes (FIG. 4G, panel 2). Similar results were obtained when nocodazole-treated mitotic cells were mechanically isolated from culture dishes and re-plated. The isolated cells remained in cytokinesis up to 45 minutes longer than controls (FIG. 4G, panel 3).

Cytokinesis defects and delays were also observed in another human cell line (HeLa), with a second set of siRNAs targeting a different centriolin sequence and with morpholino antisense DNA oligonucleotides targeting centriolin in a third cell line (HME1).

Example 3

Centriolin Shares Homology to Yeast Proteins of the MEN and SIN

Insights into the mechanism by which centriolin induced cytokinesis delays and defects came from analysis of the centriolin cDNA sequence (see experimental procedures). The full-length centriolin cDNA contained 6975 nucleotides with an open reading frame of 2325 amino acids and predicted a molecular weight of 269 kD, consistent with the molecular weight of endogenous centriolin (FIG. 1A).

Figure 5A:
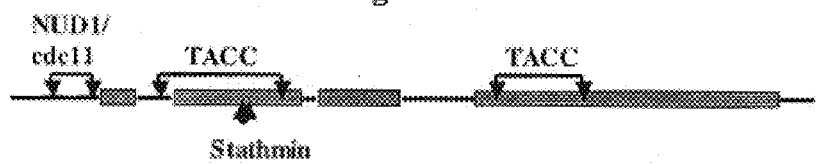
FIGS. 5A–E depict centriolin domain structure and interaction with yeast Bub2p.

The amino acid sequence of centriolin had several interesting features (FIG. 5A). It predicted a protein with several coiled-coil regions interrupted by noncoiled domains (Lupas, Science, 252:1163–1164, 1991). Two domains within the centriolin sequence shared homology with human oncogenic transforming acidic coiled coil proteins (TACC) that localize to centrosomes and are implicated in microtubule binding and stabilization and spindle function (Gergely et al., Proc Natl Acad Sci USA, 97:14352–14357, 2000). Centriolin amino acids 435–623 and 1385–1658 were 24% identical/47% similar and 20% identical/41% similar to the C-terminal half of TACCs, respectively. In addition, centriolin amino acids 879–913 were 40% identical/51% similar to amino acids 72–106 of human stathmin, an oncogenic protein involved in microtubule destabilization (Lee et al., Nat Cell Biol., 3:643–649, 2001). The carboxyl terminus of centriolin was identical to CEP110, a naturally occurring fusion to the fibroblast growth factor (FGF) receptor that localizes to centrosomes, is oncogenic and is of unknown function (Guasch et al., Blood, 95:1788–1796, 2000). CEP110 may be a smaller isoform or truncated form of centriolin.

Figure 5B:
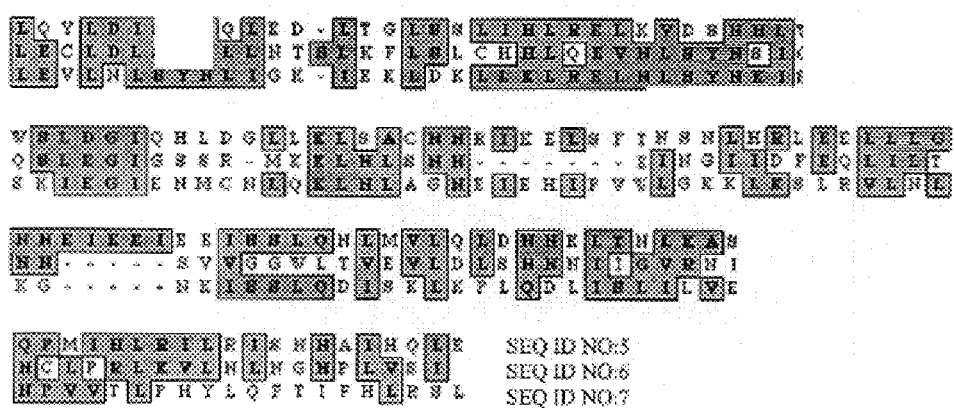
Figure 5C:
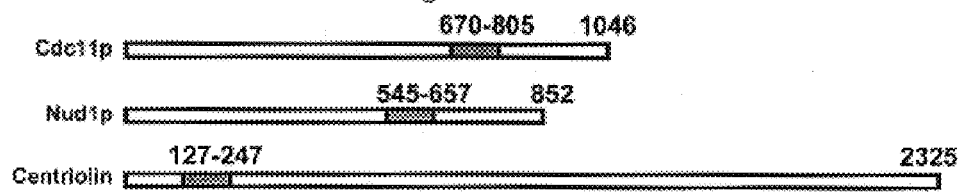

A domain of centriolin at the amino terminus (amino acids 126–234) shared homology with the carboxyl termini of budding yeast Nud1p and fission yeast Cdc11p (FIGS. 5B and C). The centriolin sequence shared the same degree of homology to each of the yeast sequences (31–35% identical, 47–50% similar) as the yeast sequences did to one another (31% identical, 48% similar). Nud1p and Cdc11p are spindle pole body/centrosome proteins that anchor components of the yeast MEN and SIN, respectively, and they are required for completion of mitosis and cytokinesis (Bardin and Amon, Nat Rev Mol Cell Biol., 2:815–826, 2001; Guertin et al., Microbiol Mol Biol Rev, 66:155–178, 2002; McCollum and Gould, Trends Cell Biol., 11:89–95, 2001; Pereira and Schiebel, Curr Opin Cell Biol., 13:762–769, 2001). A regulatory pathway homologous to the yeast MEN and SIN has not been identified in vertebrate cells.

Example 4

The Nud1 Domain of Centriolin Interacts with the Yeast Bub2p

The shared sequence homology between centriolin and Nud1p/Cdc11p and the related roles of the human and yeast genes in the completion of cytokinesis suggested that centriolin functioned in a vertebrate pathway analogous to the yeast MEN/SIN. Moreover, the centriolin Nud1 domain contained the region of Nud1p that interacted directly with the downstream MEN/SIN component Bub2p.

Figure 5D:
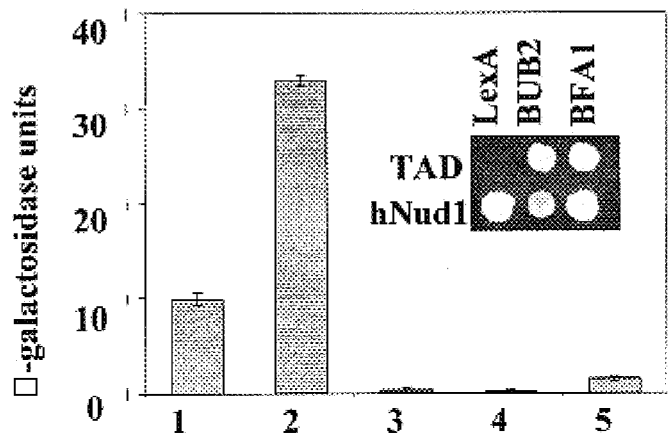
Figure 5E:
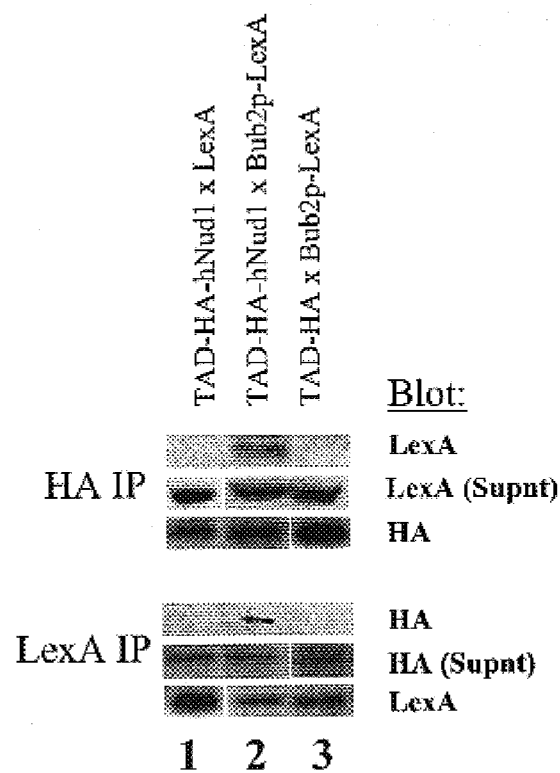

To further examine the possibility that the centriolin Nud1 domain was a member of a pathway analogous to the MEN/SIN, its ability to interact with the yeast Bub2p was tested because no vertebrate Bub2p/Cdc11p has been unequivocally identified. Directed two-hybrid analysis revealed a specific interaction between the centriolin Nud1 domain and Bub2p (FIG. 5D). No signal was observed when either protein was used alone and no binding was detected between centriolin Nud1 and the budding yeast MEN component Bfa1p, consistent with observations in budding yeast (Pereira and Schiebel, Curr Opin Cell Biol., 13:763–769, 2001). The centriolin Nud1-Bub2p interaction was confirmed by immunoprecipitation from yeast cells co-expressing the two proteins (FIG. 5E).

Example 5

Overexpression of the Centriolin Nud1-Interacting Domain Induces Cytokinesis Defects The results disclosed as part of this invention strongly suggested a role for centriolin and the Nud1 domain in particular, in regulating completion of cytokinesis. To test this more directly, the question of whether the 120 amino acid Bub2p-interacting Nud1 domain was sufficient to induce the cytokinesis defects observed in cells overexpressing the full-length protein was considered. The phenotype of cells overexpressing a GFP-tagged Nud1 domain was similar to that observed in cells expressing the full-length protein. There was a significant increase in the percent of telophase cells suggesting a delay in cytokinesis (FIG. 6D), and a dramatic increase in the proportion of binucleate cells suggesting a failure to complete cytokinesis (FIGS. 6C and E). Importantly, overexpression of the Nud1 domain had no detectable effect on the centrosomal localization of the endogenous protein (FIGS. 6A and B). The most likely explanation of these results is that the cytoplasmic overexpressed Nud1 domain sequestered proteins related to the MEN/SIN preventing them from associating with centriolin at the centrosome and inducing delays and defects in cytokinesis.

Example 6

Figure 7B:
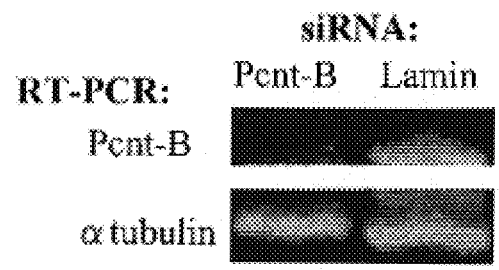
Figure 7C:
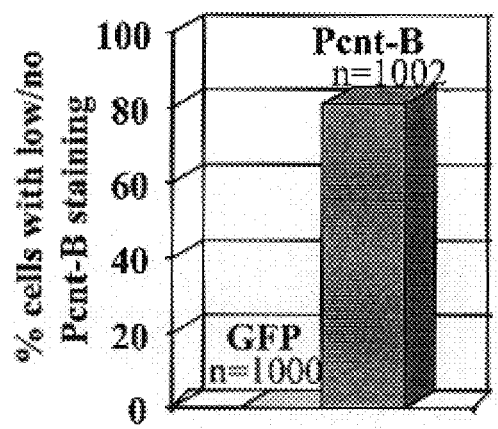
Figure 7D:
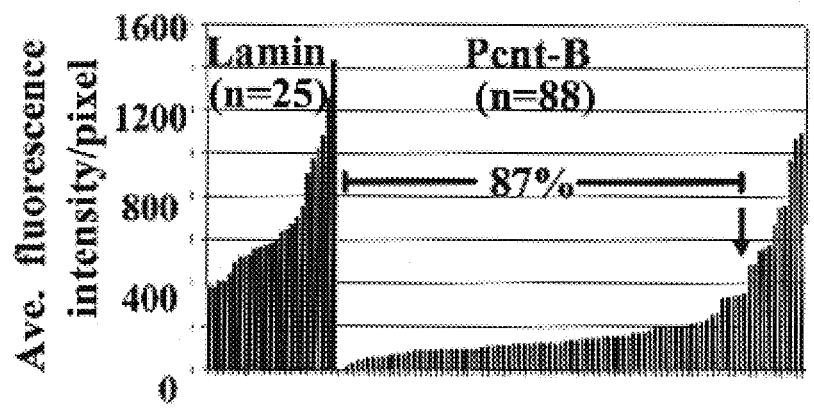
Figure 7E:
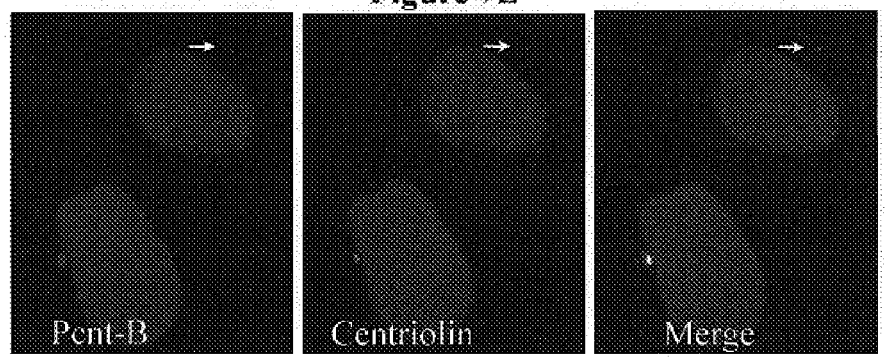
Figure 11:
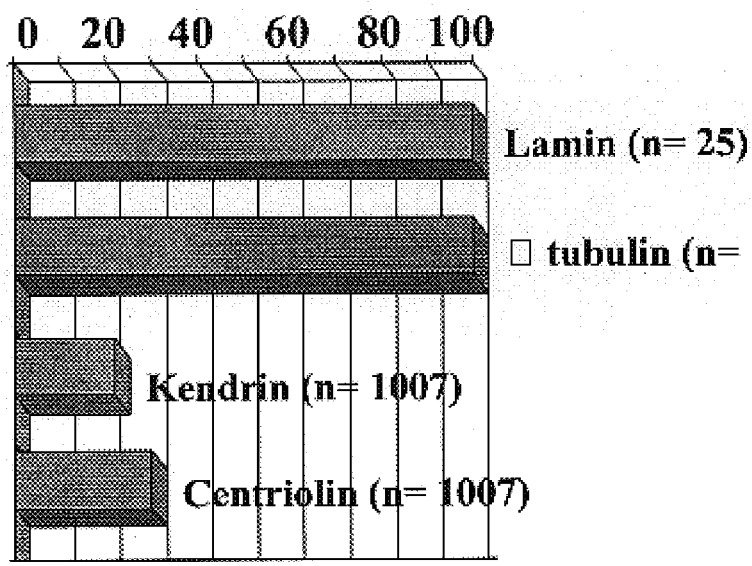
FIG. 11 is a graph that that shows that reduction in pericentrin-B levels specifically mislocalizes centrosomal centriolin. Quantification of cells whose centrosomal levels of the stated antigens are not detectably altered following treatment with siRNAs targeting pericentrin-B (Pcnt-B). n=total number of cells.

Reduction in Pericentrin-B Levels Mislocalizes Centriolin and Induces Cytokinesis Defects In a search of other candidate genes in the putative vertebrate MEN/SIN, we identified pericentrin-B (Accession#AF515282) as a centrosome anchoring protein for centriolin. Pericentrin-B appears to be a larger isoform of pericentrin-A (Doxsey et al., Cell, 76:639–650, 1994). It has a different molecular weight, cellular distribution and biochemical properties, although its function is unknown. Pericentrin-B co-localized with centriolin to the centrosome and, like centriolin, translocated to the intercellular bridge during cytokinesis (FIG. 7A). Cells treated with pericentrin-B-specific siRNAs showed a 5-fold decrease in mRNA levels and a significant loss of centrosome-associated protein (FIG. 7B–D). Essentially all centrosomes with reduced pericentrin-B also showed a dramatic reduction in centriolin (FIG. 7E; FIG. 11). Loss of centrosomal centriolin appeared to be selective since other centrosome proteins such as g tubulin were not significantly affected (100% positive; FIG. 11).

Figure 7F:
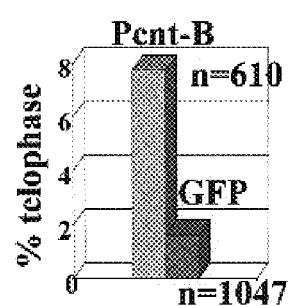
Figure 7G:
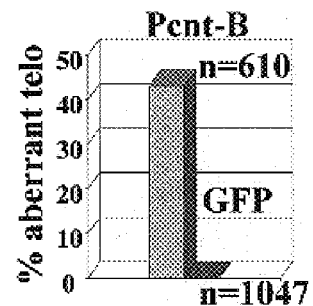

Cells treated with siRNAs targeting pericentrin-B exhibited cytokinesis delays and defects indistinguishable from those observed in cells with reduced centriolin levels (FIGS. 7F and G). Moreover, mislocalization of pericentrin-B and consequently centriolin, by overexpressing the pericentrin-B centrosomal anchoring domain (Gillingham and Munro, EMBO Rep, 1:524–529, 2000) caused cytokinesis defects in COS-7 cells. Thus, the pericentrin-B-induced mislocalization of centriolin from centrosomes suggests that centrosomal anchoring of centriolin, rather than reduction in centriolin levels, was sufficient to induce cytokinesis defects just as mislocalization of spindle pole body-associated Cdc11p and Nud1p induce defects in mitotic exit and cytokinesis. Cytokinesis defects were also observed with a second set of pericentrin-B-specific siRNAs, and in several cell lines including HeLa (FIG. 7A–G), RPE1, and HME1.

Example 7

Reduction in Centriolin and Pericentrin-B Levels Induces G1/G0 Arrest

Figure 8A:
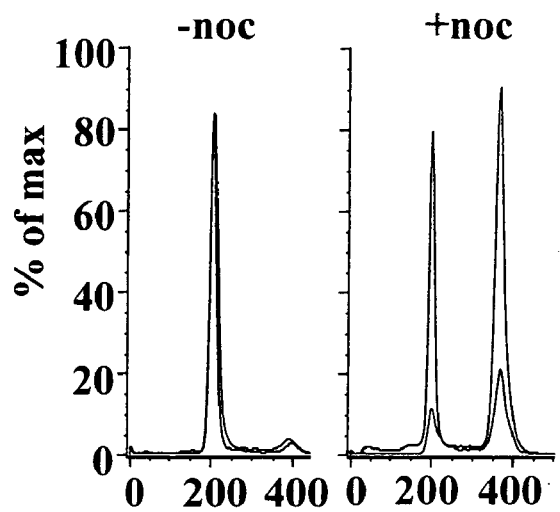
Figure 8B:
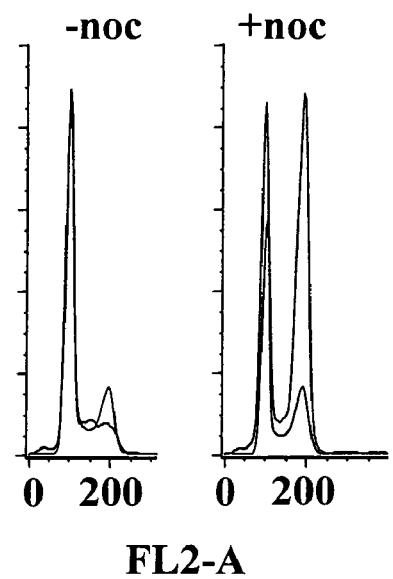
Figure 8C:
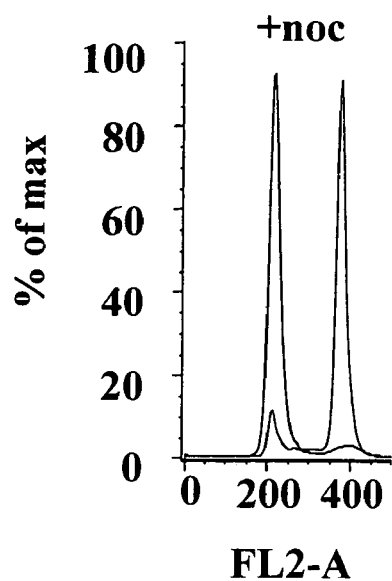
Figure 10:
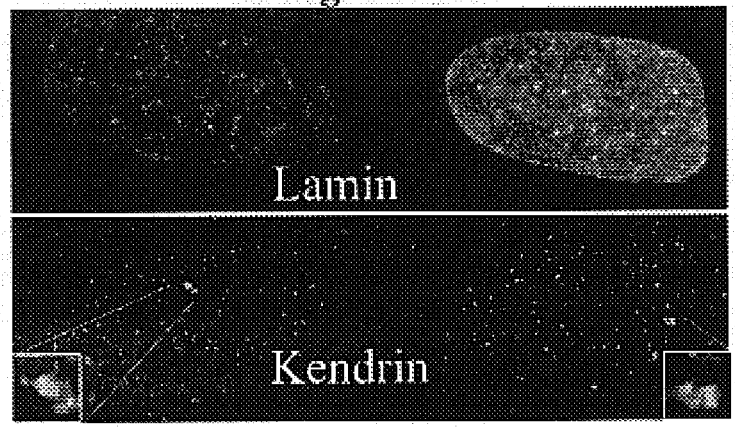
FIG. 10 depicts micrographs that show that lamin siRNA does not affect pericentrin-B localization at centrosomes. Images showing that cells in which lamin is disrupted by lamin-specific siRNAs (upper left) have normal levels of pericentrin-B (lower left), similar to cells unaffected by lamin-specific siRNAs (right, both panels). Insets, higher magnifications of centrosomes in lower panel. Bar, 7.5 μm, and Bar, 2 μm for insets. Pcnt-B, pericentrin-B.

The cytokinesis defects and delays induced by siRNAs targeting centriolin and pericentrin-B in RPE1 cells were observed at early times after treatment (FIG. 4A–G, less than 24 hours). At later times (48–72 hours post treatment) a reduction in the mitotic index was observed suggesting that the cells were arrested at some other stage of the cell cycle. This was directly tested by treating cells with nocodazole to induce mitotic arrest. Although 71% of lamin siRNA-treated control cells arrested in mitosis, only ~1% of the centriolin and pericentrin-B siRNA-treated cells arrested at this cell cycle stage. To determine the cell cycle stage of arrest, cells were analyzed by flow cytometry in the presence and absence of nocodazole. In the absence of nocodazole, cells treated with siRNAs targeting centriolin and pericentrin-B had a slightly higher percentage of cells in G1 compared with control cells treated with lamin or GFP siRNA (FIG. 9; see also FIG. 10). In the presence of nocodazole, control cells showed a significant shift from the G1 peak to the G2/M peak (FIGS. 8A and B; FIG. 9). In contrast, cells treated with siRNAs targeting both centriolin or pericentrin-B did not significantly shift into the G2/M peak in the presence of nocodazole but remained largely in G1. The inability to undergo a nocodazole-induced shift into the G2/M peak was a feature shared by cells driven into G0 by serum starvation (FIG. 8C). These results demonstrate that cells treated with centriolin and pericentrin-B siRNAs arrest prior to S phase, possibly in G1/S, G1, or G0.

Another approach was used to examine the stage of cell cycle arrest. Ki-67 is an antibody directed against a nuclear protein that stains only cycling cells or cells arrested in cycle, including those arrested in G1/S or S phase (Gerdes et al., J Immunol, 133:1710–1715, 1984). Cells that exit the cell cycle and become quiescent (G0) or undergo differentiation, are Ki-67-negative. As expected, nearly all untreated cells or control cells treated with siRNAs targeting GFP or lamins A/C were cycling and thus, positive for Ki-67 (FIG. 8E). However, treatment with siRNAs targeting centriolin and pericentrin-B eliminated Ki-67 staining in essentially all affected cells (80–85%, FIG. 8D, arrowhead, E). Nearly identical results were observed in cells driven into G0 by serum starvation (95% negative). Taken together, the results from mitotic index assays, flow cytometry and Ki-76 staining demonstrated that reduction of centriolin and pericentrin-B levels by siRNA prevented cells from entering S phase and appeared to drive them out of cycle into a G0-like state. Cell cycle arrest was also observed in another diploid cell line (HME1).

Example 8 p53 Dependence of the G1/G0 Arrest

The G1/G0 arrest observed in cells with reduced centriolin and pericentrin-B seemed to be p53-dependent. Reduction of centriolin or pericentrin-B in cells with wild type p53 (RPE1, HME1) (Morales et al., Nat Genet, 21:115–118, 1999) caused G1/G0 arrest as shown by the lack of Ki-67 staining and inability of cells to shift from G1 to G2/M in the presence of nocodazole (FIG. 8A–E). In contrast, cells with abrogated p53 function (HeLa, Saos-2) (Scheffner et al., Cell, 63:1129–11, 1990; Shew et al., Proc Natl Acad Sci USA, 87:6–10, 1990) did not arrest when centriolin or pericentrin-B levels were reduced. The majority stained for Ki-67 (FIGS. 8F and G) and shifted into the G2 peak when treated with nocodazole.

Example 9

Rb Phosphorylation

The effect of the centriolin and pericentrin-B siRNA treatment on Ki-67 staining was not cell-type specific because similar results were observed in three diploid cell lines (i.e., RPE, BJ-1, MRC-5), and two genetically unstable tumor-like cell lines with altered p53 (i.e., HeLa, COS). Similar results were obtained in cells overexpressing centriolin but not the Nud1 domain alone.

Example 10

Centriolin Silencing by siRNA Induces Cytokinesis Failure and a Novel Cytokinesis Phenotype To determine the function of centriolin, its levels were reduced using siRNAs (Fire et al., Nature, 391:806–811, 1998; Elbashir et al., Nature, 411:494–498, 2001). Treatment of telomerase-immortalized diploid human retinal pigment epithedial (RPE-1) cells (Morales et al., *Nature Genetics*, 21:115–118, 1999) with centriolin-specific siRNAs caused a significant reduction in centriolin mRNA levels (FIG. 4A). Although protein levels were not successfully examined by Western blotting of whole cell lysates due to the rare nature of this and other centrosome autoantigens (Doxsey et al., *Cell*, 76:639–650, 1994), immunofluorescence staining demonstrated that centriolin was undetectable, or greatly reduces, at centrosomes in most cells (86%; n=1,012). Quantitative analysis showed that immunofluorescence signals at individual centrosomes were significantly below those in cells treated with control lamin A/C siRNA, despite severe disruption of the nuclear lamina in the latter (FIGS. 4B and D) (Elbashir et al., *Nature*, 411: 494–498, 2001). Midbody staining of centriolin was also reduced in cells treated with siRNAs targeting centriolin.

Because centriolin shares homology with proteins known to affect microtubule organization and cytokinesis, we examined cells with reduced centriolin for defects in these functions. The most obvious cellular change detected in RPE-1 cells with reduced centriolin was a dramatic increase in the percentage of late-state mitotic cells (~70-fold increase; FIG. 4E). In addition, an increase in the percentage of binucleate cells was observed in three different cell lines, suggesting that a certain proportion of cells failed to cleave (FIG. 15B). The incidence of binucleate cells was significantly greater than controls, although somewhat lower than that observed for some other proteins involved in cytokinesis (Matuliene and Kuriyama, *Mol. Biol. Cell.* 13:1832–1845, 2002; Meraldi et al., EMBO J., 21:483–492, 2002; Mollinari et al., *J. Cell. Biol.*, 157:1175–1186, 2002). A similar cytokinesis phenotype was observed with a second set of siRNAs targeting a different centriolin sequence and with morpholino antisense DNA oligonucleotides targeting centriolin.

The dramatically high percentage of cells in late mitotic stages suggested a unique cytokinesis defect in these cells. When carefully analyzed by immunofluorescence microscopy, cells with reduced centriolin appeared to be arrested or delayed in the final stages of cytokinesis. Most cells retained intercellular bridges of varying length and thickness (FIGS. 15M and N, arrowheads). In some cases, cells remained connected even though one or both of the future daughter cells had reentered mitosis (FIGS. 15M and N). Some cells failed to cleave, forming syncytia with two, three, of four cells remaining interconnected (FIGS. 15M and N). During the early stages of cytokinesis, midbodies appeared normal.

Figure 16C:
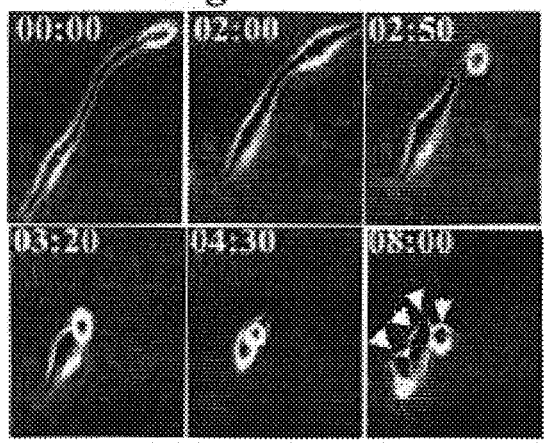
Figure 16D:
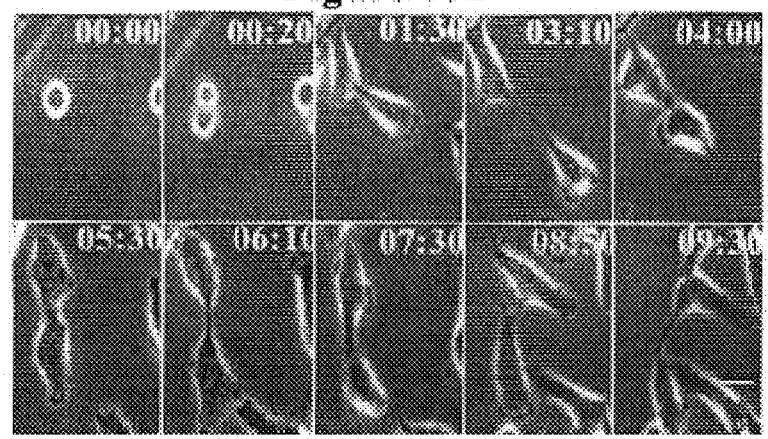
Figure 16E:
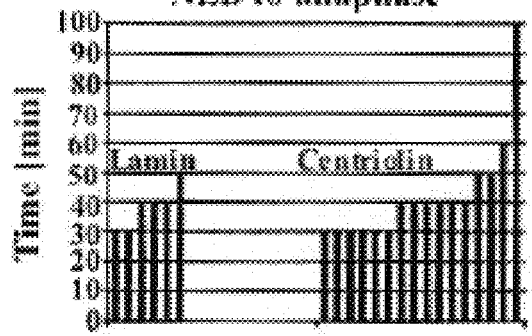
Figure 16F:
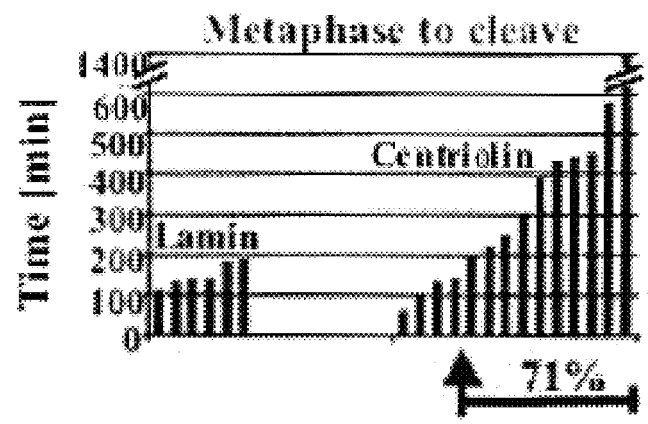

A more complete understanding of the mechanism of cytokinesis failure was obtained by imaging live HeLa cells treated with centriolin-specific siRNAs (FIG. 16A–F; see Videos 1–3, available at http://www.jcb.org/cgi/content/full/jcb.200201105/DC1). As expected, control cells (lamin siRNA) performed a distinct cell cleavage event with normal timing (average 2 h after mitosis) and immediately flattened and crawled apart (FIG. 16A). Cells silenced for centriolin progressed normally through mitosis (FIG. 15G–J; FIG. 16E) and sometimes cleaved normally, but most failed to cleave or cleaved after prolonged periods of time (up to 23.2 h after metaphase; FIG. 16B–D and F). These cells arrested or delayed in a unique post-telophase state. Most were unusually elongated, each with a persistent intercellular bridge of variable diameter that was often dynamic. Bridges alternated between thin threads of interconnecting cytoplasm to very thick interconnections of large diameter that appeared able to produce membrane ruffles (FIG. 16B, 5:50, arrow). Midbodies were not detected within persistent interconnections between cells, suggesting that they were lost sometime during the protracted period spent in cytokinesis. Interconnected cells sometimes coalesced to form single cells and then quickly moved apart again (FIG. 16D). They sometimes made multiple failed attempts at cleavage, but in no case did we observe a cell that formed a stable binucleate. This suggested that binucleate cells observed in fixed cells (FIG. 15B–D) were transient intermediates in a process that involved multiple failed attempts at cytokinesis. Cells that retained intercellular connections for long periods of time continued to progress through the cell cycle. To our surprise, some cells reentered the next mitosis while still interconnected and produced interconnected "progeny" that formed two- to four-cell syncytia, thus confirming the cell-cell interconnections observed by indirect immunofluorescence (FIGS. 15M and N). In some cases, cells that remained interconnected for long periods of time appeared to undergo apoptosis. They showed extensive blebbing, increased phase density, and decreased size and lifted from the substrate (FIG. 16B, tipper cell, 7:20).

Microtubule organization in cells with reduced centriolin appeared normal at all cell cycle stages. This included microtubules of the spindle midzone in anaphase and the Midbody in telophase (FIG. 15E–J). Microtubule nucleation from centrosomes also appeared normal (FIGS. 15K and L), although a slight delay was sometimes observed within the first minute or two. γ-Tubulin, a marker for centrosome-associated microtubule nucleation, was localized normally to centrosomes (FIGS. 4B and D), as were several other centrosome antigens, including GCP-2 (Murphy et al., *J. Cell Biol.*, 141:663–674, 1998) and cNap-1 (Fry et al., *J. Cell Biol.*, 141:1563–1574, 1998; unpublished data). Midbody markers, such as anillin (see Glotzer, *Annu. Rev. Cell. Dev. Biol.*, 17:351–386 2001) and γ-tubulin (Shu et al., *J. Cell. Sci.*, 108:2955–2962, 1995), were also localized normally. At later stages of cytokinesis in cells with long intercellular bridges, midbodies were no longer detected. These data indicate that cytokinesis failure did not result from disruption of microtubules, centrosomes, or midbodies.

Example 11

The Centriolin Nud1 Domain Interacts with the Yeast Bub2p In Vitro

Budding yeast Nud1 p anchors the MEN to the spindle pole body through direct interactions with Bub2p and perhaps other MEN components (Gruneberg et al., *EMBO J.*, 19:6475–6488, 2000; Pereira et al., *Mol. Cell.*, 6:1–10, 2000). To determine if the centriolin Nud1 homology domain (FIG. 5B) had similar properties, its ability to bind Bub2p by directed two-hybrid analysis and immunoprecipitation was tested. Because no vertebrate Bub2p homologue has been unequivocally identified (Cuif et al., *EMBO J.*, 18:1772–1782, 1999), the ability of the centriolin Nud1 domain to interact with yeast Bub2p was examined. Both two-hybrid analysis and immuno-precipitation from yeast cells coexpressing the two proteins revealed a strong and specific interaction between the centriolin Nud1 domain and Bub2p (FIGS. 5D and E). No signal was observed when either protein was used alone, and no binding was detected between the centriolin Nud1 domain and the budding yeast MEN component Bfa1p, consistent with interaction observations in budding yeast (Pereira and Schiebel, *Curr. Opin. Cell Biol.*, 13:762–769, 2001).

Example 12

Figure 17:
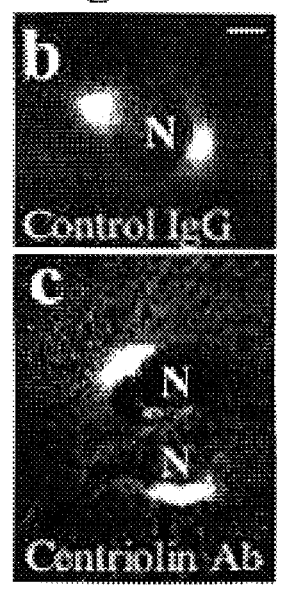
FIG. 17 is a depiction of immunofluorescence images showing two microtubule asters near a single nucleus (N) in a cell from an embryo injected with control IgG (panel above), and two nuclei and two asters in a cell from a centriolin antibody-injected cell (panel below, microtubules stained with anti-α tubulin). Bar, 10 µm.

Cleavage Failure is Observed in *Xenopus* Embryos Injected with Centriolin Antibodies Another approach was used to examine centriolin function. When affinity-purified anticentriolin antibodies (FIG. 1A) were microinjected into one cell of two-cell Xenopus embryos (Doxsey et al., *Cell*, 76:639–650, 1994), the injected cell failed to cleave, or cleaved a few times and then arrested; uninjected cells or preimmune IgG-injected cells divided normally (FIGS. 3A and B). Centriolin antibody-injected cells arrested with two nuclei and two well-organized microtubule asters, indicating that karyokinesis and microtubule organization were normal, but cells failed to complete the final event of mitosis, cell cleavage (FIG. 17B). Preimmune IgG-injected cells had a single nucleus with one or two microtubule asters, depending on their cell cycle stage, as would be expected for cells that had undergone normal cell cleavage (FIG. 17A). Taken together, the results from gene silencing, antibody injection, and protein overexpression in several experimental systems all demonstrate that centriolin plays an important role in the late stages of cytokinesis.

Example 13

SiRNA-Induced Gene Silencing of Centriolin Causes G1/G0 Arrest

Cytokinesis defects and delays induced by centriolin silencing were observed at early times after treatment of RPE-1 cells (18–24 h). At later times (48–72 h after treatment), a reduction in the mitotic index was observed, suggesting that the cells were arrested at some other stage of the cell cycle. This was directly tested by treating cells with nocodazole to induce mitotic arrest and quantifying mitotic cells in DAPI-stained preparations. Under these conditions, most lamin siRNA-treated control RPE-1 cells were arrested in mitosis (71%), whereas only a small fraction of centriolin siRNA-treated cells arrested at this cell cycle stage (<1%).

To determine the cell cycle stage of arrest, cells were analyzed by flow cytometry. In the presence of nocodazole, control cells showed a significant shift from the G1 peak to the G2/M peak (FIG. 8A, red). In contrast, cells treated with siRNAs targeting centriolin did not significantly shift into the G2/M peak in the presence of nocodazole but remained largely in G1 (FIG. 8A, blue). The inability to undergo a nocodazole-induced shift into the G2/M peak was a feature shared by cells driven into G0 by serum starvation (FIG. 8C, blue). The proportion of cells in S phase was either unaltered or slightly decreased in cells silenced for centriolin both in the presence of nocodazole (centriolin, 13%; lamin, 23%) or in its absence (centriolin, 13%; lamin, 19%). These results demonstrate that cells with reduced centriolin arrest before S phase, possibly in G1/S, G1, or G0.

Ki-67 staining was also used to examine the stage of cell cycle arrest. Ki-67 is an antibody directed against a nuclear protein that stains cycling cells or cells arrested in cycle (e.g., C1/S or S phase; Gerdes et al., *J. Immunol.*, 133: 1710–1715, 1984) but not cells that are quiescent (G0) or differentiated. As expected, nearly all untreated RPE-1 cells or control cells treated with siRNAs targeting GFP or lamins A/C were positive for Ki-67 (FIGS. 8D and E). However, most cells with reduced centriolin had undetectable levels of Ki-67 staining (FIGS. 8D and E). Taken together, results from mitotic index assays, flow cytometry, and Ki-76 staining in RPE-1 and HME-1 (human mammary epithelia) cells (unpublished data) demonstrated that reduction of centriolin levels prevented cells from entering S phase and appeared to drive them out of cycle into a G0-like state. This cell cycle arrest effectively prevents the initiation of additional rounds of centrosome duplication in cells compromised by having diminished levels of centriolin.

Other Embodiments

A number of embodiments of the invention have been described. Nevertheless, it will be understood that various modifications may be made without departing from the spirit and scope of the invention. Accordingly, other embodiments are within the scope of the following claims.

---

What is claimed is:

1. An isolated nucleic acid comprising SEQ ID NO:1, or the complementary sequence thereof.

2. An isolated nucleic acid consisting of SEQ ID NO:1, or the complementary sequence thereof.

3. A vector comprising the nucleic acid molecule of claim 1.

4. A cell comprising the vector of claim 3.

* * * * *

UNITED STATES PATENT AND TRADEMARK OFFICE
CERTIFICATE OF CORRECTION

PATENT NO.        : 7,279,566 B2                                               Page 1 of 1
APPLICATION NO.   : 10/663433
DATED             : October 9, 2007
INVENTOR(S)       : Stephen J. Doxsey It is certified that error appears in the above-identified patent and that said Letters Patent is hereby corrected as shown below:

Please insert the following paragraph in Col. 1, at Line 13:

-- FEDERALLY SPONSERED RESEARCH OR DEVELOPMENT

This invention was made with Government support under Grant No. GM051994 awarded by the National Institutes of Health. The Government has certain rights in the invention. --

Signed and Sealed this

Fourth Day of December, 2007

JON W. DUDAS
*Director of the United States Patent and Trademark Office*